US012590096B2

(12) United States Patent
Zhang et al.

(10) Patent No.: US 12,590,096 B2

(45) Date of Patent: Mar. 31, 2026

(54) IMIDAZO[2,1-F][1,2,4]TRIAZIN-4-AMINE AS TLR8 AGONISTS

(71) Applicant: BeOne Medicines I GmbH, Basel (CH)

(72) Inventors: Guoliang Zhang, Beijing (CN); Jianzhuang Miao, Beijing (CN); Ce Wang, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 1001 days.

(21) Appl. No.: 17/632,027

(22) PCT Filed: Jul. 31, 2020

(86) PCT No.: PCT/CN2020/106190
§ 371 (c)(1),
(2) Date: Feb. 1, 2022

(87) PCT Pub. No.: WO2021/023105
PCT Pub. Date: Feb. 11, 2021

(65) Prior Publication Data

US 2022/0289752 A1 Sep. 15, 2022

(30) Foreign Application Priority Data

Aug. 2, 2019 (WO) ................ PCT/CN2019/099147
Sep. 30, 2019 (CN) ......................... 201910939816.3
Nov. 29, 2019 (CN) ......................... 201911204523.7
Jan. 22, 2020 (CN) ......................... 202010075950.6

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ....... C07D 487/04; C07D 519/00; A61P 1/16; A61P 11/02; A61P 11/06; A61P 31/12; A61P 31/14; A61P 31/16; A61P 35/00; A61P 37/08; A61P 1/04; A61K 31/53
See application file for complete search history.

(56) References Cited

U.S. PATENT DOCUMENTS

| | | | |
|---|---|---|---|
| 2010/0210598 A1 | 8/2010 | Carson et al. | |
| 2013/0324547 A1 | 12/2013 | Boivin et al. | |
| 2017/0273983 A1 | 9/2017 | Ding et al. | |
| 2020/0062758 A1 | 2/2020 | Liu et al. | |

FOREIGN PATENT DOCUMENTS

| | | | | |
|---|---|---|---|---|
| CN | 102439011 A | 5/2012 | | |
| CN | 105367576 A | 3/2016 | | |
| CN | 107344941 A | 11/2017 | | |
| CN | 108069969 A | 5/2018 | | |
| WO | WO-2009132123 A1 * | 10/2009 | ............ A61K 31/12 | |
| WO | WO-2014035140 A2 | 3/2014 | | |
| WO | WO-2014056953 | 4/2014 | | |
| WO | WO-2016023511 A1 | 2/2016 | | |
| WO | WO-2016183094 A1 | 11/2016 | | |
| WO | WO-2017106607 | 6/2017 | | |
| WO | WO-2017223414 A1 | 12/2017 | | |
| WO | WO-2018095426 | 5/2018 | | |
| WO | WO-2018210298 | 11/2018 | | |
| WO | WO-2020160710 A1 * | 8/2020 | ............ A61K 31/53 | |
| WO | WO-2020160711 A1 | 8/2020 | | |
| WO | WO-2021023105 A1 | 2/2021 | | |

OTHER PUBLICATIONS

European Search Report in EP Application No. 20752173.3, mailed Oct. 7, 2022, 7 pages.
Search Report and Written Opinion in SG Application No. 11202108284T, mailed Dec. 5, 2022, 9 pages.
Adams, S., "Toll-like receptor agonists in cancer therapy," Immunotherapy 1(6):949-964 (2009).
Aranda, F. et al., "Trial Watch: Toll-like receptor agonists in oncological indications," OncoImmunology 3:6, e29179 (Aug. 2014).
Barton, G. M. et al., "Toll-like receptors and their ligands," Curr. Top. Microbiol. Immunol. 270:81-92 (2002).
International Search Report and Written Opinion for PCT/CN2020/074436, mailed Apr. 26, 2020, 10 pages.
International Search Report and Written Opinion for PCT/CN2020/074437, mailed Apr. 26, 2020, 15 pages.
International Search Report and Written Opinion for PCT/CN2020/106190, mailed Nov. 3, 2020, 24 pages.
Iwasaki, A. et al., "Toll-like receptor control of the adaptive immune responses," Nat. Immunol. 5(10):987-995 (2004).
Karroum, N. B. et al., "Novel and selective TLR7 antagonists among the Imidazo[1,2-a]pyrazines, Imidazo[1,5-a]quinoxalines, and Pyrazolo[1,5-a]quinoxalines Series," J. Med. Chem., vol. 62, Jul. 2019, pp. 7015-7031.
Lochmuller, C. H. et al., "Chromatographic resolution of enantiomers selective review," J. Chromatogr., vol. 113, No. 3 (Oct. 1975), pp. 283-302.
Monk, B. J. et al., "A phase 2, randomized, double-bind, placebo-controlled study of chemo-immunotherapy combination using motolimod with pegylated liposomal doxorubicin in recurrent or persistent ovarian cancer: a Gynecologic Oncology Group partners study," Ann Oncol. May 1, 2017;28(5):996-1004.

(Continued)

*Primary Examiner* — Amanda L. Aguirre

(74) *Attorney, Agent, or Firm* — Foley & Lardner LLP

(57) ABSTRACT

Disclosed are an imidazo[2,1-f][1,2,4]triazin-4-amine derivative used as a TLR8 agonist or a stereoisomer thereof or a pharmaceutically acceptable salt thereof, and a pharmaceutical composition containing same. Further disclosed is a method for treating cancers using the imidazo[2,1-f][1,2,4]triazin-4-amine derivative or the stereoisomer thereof or the pharmaceutically acceptable salt thereof as a TLR8 agonist.

18 Claims, No Drawings

(56) References Cited

OTHER PUBLICATIONS

Salunke, D. B. et al., "Structure-activity relationships in human toll-like receptor 8-active 2, 3-diamino-furo [2,3-c] pyridines," J. Med. Chem., vol. 55, Aug. 2012, pp. 8137-8151.
Shayan, G. et al., "Phase Ib Study of Immune Biomarker Modulation with Neoadjuvant Cetuximab and TLR8 Stimulation in Head and Neck Cancer to Overcome Suppressive Myeloid Signals," Clin. Cancer Res. Jan. 24, 2018(1):62-72.
Stary, G. et al., "Tumoricidal activity of TLR7/8-activated inflammatory dendritic cells," J. Exp. Med. 204(6):1441-1451 (2007).
Van Duin, D. et al., "Triggering TLR signaling in vaccination," Trends Immunol. 27(1):49-55 (2006).

* cited by examiner

IMIDAZO[2,1-F][1,2,4]TRIAZIN-4-AMINE AS TLR8 AGONISTS

CROSS-REFERENCE TO RELATED APPLICATIONS

This application is a U.S. National Stage Application under 35 U.S.C. § 371 of International Application No. PCT/CN2020/106190, filed Jul. 31, 2020, which claims priority to Patent Application No. PCT/CN2019/099147 (CN), filed Aug. 2, 2019 and Chinese Patent Application Nos. 201910939816.3, filed Sep. 30, 2019; 201911204523.7, filed Nov. 29, 2019; and 202010075950.6, filed Jan. 22, 2020.

FIELD OF THE INVENTION

The invention discloses an imidazo[2,1-f][1,2,4]triazin-4-amine derivative used as a TLR8 agonist or a stereoisomer thereof or a pharmaceutically acceptable salt thereof, and a pharmaceutical composition comprising the same. The invention further discloses a method for treating cancers by using the imidazo[2,1-f][1,2,4]triazin-4-amine derivative or the stereoisomer thereof or the pharmaceutically acceptable salt thereof as a TLR8 agonist.

BACKGROUND OF THE INVENTION

Toll-like receptors (TLRs), which belong to the family of pattern recognition receptors (PRRs), play a key role in early innate immune response by sensing highly conserved pathogen associated molecular patterns (PAMPs) and endogenous damage-associated molecular patterns (DAMPs) (Barton, G. M. and R. Medzhitov (2002). "Toll-like receptors and their ligands." Curr Top Microbiol Immunol 270: 81-92).

Ten different TLRs have been identified in humans. Among them. TLR7, TLR8 and TLR9 belong to the same subfamily of TLR based on their genome structure, sequence similarity and endosome localization. They have a limited expression pattern, and only expressed in some types of immune cells. TLR7 is expressed in B cells and plasma cell-like dendritic cells (pDCs); and TLR8 is expressed in monocytes and myeloid dendritic cells (mDCs) (Iwasaki, A. and R. Medzhitov (2004). "Toll-like receptor control of the adaptive immune responses." Nat Immunol 5(10): 987-995).

In addition to natural ligand single-stranded RNA, imidazoquinolone (or "imiquimod-like" ligand) and guanosine analogues also activate TLR7 and/or TLR8 with different specificity. The activation of TLR7 and/or TLR8 triggers the maturation of dendritic cells (DCs) and the secretion of pro-inflammatory cytokines (van Duin, D., et al. (2006). "Triggering TLR signaling in vaccination." Trends Immunol 27(1): 49-55). CTL and NK cells are further activated and proliferated by DC stimulated by cytokines and antigen presentation. Therefore, the characteristics of TLR agonists constitute an effective strategy to enhance the anti-cancer immunity (Adams, S. (2009). "Toll-like receptor agonists in cancer therapy." Immunotherapy 1(6): 949-964).

Imiquimod (TLR7 agonist), as a single antitumor agent with immuno-stimulating ability, has been successfully used in the treatment of many primary skin tumors and skin metastases (Stary, G., et al. (2007). "Tumoricidal activity of TLR7/8-activated inflammatory dendritic cells." J Exp Med 204(6): 1441-1451, Aranda. F., et al. (2014). "Trial Watch: Toll-like receptor agonists in oncological indications." Oncoimmunology 3: e29179).

WO2016023511 discloses that pyrrolopyrimidine compounds as a TLR7 agonist is used for preparing antiviral drugs.

Motolimod (VTX-2337) is a small molecule agonist specific for TLR8, which is used as an immunotherapy for various cancer types in clinical development. Motolimod, when used as an immunotherapy for cancer patients, has good safety, showing limited toxicity and no evidence of cytokine storms (Ann Oncol. 2017; 28: 996-1004). However, its benefits are usually limited to the subjects with injection site response (Clin Cancer Res. Jan. 1, 2018: 24 (1): 62-72. Ann Oncol. May 1, 2017; 28(5): 996-1004).

At present, a great deal of efforts have been devoted to the preclinical and clinical development of TLR agonists for cancer treatment. Therefore, it is necessary to develop more effective TLR agonists for cancer treatment.

SUMMARY OF THE INVENTION

Unexpectedly and surprisingly, the inventors found that imidazo[2,1-f][1,2,4]triazin-4-amine derivatives disclosed in the invention show more effective activity as TLR8 agonists, especially when ring A in formula (I) is a non-aromatic ring.

In first aspect, the invention discloses a compound of formula (I), (I)

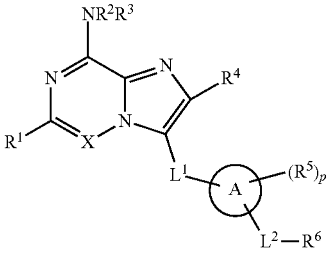

or a pharmaceutically acceptable salt thereof, or a stereoisomer thereof, wherein:

X is N or $CR^7$;

wherein $R^7$ is hydrogen, alkyl, alkenyl, alkynyl, cycloalkyl, cycloalkenyl, cycloalkynyl, heterocyclyl, aryl or heteroaryl;

$L^1$ is $—(CR^aR^b)_m—$, —O—, —S—, —S(O)—, $—SO_2—$, —C(O)—, —C(O)O—, —OC(O)—, $—NR^a—$, $—C(O)NR^a—$, $—NR^aC(O)—$, $—NR^aC(O)O—$, $—NR^aC(O)NR^b—$, $—SO_2NR^a—$, $—NR^aSO_2—$, $—NR^aS(O)_2NR^b—$, $—NR^aS(O)NR^b—$, $—C(O)NR^aSO_2—$, $—C(O)NR^aSO—$, or $—C({=}NR^a)NR^b—$, wherein m is 0 to 8, and one or two $CR^aR^b$ moieties in $—(CR^aR^b)_m—$ are not replaced or replaced by one or more moieties selected from O, S, SO, $SO_2$, C(O) and $NR^a$;

$R^a$ and $R^b$ in each occurrence are independently hydrogen, halogen, alkyl, alkenyl, alkynyl, cycloalkyl, cycloalkenyl, cycloalkynyl, heterocyclyl, aryl, heteroaryl or $—OR^c$;

wherein $R^c$ is hydrogen, alkyl, alkoxy-alkyl-, alkenyl, alkynyl, cycloalkyl, aryl, heterocyclyl or heteroaryl;

$R^1$ is $—OR^{1a}$, $—SR^{1a}$, $—NR^{1a}R^{1b}$, $—COR^{1a}$, $—SO_2R^{1a}$, $—C({=}O)OR^{1a}$, $—C({=}O)NR^{1a}R^{1b}$, $—C({=}NR^{1a})NR^{1b}R^{1c}$, $—N(R^{1a})C({=}O)R^{1b}$, $—N(R^{1a})C({=}O)OR^{1b}$, $—N(R^{1a})C(O)NR^{1b}R^{1c}$, $—N(R^{1a})S(O)NR^{1b}R^{1c}$, $—N(R^{1a})S(O)_2NR^{1b}R^{1c}$, $—NR^{1a}SO_2R^{1b}$, alkyl, alkenyl, alkynyl, cycloalkyl, cycloalkenyl, cycloalkynyl, heterocyclyl, aryl, or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{1d}$;

$R^{1a}$, $R^{1b}$ and $R^{1c}$ are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each optionally substituted with one or two or three substituents selected from: halogen, —$C_{1-8}$ alkyl optionally substituted with $R^{1c}$, cycloalkyl optionally substituted with $R^{1e}$, heterocyclyl optionally substituted with $R^{1c}$, aryl optionally substituted with $R^{1c}$, heteroaryl optionally substituted with $R^{1c}$, $CH_3$—$(OCH_2CH_2)_n$— (where n is 3 to 10) or —$OR^{1f}$;

wherein $R^{1e}$ is halogen, nitro, cyano, hydroxyl, amino (—$NH_2$), alkylamino, dialkylamino. —$C_{1-6}$ alkyl optionally substituted with halogen, carboxyl, alkoxycarbonyl, aminocarbonyl, alkylaminocarbonyl, dialkylaminocarbonyl;

wherein $R^{1f}$ is alkyl, cycloalkyl, heterocyclyl, aryl or heteroaryl, each being optionally substituted with —$C_{1-4}$alkyl or halogen;

each $R^{1d}$ in each occurrence is independently hydrogen, oxo, —CN, —$NO_2$, hydroxyl, amino (—$NH_2$), alkylamino, dialkylamino, halogen, haloalkyl, alkyl, haloalkoxy, alkoxy, alkenyl, alkynyl, cycloalkyl, cycloalkenyl, cycloalkynyl, heterocyclyl, aryl or heteroaryl;

$R^2$ and $R^3$ in each occurrence are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl is optionally substituted with 1-3 substituents selected from: oxo, —CN, —$NO_2$, amino (—$NH_2$), alkylamino, dialkylamino, halogen, hydroxyl, haloalkyl, alkyl, haloalkoxy, alkoxy, alkenyl, alkynyl, cycloalkyl, cycloalkenyl, cycloalkynyl, heterocyclyl, aryl or heteroaryl;

$R^4$ is hydrogen, halogen, cyano, —$NO_2$, —$OR^{4a}$, —$SR^{4a}$, —$NR^{4a}R^{4b}$, —$COR^{4a}$, —$SO_2R^{4a}$, —C(═O)$OR^{4a}$, —C(═O)$NR^{4a}R^{4b}$, —C(═$NR^{4a}$)$NR^{4b}R^{4c}$, —N($R^{4a}$)C(═O)$R^{4b}$, —N($R^{4a}$)C(═O)$OR^{4b}$, —N($R^{4a}$)C(O)$NR^{4b}R^{4c}$, —N($R^{4a}$)S(O)$NR^{4b}R^{4c}$, —N($R^{4a}$)$S(O)_2NR^{4b}R^{4c}$, —$NR^{4a}SO_2R^{4b}$, alkyl, alkenyl, alkynyl, cycloalkyl, cycloalkenyl, cycloalkynyl, heterocyclyl, aryl, or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{4d}$;

$R^{4a}$, $R^{4b}$ and $R^{4c}$ are independently hydrogen, alkyl, alkenyl, alkynyl, cycloalkyl, cycloalkenyl, cycloalkynyl, heterocyclyl, any or heteroaryl, wherein the alkyl, alkenyl, alkynyl, cycloalkyl, cycloalkenyl, cycloalkynyl, heterocyclyl, aryl or heteroaryl are each optionally substituted with halogen, hydroxyl, $NH_2$—, alkylamino, dialkylamino or alkoxy;

each $R^{4d}$ in each occurrence is independently hydrogen, oxo, —CN, —$NO_2$, halogen, hydroxyl, $NH_2$—, alkylamino, dialkylamino, alkyl, alkoxy, alkenyl, alkynyl, cycloalkyl, cycloalkenyl, cycloalkynyl, heterocyclyl, aryl or heteroaryl, wherein the alkyl, alkoxy, alkenyl, alkynyl, cycloalkyl, cycloalkenyl, cycloalkynyl, heterocyclyl, aryl or heteroaryl are each optionally substituted with halogen, hydroxyl, $NH_2$—, alkylamino, dialkylamino or alkoxy;

ring A is a cycloalkyl or heterocyclyl ring;

$R^5$ is halogen, oxo, hydroxyl, alkyl, haloalkyl, alkoxy, haloalkoxy or —C(═O)$OR^{5a}$, wherein $R^{5a}$ is hydrogen, alkyl or haloalkyl;

p is 0, 1, 2 or 3;

$L^2$ is a direct bond, —($CR^fR^g$)—, —O—, —S—, —S(O)—, —$SO_2$—, —C(O)—, —C(O)O—, —OC(O)—, or —$NR^d$— where $R^d$ is —$C_{1-6}$ alkyl, wherein t is 1 to 8, and one or two $CR^fR^g$ moieties in —$(CR^fR^g)_t$— are not replaced or replaced by one or more moieties selected from O, S, SO, $SO_2$, C(O) and $NR^f$;

$R^f$ and $R^g$ in each occurrence are independently hydrogen, alkyl, alkenyl, alkynyl, cycloalkyl, cycloalkenyl, cycloalkynyl, heterocyclyl, aryl or heteroaryl;

$R^6$ is hydrogen, —$NR^{6a}R^{6b}$, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{6c}$;

$R^{6a}$ and $R^{6b}$ are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each optionally substituted with halogen, hydroxyl, $NH_2$—, alkylamino, dialkylamino or alkoxy;

$R^{6c}$ is independently hydrogen, halogen, cyano, —$NO_2$, —$OR^{6d}$, —$SR^{6d}$, —$NR^{6d}R^{6e}$, —$COR^{6d}$, —$SO_2R^{6d}$, —C(═O)$OR^{6d}$, —C(═O)$NR^{6d}R^{6e}$, —C(═$NR^{6d}$)$NR^{6e}R^{6f}$, —N($R^{6d}$)C(═O)$R^{6e}$, —N($R^{6d}$)C(═O)$OR^{6e}$. —N($R^{6d}$)C(O)$NR^{6e}R^{6f}$, —N($R^{6d}$)S(O)$NR^{6e}R^{6f}$, —N($R^{6d}$)$S(O)_2NR^{6e}R^{6f}$. —$NR^{6d}SO_2R^{6e}$, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{6g}$;

$R^{6d}$, $R^{6e}$ and $R^{6f}$ are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each optionally substituted with one or two or three substituents $R^{6g}$;

each $R^{6g}$ in each occurrence is independently hydrogen, halogen, cyano, —$NO_2$, —$OR^{6h}$, —$SR^{6h}$, —$NR^{6h}R^{6i}$, —$COR^{6h}$, —$SO_2R^{6h}$, —C(═O)$OR^{6h}$, —C(═O)$NR^{6h}R^{6i}$, —C(═$NR^{6h}$)$NR^{6i}R^{6j}$, —N($R^{6h}$)C(═O)$R^{6i}$, —N($R^{6h}$)C(═O)$OR^{6i}$, —N($R^{6h}$)C(O)$NR^{6i}R^{6j}$, —N($R^{6h}$)S(O)$NR^{6i}R^{6j}$, —N($R^{6h}$)$S(O)_2NR^{6i}R^{6h}$, —$NR^{6h}SO_2R^{6i}$, alkyl, alkenyl, alkynyl, cycloalkyl, cycloalkenyl, cycloalkynyl, heterocyclyl, aryl or heteroaryl; and $R^{6h}$, $R^{6i}$ and $R^{6j}$ are independently hydrogen, alkyl, alkoxy, alkenyl, alkynyl, cycloalkyl, cycloalkenyl, cycloalkynyl, heterocyclyl, aryl or heteroaryl, wherein the alkyl, alkoxy, alkenyl, alkynyl, cycloalkyl, cycloalkenyl, cycloalkynyl, heterocyclyl, aryl or heteroaryl are each independently and optionally substituted with one or two or three substituents selected from: halogen, $-C_{1-4}$ alkyl, $-C_{1-4}$ alkoxy, hydroxyl, nitro, $-NH_2$, alkylamino, dialkylamino or cyano.

Definition of X

In some embodiments, X is N. In some embodiments, X is $CR^7$, wherein $R^7$ is as defined for formula (I). In some embodiments, X is CH.

Definition of $L^1$

In some embodiments, m is 0 to 5, or 1 to 3, or 1.

In some embodiments, $L^1$ is $-CR^aR^b-$, $-O-$, $-S-$, $-S(O)-$, $-SO_2-$ or $-C(O)-$, wherein $R^a$ and $R^b$ in each occurrence are independently hydrogen, halogen, $-C_{1-8}$ alkyl or $-OR^c$, wherein $R^c$ is hydrogen or $-C_{1-4}$ alkyl. In other embodiments, $L^1$ is $-CR^aR^b-$, wherein $R^a$ and $R^b$ in each occurrence are independently hydrogen, halogen. $-C_{1-8}$ alkyl (preferably $-C_{1-4}$alkyl, and more preferably methyl) or $-OH$. In some embodiments, $L^1$ is $-CH_2-$, $-CH(OH)-$ or $-CH(CH_3)-$. In some embodiments, $L^1$ is $-CH_2-$.

Definition of $R^1$

In some embodiments, $R^1$ is $-OR^{1a}$ or $-NR^{1a}R^{1b}$, wherein $R^{1a}$ and $R^{1b}$ are as defined for formula (I).

In some embodiments, $R^1$ is $-OR^{1a}$ or $-NR^{1a}R^{1b}$, wherein $R^{1a}$ and $R^{1b}$ are independently hydrogen. $-C_{1-8}$ alkyl or $-C_{2-8}$ alkenyl, and the $-C_{1-8}$ alkyl or $-C_{2-8}$ alkenyl are each optionally substituted with one or two or three substituents selected from, heterocyclyl optionally substituted with $R^{1e}$, aryl optionally substituted with $R^{1e}$, $CH_3-(OCH_2CH_2)_n-$ (where n is 3 to 10, preferably 4-8, and more preferably 5-7), or $-OR^{1f}$.

wherein $R^{1e}$ is halogen, $-C_{1-6}$ alkyl optionally substituted with halogen, carboxyl, alkoxycarbonyl, aminocarbonyl, alkylaminocarbonyl, dialkylaminocarbonyl;

wherein $R^{1f}$ is $-C_{1-8}$ alkyl, aryl or heteroaryl, each of which is optionally substituted with $-C_{1-4}$ alkyl or halogen.

In some embodiments, $R^1$ is $-OR^{1a}$, wherein $R^{1a}$ is hydrogen.

In some embodiments, $R^1$ is $-OR^{1a}$, wherein $R^{1a}$ is $-C_{1-8}$ alkyl optionally substituted with one or two or three substituents selected from: halogen, $-C_{1-8}$ alkyl optionally substituted with $R^{1e}$, cycloalkyl optionally substituted with $R^{1e}$, heterocyclyl optionally substituted with $R^{1e}$, aryl optionally substituted with $R^{1e}$, heteroaryl optionally substituted with $R^{1e}$, $CH_3-(OCH_2CH_2)_n-$ (where n is 3 to 10), or $-OR^{1f}$, wherein $R^{1e}$ and $R^{1f}$ are as defined for formula (I).

In some embodiments, $R^1$ is $-OR^{1a}$, wherein $R^{1a}$ is substituted $C_{1-8}$ alkyl. In some embodiments, $R^1$ is $-OR^{1a}$, wherein $R^{1a}$ is linear. In some embodiments, $R^1$ is $-OR^{1a}$, wherein $R^{1a}$ is branched alkyl. In some embodiments, $R^1$ is $-OR^{1a}$, wherein $R^{1a}$ is branched alkyl, preferably $-C_{4-8}$ alkyl, wherein the branched substituent is at the $\alpha$ position relative to the oxygen atom, including but not limited to but-2-yl, pent-2-yl, pent-3-yl, hept-2-yl, hept-3-yl, hept-4-yl, oct-2-yl, oct-3-yl, oct-4-yl, or oct-5-yl. In some embodiments, $R^1$ is methoxy, ethoxy, propoxy, butoxy, pentoxy, hexyloxy, heptyloxy or octoxy. In some embodiments, $R^1$ is preferably propoxy, isopropoxy, n-butoxy, isobutoxy, but-2-yloxy (sec-butoxy), pent-2-yloxy, pent-3-yloxy, 2-methylbutoxy, hep-2-yloxy, hep-3-yloxy, hep-4-yloxy, oct-2-yloxy, oct-3-yloxy, oct-4-yloxy, or oct-5-yloxy. In some embodiments, $R^1$ is n-butoxy, but-2-yloxy (sec-butoxy), pent-2-yloxy, pent-3-yloxy, hept-2-yloxy, hept-3-yloxy, hept-4-yloxy, oct-2-yloxy, oct-3-yloxy, oct-4-yloxy, or oct-5-yloxy.

In some embodiments, $R^1$ is $-OR^{1a}$, wherein $R^{1a}$ is $-C_{1-4}$ alkyl, preferably $-C_{4-5}$ alkyl, wherein the alkyl is substituted with 1-3 halogens, such as fluorine.

In some embodiments, $R^1$ is $-OR^{1a}$, wherein $R^{1a}$ is $-C_{1-8}$ alkyl, preferably $-C_{1-3}$ alkyl, wherein the alkyl is substituted with cycloalkyl optionally substituted with $R^{1e}$, heterocyclyl optionally substituted with $R^{1e}$, aryl optionally substituted with $R^{1e}$ or heteroaryl optionally substituted with $R^{1e}$, wherein $R^{1e}$ is as defined for formula (I).

In some embodiments, $R^1$ is $-OR^{1a}$, wherein $R^{1a}$ is $-C_{1-8}$ alkyl, preferably $-C_{1-3}$ alkyl, wherein the alkyl is substituted with heteroaryl, such as 5-6 membered heteroaryl comprising one or two or three heteroatoms selected from oxygen, nitrogen or optionally oxidized sulfur as ring members, wherein the heteroaryl is optionally substituted with $-C_{1-6}$ alkyl, preferably $-C_{1-4}$ alkyl, and more preferably methyl. In some embodiments, heteroaryl is pyridinyl or imidazolyl or isoxazolyl. In some embodiments, $R^1$ is pyridin-3-ylmethoxy, 2-(1H-imidazol-1-yl)ethoxy or (5-methylisoxazol-3-yl)methoxy.

In some embodiments, $R^1$ is $-OR^{1a}$, wherein $R^{1a}$ is $-C_{1-8}$ alkyl, and preferably $-C_{1-3}$ alkyl, wherein the alkyl is substituted with aryl such as phenyl. In some embodiments, $R^1$ is 2-phenylethoxy or 3-phenylpropoxy.

In some embodiments, $R^1$ is $-OR^{1a}$, wherein $R^{1a}$ is $-C_{1-8}$ alkyl, preferably $-C_{1-3}$ alkyl, wherein the alkyl is substituted with $-OR^{1f}$, wherein $R^{1f}$ is $-C_{1-8}$ alkyl or aryl (e.g., phenyl). In some embodiments, $R^1$ is 2-methoxyethoxy or 2-phenoxyethoxy.

In some embodiments, $R^1$ is $-OR^{1a}$, wherein $R^{1a}$ is $-C_{1-8}$ alkyl, and preferably $-C_{1-3}$ alkyl, wherein the alkyl is substituted with $CH_3-(OCH_2CH_2)_n-$, wherein n is 3 to 10, preferably 3 or 4 or 5. In some embodiments, $R^1$ is 2,5,8,11-tetraoxatridecan-13-yloxy.

In some embodiments, $R^1$ is $-OR^{1a}$, wherein $R^{1a}$ is $-C_{2-8}$ alkenyl; preferably $-C_{2-6}$ alkenyl; and most preferably $-C_{4-6}$ alkenyl. In one example, $R^1$ is but-3-enyloxy.

In some embodiments, $R^1$ is $-NR^{1a}R^{1b}$, wherein $R^{1a}$ and $R^{1b}$ are each hydrogen or $-C_{1-8}$ alkyl, and preferably $-C_{1-6}$ alkyl, wherein the alkyl is optionally substituted with one or two or three substituents selected from: halogen, $-C_{1-8}$ alkyl optionally substituted with $R^{1e}$, cycloalkyl optionally substituted with $R^{1e}$, heterocyclyl optionally substituted with $R^{1e}$, aryl optionally substituted with $R^{1e}$ or heteroaryl optionally substituted with $R^{1e}$, wherein $R^{1e}$ is $-C_{1-6}$ alkyl, such as methyl.

In some embodiments, $R^1$ is $-NR^{1a}R^{1b}$, wherein $R^{1a}$ is hydrogen, and $R^{1b}$ is linear or branched $-C_{1-8}$ alkyl. In some embodiments, $R^1$ is $-NR^{1a}R^{1b}$, wherein $R^{1a}$ is hydrogen, $R^{1b}$ is branched alkyl, and preferably-$C_{4-8}$ alkyl, wherein the branched substituent is at the $\alpha$ position relative to the oxygen atom, including but not limited to but-2-yl, pent-2-yl, pent-3-yl, hept-2-yl, hept-3-yl, hept-4-yl, oct-2-yl, oct-3-yl, oct-4-yl, or oct-5-yl.

In some embodiments, $R^1$ is butylamino, N-butyl-N-methylamino or isopentylamino.

In some embodiments, $R^1$ is optionally partially or completely deuterated, that is, one or more carbon-bonded hydrogen atoms in the definition of $R^1$ are replaced by one or more deuterium atoms.

Definition of $R^2$ and $R^3$

In some embodiments, $R^2$ and $R^3$ in each occurrence are independently hydrogen or $C_{1-8}$ alkyl, and preferably $C_{1-6}$ alkyl. In some embodiments, $R^2$ and $R^3$ are both hydrogen.

Definition of $R^4$

In some embodiments, $R^4$ is hydrogen.

Definition of $R^5$

In some embodiments, $R^5$ is halogen, oxo, hydroxyl, $C_{1-8}$ alkyl, halogenated $C_{1-8}$ alkyl, $C_{1-8}$ alkoxy, halogenated $C_{1-8}$ alkoxy, or —C(═O)$OR^{5a}$, wherein $R^{5a}$ is hydrogen. $C_{1-8}$ alkyl, or halogenated $C_{1-8}$ alkyl; and p is 0, 1, or 2.

In some embodiments, $R^5$ is halogen, oxo, $C_{1-3}$ alkyl, halogenated $C_{1-3}$ alkyl, $C_{1-3}$ alkoxy, or halogenated $C_{1-8}$ alkoxy. In some embodiments, $R^5$ is methyl, ethyl, propyl, methoxy, ethoxy, propoxy, isopropoxy, trifluoromethoxy or trifluoromethyl. In some embodiments, $R^5$ is methyl.

In some embodiments, p is 1.

In some embodiments, $R^5$ and $L^2$-$R^5$ are on ortho-positions of ring A.

Definition of Ring A

In some embodiments, ring A is heterocyclyl.

In some embodiments, ring A is 4-, 5-, 6-, 7-, 8- or 9-membered monocyclic heterocyclyl, which comprises one or two or three heteroatoms selected from oxygen, nitrogen or optionally oxidized sulfur as ring members, preferably 5- or 6-membered heteroaryl comprising one or two nitrogen atoms as ring members; and more preferably, 5- or 6-membered heteroaryl comprising one nitrogen atom as a ring member. In some embodiments, ring A is azetidinyl (e.g., azetidin-1-yl, azetidin-2-yl, azetidin-3-yl, azetidin-4-yl), pyrrolidinyl (e.g., pyrrolidin-1-yl, pyrrolidin-2-yl, pyrrolidin-3-yl), piperidinyl (e.g., piperidin-1-yl, piperidin-2-yl, piperidin-3-yl, piperidin-4-yl), or azepanyl (e.g., azepan-1-yl, azepan-2-yl, azepan-3-yl, azepan-4-yl); and preferably piperidinyl (e.g., piperidin-1-yl, piperidin-4-yl). In some embodiments, ring A is piperazinyl (e.g., piperazin-1-yl or piperazin-2-yl).

In some embodiments, the heterocyclyl ring may comprise one or more double bonds (C═C or C═N), but it is not aromatic. However, the heterocyclyl ring is preferably saturated.

In some embodiments, ring A is spiro heterocyclyl or bridged heterocyclyl, such as 5-20-membered, preferably 6-14-membered, and more preferably 7-12-membered heterocyclyl. In some embodiments, the heterocyclyl is 7-azaspiro[3.5]nonyl, 3-azaspiro[3.1.0]hexyl, 2-azaspiro[3.3]heptyl, 7-azaspiro[3.5]nonyl, 2-azaspiro[3.5]nonyl, 2-azabicyclo[2.2.1]heptyl, 8-azabicyclo[3.2.1]octyl or 2-azabicyclo[4.1.0]heptyl. More specifically, spiro heterocyclyl is 7-azaspiro[3.5]non-2-yl, 3-azabicyclo[3.1.0]hex-6-yl, 2-azaspiro[3.3]hept-6-yl, 7-azaspiro[3.5]non-2-yl, 2-azaspiro[3.5]non-7-yl, 2-azabicyclo[2.2.1]hept-5-yl, 8-azabicyclo[3.2.1]oct-3-yl or 2-azabicyclo[4.1.0]hept-5-yl.

In some embodiments, ring A is a cycloalkyl ring, such as 3-8-membered monocyclic cycloalkyl or 6-12-membered bicyclic cycloalkyl selected from spiro-cycloalkyl, fused cycloalkyl or bridged cycloalkyl, such as bicyclo[1.1.1]pentyl (e.g., bicyclo[1.1.1]pent-1-yl). In some embodiments, ring A is cycloalkenyl or cycloalkynyl.

Definition of $L^2$-$R^6$

In some embodiments, $L^2$ is a direct bond, —$(CH_2)_t$—, —O—, —S—, —S(O)—, —$SO_2$—, —C(O)—, —C(O)O—, —OC(O)—, or —$NR^d$— where $R^d$ is —$C_{1-6}$ alkyl, wherein t is 1 to 8, preferably 1 to 5, and more preferably 1 or 2 or 3; and $R^d$ is —$C_{1-6}$ alkyl.

In some embodiments, $L^2$ is a bond, —$CH_2$—, —$CH_2CH_2$—, —$CH_2CH_2CH_2$—, —O—, or —$NR^d$—, wherein $R^d$ is —$C_{1-6}$ alkyl, preferably —$C_{1-4}$ alkyl, and more preferably methyl.

In some embodiments, $R^6$ is hydrogen, —$NR^{6a}R^{6b}$, —$C_{1-8}$ alkyl, —$C_{2-8}$ alkenyl, —$C_{2-8}$ alkynyl, -cycloalkyl, heterocyclyl, aryl or heteroaryl, wherein the —$C_{1-8}$ alkyl, —$C_{2-8}$ alkenyl, —$C_{2-8}$ alkynyl, -cycloalkyl, heterocyclyl, aryl or heteroaryl are each independently and optionally substituted with one or two or three substituents $R^1$;

$R^{6a}$ and $R^{6b}$ are independently hydrogen or —$C_{1-8}$ alkyl;

$R^{6c}$ is independently hydrogen, halogen, —$OR^{6d}$, —$SR^{6d}$, —$NR^{6d}R^{6e}$, —$COR^{6d}$, —$SO_2R^{6d}$, —C(═O)$NR^{6d}R^{6e}$ or —$C_{1-8}$ alkyl, wherein the —$C_{1-8}$ alkyl is independently and optionally substituted with one or two or three substituents $R^{68}$;

$R^{6d}$ and $R^{6e}$ are independently hydrogen, —$C_{1-8}$ alkyl, —$C_{2-8}$ alkenyl, heterocyclyl or aryl, wherein the —$C_{1-8}$ alkyl, —$C_{2-8}$ alkenyl, heterocyclyl or aryl is each optionally substituted with one or two or three substituents $R^{6g}$;

$R^{6g}$ in each occurrence is independently hydrogen, halogen, —$OR^{6h}$, —$SR^{6h}$, —$NR^{6h}R^{6i}$, —N($R^{6h}$)C(═O)$OR^{6i}$, —$C_{1-8}$ alkyl, heterocyclyl, aryl or heteroaryl, wherein $R^{6h}$ and $R^{6i}$ are independently hydrogen or —$C_{1-8}$ alkyl.

Definition of $L^2$-$R^6$, Wherein $L^2$ is —$(CR^fR^g)_t$— and $R^6$ is Heterocyclyl In some embodiments, $L^2$ is —$(CR^fR^g)_t$— (where t, $R^f$ and $R^g$ are as defined for formula (I)), preferably —$CH_2$— or —$CH_2CH_2$—, and $R^6$ is heterocyclyl optionally substituted with one or two substituents $R^{6c}$, wherein $R^{6c}$ is as defined for formula (I).

In some embodiments, the heterocyclyl as $R^6$ is monocyclic. In some embodiments, the heterocyclyl is bicyclic. In some embodiments, the heterocyclyl is saturated. In some embodiments, the heterocyclyl is a 5-8-membered saturated monocyclic ring which comprises one, two or three heteroatoms selected from oxygen, nitrogen or optionally oxidized sulfur as ring members. In some embodiments, the heterocyclyl is a 5-, 6-, 7- or 8-membered saturated monocyclic ring comprising one or two or three nitrogen heteroatoms as ring members.

In some embodiments, the heterocyclyl as $R^6$ is pyrrolidinyl (e.g., pyrrolidin-1-yl, pyrrolidin-2-yl, pyrrolidin-3-yl), piperidinyl (e.g., piperidin-1-yl, piperidin-2-yl, piperidin-3-yl, piperidin-4-yl, piperidin-5-yl), triazolyl (e.g., 1H-1,2,4-triazol-1-yl), azepanyl (e.g., azepan-2-yl, azepan-3-yl, azepan-4-yl, azepan-5-yl), piperazinyl (e.g., piperazin-1-yl, piperazin-2-yl, piperazin-3-yl) or morpholino. In some embodiments, the heterocyclyl is bicyclic and comprises one, two or three heteroatoms selected from oxygen, nitrogen or optionally oxidized sulfur as ring members. In some examples, the heterocyclyl is (1S,4S)-2,5-diazabicyclo[2.2.1]hept-2-yl. In the above embodiments, the heterocyclyl as $R^6$ is further optionally substituted with one or two substituents $R^{6c}$. In some embodiments, $R^{6c}$ is —$NR^{6d}R^{6e}$, —$COR^{6d}$, —$OR^{6d}$ or —$C_{1-8}$ alkyl optionally substituted with hydroxyl, wherein $R^{6d}$ and $R^{6e}$ are independently hydrogen or —$C_{1-8}$ alkyl (preferably —$C_{1-3}$ alkyl) or phenyl, wherein the alkyl is optionally substituted with $NH_2$—, alkylamino or dialkylamino. In some embodiments, $R^{6e}$ is amino, dimethylamino, 2-(dimethylamino)acetyl, methyl, 3-hydroxypropyl or phenoxy. In some embodiments, $L^2$ is —$CH_2$— or —$CH_2CH_2$—. In some embodiments, $R^6$ is pyrrolidin-1-yl, morpholino, piperidin-1-yl, 4-methylpiperazin-1-yl, piperazin-1-yl, piperidin-4-yl, 4-(2-(dimethylamino)acetyl)piperazin-1-yl, (1S,4S)-2,5-diazabicyclo[2.2.1]hept-2-yl, 4-aminopiperidin-1-yl, 3-(dimethylamino)pyrrolidin-1-yl, 4-phenoxypiperidin-1-yl, 1H-1,2,4-triazol-1-yl, 4-(3-hydroxypropyl)piperazin-1-yl or piperidin-3-yl.

Definition of $L^2$-$R^6$, Wherein $L^2$ is —$(CR^fR^g)$— and $R^6$ is —$NR^{6a}R^{6b}$ In some embodiments, $L^2$ is —$(CR^fR^g)_t$— (where t, $R^f$ and $R^g$ are as defined for formula (I)), preferably —$CH_2$— or —$CH_2CH_2$—, and $R^6$ is —$NR^{6a}R^{6b}$, wherein $R^{6a}$ and $R^{6b}$ are as defined for formula (I). In some embodiments, $L^2$ is —$(CH_2)_t$— (where t is 1 to 8, preferably 1 to 5, and more preferably 1 or 2 or 3), preferably —$CH_2$— or —$CH_2CH_2$—, and $R^6$ is —$NR^{6a}R^{6b}$, wherein $R^{6a}$ and $R^{6b}$ are independently hydrogen or $C_{1-8}$ alkyl, and preferably $C_{1-6}$ alkyl. In some embodiments, $L^2$-$R^6$ are aminomethyl.

Definition of $L^2$-$R^6$, Wherein $L^2$ is a Bond and $R^6$ is Alkyl, Alkenyl or Alkynyl In some embodiments, $L^2$ is a bond and $R^6$ is —$C_{1-8}$ alkyl, —$C_{2-8}$ alkenyl, or —$C_{2-8}$ alkynyl.

Definition of $L^2$-$R^6$, Wherein $L^2$ is —O— or —$NR^{d-}$ and $R^6$ is Alkyl, Alkenyl, Alkynyl, Heterocyclyl, Aryl or Heteroaryl In some embodiments, $L^2$ is —O—, and $R^6$ is —$C_{1-8}$ alkyl or heterocyclyl, wherein the —$C_{1-8}$ alkyl and heterocyclyl are optionally substituted with one or two $R^{6c}$. In some embodiments, $R^{6c}$ is —$C_{1-8}$ alkyl, —$NR^{6d}R^{6e}$ and —$COR^{6d}$, wherein $R^{6d}$ and $R^{6e}$ are independently —$C_{1-8}$ alkyl (preferably —$C_{1-3}$ alkyl) optionally substituted with $NH_2$—, alkylamino or dialkylamino.

In some embodiments, $L^2$ is —$NR^d$— where $R^d$ is —$C_{1-6}$ alkyl, and $R^6$ is —$C_{1-8}$ alkyl, —$C_{2-8}$ alkenyl or —$C_{2-8}$ alkynyl, each of which is optionally substituted with one or two $R^{6c}$. In some embodiments, $R^{6c}$ is —$C_{1-8}$ alkyl or —$NR^{6d}R^{6e}$, where $R^{6d}$ and $R^{6e}$ are independently —$C_{1-8}$ alkyl (preferably —$C_{1-3}$ alkyl). In some embodiments. $L^2$-$R^6$ is (2-(dimethylamino)ethyl)(methyl)amino.

Definition of $L^2$-$R^6$, Wherein $L^2$ is a Direct Bond and $R^6$ is Cycloalkyl, Heterocyclyl, Aryl or Heteroaryl In some embodiments, $L^2$ is a direct bond, and $R^6$ is cycloalkyl, heterocyclyl, aryl or heteroaryl, each of which is independently and optionally substituted with one or two or three substituents $R^{6c}$.

In some embodiments, $L^2$ is a direct bond, and $R^6$ is heterocyclyl, which is optionally substituted with one or two or three substituents $R^{6c}$.

As $R^6$, in some embodiments, the heterocyclyl is monocyclic; in some embodiments, the heterocyclyl is fused bicyclic heterocyclyl; and in some embodiments, the heterocyclyl is spirobicyclic heterocyclyl.

In some embodiments, the heterocyclyl is saturated. In some embodiments, the heterocyclyl is a 4-, 5-, 6-, 7-, or 8-membered saturated monocyclic ring, which comprises one, two or three heteroatoms selected from oxygen, nitrogen or optionally oxidized sulfur as ring members. In some embodiments, the heterocyclyl is a 5-, 6-, 7- or 8-membered saturated monocyclic ring comprising one or two or three nitrogen heteroatoms as ring members. In some embodiments, the heterocyclyl is a 5- or 6-membered saturated monocyclic ring comprising one or two nitrogen heteroatoms as ring members. In some embodiments, the heterocyclyl is pyrrolidinyl (e.g., pyrrolidin-1-yl, pyrrolidin-2-yl, pyrrolidin-3-yl), piperidinyl (e.g., piperidin-1-yl, piperidin-2-yl, piperidin-3-yl, piperidin-4-yl, piperidin-5-yl), triazolyl (e.g., 1H-1,2,4-triazol-1-yl), azepanyl (e.g., azepan-2-yl, azepan-3-yl, azepan-4-yl, azepan-5-yl), diazepinyl (e.g., 1,4-diazepin-1-yl, 1,4-diazepin-2-yl, 1,4-diazepin-3-yl, 1,4-diazepin-4-yl), piperazinyl (e.g., piperazin-1-yl, piperazin-2-yl, piperazin-3-yl), or morpholino.

In some embodiments, the heterocyclyl is bicyclic and comprises one, two or three heteroatoms selected from oxygen, nitrogen or optionally oxidized sulfur as ring members. In some examples, the heterocyclyl is 2,5-diazabicyclo[2.2.1]hept-2-yl.

In some embodiments, the heterocyclyl is 6-14-membered, and more preferably 7-10-membered spirobicyclic heterocyclyl. In some embodiments, the heterocyclyl is spiroheptyl, spirodecyl or spirononyl comprising one or two nitrogen atoms as ring members. In some embodiments, the heterocyclyl is 8-azaspiro[4.5]dec-8-yl, 2,7-diazspiro[3.5]non-7-yl, 2,8-diazspiro[4.5]dec-2-yl, 2,7-diazspiro[3.5]non-2-yl, and 2,8-diazspiro[4.5]dec-8-yl.

In the above embodiments, the heterocyclyl as $R^6$ is further optionally substituted with one or two substituents $R^{6c}$.

In some embodiments, $R^{6c}$ is —$COR^{6d}$, wherein $R^{6d}$ is —$C_{1-8}$ alkyl optionally substituted with one or two substituents $R^{6g}$, wherein $R^{6g}$ is —$NR^{6h}R^{6i}$, —$N(R^{6h})C(=O)R^{6i}$, —$C_{1-8}$ alkyl, aryl or heteroaryl, wherein $R^{6h}$ and $R^{6i}$ are as defined for formula (I). In some embodiments, $R^{6c}$ is —$COR^{6d}$, wherein $R^{6d}$ is —$C_{1-8}$ alkyl (preferably $C_{1-6}$ alkyl, and more preferably $C_{1-4}$ alkyl) optionally substituted with one or two substituents $R^{6g}$, wherein $R^{6g}$ is —$NR^{6h}R^{6i}$, —$N(R^{6h})C(=O)R^{6i}$, —$C_{1-8}$ alkyl, aryl or heteroaryl, wherein $R^{6h}$ and $R^{6i}$ are each independently hydrogen or —$C_{1-8}$ alkyl (preferably $C_{1-6}$ alkyl, and more preferably $C_{1-4}$ alkyl).

In some embodiments, $R^{6c}$ is —$COR^{6d}$, wherein $R^{6d}$ is —$C_{2-8}$ alkenyl.

In some embodiments, $R^{6c}$ is —$COR^{6d}$, wherein $R^{6d}$ is heterocyclyl.

In some embodiments, $R^{6c}$ is acetyl, 2-(dimethylamino)acetyl, 2-(dimethylamino)acetyl, aminoacetyl, 2-(methylamino)acetyl, 3-(dimethylamino)propionyl, 4-(dimethylamino)butyryl, 5-(dimethylamino)valeryl, (2S,3S)-2-amino-3-methylvaleryl, 2-(methylamino)acetyl, 2-amino-4-methylvaleryl, 2-amino-3-methylbutyryl, 2-(dimethylamino)acetyl, phenylpropionyl, 2-(piperazin-1-yl)acetyl, acryloyl, piperazin-2-carbonyl, piperidin-4-carbonyl, pyrrolidin-2-carbonyl or 2-(N-methylacetamino)acetyl.

In some embodiments, $R^{6c}$ is —$C_{1-8}$ alkoxy, preferably —$C_{1-6}$ alkoxy, such as methoxy.

In some embodiments, $R^{6c}$ is —$C_{1-8}$ alkyl, preferably —$C_{1-6}$alkyl, which is optionally substituted with one or two substituents $R^{6g}$, wherein $R^{6g}$ is —$OR^{6h}$, —$NR^{6h}R^{6i}$, heterocyclyl, aryl, wherein $R^{6h}$ and $R^{6i}$ are as defined for formula (I). In some aspects, $R^{6c}$ is —$C_{1-8}$ alkyl, preferably —$C_{1-6}$ alkyl, which is optionally substituted with a substituent $R^{6g}$, wherein $R^{6g}$ is —$OR^{6h}$, —$NR^{6h}R^{6i}$, heterocyclyl (e.g., morpholino), aryl (e.g., phenyl), wherein $R^{6h}$ and $R^{6i}$ are —$C_{1-4}$ alkyl, and preferably methyl. In some embodiments, $R^{6c}$ is methyl, ethyl, isobutyl, methoxymethyl, 2-methoxyethyl, (methylamino)methyl, 2-(dimethylamino)ethyl, (dimethylamino)methyl, 2-aminoethyl, 2-(methylamino)ethyl 2-(dimethylamino)ethyl, morpholinomethyl or phenethyl.

In some embodiments, $R^{6c}$ is heterocyclyl, which is optionally substituted with a substituent $R^{6g}$. In some embodiments, $R^{6c}$ is heterocyclyl, which is optionally substituted with a substituent $R^{6g}$ which is heterocyclyl. In some embodiments, $R^{6c}$ is 4-morpholinopiperidin-1-yl.

In some embodiments, $R^{6c}$ is —$C(=O)NR^{6d}R^{6e}$, wherein $R^{6d}$ and $R^{6e}$ are independently hydrogen, —$C_{1-8}$ alkyl (preferably —$C_{1-3}$ alkyl) or aryl, wherein the —$C_{1-8}$ alkyl or aryl is independently and optionally substituted with halogen or —$C_{1-4}$ alkyl. In some embodiments, $R^{6c}$ is —$C(=O)NR^{6d}R^{6e}$, wherein $R^{6d}$ and $R^{6e}$ are independently hydrogen and —$C_{1-4}$ alkyl. In some embodiments, $R^{6c}$ is —C(=O)

$NR^{6d}R^{6e}$, wherein $R^{6d}$ and $R^{6e}$ are independently hydrogen and aryl optionally substituted with halogen. In some embodiments, $R^{6c}$ is dimethylcarbamoyl, isopropylcarbamoyl or 2,4,5-trifluorophenylcarbamoyl.

In some embodiments, $R^{6c}$ is —$NR^{6d}R^{6e}$, wherein $R^{6d}$ and $R^{6e}$ are independently hydrogen or —$C_{1-8}$ alkyl (preferably —$C_{1-6}$ alkyl, more preferably —$C_{1-3}$ alkyl, and most preferably methyl). In some embodiments, $R^{6e}$ is dimethylamino or amino.

In some embodiments, $R^{6c}$ is —$SO_2R^{6d}$, wherein $R^{6d}$ is —$C_{1-8}$ alkyl, —$C_{2-8}$ alkenyl, —$C_{2-8}$ alkynyl, cycloalkyl, cycloalkenyl, cycloalkynyl, heterocyclyl, aryl or heteroaryl. In some embodiments, $R^{6c}$ is —$SO_2R^{6d}$, wherein $R^{6d}$ is —$C_{1-8}$ alkyl (preferably —$C_{1-6}$ alkyl). In some embodiments, $R^{6c}$ is propylsulfonyl.

In some embodiments, $L^2$ is a direct bond, and $R^6$ is pyrrolidinyl, which is optionally substituted with one or two or three substituents selected from methyl, (dimethylamino) methyl or dimethylamino.

In some embodiments, $L^2$ is a direct bond, and $R^6$ is piperazinyl, which is optionally substituted with one or two or three substituents selected from: acryloyl, 2-(dimethylamino)acetyl, aminoacetyl, 2-(methylamino)acetyl, 3-(dimethylamino)propionyl, 2-(piperazin-1-yl)acetyl, piperazin-2-carbonyl, 4-(dimethylamino)butyryl, 5-(dimethylamino) valeryl, methyl, piperidin-4-carbonyl, acetyl, 2-(N-methylacetamino)acetyl, isopropylcarbamoyl, 2,4,5-trifluorophenylcarbamoyl, (2S,3S)-2-amino-3-methylvaleryl, 2-methoxyethyl, 2-(methylamino)acetyl, ethyl, isobutyl, pyrrolidin-2-carbonyl, 2-amino-4-methylvaleryl, 2-amino-3-methylbutyryl, 2-(dimethylamino) acetyl, 2-(methylamino)ethyl, 2-(dimethylamino)ethyl, amino, phenylpropionyl, propylsulfonyl or 2-aminoethyl.

In some embodiments, $L^2$ is a direct bond, and $R^6$ is piperidyl, optionally substituted with one or two or three substituents selected from: 2-(dimethylamino)acetyl, methoxy, methoxymethyl, (methylamino)methyl, 4-morpholinopiperidin-1-yl, morpholinomethyl, 2-(dimethylamino)ethyl, phenethyl, (dimethylamino)methyl, amino, dimethylamino or dimethylcarbamoyl.

Definitions of ring A, $R^5$ and $L^2$-$R^6$

In some embodiments, ring A is azetidin-3-yl, azepan-4-yl; piperidin-2-yl, piperidin-3-yl, piperidin-4-yl; pyrrolidin-1-yl, pyrrolidin-2-yl, pyrrolidin-3-yl: piperazin-1-yl; 7-azaspiro[3.5]non-2-yl, 2-azaspiro[3.3]hept-6-yl, 7-azaspiro[3.5]non-2-yl, 2-azaspiro[3.5]non-7-yl; 3-azabicyclo[3.1.0]hex-6-yl, 2-azabicyclo[2.2.1]hept-5-yl, 8-azabicyclo[3.2.1]oct-3-yl, 2-azabicyclo[4.1.0]hept-5-yl: cyclobutyl, bicyclo[1.1.1]pent-1-yl; bicyclo[1.1.1]pent-1-yl; or 1,2,3,6-tetrahydropyridin-4-yl. In some embodiments, ring A is piperidinyl, preferably piperidin-1-yl or piperidin-4-yl.

p is 0 or 1.

In some embodiments, $R^5$ and $L^2$-$R^6$ are each independently methyl, ethyl, isopropyl; 2-(methylamino)ethyl; benzyl; piperidin-4-yl-methyl; (methylamino)methyl: 2-(methylamino)ethyl; hydroxymethyl; trifluoromethyl; pyrrolidin-3-yl, pyrrolidin-2-yl, piperidin-4-yl: hydroxyl; oxo; fluorine; ethoxycarbonyl; phenyl; methylamino or amino.

In some embodiments, the moiety

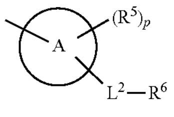

is piperidin-4-yl, 1-methylpiperidin-4-yl, 1-(2-(methylamino)ethyl)piperidin-4-yl, 1-(pyrrolidin-3-yl)piperidin-4-yl, 1-(pyrrolidin-2-yl)piperidin-4-yl, 1-(piperidin-4-yl)piperidin-4-yl, 4-methylpiperidin-4-yl, 3-hydroxypiperidin-4-yl, 3-oxopiperidin-4-yl, 3-fluoropiperidin-4-yl, 3,3-difluorpiperidin-4-yl, 3-benzylpiperidin-4-yl, 1-(piperidin-4-ylmethyl)piperidin-4-yl, 4-((methylamino)methyl) piperidin-1-yl, 2-ethylpiperidin-4-yl, 2-ethoxycarbonylpiperidin-4-yl, 2-hydroxymethylpiperidin-4-yl, 1-methyl-2-((methylamino)methyl)piperidin-4-yl, 1-isopropyl-2-((methylamino)methyl)piperidin-4-yl, 2,6-dimethylpiperidin-4-yl, 2,2-dimethylpiperidin-4-yl, 2-(trifluoromethyl)piperidin-4-yl, 2-phenylpiperidin-4-yl, 4-(methylamino)piperidin-1-yl; piperidin-2-yl; pyrrolidin-3-yl; azetidin-3-yl; azepan-4-yl; (R)-3-methylpiperazin-1-yl; (S)-3-methylpiperazin-1-yl; (S)-3-methylpiperazin-1-yl; (R)-3-methylpiperazin-1-yl; 2-hydroxy-7-azaspiro[3.5]non-2-yl; 3-azabicyclo[3.1.0]hex-6-yl; 2-azaspiro[3.3]hept-6-yl; 7-azaspiro[3.5]non-2-yl; 2-azaspiro[3.5]non-7-yl; 2-azabicyclo[2.2.1]hept-5-yl; 8-azabicyclo[3.2.1]oct-3-yl; 3-aminocyclobutyl; 1-(2-(methylamino)ethyl)-2-oxo-piperidin-4-yl; 2-azabicyclo[4.1.0]hept-5-yl; 1,2,3,6-tetrahydropyridin-4-yl; 3-aminobicyclo[1.1.1]pent-1-yl; 3-((methy lamino) methyl) bicyclo[1.1.1]pent-1-yl.

In second aspect, the invention discloses a compound of formula (II), (II)

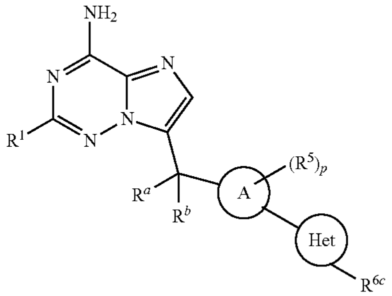

or a pharmaceutically acceptable salt thereof, or a stereoisomer thereof, wherein:

$R^a$ and $R^b$ in each occurrence are independently hydrogen, halogen, alkyl, alkenyl, alkynyl, cycloalkyl, cycloalkenyl, cycloalkynyl, heterocyclyl, aryl, heteroaryl or -ORG;

wherein $R^c$ is hydrogen, alkyl, alkoxy-alkyl-, alkenyl, alkynyl, cycloalkyl, aryl, heterocyclyl or heteroaryl;

$R^1$ is —$OR^{1a}$, —$SR^{1a}$, —$NR^{1a}R^{1b}$, —$COR^{1a}$, —$SO_2R^{1a}$, —C(═O)$OR^{1a}$, —C(═O)$NR^{1a}R^{1b}$, —C(═$NR^{1a}$)$NR^{1b}R^{1c}$, —N($R^{1a}$)C(═O)$R^{1b}$, —N($R^{1a}$)C(═O)$OR^{1b}$, —N($R^{1a}$)C(O)$NR^{1b}R^{1c}$, —N($R^{1a}$)S(O)$NR^{1b}R^{1c}$, —N($R^{1a}$)$S(O)_2NR^{1b}R^{1c}$, —$NR^{1a}SO_2R^{1b}$, alkyl, alkenyl, alkynyl, cycloalkyl, cycloalkenyl, cycloalkynyl, heterocyclyl, aryl, or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{1d}$;

$R^{1a}$, $R^{1b}$ and $R^{1c}$ are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each optionally substituted with one or two or three substituents selected from: halogen, $-C_{1-8}$ alkyl optionally substituted with $R^{1e}$, cycloalkyl optionally substituted with $R^{1e}$, heterocyclyl optionally substituted with $R^{1e}$, aryl optionally substituted with $R^{1e}$, heteroaryl optionally substituted with $R^{1e}$, $CH_3-(OCH_2CH_2)_n-$ (where n is 3 to 10) or $-OR^{1f}$;

wherein $R^{1e}$ is halogen, nitro, cyano, hydroxyl, amino ($-NH_2$), alkylamino, dialkylamino, $-C_{1-6}$ alkyl optionally substituted with halogen, carboxyl, alkoxycarbonyl, aminocarbonyl, alkylaminocarbonyl, and dialkylaminocarbonyl;

wherein $R^{1f}$ is alkyl, cycloalkyl, heterocyclyl, aryl or heteroaryl, each of which is optionally substituted with $-C_{1-4}$ alkyl or halogen;

$R^{1d}$ in each occurrence is independently hydrogen, oxo, $-CN$, $-NO_2$, hydroxyl, amino ($-NH_2$), alkylamino, dialkylamino, halogen, haloalkyl, alkyl, haloalkoxy, alkoxy, alkenyl, alkynyl, cycloalkyl, cycloalkenyl, cycloalkynyl, heterocyclyl, aryl or heteroaryl;

ring A is a cycloalkyl or heterocyclyl ring;

Het is heterocyclyl;

$R^5$ is halogen, hydroxyl, alkyl, haloalkyl, alkoxy, haloalkoxy or $-C(=O)OR^{5a}$, wherein $R^{5a}$ is hydrogen, alkyl or haloalkyl;

p is 0, 1, 2 or 3;

$R^{6c}$ is independently hydrogen, halogen, cyano, $-NO_2$, $-OR^{6d}$, $-SR^{6d}$, $-NR^{6d}R^{6e}$, $-COR^{6d}$, $-SO_2R^{6d}$, $-C(=O)OR^{6d}$, $-C(=O)NR^{6d}R^{6e}$, $-C(=NR^{6d})NR^{6e}R^{6f}$, $-N(R^{6d})C(=O)R^{6e}$, $-N(R^{6d})C(=O)OR^{6e}$, $-N(R^{6d})C(O)NR^{6e}R^{6f}$, $-N(R^{6d})S(O)NR^{6e}R^{6f}$, $-N(R^{6d})S(O)_2NR^{6e}R^{6f}$, $-NR^{6d}SO_2R^{6e}$, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{6g}$;

$R^{6d}$, $R^{6e}$ and $R^{6f}$ are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each optionally substituted with one or two or three substituents $R^{6g}$;

$R^{6g}$ in each occurrence is independently hydrogen, halogen, cyano, $-NO_2$, $-OR^{6h}$, $-SR^{6h}$, $-NR^{6h}R^{6i}$, $-COR^{6h}$, $-SO_2R^{6h}$, $-C(=O)OR^{6h}$, $-C(=O)NR^{6h}R^{6i}$, $-C(=NR^{6h})NR^{6i}R^{6j}$, $-N(R^{6h})C(=O)R^{6i}$, $-N(R^{6h})C(=O)OR^{6i}$, $-N(R^{6h})C(O)NR^{6i}R^{6j}$, $-N(R^{6h})S(O)NR^{6i}R^{6j}$, $-N(R^{6h})S(O)_2NR^{6i}R^{6h}$, $-NR^{6h}SO_2R^{6i}$, alkyl, alkenyl, alkynyl, cycloalkyl, cycloalkenyl, cycloalkynyl, heterocyclyl, aryl or heteroaryl, $R^{6h}$, $R^{6i}$ and $R^{6j}$ are independently hydrogen, alkyl, alkoxy, alkenyl, alkynyl, cycloalkyl, cycloalkenyl, cycloalkynyl, heterocyclyl, aryl or heteroaryl, wherein the alkyl, alkoxy, alkenyl, alkynyl, cycloalkyl, cycloalkenyl, cycloalkynyl, heterocyclyl, aryl or heteroaryl are each independently and optionally substituted with one or two or three substituents selected from: halogen, $-C_{1-4}$alkyl, $-C_{1-4}$ alkoxy, hydroxyl, nitro, $-NH_2$, alkylamino, dialkylamino or cyano.

Definition of $R^1$

In some embodiments, $R^1$ is $-OR^{1a}$ or $-NR^{1a}R^{1b}$, wherein $R^{1a}$ and $R^{1b}$ are as defined for formula (II).

In some embodiments, $R^1$ is $-OR^{1a}$ or $-NR^{1a}R^{1b}$, wherein $R^{1a}$ and $R^{1b}$ are independently hydrogen, $-C_{1-8}$ alkyl or $-C_{2-8}$ alkenyl, wherein the $-C_{1-8}$ alkyl or $-C_{2-8}$ alkenyl is each optionally substituted with one or two or three substituents selected from: heterocyclyl optionally substituted with $R^{1c}$, aryl optionally substituted with $R^{1c}$, $CH_3-(OCH_2CH_2)_n-$ (where n is 3 to 10, preferably 4-8, and more preferably 5-7), or $-OR^{1f}$;

wherein $R^{1e}$ is halogen, $-C_{1-6}$ alkyl optionally substituted with halogen, carboxyl, alkoxycarbonyl, aminocarbonyl, alkylaminocarbonyl or dialkylaminocarbonyl, wherein $R^{1f}$ is $-C_{1-8}$ alkyl, aryl or heteroaryl, each of which is optionally substituted with $-C_{1-4}$ alkyl or halogen.

In some embodiments, $R^1$ is $-OR^{1a}$, wherein $R^{1a}$ is hydrogen.

In some embodiments, $R^1$ is $-OR^{1a}$, wherein $R^{1a}$ is $-C^{1-8}$ alkyl optionally substituted with one or two or three substituents selected from: halogen, $-C_{1-8}$ alkyl optionally substituted with $R^{1e}$, cycloalkyl optionally substituted with $R^{1e}$, heterocyclyl optionally substituted with $R^{1e}$, aryl optionally substituted with $R^{1e}$, heteroaryl optionally substituted with $R^{1e}$, $CH_3-(OCH_2CH_2)_n-$ (where n is 3 to 10), or $-OR^{1f}$, wherein $R^{1e}$ and $R^{1f}$ are as defined for formula (II).

In some embodiments, $R^1$ is $-OR^{1a}$, wherein $R^{1a}$ is substituted $C_{1-8}$ alkyl. In some embodiments, $R^1$ is $-OR^{1a}$, wherein $R^{1a}$ is linear. In some embodiments, $R^1$ is $-OR^{1a}$, wherein $R^{1a}$ is branched alkyl. In some embodiments, $R^1$ is $-OR^{1a}$, wherein $R^{1a}$ is branched alkyl, preferably $-C_{4-8}$ alkyl group, wherein the branched substituent is at the α position relative to the oxygen atom, including but not limited to but-2-yl, pent-2-yl, pent-3-yl, hept-2-yl, hept-3-yl, hept-4-yl, oct-2-yl, oct-3-yl, oct-4-yl, or oct-5-yl. In some embodiments, $R^1$ is methoxy, ethoxy, propoxy, butoxy, pentoxy, hexyloxy, heptyloxy or octoxy. In some embodiments, $R^1$ is preferably propoxy, isopropoxy, n-butoxy, isobutoxy, but-2-yloxy (sec-butoxy), pent-2-yloxy, pent-3-yloxy, 2-methylbutoxy, hep-2-yloxy, hep-3-yloxy, hep-4-yloxy, oct-2-yloxy, oct-3-yloxy, oct-4-yloxy, or oct-5-yloxy. In some embodiments, $R^1$ is n-butoxy, but-2-yloxy (sec-butoxy), pent-2-yloxy, pent-3-yloxy, hept-2-yloxy, hept-3-yloxy, hept-4-yloxy, oct-2-yloxy, oct-3-yloxy, oct-4-yloxy, or oct-5-yloxy.

In some embodiments, $R^1$ is $-OR^{1a}$, wherein $R^{1a}$ is $-C_{1-8}$ alkyl, and preferably $-C_{4-5}$ alkyl, wherein the alkyl is substituted with 1-3 halogens, such as fluorine.

In some embodiments, $R^1$ is $-OR^{1a}$, where $R^{1a}$ is $-C_{1-8}$ alkyl, and preferably $-C_{1-3}$ alkyl, wherein the alkyl is substituted with cycloalkyl optionally substituted with $R^{1e}$, heterocyclyl optionally substituted with $R^{1e}$, aryl optionally substituted with $R^{1e}$ or heteroaryl optionally substituted with $R^{1e}$, wherein $R^{1e}$ is as defined for formula (II).

In some embodiments, $R^1$ is $-OR^{1a}$, wherein $R^{1a}$ is $-C_{1-8}$ alkyl, and preferably $-C_{1-3}$ alkyl, wherein the alkyl is substituted with heteroaryl, such as 5-6-membered heteroaryl comprising one or two or three heteroatoms selected from oxygen, nitrogen or optionally oxidized sulfur as ring members, wherein the heteroaryl is optionally substituted with $-C_{1-6}$ alkyl, preferably $-C_{1-4}$ alkyl, and more preferably methyl. In some embodiments, the heteroaryl is pyridinyl or imidazolyl or isoxazolyl. In some embodiments, $R^1$ is pyridin-3-ylmethoxy, 2-(1H-imidazol-1-yl)ethoxy or (5-methylisoxazol-3-yl)methoxy.

In some embodiments, $R^1$ is $-OR^{1a}$, wherein $R^{1a}$ is $-C_{1-8}$ alkyl, and preferably $-C_{1-3}$ alkyl, wherein the alkyl is substituted with aryl such as phenyl. In some embodiments, $R^1$ is 2-phenylethoxy or 3-phenylpropoxy.

In some embodiments, $R^1$ is $-OR^{1a}$, wherein $R^{1a}$ is $-C_{1-8}$ alkyl, and preferably $-C_{1-3}$ alkyl, wherein the alkyl is substituted with $-OR^{1f}$, wherein $R^{1f}$ is $-C_{1-8}$ alkyl or aryl (e.g., phenyl). In some embodiments, $R^1$ is 2-methoxyethoxy or 2-phenoxyethoxy.

In some embodiments, $R^1$ is $-OR^{1a}$, wherein $R^{1a}$ is $-C_{1-8}$ alkyl, and preferably $-C_{1-3}$ alkyl, wherein the alkyl is substituted with $CH_3-(OCH_2CH_2)_n-$, where n is 3 to 10, preferably 3 or 4 or 5. In some embodiments, $R^1$ is 2,5,8,11-tetraoxatridec-13-yloxy.

In some embodiments, $R^1$ is $-OR^{1a}$, wherein $R^{1a}$ is $-C_{2-8}$ alkenyl; preferably $-C_{2-6}$ alkenyl; and most preferably $-C_{4-6}$ alkenyl. In one example, $R^1$ is but-3-enyloxy.

In some embodiments, $R^1$ is $-NR^{1a}R^{1b}$, wherein $R^{1a}$ and $R^{1b}$ are each hydrogen or $-C_{1-8}$ alkyl, preferably $-C_{1-6}$ alkyl, wherein the alkyl is optionally substituted with one or two or three substituents selected from: halogen, $-C_{1-8}$ alkyl optionally substituted with $R^{1e}$, cycloalkyl optionally substituted with $R^{1e}$, heterocyclyl optionally substituted with $R^{1e}$, aryl optionally substituted with $R^{1e}$ or heteroaryl optionally substituted with $R^{1e}$, wherein $R^{1e}$ is $-C_{1-6}$ alkyl, such as methyl.

In some embodiments, $R^1$ is $-NR^{1a}R^{1b}$, where $R^{1a}$ is hydrogen and $R^{1b}$ is linear or branched $-C_{1-8}$ alkyl. In some embodiments, $R^1$ is $-NR^{1a}R^{1b}$, wherein $R^{1a}$ is hydrogen, $R^{1b}$ is branched alkyl, preferably $-C_{4-8}$ alkyl, wherein the branched substituent is at the $\alpha$ position relative to the oxygen atom, including but not limited to but-2-yl, pent-2-yl, pent-3-yl, hept-2-yl, hept-3-yl, hept-4-yl, oct-2-yl, oct-3-yl, oct-4-yl, or oct-5-yl.

In some embodiments, $R^1$ is butylamino, N-butyl-N-methylamino or isopentylamino.

In some embodiments, $R^1$ is optionally partially or completely deuterated, that is, one or more carbon-bonded hydrogen atoms in the definition of $R^1$ are replaced by one or more deuterium atoms.

Definition of $R^5$

In some embodiments, $R^5$ is halogen, oxo, hydroxyl, $C_{1-8}$ alkyl, halogenated $C_{1-8}$ alkyl, $C_{1-8}$ alkoxy, halogenated $C_{1-8}$ alkoxy, or $-C(=O)OR^{5a}$, wherein $R^{5a}$ is hydrogen, $C_{1-8}$ alkyl, or halogenated $C_{1-8}$ alkyl; and p is 0, 1, or 2.

In some embodiments, $R^5$ is halogen, oxo, $C_{1-3}$ alkyl, halogenated $C_{1-3}$ alkyl, $C_{1-3}$ alkoxy, or halogenated $C_{1-8}$ alkoxy. In some embodiments, $R^5$ is methyl, ethyl, propyl, methoxy, ethoxy, propoxy, isopropoxy, trifluoromethoxy or trifluoromethyl. In some embodiments, $R^5$ is methyl.

In some embodiments, p is 1.

In some embodiments, $R^5$ and Het-$R^{6c}$ are on ortho-positions of ring A.

Definition of Ring A

In some embodiments, ring A is heterocyclyl.

In some embodiments, ring A is 4-, 5-, 6-, 7-, 8- or 9-membered monocyclic heterocyclyl, which comprises one or two or three heteroatoms selected from oxygen, nitrogen or optionally oxidized sulfur as ring members; preferably 5- or 6-membered heteroaryl comprising one or two nitrogen atoms as ring members; and more preferably, 5- or 6-membered heteroaryl comprising one nitrogen atom as a ring member. In some embodiments, ring A is azetidinyl (e.g., azetidin-1-yl, azetidin-2-yl, azetidin-3-yl, azetidin-4-yl), pyrrolidinyl (e.g., pyrrolidin-1-yl, pyrrolidin-2-yl, pyrrolidin-3-yl), piperidinyl (e.g., piperidin-1-yl, piperidin-2-yl, piperidin-3-yl, piperidin-4-yl), or azepanyl (e.g., azepan-1-yl, azepan-2-yl, azepan-3-yl, azepan-4-yl); and preferably piperidinyl (e.g., piperidin-1-yl, piperidin-4-yl). In some embodiments, ring A is piperazinyl (e.g., piperazin-1-yl or piperazin-2-yl).

In some embodiments, the heterocyclyl ring may comprise one or more double bonds (C=C or C=N), but it is not aromatic. However, the heterocyclyl ring is preferably saturated.

In some embodiments, ring A is spiro heterocyclyl or bridged heterocyclyl, such as 5-20-membered, preferably 6-14-membered, and more preferably 7-12-membered heterocyclyl. In some embodiments, the heterocyclyl is 7-azaspiro[3.5]nonyl, 3-azaspiro[3.1.0]hexyl, 2-azaspiro[3.3]heptyl, 7-azaspiro[3.5]nonyl, 2-azaspiro[3.5]nonyl, 2-azabicyclo[2.2.1]heptyl, 8-azabicyclo[3.2.1]octyl or 2-azabicyclo[4.1.0]heptyl. More specifically, the spiro heterocyclyl is 7-azaspiro[3.5]non-2-yl, 3-azabicyclo[3.1.0]hex-6-yl, 2-azaspiro[3.3]hept-6-yl, 7-azaspiro[3.5]non-2-yl, 2-azaspiro[3.5]non-7-yl, 2-azabicyclo[2.2.1]hept-5-yl, 8-azabicyclo[3.2.1]oct-3-yl or 2-azabicyclo[4.1.0]hept-5-yl.

In some embodiments, ring A is a cycloalkyl ring, such as 3-8-membered monocyclic cycloalkyl or 6-12-membered bicyclic cycloalkyl selected from spiro-cycloalkyl, fused cycloalkyl or bridged cycloalkyl, such as bicyclo[1.1.1]pentyl (e.g., bicyclo[1.1.1]pent-1-yl). In some embodiments, ring A is cycloalkenyl or cycloalkynyl.

Definition of Het

In some embodiments, Het is monocyclic heterocyclyl; in some embodiments, Het is fused bicyclic heterocyclyl: in some embodiments, Het is spirobicyclic heterocyclyl.

In some embodiments. Het is saturated heterocyclyl. In some embodiments, Het is a 4-, 5-, 6-, 7-, or 8-membered saturated monocyclic heterocyclyl ring, which comprises one, two or three heteroatoms selected from oxygen, nitrogen or optionally oxidized sulfur as ring members. In some embodiments, Het is a 5-, 6-, 7- or 8-membered saturated monocyclic heterocyclyl ring comprising one or two or three nitrogen heteroatoms as ring members. In some embodiments, Het is a 5- or 6-membered saturated monocyclic heterocyclyl ring comprising one or two nitrogen heteroatoms as ring members. In some embodiments, Het is pyrrolidinyl (e.g., pyrrolidin-1-yl, pyrrolidin-2-yl, pyrrolidin-3-yl), piperidinyl (e.g., piperidin-1-yl, piperidin-2-yl, piperidin-3-yl, piperidin-4-yl, piperidin-5-yl), triazolyl (e.g., 1H-1,2,4-triazol-1-yl), azepanyl (e.g., azepan-2-yl, azepan-3-yl, azepan-4-yl, azepan-5-yl), diazepinyl (e.g., 1,4-diazepin-1-yl, 1,4-diazepin-2-yl, 1,4-diazepin-3-yl, 1,4-diazepin-4-yl), piperazinyl (e.g., piperazin-1-yl, piperazin-2-yl, piperazin-3-yl), or morpholino.

In some embodiments, Het is a bicyclic heterocyclyl ring comprising one, two or three heteroatoms selected from oxygen, nitrogen or optionally oxidized sulfur as ring members. In some examples, Het is 2,5-diazabicyclo[2.2.1]hept-2-yl.

In some embodiments, Het is 6-14-membered, and more preferably 7-10-membered spirobicyclic heterocyclyl. In some embodiments, the heterocyclyl is spiroheptyl, spirodecyl or spirononyl comprising one or two nitrogen atoms as ring members. In some embodiments, the heterocyclyl is 8-azaspiro[4.5]dec-8-yl, 2,7-diazspiro[3.5]non-7-yl, 2,8-diazspiro[4.5]dec-2-yl, 2,7-diazspiro[3.5]non-2-yl, and 2,8-diazspiro[4.5]dec-8-yl.

Definition of $R^{6c}$

In some embodiments, Het is optionally substituted with one or two or three substituents $R^c$.

In some embodiments, Het is optionally substituted with one $R^{6c}$.

In some embodiments, $R^{6c}$ is independently hydrogen, halogen $-OR^{6d}$, $-SR^{6d}$, $-NR^{6d}R^{6e}$, $-COR^{6s}$, $-SO_2R^{6d}$, $-C(=O)NR^{6d}R^{6e}$ or $-C_{1-8}$ alkyl, wherein the —$C_{1-8}$ alkyl is independently and optionally substituted with one or two or three substituents $R^{6g}$;

$R^{6d}$ and $R^{6e}$ are independently hydrogen, —$C_{1-8}$ alkyl, —$C_{2-8}$ alkenyl, heterocyclyl or aryl, wherein the —$C_{1-8}$ alkyl, —$C_{2-8}$ alkenyl, heterocyclyl or aryl is each optionally substituted with one or two or three substituents $R^{6g}$;

$R^{6g}$ in each occurrence is independently hydrogen, halogen. —$OR^{6h}$, —$SR^{6h}$, —$NR^{6h}R^{6i}$, —$N(R^{6h})C(=O)OR^{6i}$, —$C_{1-8}$ alkyl, heterocyclyl, aryl or heteroaryl, $R^{6h}$ and $R^{6i}$ are independently hydrogen or —$C_{1-8}$ alkyl.

In some embodiments, $R^6$ is —$COR^{6d}$, wherein $R^{6d}$ is —$C_{1-8}$ alkyl optionally substituted with one or two substituents $R^{6g}$, wherein $R^{6g}$ is —$NR^{6h}R^{6i}$, —$N(R^{6h})C(=O)R^{6i}$, —$C_{1-8}$ alkyl, aryl or heteroaryl, wherein $R^{6h}$ and $R^{6i}$ are as defined for formula (II). In some embodiments, $R^{6c}$ is —$COR^{6d}$, wherein $R^{6d}$ is —$C_{1-4}$ alkyl (preferably $C_{1-4}$ alkyl, and more preferably $C_{1-4}$ alkyl) optionally substituted with one or two substituents $R^{6g}$, where $R^{6g}$ is —$NR^{6h}R^{6i}$, —$N(R^{6h})C(=O)R^{6i}$, —$C_{1-8}$ alkyl, aryl or heteroaryl, wherein $R^{6h}$ and $R^{6i}$ are each independently hydrogen or —$C_{1-8}$ alkyl (preferably $C_{1-6}$ alkyl, and more preferably $C_{1-4}$ alkyl).

In some embodiments, $R^{6c}$ is —$COR^{6d}$, wherein $R^{6d}$ is —$C_{2-8}$ alkenyl.

In some embodiments, $R^{6c}$ is —$COR^{6d}$, wherein $R^{6d}$ is heterocyclyl.

In some embodiments, $R^{6c}$ is acetyl, 2-(dimethylamino) acetyl, 2-(dimethylamino)acetyl, aminoacetyl, 2-(methylamino)acetyl, 3-(dimethylamino)propionyl, 4-(dimethylamino)butyryl, 5-(dimethylamino)valeryl, (2S,3S)-2-amino-3-methylvaleryl, 2-(methylamino)acetyl, 2-amino-4-methylvaleryl, 2-amino-3-methylbutyryl, 2-(dimethylamino)acetyl, phenylpropionyl, 2-(piperazin-1-yl)acetyl, acryloyl, piperazin-2-carbonyl, piperidin-4-carbonyl, pyrrolidin-2-carbonyl or 2-(N-methylacetamino)acetyl.

In some embodiments, $R^{6c}$ is —$C_{1-8}$ alkoxy, preferably —$C_{1-6}$ alkoxy, such as methoxy.

In some embodiments, $R^{6c}$ is —$C_{1-8}$ alkyl, preferably —$C_{1-6}$ alkyl, which is optionally substituted with one or two substituents $R^{6g}$, wherein $R^{6g}$ is —$OR^{6h}$, —$NR^{6h}R^{6i}$, heterocyclyl, aryl, wherein $R^{6h}$ and $R^{6i}$ are as defined for formula (II). In some aspects. $R^{6c}$ is —$C_{1-8}$ alkyl, preferably —$C_{1-6}$ alkyl, which is optionally substituted with a substituent $R^{6g}$, wherein $R^{6g}$ is —$OR^{6i}$, —$NR^{6h}R^{6i}$, heterocyclyl (e.g., morpholino), aryl (e.g., phenyl), wherein $R^{6h}$ and $R^{6i}$ are —$C_{1-4}$ alkyl, and preferably methyl. In some embodiments, $R^{6c}$ is methyl, ethyl, isobutyl, methoxymethyl, 2-methoxyethyl, (methylamino)methyl, 2-(dimethylamino) ethyl, (dimethylamino)methyl, 2-aminoethyl, 2-(methylamino)ethyl 2-(dimethylamino)ethyl, morpholinomethyl or phenethyl.

In some embodiments $R^{6c}$ is heterocyclyl, which is optionally substituted with a substituent $R^{6g}$. In some embodiments, $R^{6c}$ is heterocyclyl, which is optionally substituted with a substituent $R^{6g}$ which is heterocyclyl. In some embodiments, $R^{6c}$ is 4-morpholinopiperidin-1-yl.

In some embodiments, $R^{6c}$ is —$C(=O)NR^{6d}R^{6e}$, wherein $R^{6d}$ and $R^{6e}$ are independently hydrogen, —$C_{1-8}$ alkyl (preferably —$C_{1-3}$ alkyl) or aryl, wherein the —$C_{1-8}$ alkyl or aryl is independently and optionally substituted with halogen or —$C_{1-4}$ alkyl. In some embodiments, $R^{6c}$ is —$C(=O)NR^{6d}R^{6e}$, wherein $R^{6d}$ and $R^{6e}$ are independently hydrogen and —$C_{1-4}$ alkyl. In some embodiments, $R^{6c}$ is —$C(=O)NR^{6d}R^{6e}$, wherein $R^{6d}$ and $R^{6e}$ are independently hydrogen and aryl optionally substituted with halogen. In some embodiments, $R^{6c}$ is dimethylcarbamoyl, isopropylcarbamoyl or 2,4,5-trifluorophenylcarbamoyl.

In some embodiments, $R^{6c}$ is —$NR^{6d}R^{6e}$, wherein $R^{6d}$ and $R^{6e}$ are independently hydrogen or —$C_{1-8}$ alkyl (preferably —$C_{1-6}$ alkyl, more preferably —$C_{1-3}$ alkyl, and most preferably methyl). In some embodiments, $R^{6e}$ is dimethylamino or amino.

In some embodiments, $R^{6c}$ is —$SO_2R^{6d}$, wherein $R^{6d}$ is —$C_{1-8}$ alkyl, —$C_{2-8}$ alkenyl, —$C_{2-8}$ alkynyl, cycloalkyl, cycloalkenyl, cycloalkynyl, heterocyclyl, aryl or heteroaryl. In some embodiments, $R^{6c}$ is —$SO_2R^{6d}$, wherein $R^{6d}$ is —$C_{1-8}$ alkyl (preferably —$C_{1-6}$ alkyl). In some embodiments, $R^{6c}$ is propylsulfonyl.

In some embodiments, Het is pyrrolidinyl, which is optionally substituted with one or two or three substituents selected from methyl, (dimethylamino)methyl or dimethylamino. In some embodiments, Het is 1-methylpyrrolidin-3-yl, pyrrolidin-1-yl, 3-((dimethylamino)methyl) pyrrolidin-1-yl or 3-(dimethylamino)pyrrolidin-1-yl.

In some embodiments. Het is piperazinyl, optionally substituted with one or two or three substituents selected from: acryloyl, 2-(dimethylamino)acetyl, aminoacetyl, 2-(methylamino)acetyl, 3-(dimethylamino)propionyl, 2-(piperazin-1-yl)acetyl, piperazin-2-carbonyl, 4-(dimethylamino)butyryl, 5-(dimethylamino)valeryl, methyl, piperidin-4-carbonyl, acetyl, 2-(N-methylacetamino)acetyl, isopropylcarbamoyl, 2,4,5-trifluorophenylcarbamoyl, (2S,3S)-2-amino-3-methylvaleryl, 2-methoxyethyl, 2-(methylamino)acetyl, ethyl, isobutyl, pyrrolidin-2-carbonyl, 2-amino-4-methylvaleryl, 2-amino-3-methylbutyryl, 2-(dimethylamino)acetyl, 2-(methylamino)ethyl, 2-(dimethylamino)ethyl, amino, phenylpropionyl, propylsulfonyl or 2-aminoethyl. In some embodiments, Het is piperazin-1-yl, 4-acrylpiperazin-1-yl, 4-(2-(dimethylamino)acetyl)piperazin-1-yl. (4-aminoacetyl)piperazin-1-yl, piperazin-1-yl, 4-(2-(methylamino)acetylpiperazin-1-yl), 4-(3-(dimethylamino)propionyl)piperazin-1-yl, 4-(2-(piperazin-1-yl) acetyl)piperazin-1-yl, 4-(piperazin-2-carbonyl)piperazin-1-yl, 4-acryloylpiperazin-1-yl, 4-(4-(dimethylamino)butyryl) piperazin-1-yl, 4-(5-(dimethylamino)valeryl)piperazin-1-yl, 3,5-dimethylpiperazin-1-yl, 4-(piperidin-4-carbonyl)piperazin-1-yl, 4-acetylpiperazin-1-yl, 4-(2-(N-methylacetylamino)acetyl)piperazin-1-yl, 4-(isopropylcarbamoyl)piperazin-1-yl, 4-(2,4,5-trifluorophenylcarbamoyl)piperazin-1-yl, 4-(3,5-dimethylpiperazin-1-yl, 4-((2S,3S)-2-amino-3-methylvaleryl)piperazin-1-yl, 4(2-methoxyethyl)piperazin-1-yl, 4-(2-(methylamino)acetyl)piperazin-1-yl, 4-ethylpiperazin-1-yl, 4-isobutylpiperazin-1-yl, 4-(pyrrolidin-2-carbonyl)piperazin-1-yl, 4-(2-amino-4-methylvaleryl) piperazin-1-yl, 4-(2-amino-3-methylbutyryl)piperazin-1-yl, 4-(2-(dimethylamino)acetyl)piperazin-1-yl, (S)-2-methylpiperazin-1-yl, (R)-2-methylpiperazin-1-yl, 4-(2-(methylamino)ethyl)piperazin-1-yl, 4-(2-(dimethylamino)ethyl)piperazin-1-yl, 4-(2-amino-3-phenylpropionyl)piperazin-1-yl, 4-(propylsulfonyl)piperazin-1-yl, 4-(2-aminoethyl)piperazin-1-yl or 3-methylpiperazin-1-yl.

In some embodiments, Het is piperidinyl, which is optionally substituted with one or two or three substituents selected from: 2-(dimethylamino)acetyl, methoxy, methoxymethyl, (methylamino)methyl, 4-morpholinopiperidin-1-yl, morpholinomethyl, 2-(dimethylamino)ethyl, phenethyl, (dimethylamino)methyl, amino, dimethylamino or dimethylcarbamoyl. In some embodiments, Het is piperidin-4-yl, 4-(2-(dimethylamino)acetyl)piperidin-1-yl, piperidin-3-yl, piperidin-4-yl, piperidin-1-yl, piperidin-4-yl, 4-methoxypiperidin-1-yl, 4-(methoxymethyl)piperidin-1-yl, 4-((methylamino)methyl)piperidin-1-yl, (4-morpholinopiperidin-1-yl)

pyridin-3-yl, 4-(morpholinomethyl)piperidin-1-yl, 4-(2-(dimethylamino)ethyl)piperidin-1-yl, 1-phenethylpiperidin-4-yl, 4-((dimethylamino)methyl)piperidin-1-yl, 4-aminopiperidin-1-yl, 4-(dimethylamino)piperidin-1-yl or 4-(dimethylcarbamoyl)piperidin-1-yl.

In some embodiments, Het is azepan-1-yl or 1,4-diazepan-1-yl.

In some embodiments. Het is octahydro-2H-isoindol-2-yl.

In some embodiments, Het is morpholino.

In some embodiments, Het is 8-azaspiro[4.5]dec-8-yl, 2,7-diazspiro[3.5]non-7-yl, 2,8-diazspiro[4.5]dec-2-yl, 2,7-diazspiro[3.5]non-2-yl, 2,8-diazspiro[4.5]dec-8-yl, (1R,4R)-2,5-diazabicyclo[2.2.1]hept-2-yl.

In some embodiments, ring A is piperidinyl, preferably piperidin-1-yl or piperidin-4-yl.

In some embodiments, the invention discloses a compound of formula (IIIA) or (IIIB), (IIIA)

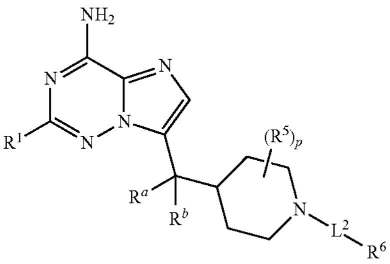

or (IIIB)

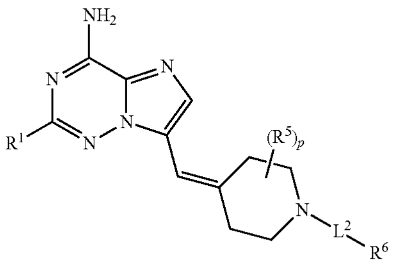

or a pharmaceutically acceptable salt thereof, or a stereoisomer thereof, wherein the variables $R^a$, $R^b$, $L^2$, $R^5$, $R^6$ and p are as defined above.

In some embodiments, the invention discloses a compound selected from the specific compounds exemplified by the invention, or pharmaceutically acceptable salts thereof or stereoisomers thereof:

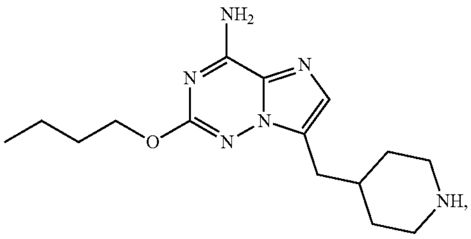

-continued

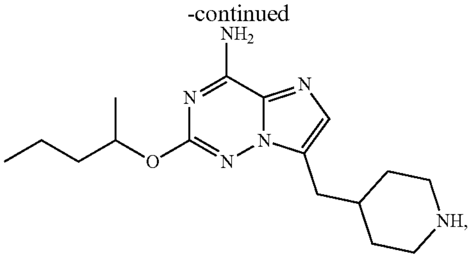

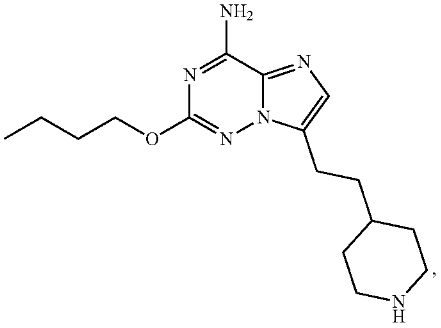

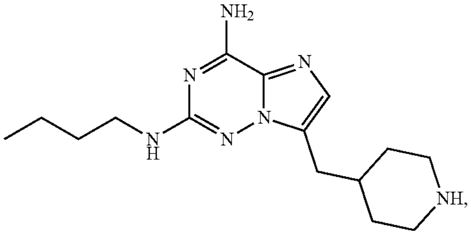

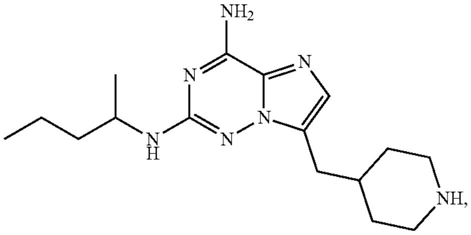

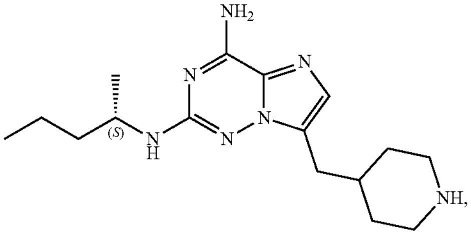

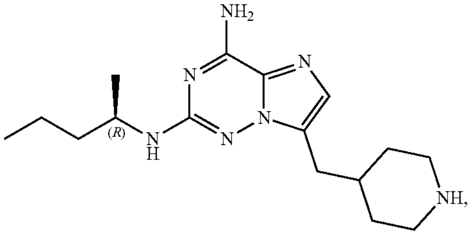

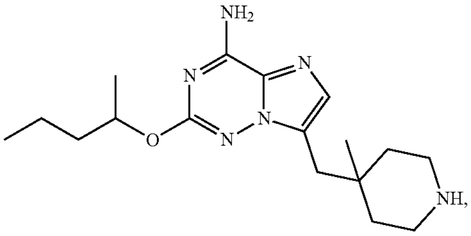

-continued
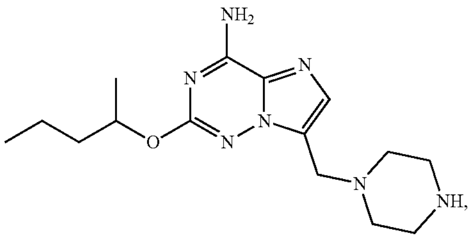
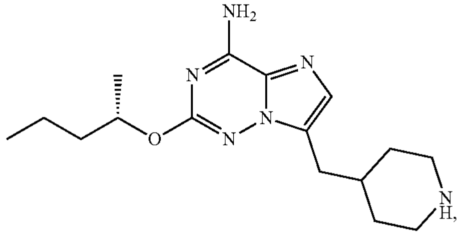
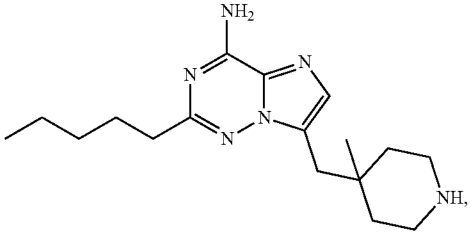
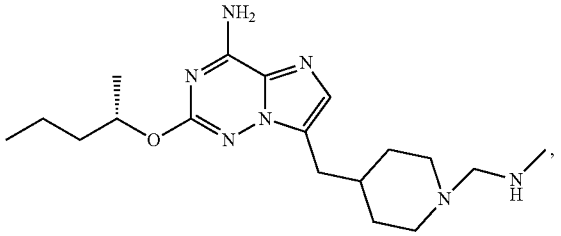
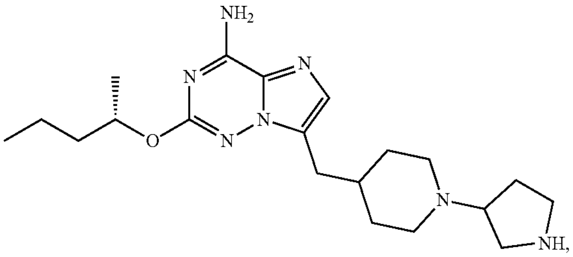
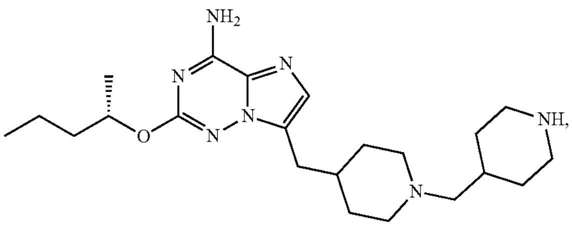
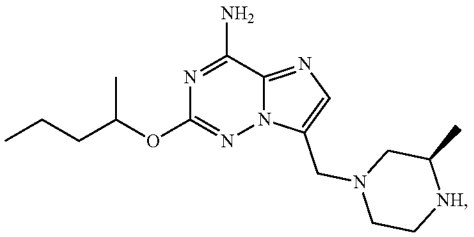
-continued
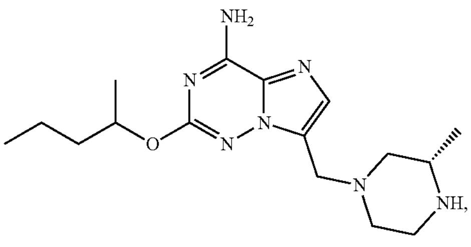
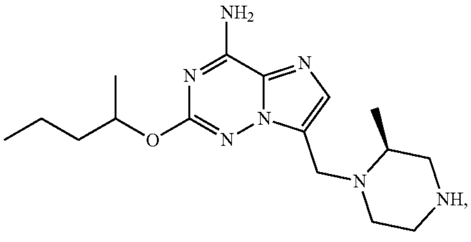
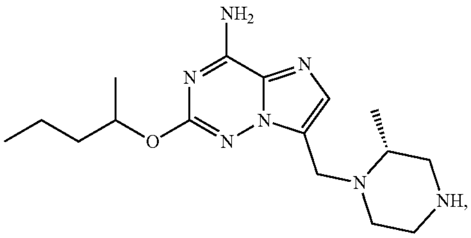
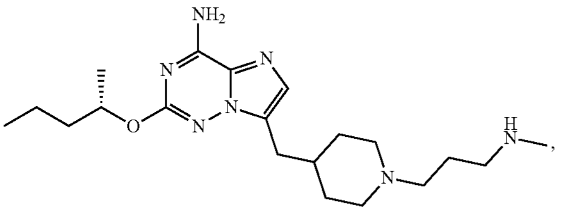
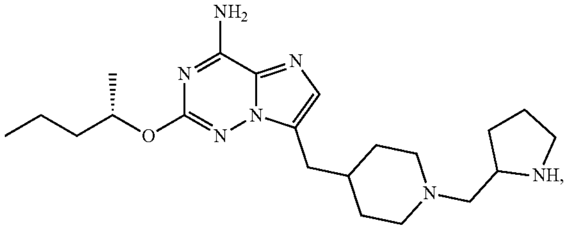
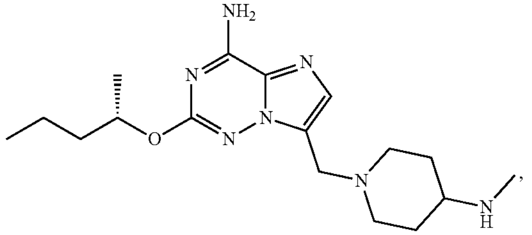
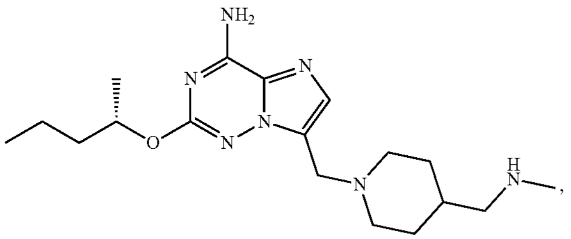

-continued
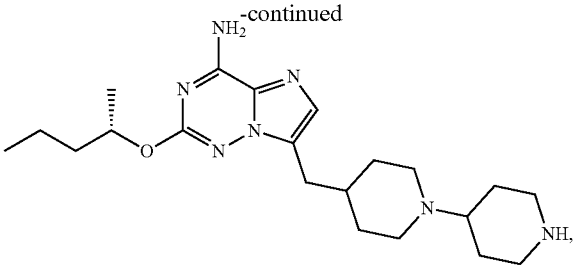
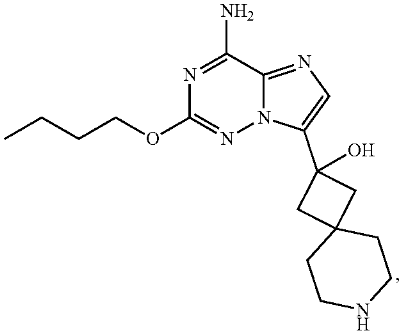
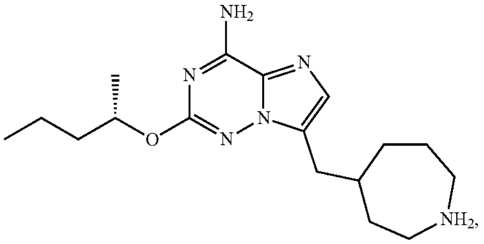
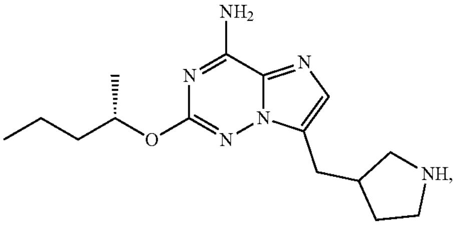
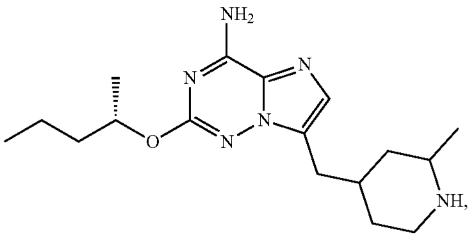
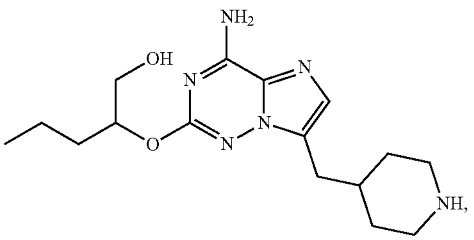
-continued
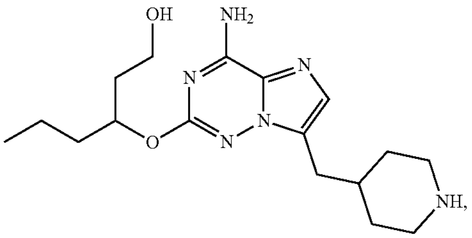
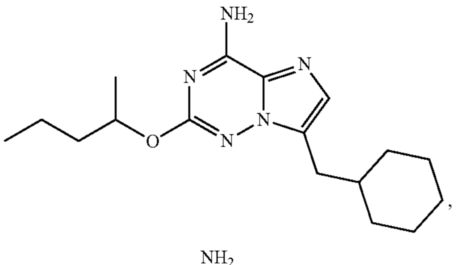
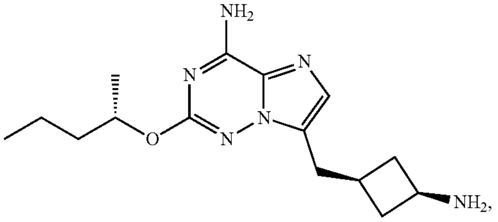
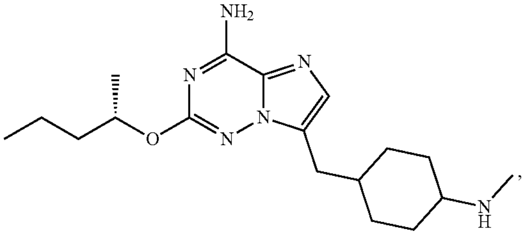
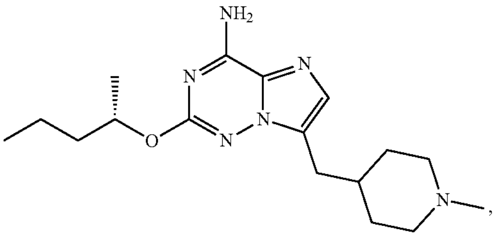
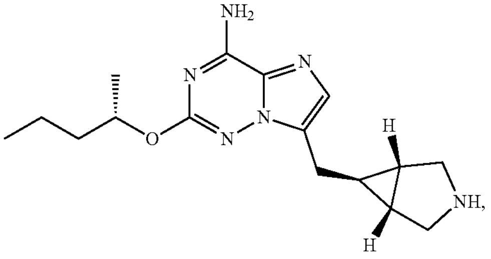
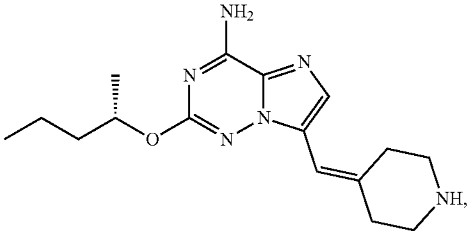

-continued
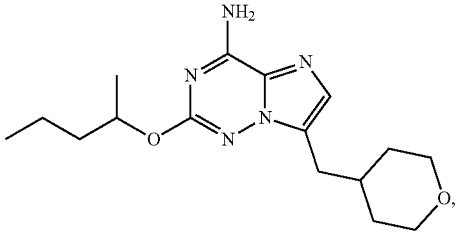
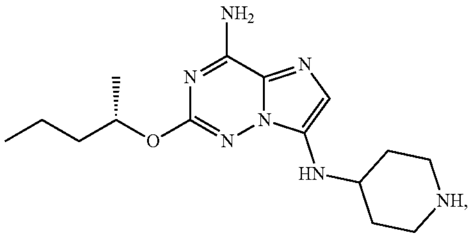
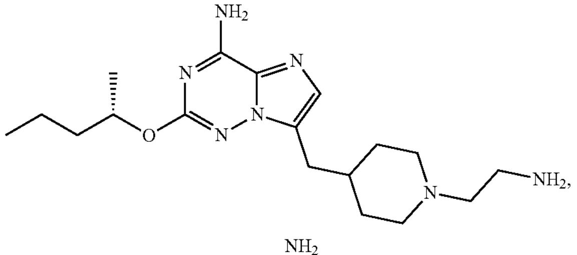
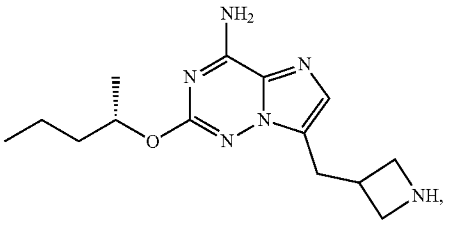
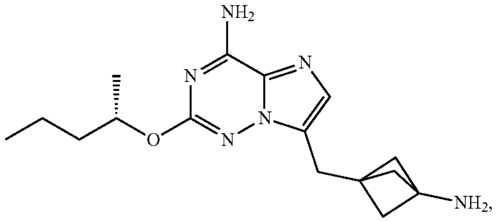
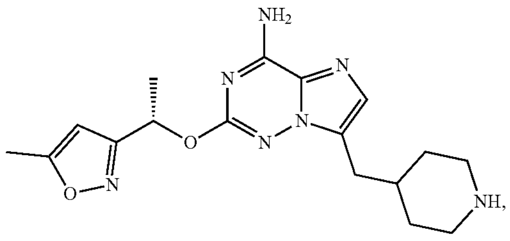
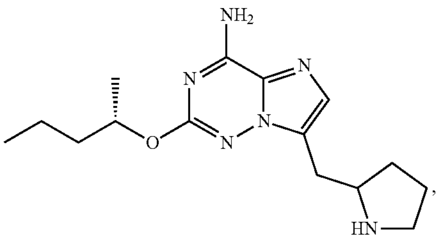
-continued
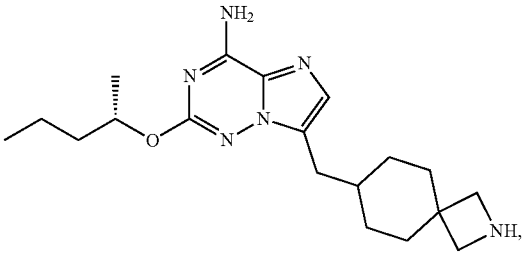
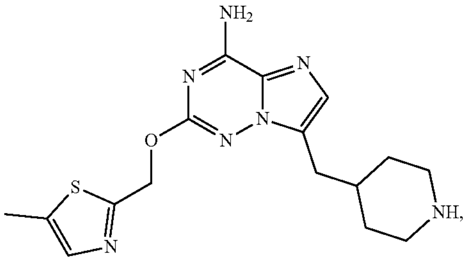
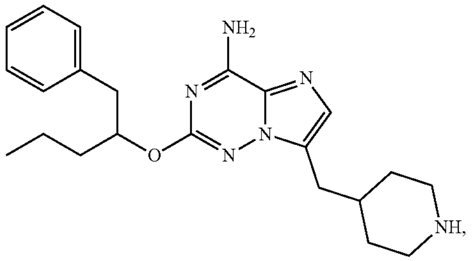
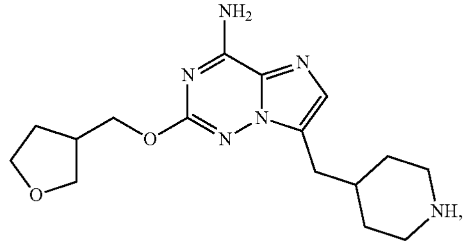
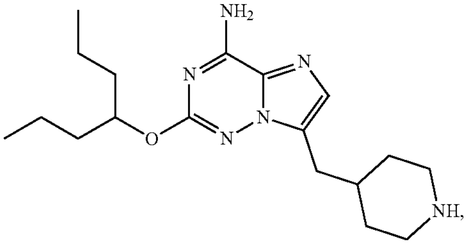
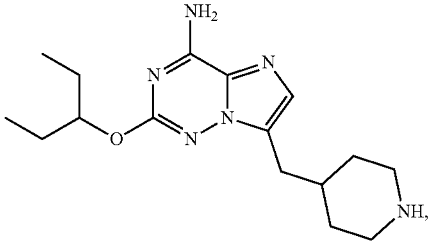

-continued
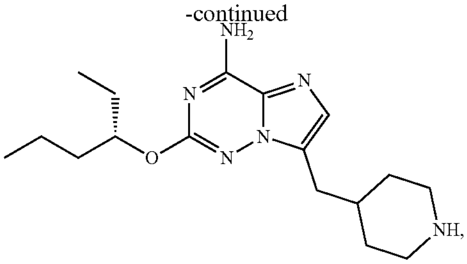
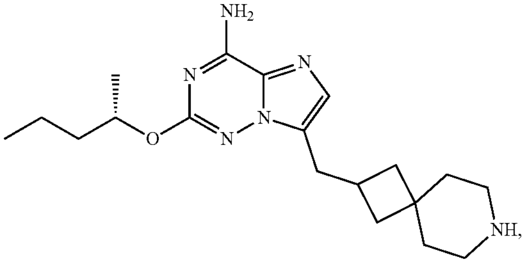
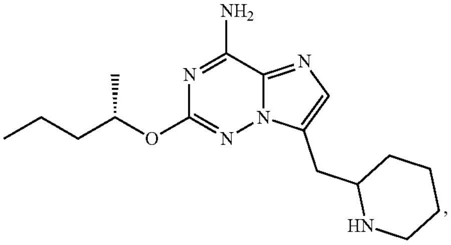
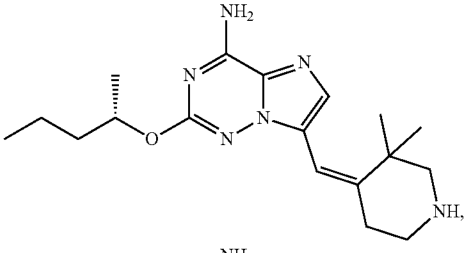
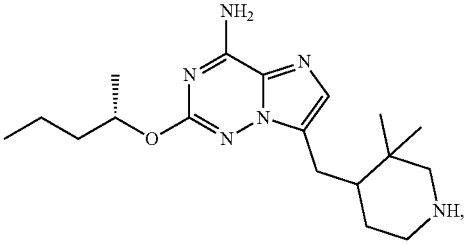
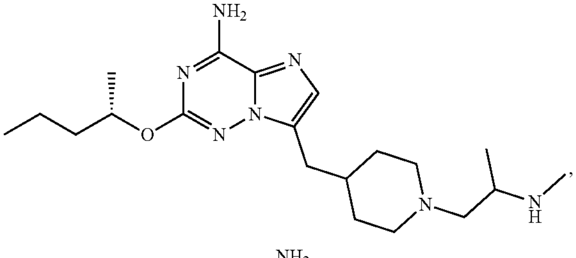
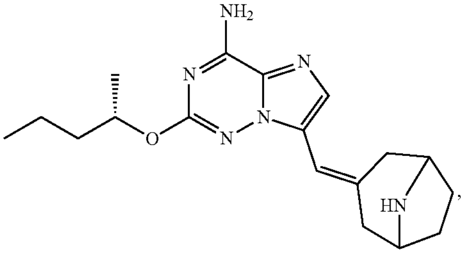
-continued
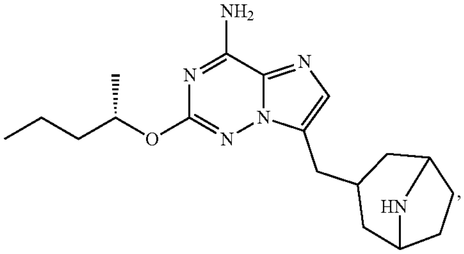
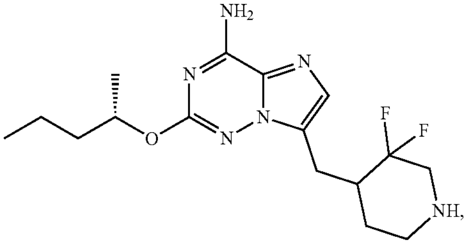
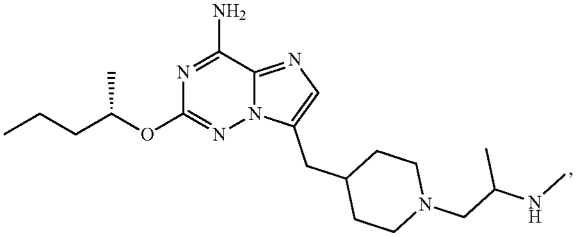
OPTICAL ISOMER 1
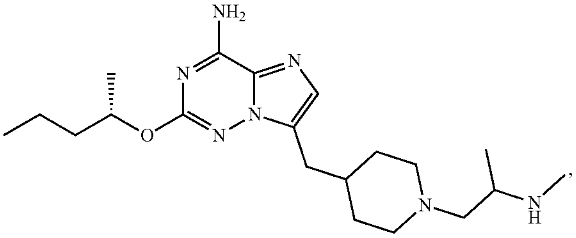
OPTICAL ISOMER 2
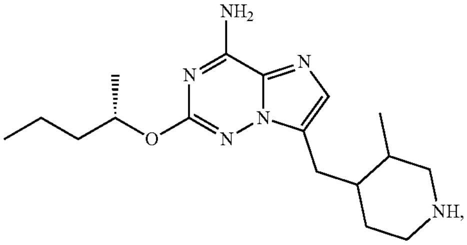
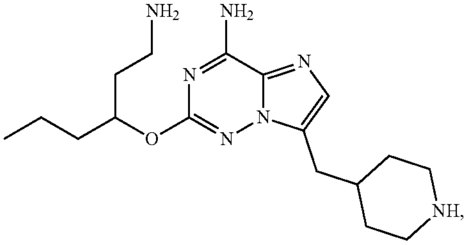

-continued
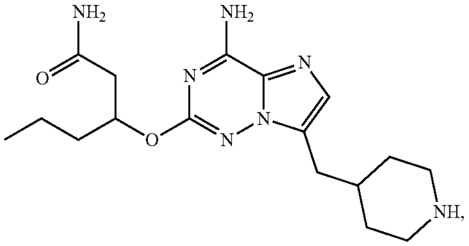
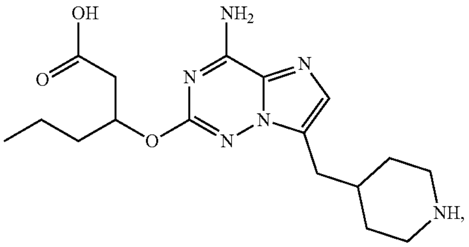
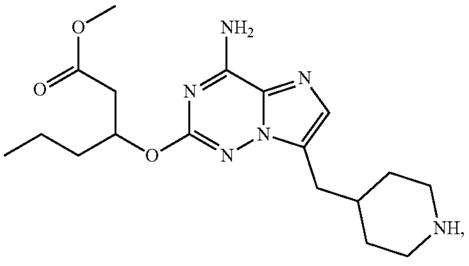
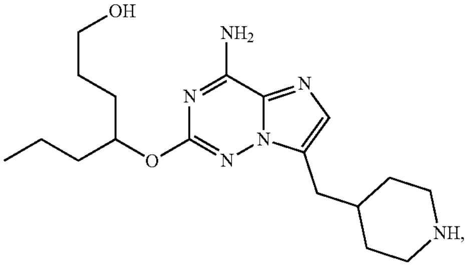
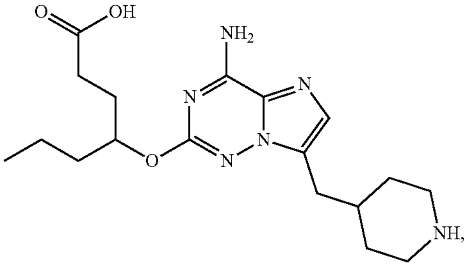
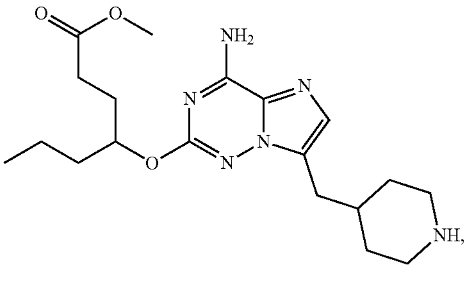
-continued
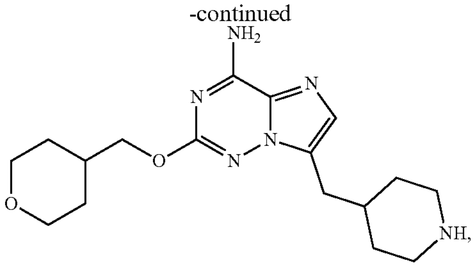
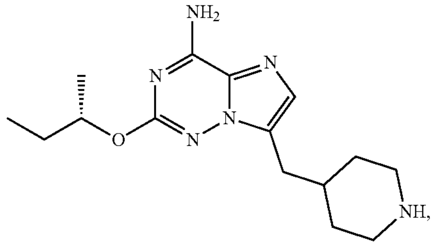
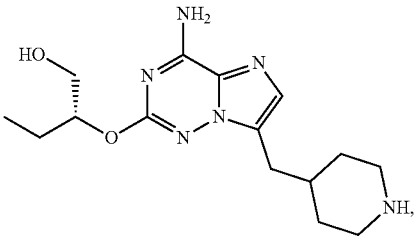
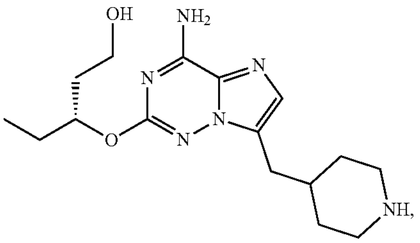
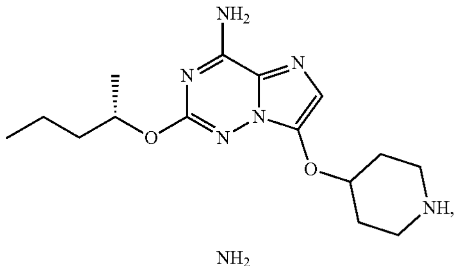
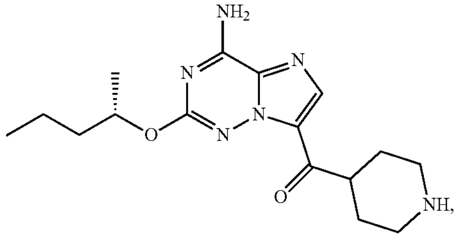
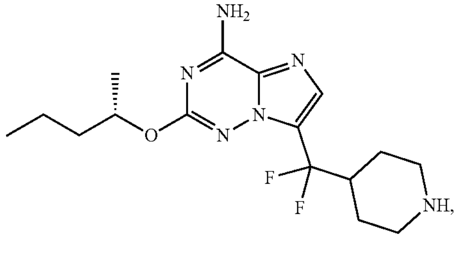

-continued
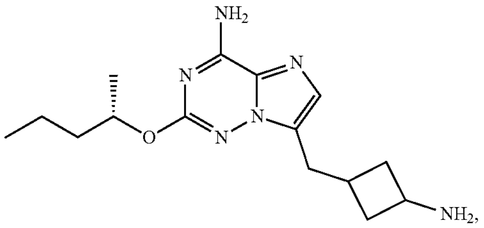
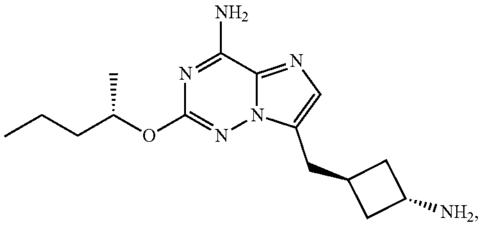
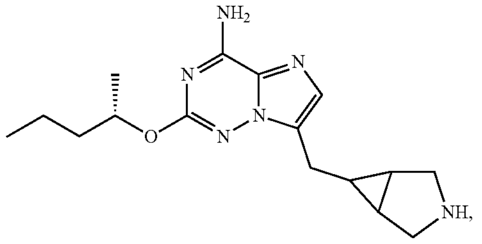
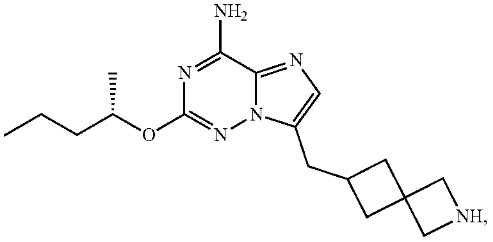
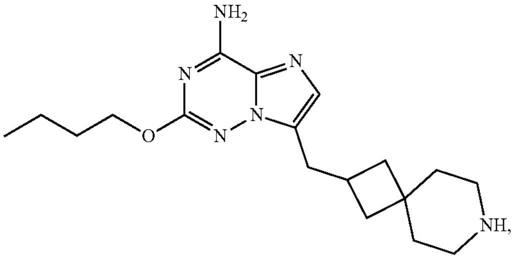
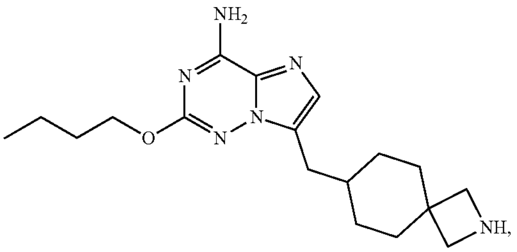
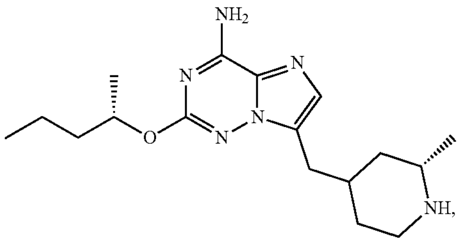
-continued
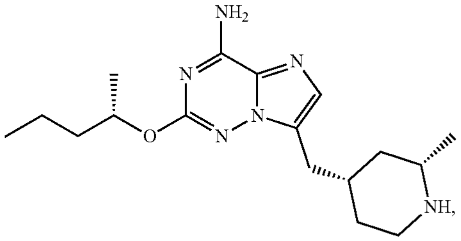
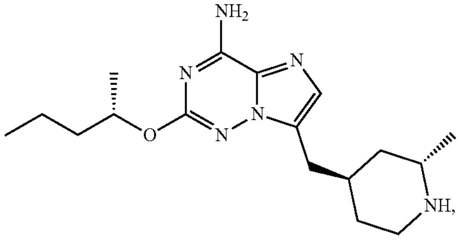
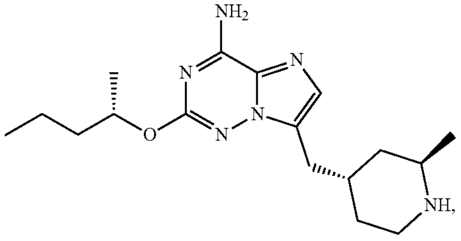
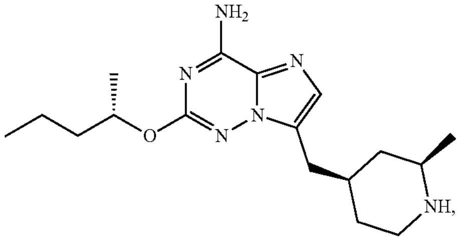
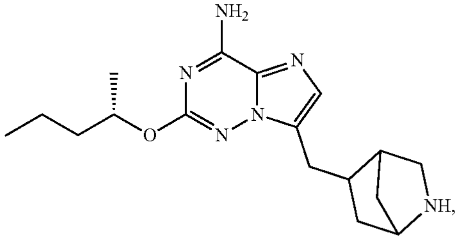
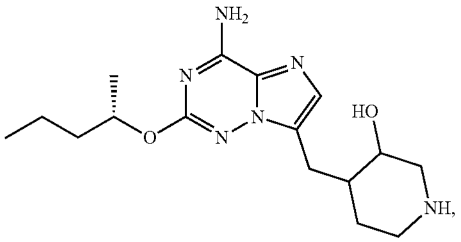
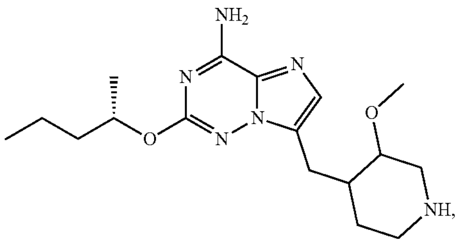

-continued
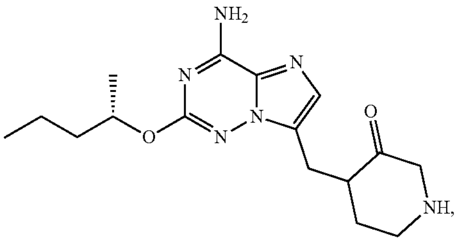
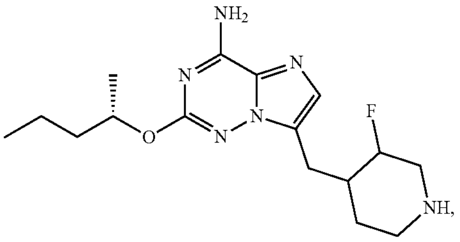
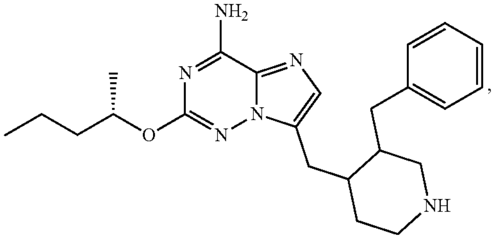
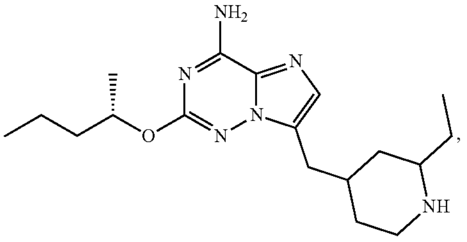
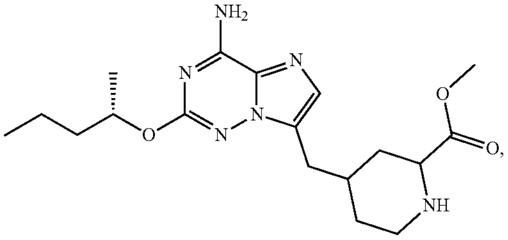
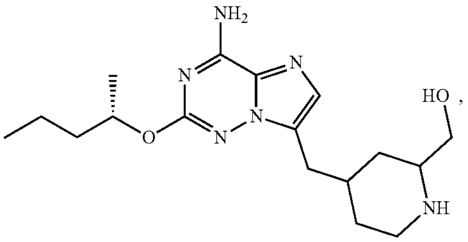
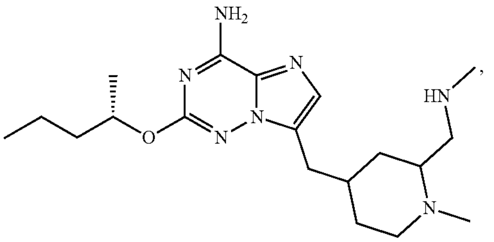
-continued
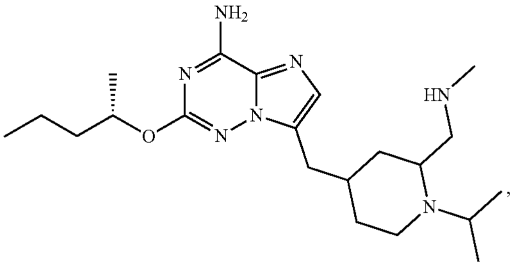
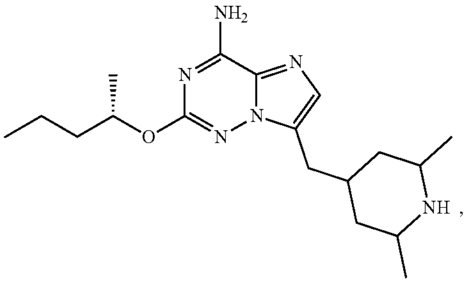
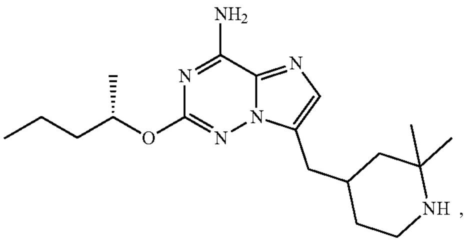
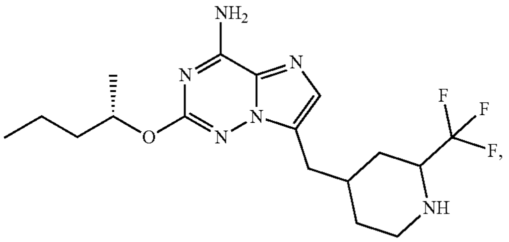
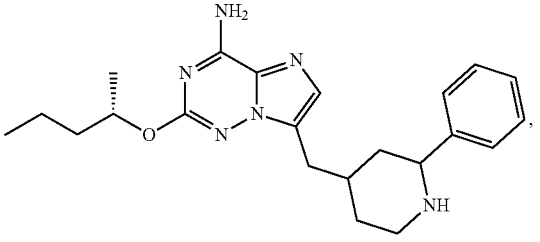
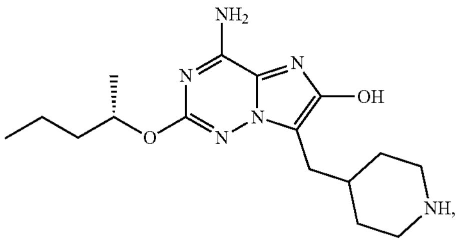

-continued

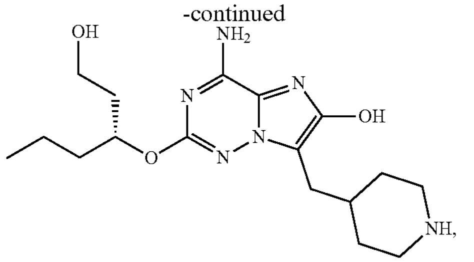

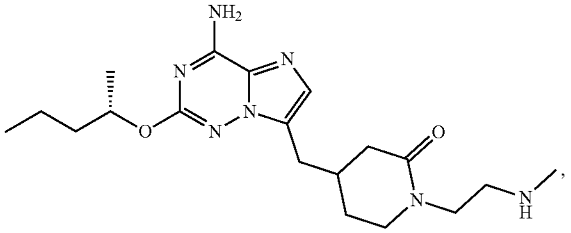

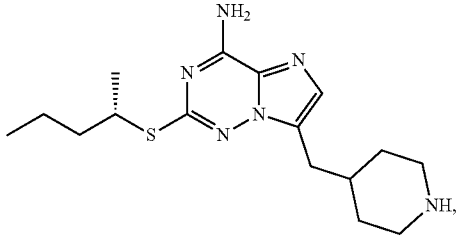

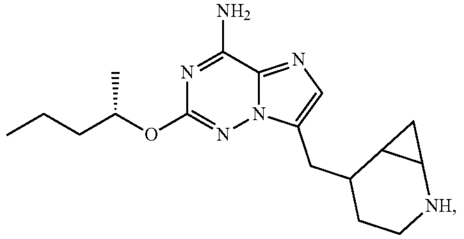

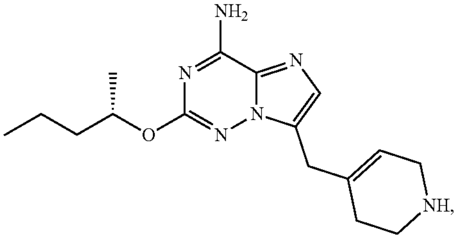

or

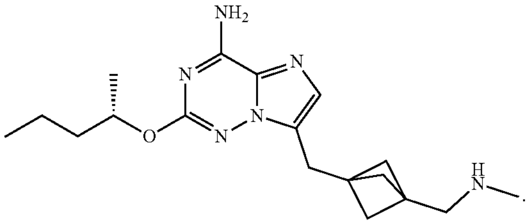

In third aspect, the invention discloses a pharmaceutical composition comprising the compounds disclosed herein, including compounds of formula (I) or (II) or specific compounds exemplified by the invention, or pharmaceutically acceptable salts thereof, and at least one pharmaceutically acceptable carrier or excipient.

In fourth aspect, the invention discloses a method for regulating TLR8, which comprises administering to an individual the compound disclosed herein or a pharmaceutically acceptable salt thereof, including the compound of formula (I) or (II) or the specific compounds exemplified by the invention.

In fifth aspect, the invention discloses a method for treating a disease or disorder in a patient, which comprises administering to the patient a therapeutically effective amount of the compound disclosed herein or a pharmaceutically acceptable salt thereof as a TLR8 agonist, wherein the compound disclosed herein includes a compound of formula (I) or (II) or the specific compounds exemplified by the invention. In some embodiments, the disease or disorder is related to the regulation of TLR, such as TLR-8 (e.g., the agitation of TLR-8). In some embodiments, the disease or disorder includes viral infections caused by viruses selected from dengue virus, yellow fever virus, west Nile virus, Japanese encephalitis virus, tick-borne encephalitis virus, kunjin virus, Murray Valley encephalitis virus. St. Louis encephalitis virus, Omsk hemorrhagic fever virus, bovine viral diarrhea virus, Zika virus and hepatitis C. In some embodiments, the disease or disorder includes melanoma, non-small cell lung cancer, hepatocellular carcinoma, basal cell carcinoma, renal cell carcinoma, myeloma, allergic rhinitis, asthma, COPD, ulcerative colitis, liver fibrosis, HBV, HCV, HPV, RSV, SARS, HIV or influenza. Preferably, the disease or disorder is cancer.

DETAILED DESCRIPTION OF THE INVENTION

The following terms have the meanings indicated throughout the specification.

As used herein (including the appended claims), unless the context clearly indicates otherwise, singular words such as "a", "an" and "the" include their corresponding plural referents.

Unless the context clearly indicates otherwise, the term "or" is used to mean the term "and/or" and can be used interchangeably with the term "and/or".

The term "alkyl" herein refers to a hydrocarbon group selected from linear saturated hydrocarbon groups and branched saturated hydrocarbon groups, which comprises 1 to 18 (such as 1 to 12, further such as 1 to 10, still further such as 1 to 8 or 1 to 6 or 1 to 4) carbon atoms.

Examples of alkyl comprising 1 to 6 carbon atoms (i.e. $C_{1-6}$ alkyl) include, but are not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or sec-butyl ("s-Bu"), 1,1-dimethylethyl or tert-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

The term "alkoxy" or "alkyloxy" refers to the alkyl as previously defined which is attached to a parent molecular moiety through an oxygen atom.

The term "amino" refers to $—NH_2$. The term "alkylamino" refers to —NH(alkyl). The term "dialkylamino" refers to $—N(alkyl)_2$. As used herein, the term "halogen" refers to fluorine (F), chlorine (Cl), bromine (Br) and iodine (I).

As used herein, the term "haloalkyl" refers to an alkyl group in which one or more hydrogen atoms are replaced by one or more halogen atoms (e.g., fluorine, chlorine, bromine and iodine).

Examples of haloalkyl include halogenated $C_{1-8}$ alkyl, halogenated $C_{1-6}$ alkyl or halogenated $C_{1-4}$ alkyl, but are not limited to $—CF_3$, $—CH_2Cl$, $—CH_2CF_3$, $—CCl_2$, $CF_3$ etc.

As used herein, the term "alkenyl" refers to a hydrocarbon group selected from linear hydrocarbon groups and branched hydrocarbon groups, which comprises at least one C═C double bond and 2 to 18 (such as 2 to 8, further such as 2 to 6) carbon atoms. Examples of alkenyl such as $C_{2-6}$ alkenyl include, but are not limited to, ethenyl (or vinyl), prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl and hexa-1,3-dienyl.

The term "alkynyl" herein refers to a hydrocarbon group selected from linear hydrocarbon groups and branched hydrocarbon groups, which comprises at least one C≡C triple bond and 2 to 18 (such as 2 to 8, further such as 2 to 6) carbon atoms. Examples of alkynyl such as $C_{2-6}$ alkynyl include but are not limited to ethynyl, 1-propynyl, 2-propynyl (propargyl), 1-butynyl, 2-butynyl and 3-butynyl.

As used herein, the term "alkyloxy" or "alkoxy" refers to the alkyl as defined above which is attached to a parent molecular moiety through an oxygen atom. Examples of alkoxy such as $C_{1-6}$ alkoxy or C1-4 alkoxy include but are not limited to methoxy, ethoxy, isopropoxy, propoxy, n-butoxy, tert-butoxy, pentoxy and hexyloxy, etc.

The term "alkoxy-alkyl-" refers to the alkyl as defined above which is further substituted with the alkoxy as defined above. Examples of alkoxy-alkyl- such as C1-8 alkoxy-C1-8 alkyl- or C1-6 alkoxy-$C_{1-6}$ alkyl- include but are not limited to methoxymethyl, ethoxymethyl, ethoxyethyl, isopropoxymethyl or propoxymethyl, etc.

The term "cycloalkyl" refers to a hydrocarbon group selected from saturated cyclic hydrocarbon groups, which includes monocyclic and polycyclic (such as bicyclic and tricyclic) groups, including fused, bridged or spiro cycloalkyl.

For example, cycloalkyl may comprise 3 to 12 (such as 3 to 10, further such as 3 to 8, further such as 3 to 6, 3 to 5 or 3 to 4) carbon atoms. Even further, for example, cycloalkyl can be selected from monocyclic groups comprising 3 to 12 (such as 3 to 10, further such as 3 to 8, 3 to 6) carbon atoms. Examples of monocyclic cycloalkyl include cyclopropyl, cyclobutyl, cyclopentyl, 1-cyclopent-1-enyl, 1-cyclopent-2-enyl, I-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Particularly, examples of saturated monocyclic cycloalkyl such as $C_{3-8}$ cycloalkyl include but are not limited to cyclopropyl, cyclobutyl, cyclopentyl, cyclohexyl, cycloheptyl and cyclooctyl. In a preferred embodiment, cycloalkyl is a monocyclic ring comprising 3 to 6 carbon atoms (abbreviated as $C_{3-6}$ cycloalkyl), which includes but is not limited to cyclopropyl, cyclobutyl, cyclopentyl and cyclohexyl. Examples of bicyclic cycloalkyl include those having 7 to 12 ring atoms, which are arranged as fused bicyclic rings selected from [4,4], [4,5], [5,5], [5,6] or [6,6] ring systems, or bridged bicyclic rings selected from bicyclo[2.2.1]heptane, bicyclo[2.2.2]octane, and bicyclo [3.2.2]nonane. Other examples of bicyclic cycloalkyl include those arranged as bicyclic rings selected from [5,6] and [6,6] ring systems.

The term "spiro-cycloalkyl" includes a cyclic structure comprising carbon atoms and formed by at least two rings sharing one atom. The term "7-12-membered spiro-cycloalkyl" includes a cyclic structure comprising 7 to 12 carbon atoms and formed by at least two rings sharing one atom.

The term "fused cycloalkyl" includes bicyclic cycloalkyl as defined herein, which is saturated and formed by two or more rings sharing two adjacent atoms.

The term "bridged cycloalkyl" includes a cyclic structure comprising carbon atoms and formed by two rings sharing two atoms that are not adjacent to each other. The term "7-10-membered bridged cycloalkyl" includes a cyclic structure comprising 7 to 12 carbon atoms and formed by two rings sharing two atoms that are not adjacent to each other.

The term "cycloalkenyl" refers to a non-aromatic cyclic alkyl group with 3 to 10 carbon atoms having one or more rings and at least one double bond and preferably 1-2 double bonds. In one embodiment, the cycloalkenyl is cyclopentenyl or cyclohexenyl, preferably cyclohexenyl.

The term "cycloalkynyl" refers to a non-aromatic cycloalkyl group with 5 to 10 carbon atoms having one or more rings and at least one triple bond.

The term "deuterated" is used here to modify chemical structures or organic groups, in which one or more hydrogen atoms bonded to carbon are replaced by one or more deuterium atoms, such as deuterated alkyl, deuterated cycloalkyl, deuterated heterocycloalkyl, deuterated aryl, deuterated morpholinyl, etc. For example, the term "deuterated alkyl" defined above refers to alkyl as defined herein, in which at least one hydrogen atom bonded to carbon is replaced by deuterium. In the deuterated alkyl, at least one carbon atom is bonded to deuterium: the carbon atom can be bonded with more than one deuterium atoms; more than one carbon atoms in the alkyl group can also be bonded to deuterium.

The term "aryl" used alone or in combination with other terms refers to a group selected from:

- 5- and 6-membered carbocyclic aromatic rings such as phenyl;
- bicyclic systems, such as 7-12-membered bicyclic systems, in which at least one ring is carbocyclic and aromatic, such as naphthyl and indenyl; and
- tricyclic systems, such as 10-15-membered tricyclic systems, in which at least one ring is carbocyclic and aromatic, such as fluorenyl.

The terms "aromatic hydrocarbon ring" and "aryl" are used interchangeably in the disclosure herein. In some embodiments, monocyclic or bicyclic aromatic hydrocarbon rings have 5 to 10 ring-forming carbon atoms (i.e., $C_{5-10}$ aryl). Examples of monocyclic or bicyclic aromatic hydrocarbon rings include, but are not limited to, phenyl, naphthalen-1-yl, naphthalen-2-yl, anthracyl, phenanthryl, etc. In some embodiments, the aromatic hydrocarbon ring is a naphthalene ring (naphthalen-1-yl or naphthalen-2-yl) or a benzene ring. In some embodiments, the aromatic hydrocarbon ring is a benzene ring.

As used herein, the term "heteroaryl" refers to a group selected from: 5-, 6- or 7-membered aromatic monocyclic rings comprising at least one heteroatom, such as 1 to 4 heteroatoms, or 1 to 3 heteroatoms in some embodiments and 1 to 2 heteroatoms in some embodiments, wherein the heteroatoms are selected from nitrogen (N), sulfur (S) and oxygen (O), and the remaining ring atoms are carbon:

7-12-membered bicyclic rings comprising at least one heteroatom, such as 1 to 4 heteroatoms, or 1 to 3 heteroatoms in some embodiments, or 1 or 2 heteroatoms in other embodiments, wherein the heteroatoms are selected from nitrogen, oxygen or optionally oxidized sulfur (as one or more ring members), the remaining ring atoms are carbon, and at least one ring is aromatic and there is at least one heteroatom in the aromatic ring; and 11-14-membered tricyclic rings comprising at least one heteroatom, such as 1 to 4 heteroatoms, or 1 to 3 heteroatoms in some embodiments, or 1 or 2 heteroatoms in other embodiments, wherein the heteroatoms are selected from nitrogen, oxygen or optionally oxidized sulfur (as one or more ring members), and the remaining ring atoms are carbon, and wherein at least one ring is aromatic and there is at least one heteroatom in the aromatic ring.

When the total number of S and O atoms in the heteroaryl exceeds 1, these heteroatoms are not adjacent to each other. In some embodiments, the total number of S and O atoms in the heteroaryl is not more than 2. In some embodiments, the total number of S and O atoms in the aromatic heterocyclic ring is not more than 1. When the heteroaryl comprises more than one heteroatom ring members, the heteroatoms may be the same or different. Nitrogen atoms in one or more rings of the heteroaryl can be oxidized to form N-oxides.

As used herein, the term "optionally oxidized sulfur" refers to S, SO or $SO_2$.

The terms "aromatic heterocyclic ring" and "heteroaryl" are used interchangeably in the disclosure herein. In some embodiments, the monocyclic or bicyclic aromatic heterocyclic ring has 5, 6, 7, 8, 9 or 10 ring-forming members, in which 1, 2, 3 or 4 heteroatom ring members are independently selected from nitrogen (N), sulfur (S) and oxygen (O), and the remaining ring members are carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5-6-membered heteroaryl ring which is monocyclic and has 1 or 2 heteroatom ring members independently selected from nitrogen (N), sulfur (S) and oxygen (O). In some embodiments, the monocyclic or bicyclic aromatic heterocyclic ring is an 8-10-membered heteroaryl ring, which is bicyclic and has 1 or 2 heteroatom ring members independently selected from nitrogen, sulfur and oxygen.

Examples of heteroaryl or monocyclic or bicyclic aromatic heterocyclic ring include, but are not limited to (numbering starts from the connection position specified as 1 in terms of priority) pyridinyl (e.g., 2-pyridinyl, 3-pyridinyl or 4-pyridinyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl (e.g., 1,2,3-thiadiazoly, 1,2,4-thiadiazolyl or 1,3,4-thiadiazolyl), tetrazolyl, thienyl (e.g., thien-2-yl, thien-3-yl), triazinyl, benzothionyl, furyl (or furanyl), benzofuranyl, benzimidazolyl, indolyl, isoindolyl, dihydroindolyl, oxadiazolyl (e.g., 1,2,3-oxadiazolyl, 1,2,4-oxadiazolyl or 1,3,4-oxadiazolyl), phthalazinyl, pyrazinyl, pyridazinyl, pyrrolyl, triazolyl (e.g., 1,2,3-triazolyl, 1,2,4-triazolyl or 1,3,4-triazolyl), quinolyl, isoquinolyl, pyrazolyl, pyrrolopyridinyl (e.g., 1H-pyrrolo[2,3-b]pyridin-5-yl), pyrazolopyridyl (e.g., 1H-pyrazolo[3,4-b]pyridin-5-yl), benzoxazolyl (e.g., benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thiaza-2,3-diazolyl, 1-thiaza-2,4-diazolyl, 1-thiaza-2,5-diazolyl, 1-thiaza-3,4-diazolyl, furazanyl (e.g., furazan-2-yl, furazan-3-yl), benzofurazanyl, benzothiophenyl, benzothiazolyl, benzoxazolyl, quinazolyl, quinoxalinyl, naphthyridinyl, furanopyridinyl, benzothiazolyl (e.g., benzo[d]thiazol-6-yl), indozolyl (e.g., 1H-indazol-5-yl) and 5,6,7,8-tetrahydroisoquinolinyl.

"Heterocyclyl", "heterocyclic ring" and "heterocyclic" are interchangeable and refer to non-aromatic heterocyclic groups comprising one or more heteroatoms selected from nitrogen, oxygen or optionally oxidized sulfur as ring members (the remaining ring members are carbon), which include monocyclic ring, fused ring, bridged ring and spiro ring, that is, comprise monocyclic heterocyclyl, bridged heterocyclyl, spiro heterocyclyl and fused heterocyclyl.

The term "monocyclic heterocyclyl" refers to a monocyclic group in which at least one ring member is a heteroatom selected from nitrogen, oxygen or optionally oxidized sulfur. Heterocyclic rings can be saturated or partially saturated.

Exemplary monocyclic 4-9-membered heterocyclic groups include, but are not limited to (numbering starts from the connection position specified as 1 in terms of priority), pyrrolidin-1-yl, pyrrolidin-2-yl, pyrrolidin-3-yl, imidazolidin-2-yl, imidazolidin-4-yl, pyrazolin-2-yl, pyrazolin-3-yl, piperidin-1-yl, piperidin-2-yl, piperidin-3-yl, piperidin-4-yl, 2,5-piperazinyl, pyranyl, morpholinyl, morpholino, morpholin-2-yl, morpholin-3-yl, oxiranyl, aziridin-1-yl, aziridin-2-yl, aracyclooctan-1-yl, azacyclooctan-2-yl, azacyclooctan-3-yl, azacyclooctan-4-yl, azacyclooctan-5-yl, thiiranyl, azetidin-1-yl, azetidin-2-yl, azetidin-3-yl, oxetanyl, thiacyclobutanyl, 1,2-dithiacyclobutanyl, 1,3-dithiacyclobutanyl, dihydropyridinyl, tetrahydropyridinyl, thiomorpholinyl, thioxanyl, piperazinyl, homopiperazinyl, homopiperidyl, azepan-1-yl, azepan-2-yl, azepan-3-yl, azepan-4-yl, oxepanyl, thiepanyl, 1,4-oxathianyl, 1,4-dioxepanyl, 1,4-oxapanyl, 1,4-oxazepanyl, 1,4-dithiepanyl, 1,4-azapanyl and 1,4-diazepanyl, 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothiophenyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxolanyl, 1,3-dioxolanyl, pyrazolinyl, pyrazolyl, dithianyl, dithiolanyl, pyrazolidinyl, imidazolinyl, pyrimidinonyl, or 1,1-dioxo-thiomorpholinyl.

The term "spiro heterocyclyl" refers to a 5-20-membered polycyclic heterocyclyl whose rings are connected by a common carbon atom (called spiro-atom), which comprises one or more heteroatoms selected from nitrogen, oxygen or optionally oxidized sulfur as ring members, and the remaining ring members are carbon. One or more rings of the spiro heterocyclyl may comprise one or more double bonds, but none of these rings has a fully conjugated n electron system. Preferably, the spiro heterocyclyl is 6-14-membered, more preferably 7-12-membered. According to the number of shared sprio-atoms, the spiro heterocyclyl is divided into mono-spiro heterocyclyl, di-spiro heterocyclyl or multi-spiro heterocyclyl, and preferably refers to mono-spiro heterocyclyl or di-spiro heterocyclyl, and more preferably 4-membered/4-membered, 3-membered/5-membered, 4-membered/5-membered, 4-membered/6-membered, 5-membered/5-membered, or 5-membered/6-membered mono-spiro heterocyclyl. For example, the spiro heterocyclyl is 7-azaspiro[3.5]nonyl, 2-azaspiro[3.3]heptyl, 7-azaspiro[3.5]nonyl or 2-azaspiro[3.5]nonyl. More specifically, the spiro heterocyclyl is 7-azaspiro[3.5]non-2-yl, 2-azaspiro[3.3]hept-6-yl, 7-azaspiro[3.5]non-2-yl or 2-azaspiro[3.5]non-7-yl.

The term "fused heterocyclyl" refers to 5-20-membered polycyclic heterocyclyl, in which each ring in the system shares an adjacent pair of atoms (carbon and carbon atoms or carbon and nitrogen atoms) with another ring, which comprises one or more heteroatoms selected from nitrogen, oxygen or optionally oxidized sulfur as ring members, and the remaining ring members are carbon.

One or more rings of fused heterocyclyl may comprise one or more double bonds, but none of these rings has a fully conjugated n electron system. Preferably, the fused heterocyclyl is 6-14-membered, and more preferably 7-10-membered. According to the number of membered rings, the fused heterocyclyl is divided into bicyclic, tricyclic, tetracyclic or polycyclic fused heterocyclyl, preferably bicyclic or tricyclic fused heterocyclyl, and more preferably 5-membered/5-membered or 5-membered/6-membered bicyclic fused heterocyclyl. Representative examples of fused heterocyclic rings include, but are not limited to: octahydro cyclopentano[c]pyrrolyl (e.g., octahydrocyclopentano[c] pyrrol-2-yl), octahydropyrrolo[3,4-c]pyrrolyl, octahydroisoindolyl, isoindolinyl (e.g., isoindolin-2-yl), octahydrobenzo[b][1,4]dioxinyl.

The term "bridged heterocyclyl" refers to 5-14-membered polycyclic heterocyclic alkyl, in which every two rings in the system share two unconnected atoms, comprise one or more heteroatoms selected from nitrogen, oxygen or optionally oxidized sulfur as ring members, and the remaining ring members are carbon. One or more rings of the bridged heterocyclyl may comprise one or more double bonds, but none of these rings has a fully conjugated n electron system. Preferably, the bridged heterocyclyl is 6-14-membered, and more preferably 7-10-membered. According to the number of membered rings, the bridged heterocyclyl is divided into bicyclic, tricyclic, tetracyclic or polycyclic bridged heterocyclyl, and preferably refers to bicyclic, tricyclic or tetracyclic bridged heterocyclyl, and more preferably bicyclic or tricyclic bridged heterocyclyl. Representative examples of bridged heterocyclyl include but are not limited: 2-azabicyclo[2.2.1]heptyl, azabicyclo[3.1.0]hexyl, 2-azabicyclo [2.2.2]octyl and 2-azabicyclo[3.3.2]decyl, 3-azabicyclo [3.1.0]hexyl, 2-azabicyclo[2.2.1]heptyl, 8-azabicyclo[3.2.1] octyl or 2-azabicyclo[4.1.0]heptyl, such as 3-azabicyclo [3.1.0]hex-6-yl, 2-azabicyclo[2.2.1]hept-5-yl, 8-azabicyclo [3.2.1]oct-3-yl, or 2-azabicyclo[4.1.0]hept-5-yl.

The compounds disclosed herein may comprise asymmetric centers, and thus may exist as enantiomers. "Enantiomer" refers to two stereoisomers of a compound, which are non-overlapping mirror images of each other. When the compounds disclosed herein have two or more asymmetric centers, they may additionally exist as diastereomers Enantiomers and diastereomers belong to a broader category of stereoisomers. It is intended to include all such possible stereoisomers as substantially pure resolved enantiomers, racemic mixtures thereof, and diastereomer mixtures. It is intended to include all stereoisomers of the compounds disclosed herein and/or pharmaceutically acceptable salts thereof. Unless otherwise explicitly mentioned, the reference to one isomer applies to any possible isomer. Whenever the isomer composition is not specified, all possible isomers are included.

As used herein, the term "substantially pure" means that the target stereoisomer comprises no more than 35% by weight (such as no more than 30%, further such as no more than 25%, even further such as no more than 20%) of any other stereoisomer. In some embodiments, the term "substantially pure" means that the target stereoisomer comprises no more than 10% by weight (for example, no more than 5%, such as no more than 1%) of any other stereoisomer.

When the compounds disclosed herein comprise olefinic double bonds, unless otherwise specified, such double bonds are intended to include E and Z geometric isomers.

When the compound disclosed herein comprises disubstituted cyclohexyl or cyclobutyl, the substituents found on the cyclohexyl or cyclobutyl ring can adopt cis and trans configurations. Cis-configuration means that two substituents are found on the upper side of the two substituent positions on the carbon, while trans-configuration means that they are on the opposite side.

It may be advantageous to separate the reaction products from each other and/or from the starting materials. The desired products of each step or a series of steps are separated and/or purified (hereinafter separated) to the desired degree of homogeneity by the common techniques in the art. Generally, such separation involves multi-phase extraction, crystallization from solvent or solvent mixture, distillation, sublimation or chromatography. Chromatography can include many methods, including, for example, reverse phase and normal phase; size exclusion; ion exchange; high, medium and low pressure liquid chromatography and apparatus; small-scale analysis; simulated moving bed (SMB) and preparative thin-layer or thick-layer chromatography, as well as small-scale thin-layer and fast chromatography technology. Those skilled in the art will apply the technology that is most likely to achieve the required separation.

"Diastereomer" refers to stereoisomers of a compound with two or more chiral centers, but they are not mirror images of each other. By methods well known to those skilled in the art, such as chromatography and/or fractional crystallization, diastereomer mixtures can be separated into their individual diastereomers based on their physical and chemical differences. Enantiomers can be separated by converting the mixture of enantiomers into a mixture of diastereomers by reacting with suitable optically active compounds (e.g., chiral auxiliaries such as chiral alcohol or Mosher's acid chloride), separating the diastereomers and converting (e.g., hydrolyzing) the respective diastereomers into corresponding pure enantiomers. Chiral HPLC columns can also be used to separate enantiomers.

A single stereoisomer (e.g., substantially pure enantiomer) can be obtained by resolving the racemic mixture using a method of forming diastereomers with optically active resolving agents, for example (Eliel, E. and Wilen, S. Stereochemistry of Organic Compounds. New York: John Wiley & Sons, Inc., 1994; Lochmuller, C. H. et al., "Chromatographic resolution of enantiomers: Selective review." J. Chromatogr., 113(3) (1975): pp. 283-302). The racemic mixture of chiral compounds of the invention can be separated by any suitable method, including: (1) forming ions and diastereomeric salts using chiral compounds and separating them by fractional crystallization or other methods; (2) forming diastereomeric compounds using chiral derivatives, separating diastereomers and converting them into pure stereoisomers; and (3) directly separating substantially pure or enriched stereoisomers under chiral conditions. See: Wainer, Irving W., Ed. Drug Stereochemistry. Analytical Methods and Pharmacology. New York: Marcel Dekker, Inc., 1993.

"Pharmaceutically acceptable salt" refers to a salt described below, which is suitable for contact with the tissues of human beings and lower animals within the scope of reliable medical judgment without excessive toxicity, irritation, allergic reaction, etc., and has a reasonable benefit/risk ratio. Pharmaceutically acceptable salts can be prepared in situ during the final separation and purification of compounds disclosed herein, or prepared separately by reacting free base functional groups with suitable organic acids or by reacting acidic groups with suitable bases.

In addition, if the compound disclosed herein is obtained as an acid addition salt, the free base can be obtained by alkalizing the solution of the acid salt. Conversely, if the product is a free base, an addition salt, such as a pharmaceutically acceptable addition salt, can be produced by dissolving a free base in a suitable organic solvent and treating the solution with an acid according to the conventional procedure for preparing acid addition salts from basic compounds. Those skilled in the art will recognize various synthetic methods that can be used to prepare nontoxic pharmaceutically acceptable addition salts without undue experimentation.

As defined herein, "pharmaceutically acceptable salts thereof" includes at least one salt of a compound of formula (I) and a salt of a stereoisomer of the compound of formula (I), such as a salt of an enantiomer and/or a salt of a diastereomer.

When applied to animals, human, experimental subjects, cells, tissues, organs or biological fluids, the terms "administration", "administering", "treating" and "treatment" mean the contact of exogenous drugs, therapeutic agents, diagnostic agents or compositions with animals, human, subjects, cells, tissues, organs or biological fluids. The treatment of cells includes the contact of reagents with cells, and the contact of reagents with fluids, wherein the fluids are in contact with the cells. The terms "administration", "administering", "treating" and "treatment" also mean in vitro and ex vivo treatment of cells, for example, by using reagents, diagnostic agents, binding compounds or by using another cell. The term "subject" herein includes any organism, preferably an animal, more preferably a mammal (e.g., rat, mouse, dog, cat, rabbit) and most preferably a human.

The term "effective amount" or "therapeutically effective amount" refers to the amount of an active ingredient (such as a compound) that is sufficient to affect the treatment of a disease or at least one clinical symptom of the disease or disorder when the compound is administered to a subject to treat the disease or at least one clinical symptom of the disease or disorder. The "therapeutically effective amount" may vary with the following factors: the compound, the disease, disorder and/or symptoms of the disease or disorder, the severity of the disease, disorder and/or symptoms of the disease or disorder, the age of the subject to be treated and/or the weight of the subject to be treated. In any given example, the appropriate amount is clear to those skilled in the art, or can be determined by routine experiments. In some embodiments, a "therapeutically effective amount" is an amount of at least one compound disclosed herein and/or at least one stereoisomer thereof and/or at least one pharmaceutically acceptable salt thereof that is effective in "treating" (as defined above) a disease or disorder of a subject. In the case of combination therapy, the "therapeutically effective amount" refers to the total amount of combined objects used to effectively treat diseases, disorders or symptoms.

Pharmaceutical compositions comprising the compounds disclosed herein can be administered to subjects in need thereof via oral, inhalation, rectal, parenteral or local administration. For oral administration, the pharmaceutical composition can be conventional solid formulations such as tablets, powders, granules, capsules, etc., liquid formulations such as water or oil suspension, or other liquid formulations such as syrup, solution, suspension, etc. For parenteral administration, the pharmaceutical composition can be solution, aqueous solution, oil suspension concentrate, lyophilized powder, etc. Preferably, the formulation of the pharmaceutical composition is selected from tablets, coated tablets, capsules, suppositories, nasal sprays or injections, and more preferably tablets or capsules. The pharmaceutical composition can be administered in a single unit with an accurate dose. In addition, the pharmaceutical composition may also comprise additional active ingredients.

All formulations of the pharmaceutical compositions disclosed herein can be prepared by conventional methods in the pharmaceutical field. For example, the active ingredient can be mixed with one or more excipients, and then prepared into the desired formulation. "Pharmaceutically acceptable excipients" refer to conventional pharmaceutical carriers suitable for the required pharmaceutical formulations, such as diluents, vehicles (such as water, various organic solvents), fillers (such as starch, sucrose) and binders (such as cellulose derivatives, alginates, gelatin and polyvinylpyrrolidone (PVP)); wetting agents such as glycerin; disintegrants such as agar, calcium carbonate and sodium bicarbonate; absorption promoters such as quaternary ammonium compounds; surfactants such as cetyl alcohol; absorbing carriers such as kaolin and bentonite; lubricants such as talc, calcium stearate, magnesium stearate, polyethylene glycol. In addition, the pharmaceutical composition also comprises other pharmaceutically acceptable excipients, such as dispersants, stabilizers, thickeners, complexing agents, buffers, permeation enhancers, polymers, flavoring agents, sweeteners and dyes.

The term "disease" refers to any disease, discomfort, illness, symptom or indication, and is interchangeable with the term "disorder" or "condition".

Throughout the specification and the following claims, unless the context requires otherwise, the terms "comprise" and variations thereof such as "comprises" and "comprising" are intended to explain the existence of subsequent features, but do not exclude the existence or addition of one or more other functions. As used herein, the term "comprise" can be replaced by the terms "contain", "include" or sometimes "have".

Throughout the specification and the following claims, the term "Cn-m" means a range including endpoints, where n and m are integers and represent carbon numbers. Examples include C1-8, C1-6, etc.

Unless explicitly defined elsewhere in this document, all other technical and scientific terms used herein have the meanings commonly understood by those of ordinary skill in the art to which the invention belongs.

General Synthesis

The compounds disclosed herein (including their salts) can be prepared using known organic synthesis techniques and can be synthesized according to any one of many possible synthesis routes.

The reactions for preparing the compounds disclosed herein can be carried out in suitable solvents, which can be easily selected by those skilled in the field of organic synthesis. A suitable solvent may not substantially react with the starting materials, intermediates or products at the reaction temperature which, for example, may range from room temperature to the boiling temperature of the solvent. A given reaction can be carried out in a solvent or solvent mixture.

Those skilled in the art can easily determine the selection of appropriate protecting groups.

The reaction can be monitored according to any suitable method known in the art, such as NMR, UV, HPLC, LC-MS and TLC. Compounds can be purified by various methods, including HPLC and normal phase silica gel chromatography.

Chiral HPLC is used to analyze the retention time of different chiral examples. According to the column, mobile phase and solvent ratio used, the conditions are divided into the following methods.

SCHEME I

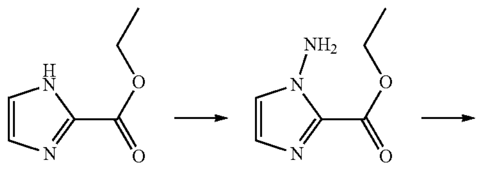

1 2

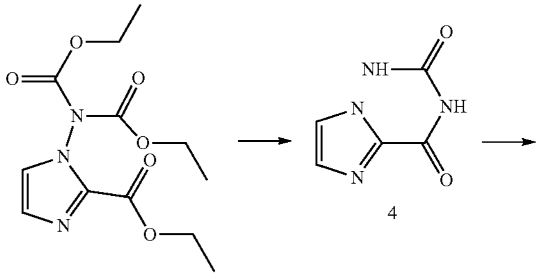

3 4

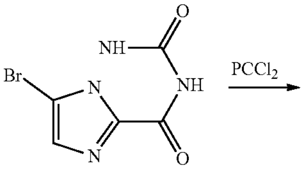

5

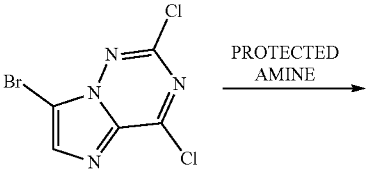

6

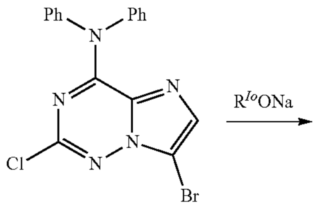

7

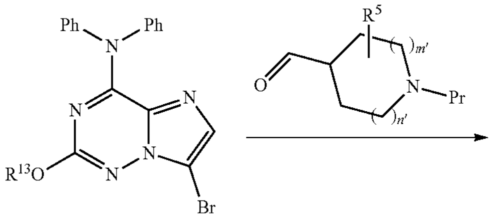

8

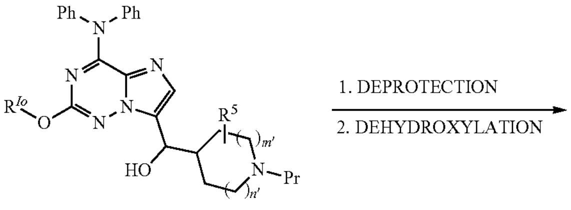

9A

-continued

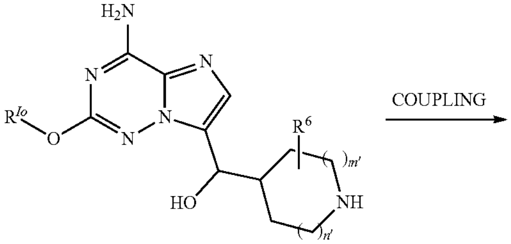

Pr = PROTECTING GROUP

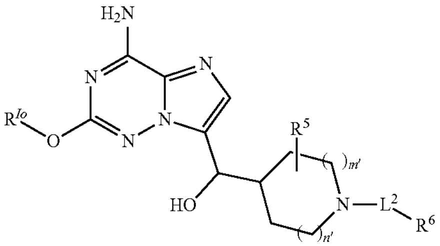

FORMULA IA wherein:

$R^{1a}$, $R^5$, $L^2$ and $R^6$ are as defined for formula (I), m' is 0, 1, 2 or 3, and n' is 1, 2 or 3.

In scheme I, commercially available ethyl 1H-imidazol-2-carboxylate reacts with 2-O-(4-nitrobenzoyl) hydroxylamine to form compound 2, which reacts with ethyl chloroformate, and then ring closure reaction is carried out in the presence of ammonium hydroxide to obtain imidazo [2,1-f][1,2,4]triazin-2,4 (1H,3H)-dione 4. After introducing a Br atom using a brominating agent, compound 5 is obtained, and then diketone is chlorinated to form compound 6. One chlorine atom is replaced by a protected amine, and the other chlorine atom reacts with $R^1$ONa to form key intermediate 8, which then reacts with different aldehydes under alkaline conditions to form formula 9A. The protecting group and hydroxyl on the amine are removed to obtain formula 10A. After formula 10A is coupled with different acids under alkaline conditions or with different aldehydes in the presence of reducing agents, the compound of formula IA is obtained.

Scheme II

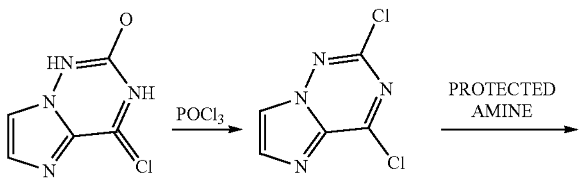

4 11

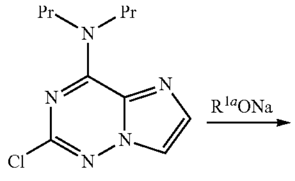

12

-continued

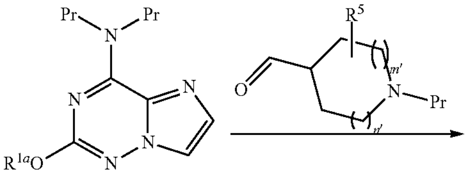

13

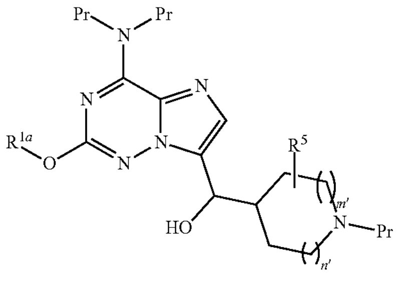

9A wherein $R^{1a}$ and $R^5$ are as defined for formula (I), m' is 0, 1, 2 or 3, and n' is 1, 2 or 3.

In scheme II, this method can also be used to prepare Formula 9A. Imidazo[2,1-f][1,2,4]triazin-2,4 (1H,3H)-dione 4 is chlorinated to form compound 11. One chlorine atom is replaced by a protected amine, and the other chlorine atom reacts with $R^1ONa$ to form key intermediate 13, which then reacts with different aldehydes under alkaline conditions to form formula 9A.

Scheme III

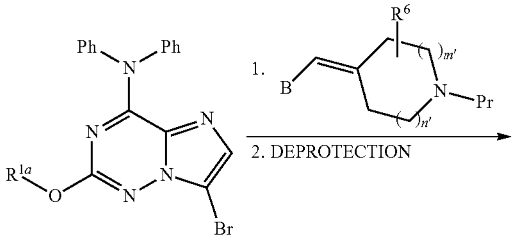

8

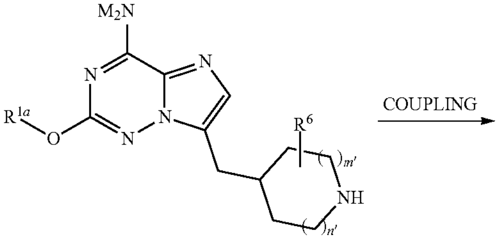

10A

-continued

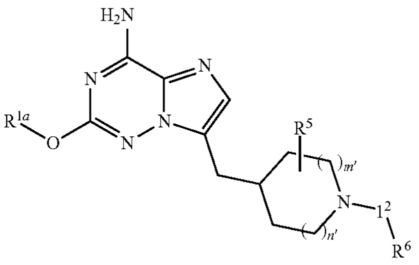

FORMULA IA

In scheme III, the key intermediate 8 reacts with different borates in the coupling reaction with or without metals, and then the protecting group on the amine is removed to obtain formula 10A. After formula 10A is coupled with different acids under alkaline conditions or with different aldehydes in the presence of reducing agents, the compound of formula IA is obtained.

SCHEME IV

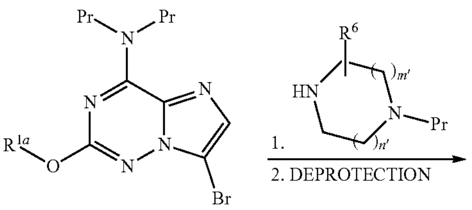

8

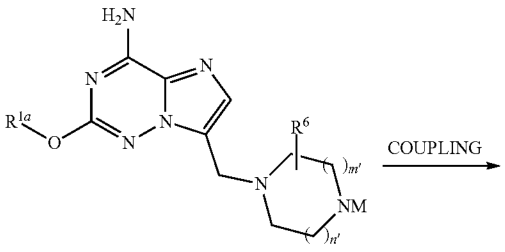

14

Pr = PROTECTING GROUP

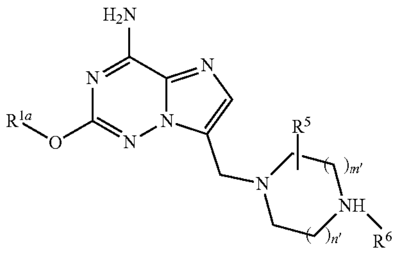

FORMULA II

X = 0, NH

In scheme IV, the key intermediate 8 reacts with different alkyl amines and alkyl alcohols in the coupling reaction with or without metals. The protecting group on the amine is removed to obtain formula 14. After deprotection and coupling with different acids under alkaline conditions or with different aldehydes in the presence of reducing agents, the compound of formula II is obtained.

SCHEME V

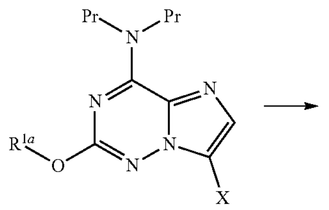

8: X = B/
13: X = H

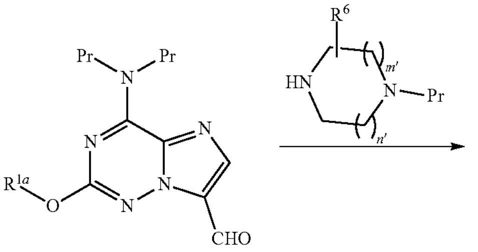

15

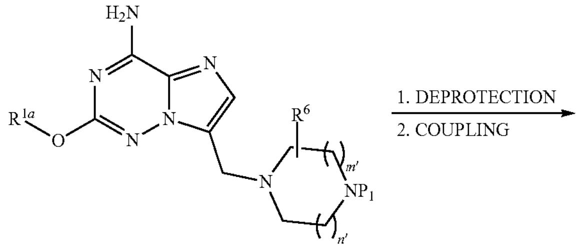

FORMULA 10B

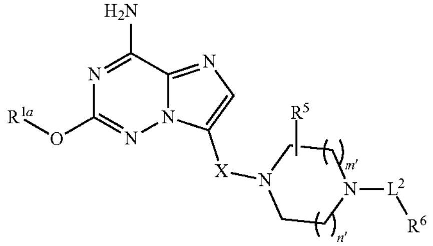

FORMULA IB

In scheme V, the key intermediate 8 or 13 reacts with DMF or morpholin-4-formaldehyde under alkaline conditions to form aldehyde 15, which reacts with different amines in the presence of reducing agent to form formula 10B. After deprotection and coupling with different acids under alkaline conditions or with different aldehydes in the presence of reducing agents, the compound of formula IB is obtained.

EXAMPLES

The following examples are intended to be exemplary only and should not be considered as limiting in any way. Unless otherwise stated, the experimental methods in the following examples are conventional methods. Unless otherwise stated, reagents and materials are commercially available. All solvents and chemicals used are analytical or chemically pure. Solvents should be distilled again before use. Anhydrous solvents are prepared according to standard methods or reference methods. Silica gel (100-200 mesh) for column chromatography and silica gel (GF254) for thin layer chromatography (TLC) can be obtained commercially from Tsingdao Haiyang Chemical Co., Ltd. or Yantai Chemical Co., Ltd in China; unless otherwise stated, all of them are eluted with petroleum ether (60-90° C.)/ethyl acetate (v/v) and developed with iodine or phosphomolybdic acid solution in ethanol. Unless otherwise stated, all extraction solvents are dried over anhydrous $Na_2SO_4$. $^1H$ NMR spectrum is recorded on Bruck-400 NMR spectrometer with TMS (tetramethylsilane) as internal standard. LC/MS data are recorded by using Agilent1100 high performance liquid chromatography-ion trap mass spectrometer (LC-MSD Trap) equipped with diode array detector (DAD) for detection at 214 nm and 254 nm and ion trap (ESI source). The names of all compounds except reagents are generated by ChemDraw®.

In the following examples, the following abbreviations are used;

AcOH Acetic acid
Aq. Aqueous
BINAP 2,2'-bis(diphenylphosphino)-1,1'-binaphthyl
Brine Saturated aqueous sodium chloride solution
Bn Benzyl
BnBr Benzyl bromide
BPO Benzoyl peroxide
BSA N,O-bis(trimethylsilyl)acetamide
$CH_2Cl_2$ or DCM Dichloromethane
DIAD Diisopropyl azodiformate
DMF N,N-dimethylformamide
Dppf 1,1'-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethylsulfoxide
EtOAc or EA Ethyl acetate
EtOH Ethanol
$Et_2O$ or ether Diethyl ether
g Gram
h or hr hour
HATU O-(7-azabenzotriazol-1-yl)-N,N,N',N'-tetramethyluronium hexafluorophosphate
Hex hexane
HCl Hydrochloric acid
HMDS Hexamethyldisilazane
HPLC high performance liquid chromatography
IBX 2-iodoxybenzoic acid
IPA Isopropyl alcohol
i-PrOH Isopropanol
LCMS Liquid chromatography-mass spectrometry
mg Milligram
mL Milliliter
mmol Millimole
MeCN Acetonitrile
MeOH Methanol
Min Minute
ms or MS Mass spectrometry
MTBE Methyl tert-butyl ether
$Na_2SO_4$ Sodium sulfate
NBS N-bromosuccinimide
NMP N-methylpyrrolidone
PE Petroleum ether
PMB (4-methoxyphenyl)methylamine
prep Preparation
Rt or rt Room temperature
sat. Saturated
TBAF Tetrabutyl ammonium fluoride
TBSCl Tert-butyl dimethyl silyl chloride t-BuOK Potassium tert-butoxide
TFA Trifluoroacetic acid
THF Tetrahydrofuran
TLC Thin-layer chromatography
μL Microliter Synthesis of Intermediate I 7-bromo-2-butoxy-N,N-bis(4-methoxybenzyl)imidazo[2,1-f][1,2,4]triazin-4-amine

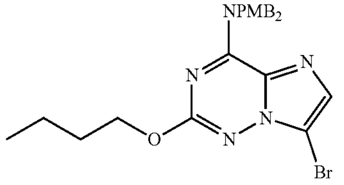

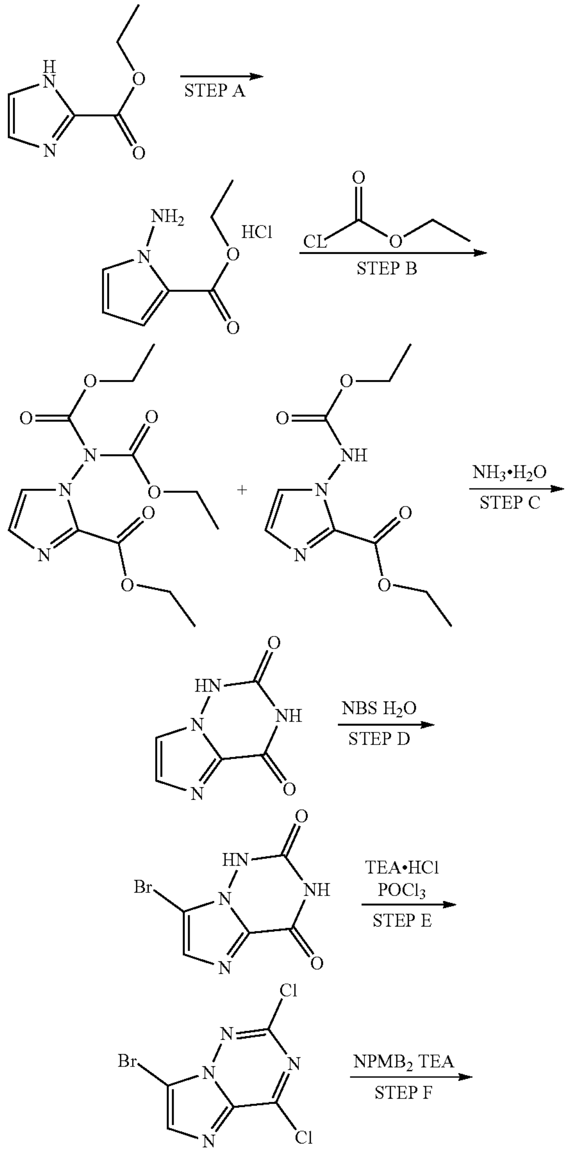

-continued

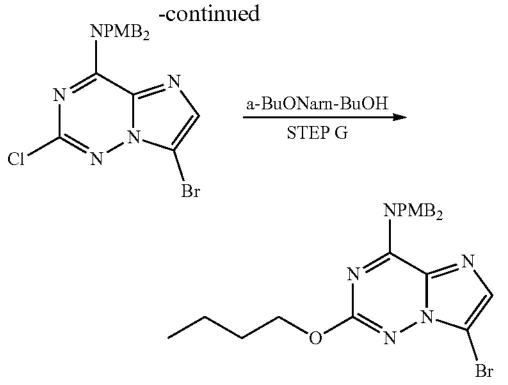

Step A: Ethyl 1-amino-1H-imidazol-2-carboxylate hydrochloride

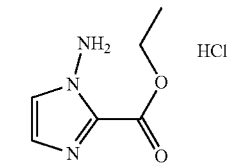

t-BuOK (1 M in THF, 440 ml, 0.44 mol) was added to a stirred solution of ethyl 1H-imidazol-2-carboxylate (56 g, 0.4 mol) in NMP (1.2 L) at 20-30° C. The mixture was stirred for 0.5 h. A solution of O-(4-nitrobenzoyl) hydroxylamine (80.08 g, 0.44 mol) in NMP (0.4 L) was added dropwise at a temperature below 30° C. The solution was stirred at room temperature for 2 h and diluted with MTBE (500 ml). HCl (4 M in EA, 100 ml) was added to quench the reaction. Diatomite (20 g) was added to the above mixture which was then stirred for 0.5 h. The mixture was filtered. The filtrate was diluted with MTBE (2 L) and HCl (4 M in EA, 200 ml) was added dropwise. The suspension was stirred for 0.5 h and filtered. The filter cake was washed with MTBE and dried in an oven to obtain the product (70 g, 91%). MS: M/e 156 $(M+1)^+$.

Step B: Mixture of ethyl 1-((ethoxycarbonyl)amino)-1H-imidazol-2-carboxylate and ethyl 1-(bis(ethoxycarbonyl)amino)-1H-imidazol-2-carboxylate (1:1)

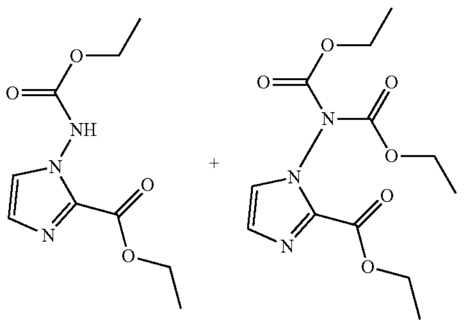 [SMILES: CCOC(=O)Nn1ccnc1C(=O)OCC ; CCOC(=O)c1nccn1N(C(=O)OCC)C(=O)OCC]

To a stirred solution of ethyl 1-amino-1H-imidazol-2-carboxylate hydrochloride (80 g, 0.42 mol) in THF (900 ml) and $H_2O$ (900 ml), $NaHCO_3$ (178.9 g, 2.1 mol) was added in several batches. Ethyl chloroformate (98.55 g, 0.9 mol) was added dropwise at a temperature below 30° C. The mixture was stirred at room temperature for 4 h, diluted with EA (1 L) and then separated. The aqueous layer was extracted with EA (800 ml). The collected organic layer was washed with brine, dried over $Na_2SO_4$, filtered and concentrated to obtain a crude product (113 g) as yellow oil, which can be directly used in the next step without further purification. MS: M/e 228 (M+1)+& M/e 300 $(M+1)^+$ Step C: Imidazo[2,1-f][1,2,4]triazin-2,4 (1H,3H)-dione

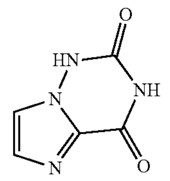 [SMILES: O=c1[nH]c(=O)c2nccn2[nH]1]

A mixture of ethyl 1-((ethoxycarbonyl)amino)-1H-imidazol-2-carboxylate and ethyl 1-(bis(ethoxycarbonyl)amino)-1H-imidazol-2-carboxylate (110 g) in ammonium hydroxide (400 ml, 3.6 V) and IPA (200 ml, 1.8 V) was added into a sealed tube. The mixture was stirred at 120° C. overnight. After cooling, the mixture was filtered. The filter cake was rinsed with MeOH. The filtrate was concentrated under reduced pressure. The resulting residue was pulped in MeOH, filtered and rinsed with MeOH. The obtained filter cake was mixed with the previous filter cake and dried in an oven to obtain the product (56 g) as a white solid. MS: M/e 153 (M+1)+.

Step D: 7-bromoimidazo[2,1-f][1,2,4]triazin-2,4-(1H,3H)-dione

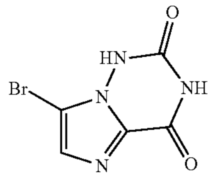 [SMILES: O=c1[nH]c(=O)c2ncc(Br)n2[nH]1]

To a solution of imidazo[2,1-f][1,2,4]triazin-2,4 (1H,3H)-dione (30 g, 0.20 mol) in $H_2O$ (1.2 L), NBS (24.6 g, 0.14 mol) was added in several batches at a temperature below 25° C. The mixture was stirred at room temperature for 1 h, and then filtered. The filtrate was concentrated to remove the solvent. The resulting residue was mixed with the previous filter cake and pulped in MeOH (20 V) and then in MeOH: $H_2O$ (1:1, 20 V) to obtain the product (30.4 g, 94%) as a white solid. MS: M/e 231 $(M+1)^+$.

Step E: 7-bromo-2,4-dichloroimidazo[2,1-f][1,2,4]triazine

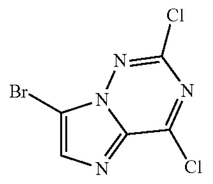 [SMILES: Clc1nc(Cl)c2ncc(Br)n2n1]

To a 350 ml sealed tube, 7-bromoimidazo[2,1-f][1,2,4]triazin-2,4 (1H,3H)-dione (10 g, 43 mmol), triethylamine hydrochloride (12 g, 88 mmol) and $POCl_3$ (100 ml) were added. The mixture was stirred at 120° C. overnight, and then concentrated to remove $POCl_3$. The residue was diluted with EA (200 ml), and saturated $NaHCO_3$ (aqueous solution) was added dropwise at a temperature below 20° C. until the pH was higher than 7. The solution was separated. The organic layer was washed with $H_2O$, dried over $Na_2SO_4$, filtered and concentrated. The resulting residue was purified by column chromatography eluted with 0-20% EA in PE to obtain the product (8.5 g, 73%) as a white solid. MS: M/e 267 (M+1)+.

Step F: 7-bromo-2-chloro-N,N-bis(4-methoxybenzyl)imidazo[2,1-f][1,2,4]triazin-4-amine

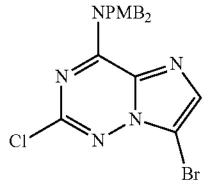

TEA (22.6 g, 0.22 mol) was added dropwise to a stirred solution of 7-bromo-2,4-dichloroimidazo[2,1-f][1,2,4]triazine (30 g, 0.11 mol) in THF (500 ml). The mixture was stirred at room temperature for 10 min. A solution of bis(4-methoxybenzyl)amine (31.6 g, 0.12 mol) in THF (80 ml) was added dropwise to the above solution. The mixture was stirred at room temperature for 2 h. The solution was quenched with $H_2O$ (300 ml) and then extracted with EA (200 ml×2). The organic layer was washed with brine, dried over $Na_2SO_4$, filtered and concentrated. The resulting residue was pulped in PE (300 ml) and filtered to obtain the product (41.4 g, 76%) as a white solid. MS: M/e 488 (M+1)+.

Step G: 7-bromo-2-butoxy-N,N-bis(4-methoxybenzyl)imidazo[2,1-f][1,2,4]triazin-4-amine

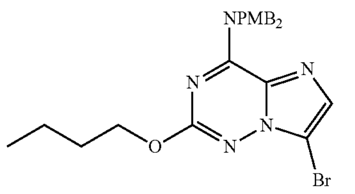

A mixture of 7-bromo-2-chloro-N,N-bis(4-methoxybenzyl)imidazo[2,1-f][1,2,4]triazin-4-amine (35 g, 71.6 mmol) and n-BuONa/n-BuOH (20%, 200 ml) was stirred at 80° C. under $N_2$ for 1 h. The solution was quenched with $H_2O$ (200 ml). The aqueous solution was extracted with EA (150 ml×2). The collected organic layer was washed with brine, dried over $Na_2SO_4$, filtered and concentrated. The resulting residue was purified by column chromatography eluted with 0-20% EA in PE to obtain the product (33 g, 88%) as colorless oil, which would be solidified after several hours. MS: M/e 526 (M+1)+.

Synthesis of Intermediate II 2-chloro-N,N-bis(2,4-dimethoxybenzyl)imidazo[2,1-f][1,2,4]triazin-4-amine

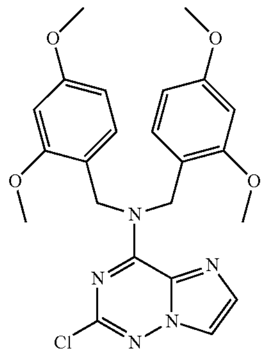

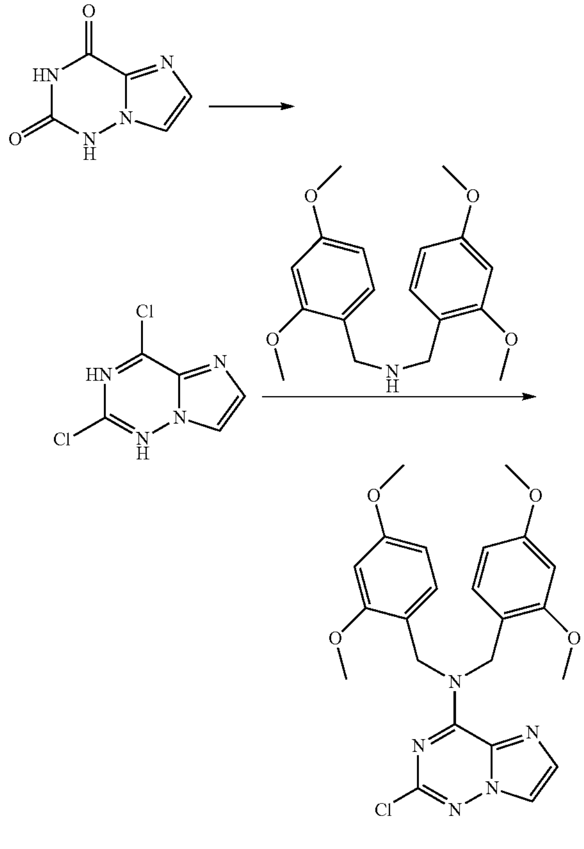

DIPEA (25.5 g, 0.20 mmol) was added to a mixture of imidazo[2,1-f][1,2,4]triazin-2,4 (1H,3H)-dione (10 g, 65.8 mmol), $POCl_3$ (50 g, 0.20 mmol) and toluene (60 mL) within 30 min at 60° C. At this time, heat release was noticed, and the temperature rose to 90° C. (The solid was gradually dissolved). After the addition was completed, the reaction was warmed to 100° C. (internal temperature was about 95° C.) and stirred overnight. The reaction was then cooled to room temperature. The mixture was concentrated under reduced pressure. The residue was dissolved in THF (100 mL), and DIPEA (25.5 g, 0.20 mmol) was then added dropwise to the mixture. The mixture was added to a solution of bis(2,4-dimethoxybenzyl)amine (31.3 g, 0.10 mol), $K_2CO_3$ (18 g, 1.32 mol), THF (260 mL) and water (260 mL) at 0° C. within 1 h. After the addition was completed, the mixture was extracted with EA (300 mL×3). The combined organic phases were washed with brine, dried over $Na_2SO_4$ and concentrated under reduced pressure. The residue was dissolved in EA (400 mL), and the mixture was stirred under reflux for 1 h and filtered at this temperature. The filtrate was concentrated under reduced pressure. EA was exchanged for MeOH, and the mixture was stirred at room temperature overnight. The mixture was filtered and the solid (off-white) was collected. The product was directly used in the next step (20 g, HPLC: 98.87%, yield: 54.5%).

Compound B1:2-butoxy-7-(piperidin-4-ylmethyl) imidazo[2,1-f][1,2,4]triazin-4-amine

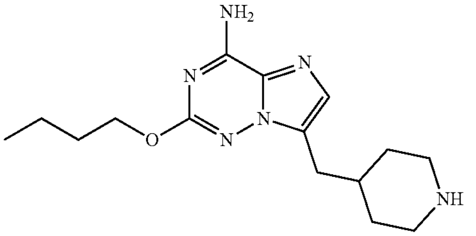

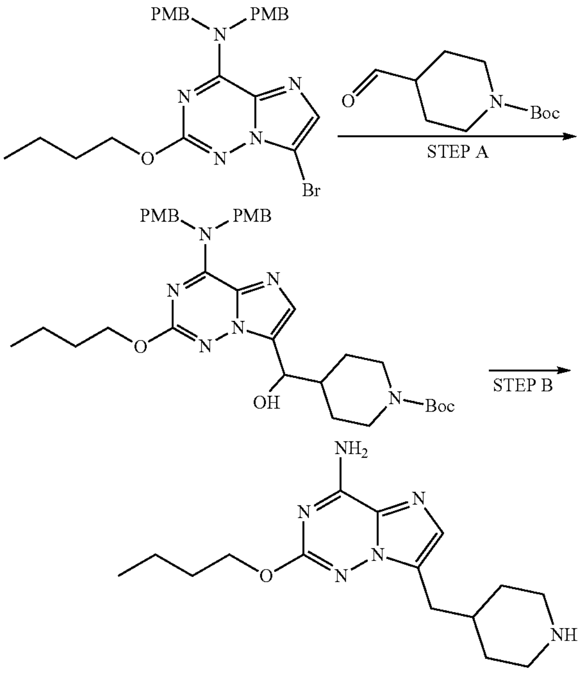

Step A: Tert-butyl 4-((4-(bis(4-methoxybenzyl)amino)-2-butoxyimidazo[2,1-f][1,2,4]triazin-7-yl)(hydroxy)methyl)piperidin-1-carboxylate

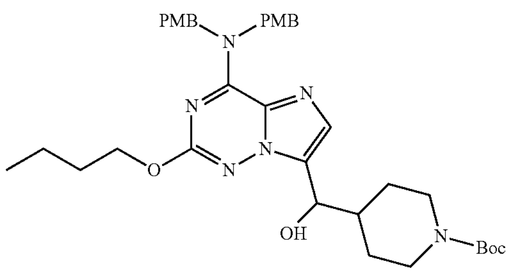

To a solution of 7-bromo-2-butoxy-N,N-bis(4-methoxybenzyl)imidazo[2,1-f][1,2,4]triazin-4-amine (200 mg, 0.38 mmol) in THF (8 mL), a solution of n-BuLi (0.4 mL, 0.6 mmol) was added dropwise at a temperature of −75° C. to −65° C. One hour later, a solution of tert-butyl 4-formylpiperidin-1-carboxylate (120 mg, 0.57 mmol) in THF (1 mL) was added dropwise. The resulting mixture was stirred at −70° C. for 1 h and then warmed to room temperature to react for 3 h. The reaction was quenched with a saturated $NH_4Cl$ solution, extracted with EtOAc (60 mL), washed with brine, dried over $Na_2SO_4$, filtered and concentrated. The residue was purified by preparative TLC to obtain the target compound (210 mg, crude). MS: M/e 661 $(M+1)^+$.

Step B: 2-butoxy-7-(piperidin-4-ylmethyl)imidazo[2,1-f][1,2,4]triazin-4-amine

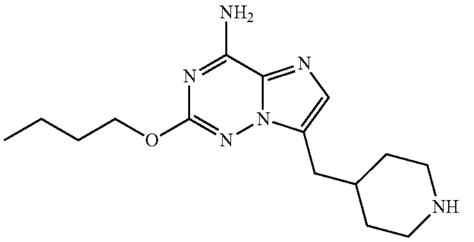 [SMILES: CCCCOc1nc(N)c2ncc(CC3CCNCC3)n2n1]

$Et_3SiH$ (2 mL) was added to a mixture of the product of step B (210 mg, crude) in TFA (6 mL). The reaction was heated at 85° C. for 72 h. The mixture was concentrated to dryness, and the residue was purified by preparative HPLC to obtain the product (20 mg, 17% for two steps). $^1$HNMR (400 MHz, DMSO-$d_6$) & 8.49 (s. 1H), 8.16 (s, 1H), 8.10 (s, 1H), 7.37 (d, J=2.0 Hz, 1H), 4.22 (t. J=6.8 Hz, 2H), 3.24 (d, J=12.0 Hz, 2H), 2.95-2.72 (m, 4H), 2.11-1.89 (m, 1H), 1.81-1.64 (m, 4H), 1.52-1.26 (m, 4H), 0.94 (t, J=7.6 Hz, 3H) ppm. MS: M/e 305 (M+1)+.

Compound B2:2-(pent-2-yloxy)-7-(piperidin-4-ylmethyl)imidazo[2,1-f][1,2,4]triazin-4-amine

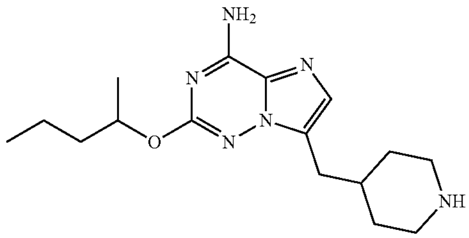

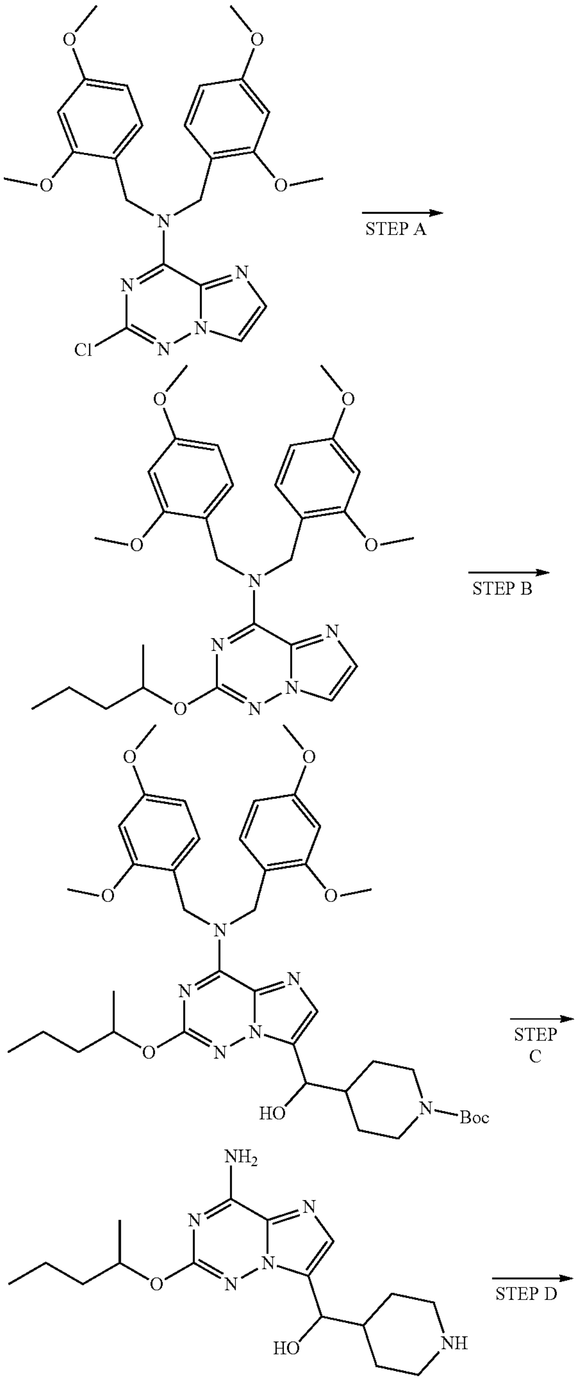

-continued

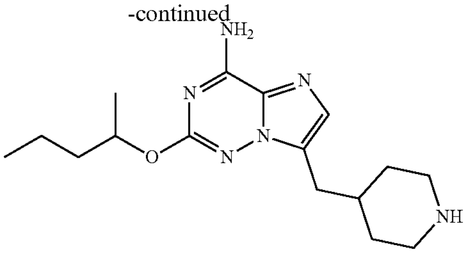

Step A: N,N-bis(2,4-dimethoxybenzyl)-2-(pent-2-yloxy)imidazo[2,1-f][1,2,4]triazin-4-amine

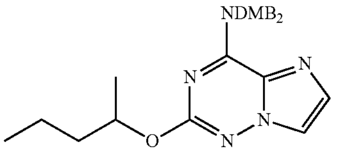

NaH (1.27 g, 31.75 mmol, 60%) was added to a solution of pentan-2-ol (2.8 g, 31.82 mmol) in THF (50 mL) at 0° C. under N2. After the mixture was stirred at 25° C. for 0.5 h, 2-chloro-N,N-2,4-dimethoxybenzyl)imidazo[2,1-f][1,2,4]triazin-4-amine (5 g, 10.64 mmol) was added. The reaction mixture was stirred at 70° C. for 16 h. Upon completion of the reaction, the reaction mixture was quenched with water (50 mL) and extracted with EtOAc (3×50 mL). The combined organic layers were dried over $Na_2SO_4$ and concentrated under vacuum to obtain a residue. The residue was purified by column chromatography on silica gel eluted with ethyl acetate (25%) in petroleum ether to obtain the title compound (4.8 g, 87%). $^1$H NMR (400 MHz, DMSO-$d_6$) δ 7.93 (s, 1H), 7.50 (s, 1H), 7.04-6.96 (m, 2H), 6.60-6.52 (m, 2H), 6.45 (m, 2H), 5.64 (m, 2H), 4.94-4.84 (m, 1H), 4.72 (m, 2H), 3.73 (t, J=9.2 Hz, 12H), 1.68-1.41 (m, 2H), 1.37-1.25 (m, 2H), 1.23 (t, J=7.2 Hz, 3H), 0.84 (t, J=7.2 Hz, 3H) ppm. MS: Me 458 $(M+1)^+$.

Step B: Tert-butyl 4-((4-(bis(2,4-dimethoxybenzyl)amino)-2-(pent-2-yloxy)imidazo[2,1-f][1,2,4]triazin-7-yl)(hydroxy)methyl)piperidin-1-carboxylate

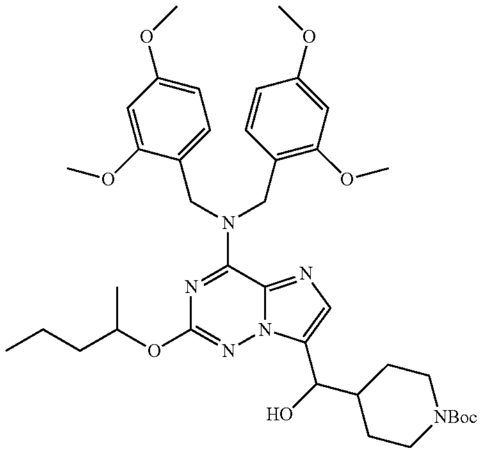 [SMILES: CCCC(C)Oc1nc(N(Cc2ccc(OC)cc2OC)Cc2ccc(OC)cc2OC)c2ncc(C(O)C3CCN(C(=O)OC(C)(C)C)CC3)n2n1]

At −78° C. under $N_2$ atmosphere, n-BuLi (1.6 M, 2.85 mL, 4.6 mmol) was added to a stirred solution of N,N-bis(2,4-dimethoxybenzyl)-2-(pent-2-yloxy)imidazo[2,1-f][1,2,4]triazin-4-amine (1.17 g, 2.3 mmol) in THF (10 mL). The mixture was stirred at −78° C. for 1 h. Then, a solution of tert-butyl 4-formylpiperidin-1-carboxylate (0.97 g, 4.6 mmol) in THF (10 mL) was added to the system at −78° C. The reaction was warmed to room temperature and stirred overnight. The reaction was quenched with a saturated aqueous solution of $NH_4Cl$ at room temperature. The mixture was extracted with EA (20 mL×3). The combined organic phases were washed with brine, dried over $Na_2SO_4$ and concentrated under reduced pressure. The residue was purified by combiflash to obtain the title compound (1.2 g, yield: 71.0%). MS: M/e 735 $(M+1)^+$.

Step C: (4-amino-2-(pent-2-yloxy)imidazo[2,1-f][1,2,4]triazin-7-yl)(piperidin-4-yl)methanol

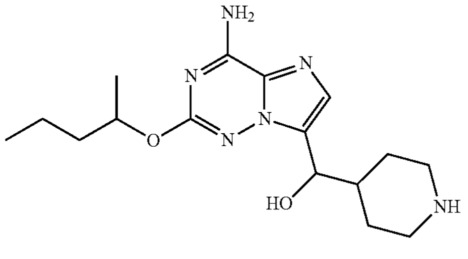 [SMILES: CCCC(C)Oc1nc(N)c2ncc(C(O)C3CCNCC3)n2n1]

A mixture of the product of step B (1.2 g, 1.6 mmol) in TFA/$H_2O$ (9:1, 12 mL) was stirred at 30° C. overnight. The reaction was cooled to room temperature and concentrated under reduced pressure. The mixture was concentrated and 20 mL of $H_2O$ was added. The mixture was stirred at room temperature for 30 min and then filtered. The filtrate was extracted with DCM (20 mL×3) to remove impurities. The aqueous layer was alkalized to pH=12 with an aqueous NaOH (2 M) solution and extracted with DCM/IPA (8:2, 20 mL×3). The combined extracts were washed with brine (20 mL), dried over $Na_2SO_4$ and concentrated to obtain the title product (350 mg, yield: 64.1%). MS: M/e 335 $(M+1)^+$.

Step D: 2-(pent-2-yloxy)-7-(piperidin-4-ylmethyl)imidazo[2,1-f][1,2,4]triazin-4-amine

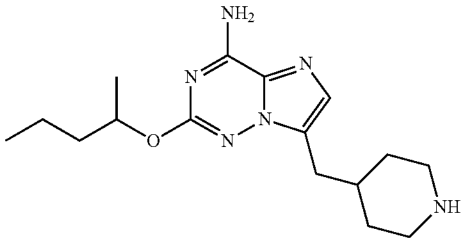 [SMILES: CCCC(C)Oc1nc(N)c2ncc(CC3CCNCC3)n2n1]

A mixture of the product of step C (350 mg, 1.05 mmol), TFA (2.5 mL) and $Et_3SiH$ (4 mL) was stirred at 60° C. overnight. As detected by LC_Ms, there was no residual starting materials. TFA (1 mL) was added to the mixture, and the resulting mixture was stirred at 60° C. overnight. The reaction was concentrated under reduced pressure. The residue was dissolved in water (15 mL) and extracted with DCM (25 mL×3). The organic phase was discarded. The inorganic phase was alkalinized with an aqueous NaOH (2 M) solution to pH=12. A white solid precipitated out of the system. The mixture was extracted with DCM/iPrOH (8:2, 20 mL×2). The combined organic phases were washed with a 20% aqueous NaCl solution, dried over $Na_2SO_4$ and concentrated. The residue was purified by combiflash to obtain the title compound (90 mg, yield: 27.0%). $^1$H NMR (400 MHz, DMSO-d6) δ 8.21-7.80 (m, 2H), 7.27 (s, 1H), 5.06-4.89 (m, 1H), 2.98-2.80 (m, 2H), 2.69 (d, J=6.6 Hz, 2H), 2.38 (t, J=12 Hz, 2H), 1.86-1.61 (m, 2H), 1.58-1.47 (m, 3H), 1.43-1.33 (m, 2H), 1.26 (t, J=6.0 Hz, 3H), 1.08 (dd, J=20.8, 12 Hz, 2H), 0.90 (t, J=7.2 Hz, 3H) ppm. MS: M/e 319 (M+1)+. MS: M/e 319 $(M+1)^+$.

Compound B3:2-butoxy-7-(2-(piperidin-4-yl)ethyl) imidazo[2,1-f][1,2,4]triazin-4-amine

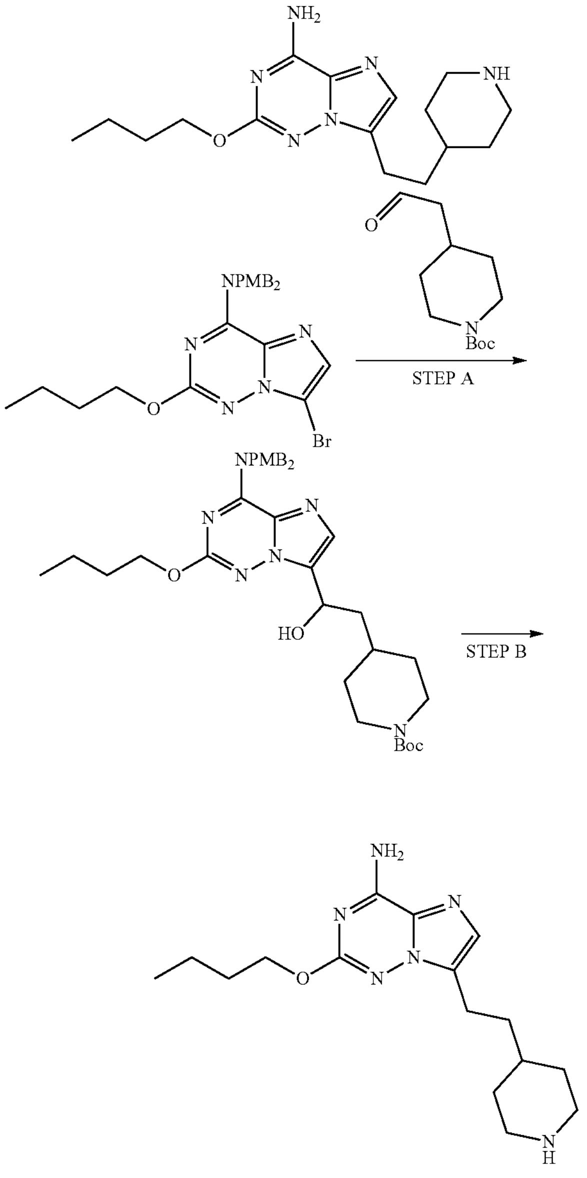

Step A: Tert-butyl 4-(2-(4-(bis(4-methoxybenzyl) amino)-2-butoxyimidazo[2,1-f][1,2,4]triazin-7-yl)-2-hydroxyethyl)piperidin-1-carboxylate

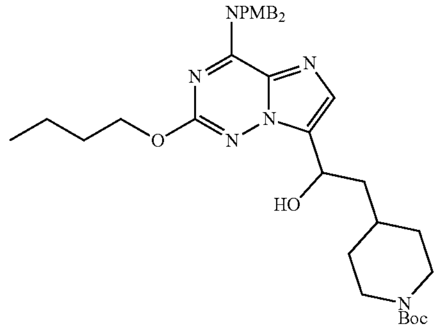

At −78° C. under $N_2$ atmosphere, n-BuLi (1.6 M, 0.57 mL) was added to a stirred solution of 7-bromo-2-butoxy-N,N-bis(4-methoxybenzyl)imidazo[2,1-f][1,2,4]triazin-4-amine (150 mg, 0.29 mmol) in THF (10 mL). The mixture was stirred at −78° C. for 1 h. Then, a solution of tert-butyl 4-(2-oxoethyl)piperidin-1-carboxylate (92 mg, 0.41 mmol) in THF (0.5 mL) was added to the system at −78° C. The reaction was warmed to room temperature and stirred overnight. The reaction was quenched with a saturated aqueous $NH_4Cl$ solution at room temperature. The mixture was extracted with EA (20 mL×3). The combined organic phases were washed with brine, dried over $Na_2SO_4$ and concentrated under reduced pressure. The residue was purified by combiflash to obtain the title compound (150 mg, yield: 76.7%). MS: M/e 675 (M+1)+.

Step B: 2-butoxy-7-(2-(piperidin-4-yl)ethyl)imidazo [2,1-f][1,2,4]triazin-4-amine

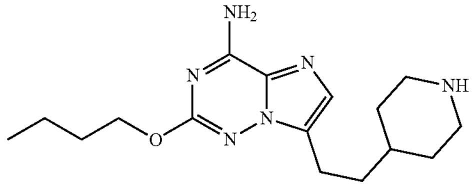 [SMILES: CCCCOc1nc(N)c2ncc(CCC3CCNCC3)n2n1]

$CF_3COOH$ (2 mL) was added to a stirred solution of the product of step A (150 mg, 0.22 mmol) in $Et_3SiH$ (4 mL) at room temperature. The mixture was stirred at 80° C. for 1 h. The reaction was cooled to room temperature and concentrated under reduced pressure. The residue was dissolved in $CF_3COOH$ (4 mL), and the mixture was stirred at 80° C. overnight. The reaction was cooled to room temperature. The mixture was concentrated under reduced pressure. The residue was purified by preparative HPLC to obtain the title compound (15 mg, yield: 21.4%). $^1$H NMR (400 MHz, DMSO-d6) δ 8.15-7.90 (m, 2H), 7.29 (s, 1H), 4.20 (t, J=6.4 Hz, 2H), 2.94 (d, J=12.0 Hz, 2H), 2.78 (t, J=7.6 Hz, 2H), 2.44 (t, J=11.6 Hz, 2H), 1.77-1.52 (m, 6H), 1.50-1.35 (m, 2H), 1.35-1.24 (m, 1H), 1.13-0.99 (m, 2H), 0.93 (t, J=7.2 Hz, 3H) ppm. MS: M/e 319 (M+1)+.

Compound B4: N2-butyl-7-(piperidin-4-ylmethyl) imidazo[2,1-f][1,2,4]triazin-2,4-diamine

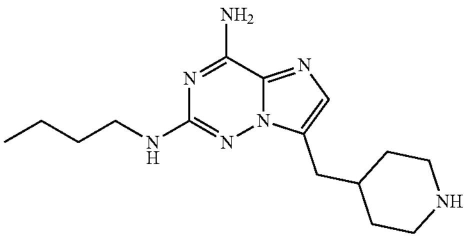

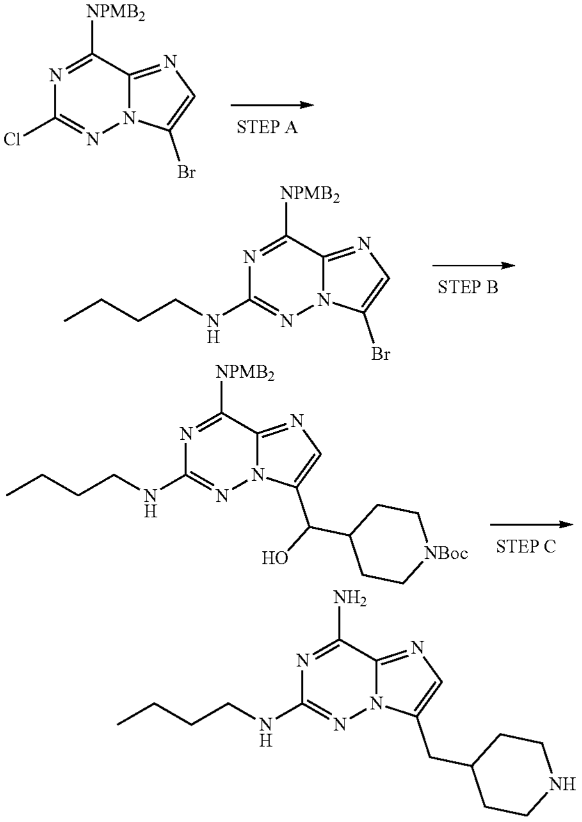

Step A: 7-bromo-N2-butyl-N4,N-bis(4-methoxybenzyl)imidazo[2,1-f][1,2,4]triazin-2,4-diamine

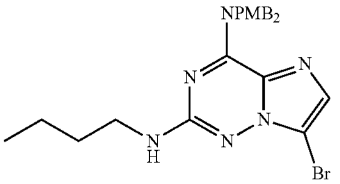

A mixture of 7-bromo-2-chloro-N,N-bis(4-methoxybenzyl)imidazo[2,1-f][1,2,4]triazin-4-amine (244 mg, 0.5 mmol), butyl-1-amine (365 mg, 5 mmol) and DIPEA (645 mg, 5 mmol) in NMP (3 mL) was stirred in a sealed tube at 220° C. for 6 h. The mixture was poured into $H_2O$ (10 mL) and extracted with EtOAc (10 mL×3). The combined organic layers were washed with brine, dried over $Na_2SO_4$, concentrated and purified by column chromatography (petroleum ether/EtOAc=20:1-5:1) to obtain the target compound (220 mg, 83.8%). MS: M/e 525/527 (M+1)+.

Step B: Tert-butyl 4-((4-(bis(4-methoxybenzyl) amino)-2-(butylamino)imidazo[2,1-f][1,2,4]triazin-7-yl)(hydroxy)methyl)piperidin-1-carboxylate

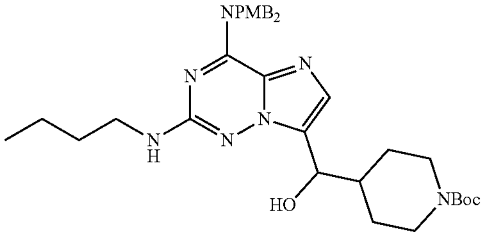

At −78° C. under N2 atmosphere, n-BuLi (1.6 M, 0.54 mL, 0.86 mmol) was added to a stirred solution of 7-bromo-N2-butyl-N4,N4-bis(4-methoxybenzyl)imidazo[2,1-f][1,2,4]triazin-2,4-diamine (150 mg, 0.29 mmol) in THF (5 mL). The mixture was stirred at −78° C. for 1 h. Then, a solution of tert-butyl 4-formylpiperidin-1-carboxylate (91 mg, 0.39 mmol) in THF (0.5 mL) was added to the system at −78° C. The reaction was warmed to room temperature and stirred overnight. The reaction was quenched with a saturated aqueous $NH_4Cl$ solution at room temperature. The mixture was extracted with EA (20 mL×3). The combined organic phases were washed with brine, dried over $Na_2SO_4$ and concentrated under reduced pressure. The residue was purified by combiflash to obtain the title compound (110 mg, yield: 58.3%) as yellow oil. MS: M/e 660 $(M+1)^+$.

Step C: N2-butyl-7-(piperidin-4-ylmethyl)imidazo [2,1-f][1,2,4]triazin-2,4-diamine

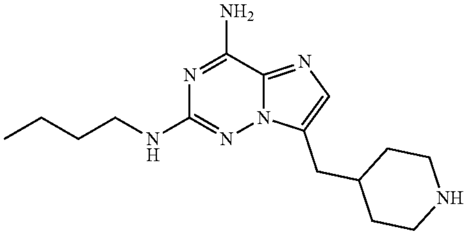 [SMILES: CCCCNc1nc(N)c2ncc(CC3CCNCC3)n2n1]

$CF_3COOH$ (2 mL) was added to a stirred solution of the product of step B (110 mg, 0.17 mmol) in $Et_3SiH$ (4 mL) at room temperature. The mixture was stirred at 80° C. for 1 h. The reaction was cooled to room temperature and concentrated under reduced pressure. The residue was dissolved in $CF_3COOH$ (4 mL), and the mixture was stirred at 80° C. overnight. The reaction was cooled to room temperature. The mixture was concentrated under reduced pressure. The residue was purified by preparative HPLC to obtain the title compound (15 mg, yield: 50.7%). $^1H$ NMR (400 MHz, DMSO-d6) δ 7.46 (br.s, 2H), 7.11 (s, 1H), 6.36-5.96 (m, 1H), 3.22-3.08 (m, 2H), 3.00-2.86 (m, 2H), 2.74-2.59 (m, 2H), 2.48-2.38 (m, 2H), 1.80 (br.s, 1H), 1.60-1.45 (m, 4H), 1.41-1.29 (m, 2H), 1.18-1.00 (m, 2H), 0.90 (t, J=7.2 Hz, 3H) ppm. MS: M/e 304 $(M+1)^+$.

Compound B5: N2-(pent-2-yl)-7-(piperidin-4-ylmethyl)imidazo[2,1-f][1,2,4]triazin-2,4-diamine

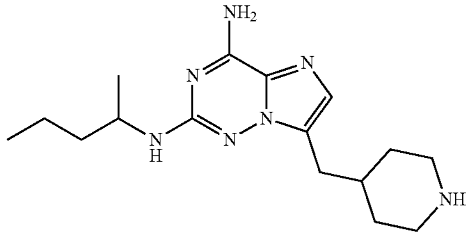

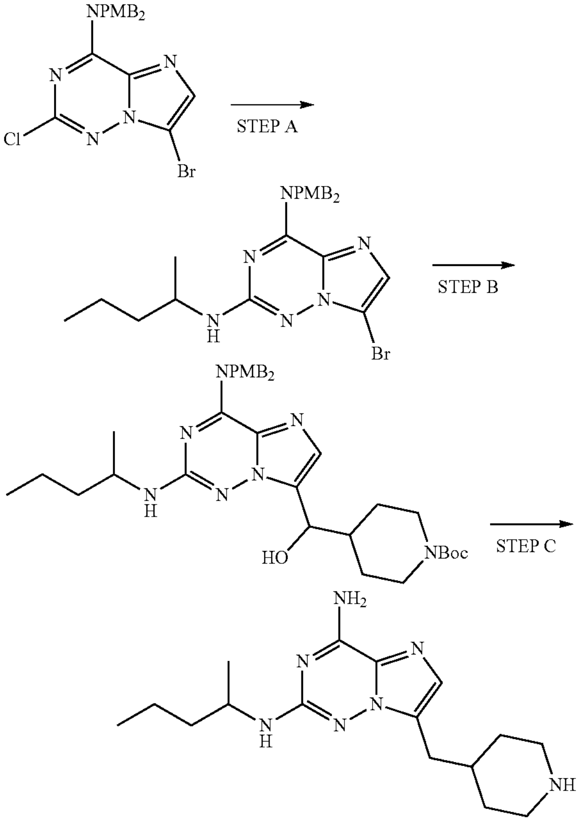

Step A: 7-bromo-N4,N4-bis(4-methoxybenzyl)-N2-(pent-2-yl)imidazo[2,1-f][1,2,4]triazin-2,4-diamine

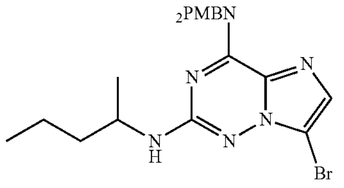

To a stirred solution of 7-bromo-2-chloro-N,N-bis(4-methoxybenzyl)imidazo[2,1-f][1,2,4]triazin-4-amine (1 g, 2.05 mmol) in NMP (10 mL), pentyl-2-amine (1 g, 11.5 mmol) and DIEA (400 mg, 3.1 mmol) were added. The reaction mixture was sealed and stirred at 220° C. for 6 h. The mixture was cooled to room temperature, $H_2O$ (20 mL) was added and the mixture was extracted with EtOAc (10 ml×3). The combined organic phases were washed with brine, dried over $Na_2SO_4$ and concentrated under vacuum. The crude product was purified by column chromatography to obtain the product (250 mg, 22.7%) as a white solid. MS: M/e 539 $(M+1)^+$.

Step B: Tert-butyl 4-((4-(bis(4-methoxybenzyl)amino)-2-(pent-2-ylamino)imidazo[2,1-f][1,2,4]triazin-7-yl)(hydroxy)methyl)piperidin-1-carboxylate

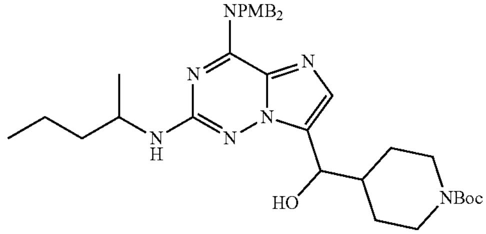

At −78° C. under N2 atmosphere, n-BuLi (1.6 M, 0.56 mL, 0.9 mmol) was added to a stirred solution of 7-bromo-2-butoxy-N,N-bis(4-methoxybenzyl)imidazo[2,1-f][1,2,4]triazin-4-amine (161 mg, 0.29 mmol) in THF (2 mL). The mixture was stirred at −78° C. for 1 h. Then, a solution of tert-butyl 4-(2-oxoethyl)piperidin-1-carboxylate (76.5 mg, 0.36 mmol) in THF (0.3 mL) was added to the system at −78° C. The reaction was warmed to room temperature and stirred overnight. The reaction was quenched with a saturated aqueous $NH_4Cl$ solution at room temperature. The mixture was extracted with EA (20 mL×3). The combined organic phases were washed with brine, dried over $Na_2SO_4$ and concentrated under reduced pressure. The residue was purified by combiflash to obtain the title compound (80 mg, yield: 39.8%) as yellow oil. MS: M/e 674 $(M+1)^+$.

Step C: $N^2$-(pent-2-yl)-7-(piperidin-4-ylmethyl)imidazo[2,1-f][1,2,4]triazin-2,4-diamine

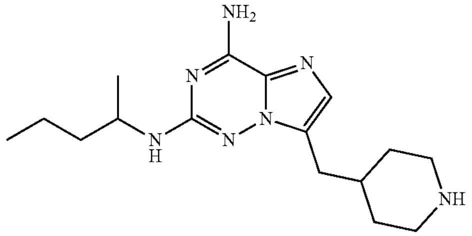 [SMILES: CCCC(C)Nc1nc(N)c2ncc(CC3CCNCC3)n2n1]

$CF_3COOH$ (2 mL) was added to a stirred solution of the product of step B (80 mg, 0.12 mmol) in $Et_3SiH$ (4 mL) at room temperature. The mixture was stirred at 80° C. for 1 h. The reaction was cooled to room temperature and concentrated under reduced pressure. The residue was dissolved in $CF_3COOH$ (4 mL), and the mixture was stirred at 80° C. overnight. The reaction was cooled to room temperature. The mixture was concentrated under reduced pressure. The residue was purified by preparative HPLC to obtain the title compound (9 mg, yield: 23.9%). $^1H$ NMR (400 MHz, DMSO-d6) δ 7.43 (br.s, 2H), 7.10 (s, 1H), 5.94 (d, J=8.0 Hz, 1H), 3.91-3.61 (m, 1H), 3.03-2.82 (m, 2H), 2.74-2.58 (m, 2H), 2.46-2.31 (m, 2H), 1.92-1.73 (m, 1H), 1.65-1.48 (m, 3H), 1.42-1.28 (m, 3H), 1.14-1.01 (m, 5H), 0.99-0.81 (m, 3H) ppm. MS: M/e 318 $(M+1)^+$.

Compound B6: (S)-2-(pent-2-yloxy)-7-(piperidin-4-ylmethyl)imidazo[2,1-f][1,2,4]triazin-4-amine

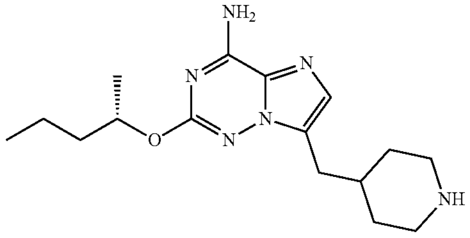

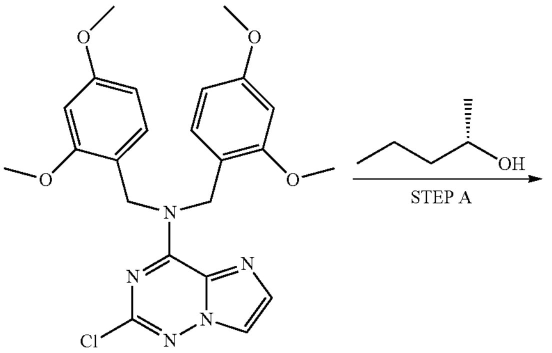

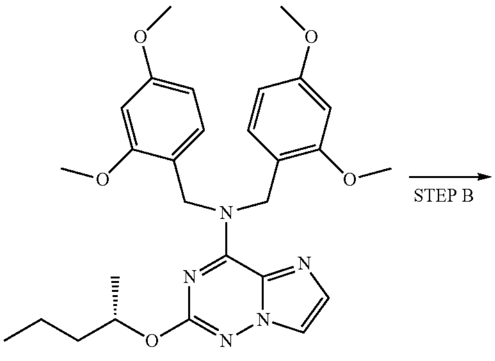

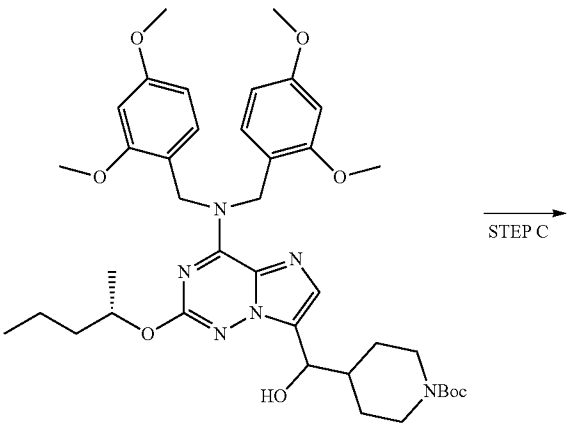

-continued

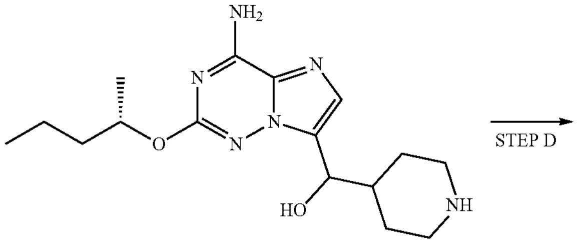

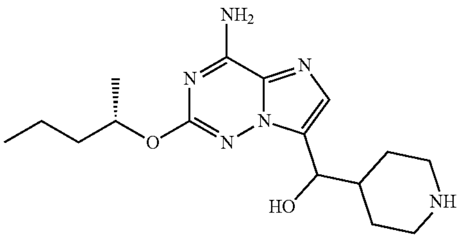

Step A: (S)-N,N-bis(2,4-dimethoxybenzyl)-2-(pent-2-yloxy)imidazo[2,1-f][1,2,4]triazin-4-amine

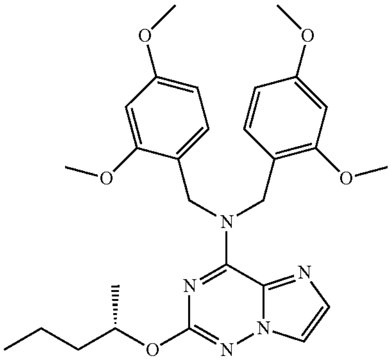 [SMILES: CCC[C@H](C)Oc1nc(N(Cc2ccc(OC)cc2OC)Cc2ccc(OC)cc2OC)c2nccn2n1]

NaH (60% in mineral oil, 1.07 g, 26.7 mmol) was slowly added to a solution of (S)-pentan-2-ol (2.35 g, 26.7 mmol) in THF (50 mL) at room temperature. The mixture was stirred at room temperature for 1 h. 2-chloro-N,N-bis(2,4-dimethoxybenzyl)imidazo[2,1-f][1,2,4]triazin-4-amine (5 g, 10.7 mmol) was added, and the resulting mixture was stirred at 60° C. overnight. The reaction was cooled to room temperature. The mixture was quenched with 80 mL of water and extracted with EA (60 mL×2). The combined organic phases were washed with brine, dried over $Na_2SO_4$ and concentrated. The residue was purified by combiflash to obtain the title product (4.5 g, yield: 81.1%) as a gel. MS: M/e 522 $(M+1)^+$.

Step B: Tert-butyl 4-((4-(bis(2,4-dimethoxybenzyl)amino)-2-(((S)-pent-2-yl)oxy)imidazo[2,1-f][1,2,4]triazin-7-yl)(hydroxy)methyl)piperidin-1-carboxylate

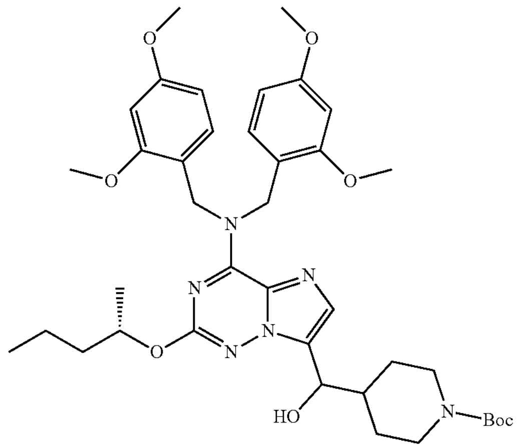 [SMILES: CCC[C@H](C)Oc1nc(N(Cc2ccc(OC)cc2OC)Cc2ccc(OC)cc2OC)c2ncc(C(O)C3CCN(C(=O)OC(C)(C)C)CC3)n2n1]

At −78° C. under $N_2$ atmosphere, n-BuLi (1.6 M, 3.8 mL, 6 mmol) was added to a stirred solution of (S)—N,N-bis(2,4-dimethoxybenzyl)-2-(pent-2-yloxy)imidazo[2,1-f][1,2,4]triazin-4-amine (1.56 g, 3 mmol) in THF (10 mL). The mixture was stirred at −78° C. for 1 h. Then, a solution of tert-butyl 4-formylpiperidin-1-carboxylate (1.3 g, 6 mmol) in THF (1 mL) was added to the system at −78° C. The reaction was kept at room temperature and stirred overnight. The reaction was quenched with a saturated aqueous $NH_4Cl$ solution at room temperature. The mixture was extracted with EA (20 mL×3). The combined organic phases were washed with brine, dried over $Na_2SO_4$ and concentrated under reduced pressure. The residue was purified by combiflash to obtain the title compound (1.6 g, yield: 72.7%). MS: M/e 735 $(M+1)^+$.

Step C: (4-amino-2-(((S)-pent-2-yl)oxy)imidazo[2,1-f][1,2,4]triazin-7-yl)(piperidin-4-yl)methanol

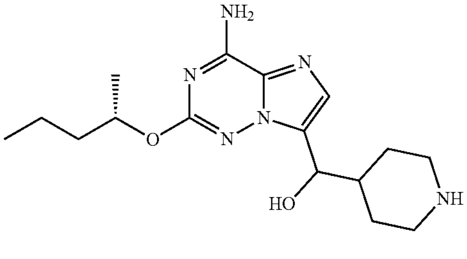 [SMILES: CCC[C@H](C)Oc1nc(N)c2ncc(C(O)C3CCNCC3)n2n1]

Tert-butyl 4-((4-(bis(2,4-dimethoxybenzyl)amino)-2-(((S)-pent-2-yl)oxy)imidazo[2,1-f][1,2,4]triazin-7-yl)(hydroxy)methyl)piperidin-1-carboxylate (1.4 g, 1.9 mmol) in TFA/$H_2O$ (9:1, 20 mL) was stirred at room temperature for 65 h. The reaction was concentrated under reduced pressure, 20 mL of $H_2O$ was added. The mixture was stirred at room temperature for 30 min and then filtered. The filtrate was extracted with DCM (20 mL×3) to remove impurities. The aqueous layer was alkalized with an aqueous NaOH (4 M) solution to pH>10, and extracted with DCM/IPA (5:1, 20 mL×5). The combined extracts were washed with brine (50 mL×3), dried over $Na_2SO_4$ and concentrated to obtain the title product (460 mg, yield: 72%). MS: M/e 335 $(M+1)^+$.

Step D: (S)-2-(pent-2-yloxy)-7-(piperidin-4-ylmethyl)imidazo[2,1-f][1,2,4]triazin-4-amine

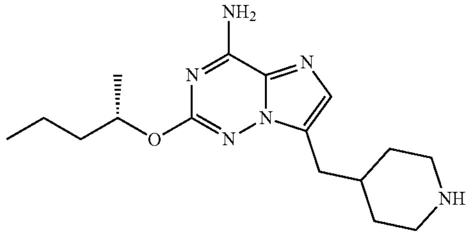 [SMILES: CCC[C@H](C)Oc1nc(N)c2ncc(CC3CCNCC3)n2n1]

A mixture of (4-amino-2-(((S)-pent-2-yl)oxy)imidazo[2,1-f][1,2,4]triazin-7-yl)(piperidin-4-yl)methanol (460 mg, 1.37 mmol), TFA (10 mL) and $Et_3SiH$ (10 mL) were stirred at 60° C. overnight. As detected by LC_MS, the starting materials disappeared. $Et_3SiH$ (5 mL) was added to the mixture and the mixture was stirred at 60° C. overnight. The reaction was concentrated under reduced pressure. The residue was dissolved in HCl (4 M, 2 mL) and extracted with DCM (5 mL×3). The organic phase was discarded. The inorganic phase was alkalized to pH=12 with an aqueous NaOH (4 M) solution. A white solid precipitated out of the system. The mixture was extracted with DCM/iPrOH (5:1, 10 mL×5). The combined organic phases were washed with brine (20 mL×2), dried over $Na_2SO_4$ and concentrated. The residue was purified by column chromatography to obtain the title compound (320 mg, yield: 72%). $^1H$ NMR (400 MHz, DMSO-d6) δ 8.04 (br.s, 1H), 7.94 (br.s, 1H), 7.27 (s, 1H), 5.03-4.89 (m, 1H), 2.87 (d, J=12.0 Hz, 2H), 2.68 (d, J=6.8 Hz, 2H), 2.36 (t, J=12.0 Hz, 2H), 1.84-1.61 (m, 2H), 1.59-1.44 (m, 3H), 1.44-1.32 (m, 2H), 1.28 (d, J=6.2 Hz, 3H), 1.14-0.99 (m, 2H), 0.91 (t, J=7.2 Hz, 3H) ppm. MS: M/e 319 $(M+1)^+$.

Compound B7: (R)-2-(pent-2-yloxy)-7-(piperidin-4-ylmethyl)imidazo[2,1-f][1,2,4]triazin-4-amine Compound B7

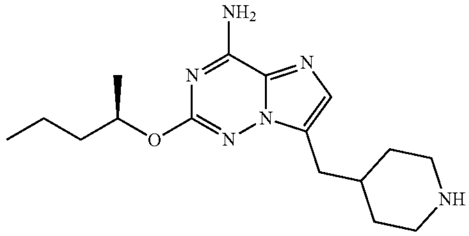 [SMILES: CCC[C@@H](C)Oc1nc(N)c2ncc(CC3CCNCC3)n2n1]

Compound B7 was obtained as follows: compound B2 was subjected to chiral resolution to obtain two chiral compounds B6 and B7.

Conditions of preparative HPLC

| Column | CHIRALPAK ID |
|---|---|
| Column size | 2 cm × 25 cm, 5 μm |
| Injection | 0.3 ml |
| Mobile phase | [(Hexane:DCM = 3:1)(0.1% isopropanolamine)(IP Amine)]:IPA = 90:10 |
| Flow rate | 20 mL/min |
| Wavelength | UV 220 nm |
| Temperature | 25° C. |
| Sample solution | 23 mg/ml in EtOH:DCM = 1:1 |
| Preparative HPLC instrument | Preparative HPLC-Gilson |

Compound B7: (R)-2-(pent-2-yloxy)-7-(piperidin-4-ylmethyl)imidazo[2,1-f][1,2,4]triazin-4-amine

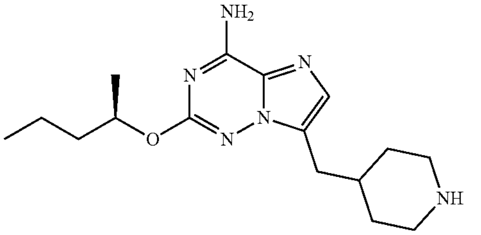

$^1$H NMR (400 MHz, DMSO-d6) δ 8.14-7.86 (m, 2H), 7.27 (s, 1H), 5.06-4.88 (m, 1H), 2.98-2.81 (m, 2H), 2.69 (d, J=6.6 Hz, 2H), 2.38 (t, J=11.6 Hz, 2H), 1.85-1.61 (m, 2H), 1.58-1.45 (m, 3H), 1.44-1.32 (m, 2H), 1.28 (d, J=6.0 Hz, 3H), 1.08 (dd, J=21.6, 11.6 Hz, 2H), 0.90 (t, J=7.2 Hz, 3H) ppm. MS: M/e 319 $(M+1)^+$.

Compound B8: 7-((4-methylpiperidin-4-yl)methyl)-2-(pent-2-yloxy)imidazo[2,1-f][1,2,4]triazin-4-amine

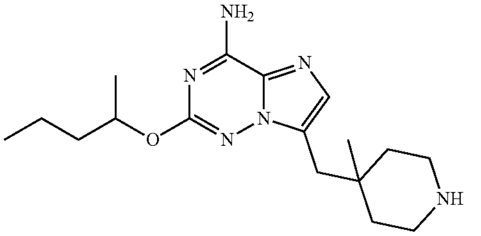

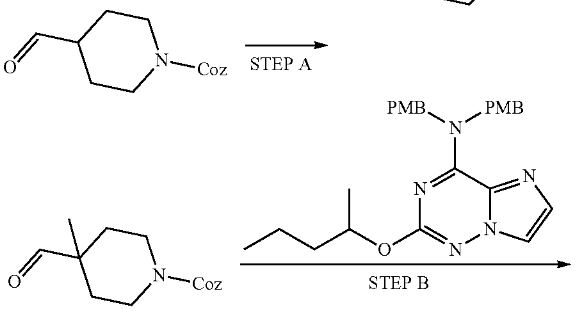

-continued

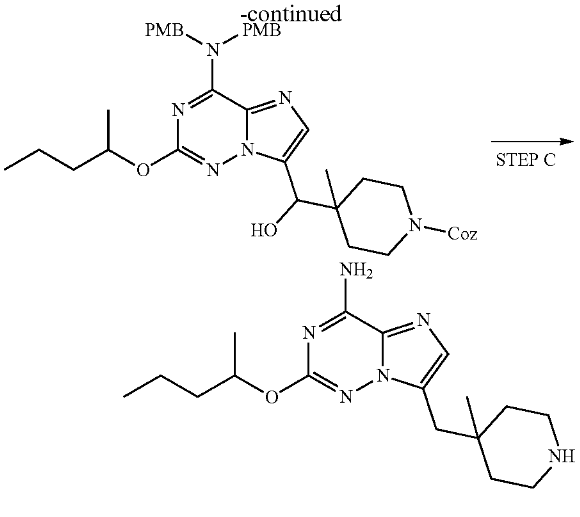

Step A: Benzyl 4-formyl-4-methylpiperidin-1-carboxylate

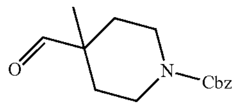 [SMILES: CC1(C=O)CCN(C(=O)OCc2ccccc2)CC1]

To a stirred mixture of benzyl 4-formylpiperidin-1-carboxylate (2 g, 8.09 mmol) in DCM (20 ml), t-BuOK (1.2 g, 10.7 mmol) and $CH_3I$ (1.55 ml, 24.9 mmol) were added. Thereafter, the reaction mixture was stirred at room temperature overnight. The reaction mixture was poured into $H_2O$ and extracted with EtOAc (15 mL×3). The combined organic phases were washed with brine, dried over $Na_2SO_4$ and concentrated under vacuum. The crude product was purified by column chromatography to obtain the title product (800 mg, 38%) $^1$H NMR (400 MHz, $CDCl_3$-d6) δ 9.45 (t, J=5.4 Hz, 1H), 7.40-7.28 (m, 5H), 5.13 (dd, J=5.8, 1.0 Hz, 2H), 3.84-3.68 (m, 2H), 3.26-3.09 (m, 2H), 1.93 (d, J=13.2 Hz, 2H), 1.42 (s, 2H), 1.08 (d, J=2.3 Hz, 3H) ppm. MS: M/e 262 $(M+1)^+$.

Step B: Benzyl 4-((4-(bis(4-methoxybenzyl)amino)-2-(pent-2-yloxy)imidazo[2,1-f][1,2,4]triazin-7-yl)(hydroxy)methyl)-4-methylpiperidin-1-carboxylate

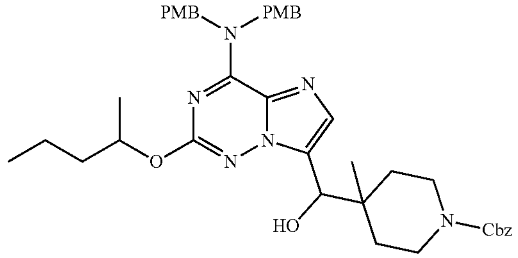

To a stirred solution of N,N-bis(4-methoxybenzyl)-2-(pent-2-yloxy)imidazo[2,1-f][1,2,4]triazin-4-amine (200 mg, 0.43 mmol) in THF (8 mL) cooled to −78° C. under nitrogen atmosphere, n-BuLi (1.6 M in hexane, 0.86 mmol, 0.54 mL) was added dropwise. After the mixture was stirred for 30 min, a solution of benzyl 4-formyl-4-methylpiperidin-1-carboxylate (226 mg, 0.86 mmol) in THF (2 mL) was slowly added. The reaction mixture was slowly warmed to room temperature and stirred overnight. The reaction mixture was poured into a saturated ammonium chloride solution and extracted with EtOAc (15 mL×3). The combined organic phases were washed with brine, dried over $Na_2SO_4$ and concentrated under vacuum. The crude product was purified by column chromatography to obtain the title product (120 mg, 38.7%). MS: M/e 723 $(M+1)^+$.

Step C: 7-((4-methylpiperidin-4-yl)methyl)-2-(pent-2-yloxy)imidazo[2,1-f][1,2,4]triazin-4-amine

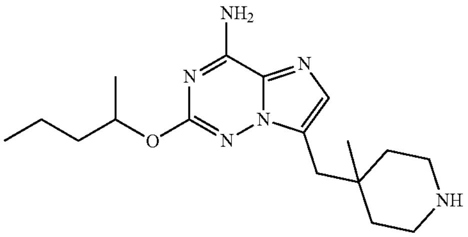 [SMILES: CCCC(C)Oc1nc(N)c2ncc(CC3(C)CCNCC3)n2n1]

$Et_3SiH$ (5 ml) was added to a stirred mixture of benzyl 4-((4-(bis(4-methoxybenzyl)amino)-2-(pent-2-yloxy)imidazo[2,1-f][1,2,4]triazin-7-yl)(hydroxy)methyl)-4-methylpiperidin-1-carboxylate (120 mg, 0.166 mmol) in TFA (5 ml). Thereafter, the reaction mixture was stirred at 80° C. for 2 h. The mixture was cooled to room temperature and concentrated under vacuum. TFA (10 ml) was added to the residue and the mixture was stirred at 80° C. overnight. The reaction mixture was cooled to room temperature and concentrated under vacuum. The residue was purified by preparative HPLC to obtain the target compound (10 mg, 22.4%). $^1H$ NMR (400 MHz, DMSO-d6) δ 8.42 (s, 1H), 8.30 (s, 1H), 8.13 (s, 1H), 8.04 (s, 1H), 7.36 (s, 1H), 4.99 (s, 1H), 3.17 (s, 2H), 3.03 (s, 2H), 2.86 (s, 2H), 1.73-1.51 (m, 4H), 1.43 (m, 4H), 1.28 (d, J=4.7 Hz, 3H), 0.98 (s, 3H), 0.90 (br.s, 3H) ppm. MS: M/e 333 $(M+1)^+$.

Compound B9:2-(pent-2-yloxy)-7-(piperazin-1-ylmethyl)imidazo[2,1-f][1,2,4]triazin-4-amine

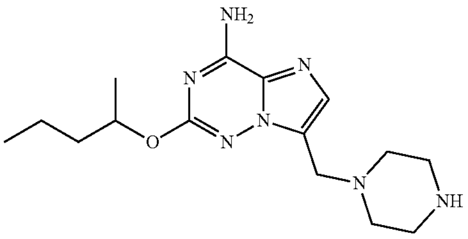

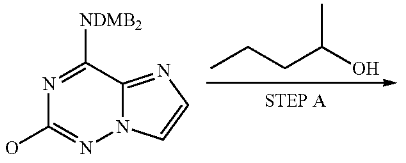

-continued

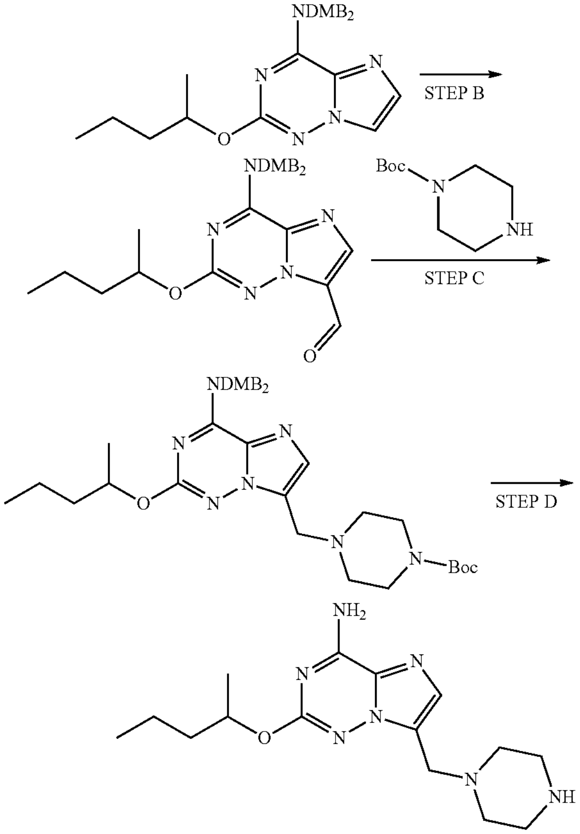

Step A: N,N-bis(2,4-dimethoxybenzyl)-2-(pent-2-yloxy)imidazo[2,1-f][1,2,4]triazin-4-amine

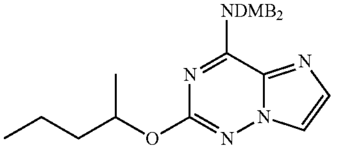

NaH (1.27 g, 31.75 mmol, 60%) was added to a solution of pentan-2-ol (2.8 g, 31.82 mmol) in THF (50 mL) at 0° C. under N2. After the mixture was stirred at 25° C. for 0.5 h, 2-chloro-N,N-bis(2,4-dimethoxybenzyl)imidazo[2,1-f][1,2,4]triazin-4-amine (5 g, 10.64 mmol) was added. The reaction mixture was stirred at 70° C. for 16 h. After completion of the reaction, the reaction mixture was quenched with water (50 mL) and extracted with EtOAc (3×50 mL). The combined organic layers were dried over $Na_2SO_4$ and concentrated under vacuum to obtain a residue. The residue was purified by column chromatography on silica gel eluted with ethyl acetate (25%) in petroleum ether to obtain the title compound (4.8 g, 87%). $^1H$ NMR (400 MHz, DMSO-d6) δ 7.93 (s, 1H), 7.50 (s, 1H), 7.04-6.96 (m, 2H), 6.60-6.52 (m, 2H), 6.45 (m, 2H), 5.64 (m, 2H), 4.94-4.84 (m, 1H), 4.72 (m, 2H), 3.73 (t, J=9.2 Hz, 12H), 1.68-1.41 (m, 2H), 1.37-1.25 (m, 2H), 1.23 (t, J==7.2 Hz, 3H), 0.84 (t, J=7.2 Hz, 3H) ppm. MS: M/e 458 $(M+1)^+$.

Step B: 4-(bis(2,4-dimethoxybenzyl)amino)-2-(pent-2-yloxy)imidazo[2,1-f][1,2,4]triazin-7-formaldehyde

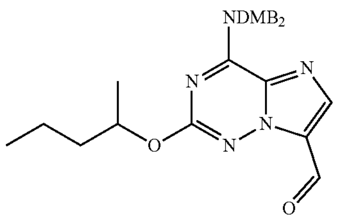

To a solution of N,N-bis(2,4-dimethoxybenzyl)-2-(pent-2-yloxy)imidazo[2,1-f][1,2,4]triazin-4-amine (3 g, 5.76 mmol) in THF (100 mL), n-BuLi (7.2 mL, 11.52 mmol) was added at −78° C. under N2. After the mixture was stirred at −78° C. for 1 h, DMF (1.7 g, 23.29 mmol) was added. The reaction mixture was warmed to 25° C. and stirred for 3 h. After completion of the reaction, the reaction mixture was quenched with an aqueous $NH_4Cl$ solution (80 mL) and extracted with EtOAc (3×100 mL). The combined organic layers were dried over $Na_2SO_4$ and concentrated under vacuum to obtain a residue. The residue was purified by column chromatography on silica gel eluted with ethyl acetate (25%) in petroleum ether to obtain the title compound (1.8 g, 57%). 1H NMR (300 MHz, DMSO-d6) δ 10.17 (s, 1H), 8.14 (s, 1H), 7.04 (d, J=8.0 Hz, 2H), 6.56 (d, J=2.4 Hz, 2H), 6.50-6.39 (m, 2H), 5.60 (m, 2H), 5.02-4.89 (m, 1H), 4.72 (m, 2H), 3.72 (m, 12H), 1.56 (m, 2H), 1.26 (m, 5H), 0.83 (t, J=7.2 Hz, 3H) ppm. MS: M/e 550 $(M+1)^+$.

Step C: Tert-butyl 4-((4-(bis(2,4-dimethoxybenzyl) amino)-2-(pent-2-yloxy)imidazo[2,1-f][1,2,4]triazin-7-yl)methyl) piperazin-1-carboxylate

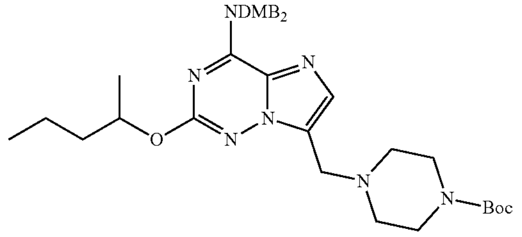

To a solution of 4-(bis(2,4-dimethoxybenzyl)amino)-2-(pent-2-yloxy)imidazo[2,1-f][1,2,4]triazin-7-formaldehyde (200 mg, 0.384 mmol) and tert-butyl piperazin-1-carboxylate (143 mg, 0.768 mmol) in THF (5 mL), AcOH (46 mg, 0.768 mmol) and $NaBH(AcO)_3$ (244 mg, 1.152 mmol) were added. The reaction mixture was stirred at 25° C. for 4 h. After completion of the reaction, the reaction mixture was quenched with water (20 mL) and extracted with EtOAc (3×30 mL). The combined organic layers were dried over $Na_2SO_4$ and concentrated under vacuum to obtain a residue. The residue was purified by column chromatography on silica gel eluted with ethyl acetate (40%) in petroleum ether to obtain the title compound (230 mg, 83%) as a white solid. MS: M/e 719.9 $(M+1)^+$.

Step D: 2-(pent-2-yloxy)-7-(piperazin-1-ylmethyl) imidazo[2,1-f][1,2,4]triazin-4-amine

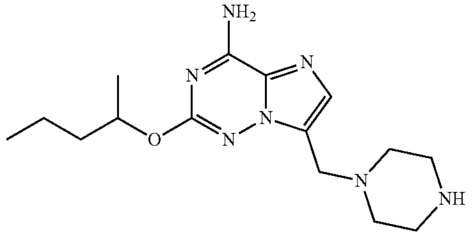 [SMILES: CCCC(C)Oc1nc(N)c2ncc(CN3CCNCC3)n2n1]

2-(pent-2-yloxy)-7-(piperazin-1-ylmethyl)imidazo[2,1-f][1,2,4]triazin-4-amine

Tert-butyl 4-((4-(bis(2,4-dimethoxybenzyl)amino)-2-(pent-2-yloxy)imidazo[2,1-f][1,2,4]triazin-7-yl)methyl) piperazin-1-carboxylate (230 mg, 0.319 mmol) was dissolved in TFA (8 mL) and $H_2O$ (0.8 mL) under N2. The reaction mixture was stirred at 70° C. for 3 h. After completion of the reaction, the reaction mixture was quenched with an aqueous $NaHCO_3$ solution (30 mL) and extracted with EtOAc (3×30 mL). The combined organic layers were dried over $Na_2SO_4$ and concentrated under vacuum to obtain a residue. The residue was purified by preparative TLC (DCM/MeOH=5/2) to obtain the title compound (23 mg, 23%). $^1$H NMR (300 MHz, DMSO-d6) δ 8.12 (m, 2H), 7.44 (s, 1H), 4.98 (dd, J=12.4, 6.4 Hz, 1H), 3.82 (s, 2H), 3.04-2.92 (m, 4H), 2.58 (s, 4H), 1.72-1.47 (m, 2H), 1.37 (m, 2H), 1.28 (d, J=6.4 Hz, 3H), 0.90 (t, J=7.2 Hz, 3H) ppm. MS: M/e 320.40 $(M+1)^+$.

Compound B10: 2—(((S)-pent-2-yl)oxy)-7-(piperidin-3-ylmethyl)imidazo[2,1-f][1,2,4]triazin-4-amine

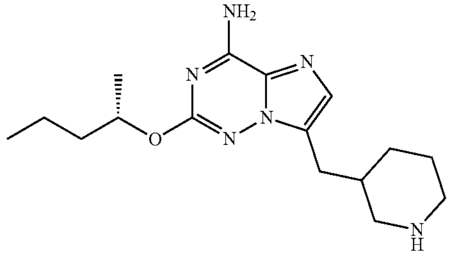

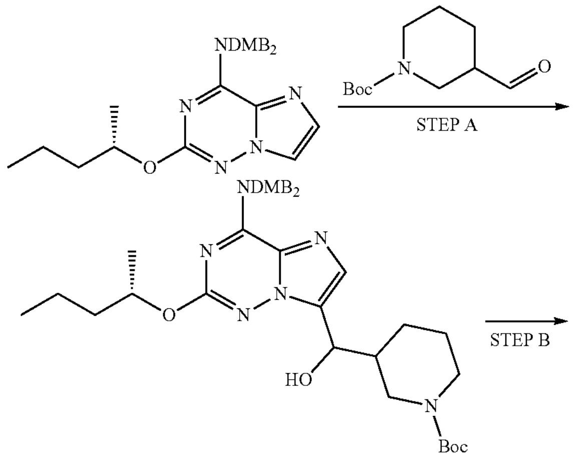

-continued

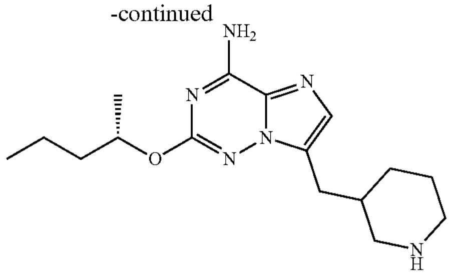

Step A: Tert-butyl 3-((4-(bis(3,4-dimethylbenzyl) amino)-2-(((S)-pent-2-yl)oxy)imidazo[2,1-f][1,2,4] triazin-7-yl)(hydroxy)methyl)piperidin-1-carboxylate

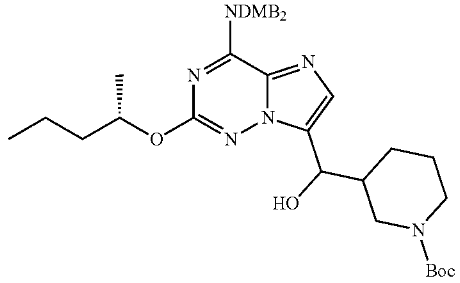

To a cooled solution of (S)-N,N-bis(3,4-dimethylbenzyl)-2-(pent-2-yloxy)imidazo[2,1-f][1,2,4]triazin-4 (200 mg, 0.38 mmol) in THF (8 mL) at −78° C. under the protection of N2, n-BuLi (1.6 M, 0.4 mL) was added dropwise. After the mixture was stirred at −78° C. for 30 min, a solution of tert-butyl 3-formylpiperidin-1-carboxylate (98 mg, 0.46 mmol) in THF (2 mL) was added. The resulting mixture was stirred at this temperature for 30 min, and then gradually warmed to room temperature to react overnight. The solution was quenched with an $NH_4Cl$ solution (5 mL) and extracted with ethyl acetate (10 mL). The organic layer was dried over $Na_2SO_4$, filtered and concentrated to obtain a crude product, which was further purified by CombiFlash (PE:EA=40%) to obtain the pure product (110 mg, 39%). MS: M/e 671 $(M+1)^+$ Step B: 2-(((S)-pent-2-yl)oxy)-7-(piperidin-3-ylmethyl)imidazo[2,1-f][1,2,4]triazin-4-amine

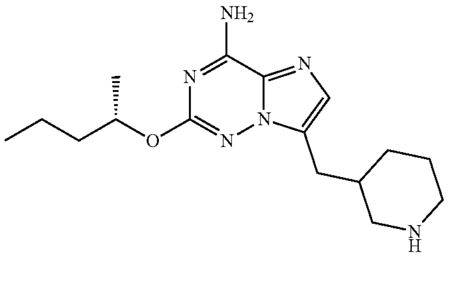 [SMILES: CCC[C@H](C)Oc1nc(N)c2ncc(CC3CCCNC3)n2n1]

A solution of the product of step A (110 mg, 0.15 mmol) in trifluoroacetic acid and water (9:1, v/v, 2 mL) was heated at 40° C. overnight. The solvent was evaporated using an oil pump to obtain a residue, water (5 mL) was added to the residue, and the mixture was pulped and filtered. The filtrate was extracted with DCM (5 mL). The aqueous phase was alkalized with a 1 M NaOH solution to pH=13, and then extracted with DCM/MeOH (10 mL, 20%). The organic layer was drying and concentrated to obtain an intermediate. The intermediate was dissolved in triethylsilane/trifluoroacetic acid (1:1, v/v, 2 mL) and heated at 80° C. overnight. After evaporation, water was added to the residue, the mixture was alkalized to pH=13 with 1 M NaOH solution, and extracted with DCM/MeOH (10 mL, 20%). The organic layer was dried, concentrated and purified by preparative TLC (DCM:$NH_3$·MeOH=9:1, 4 M $NH_3$. MeOH) to obtain the product (6 mg, 13%). $^1H$ NMR (400 MHz, DMSO-d6) δ 8.12 (s, 1H), 8.01 (s, 1H), 7.32 (s, 1H), 7.14 (s, 1H), 5.01-4.97 (m, 1H), 3.61 (t, J=4.0 Hz, 2H), 3.10 (t, J=12.0 Hz, 2H), 2.76 (d, J=8.0 Hz, 2H), 2.68 (t, J=8.0 Hz, 1H), 1.97 (br.s, 1H), 1.78-1.65 (m, 4H), 1.58-1.49 (m, 2H), 1.43-1.33 (m, 2H), 1.28 (d, J=4.0 Hz, 3H), 1.23-1.17 (m, 2H), 0.91 (t, J=8.0 Hz, 3H) ppm. MS: M/e 319 $(M+1)^+$ Compound B11:2-pentyl-7-(piperidin-4-ylmethyl) imidazo[2,1-f][1,2,4]triazin-4-amine

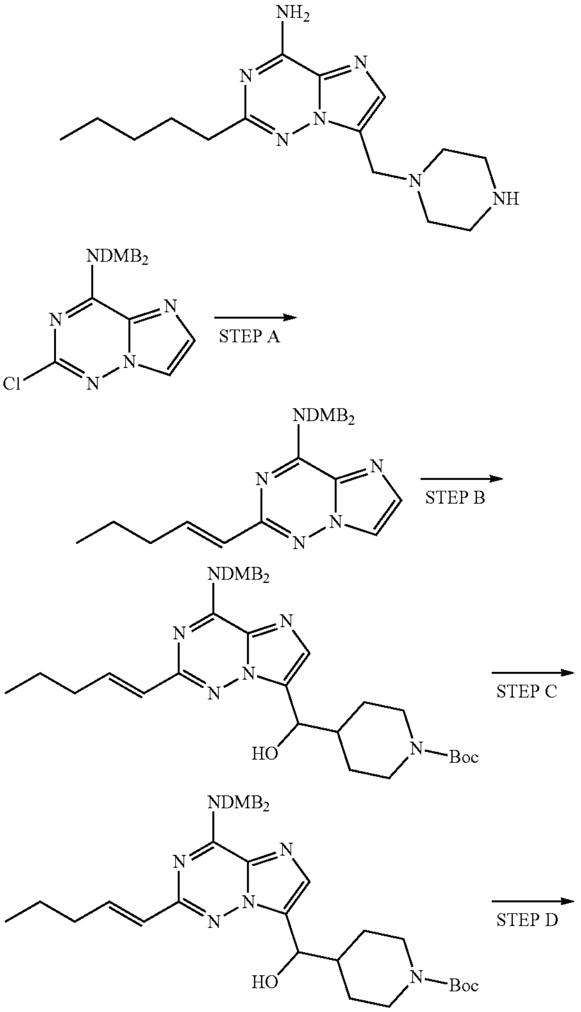

-continued

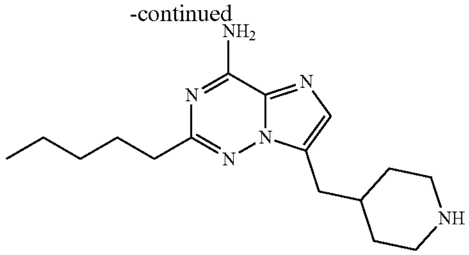

Step A: (E)-N,N-bis(4-methoxybenzyl)-2-(pent-1-en-1-yl)imidazo[2,1-f][1,2,4]triazin-4-amine

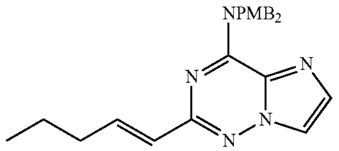

A mixture of 2-chloro-N,N-bis(4-methoxybenzyl)imidazo[2,1-f][1,2,4]triazin-4-amine (0.5 g, 1.2 mmol), a mixture of (E)-pent-1-en-1-yl boric acid (0.21 g, 1.8 mmol), $Pd(dppf)_2Cl_2$ (45 mg, 0.06 mmol) and $Na_2CO_3$ (0.26 g, 2.4 mmol) in dioxane (10 ml) and $H_2O$ (3 ml) was stirred at 80° C. under N2 atmosphere overnight. After completion of the reaction, the mixture was concentrated, diluted with EA (20 ml), and then washed with brine (10 ml). The organic layer was dried and evaporated under reduced pressure. The resulting residue was purified by flash column chromatography eluted with 0-25% EA in PE to obtain the product (0.5 g, 92%) as colorless oil. MS: M/e 444 $(M+1)^+$.

Step B: Tert-butyl (E)-4-((4-(bis(4-methoxybenzyl)amino)-2-(pent-1-en-1-yl)imidazo[2,1-f][1,2,4]triazin-7-yl)(hydroxy)methyl)piperidin-1-carboxylate

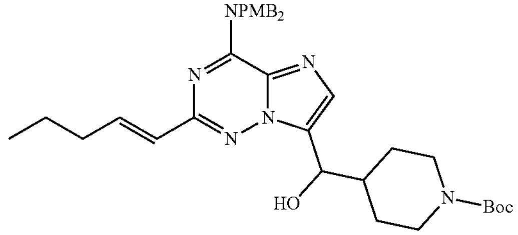

To a solution of (E)-N,N-bis(4-methoxybenzyl)-2-(pent-1-en-1-yl)imidazo[2,1-f][1,2,4]triazin-4-amine (0.5 g, 1.1 mmol) in THF (15 ml) at −70° C. under N2, n-BuLi (1.6 M, 1.4 ml, 2.2 mmol) was added dropwise. The solution was stirred at −70° C. for 0.5 h. A solution of tert-butyl 4-formylpiperidin-1-carboxylate (0.47 g, 2.2 mmol) in THF (2 ml) was added dropwise to the above solution at −70° C. over 0.5 h, and then the mixture was warmed to room temperature to react for 1 h. After completion of the reaction, the solution was quenched with $H_2O$ (15 ml) and extracted with EA (15 ml×2). The organic layer was washed with brine (10 ml), dried and concentrated. The resulting residue was purified by combi-flash eluted with 10%-70% EA in PE to obtain a white semi-solid product (0.65 g, 88%). MS: M/e 657 $(M+1)^+$.

Step C: Tert-butyl 4-((4-(bis(4-methoxybenzyl)amino)-2-pentylimidazolo[2,1-f][1,2,4]triazin-7-yl)(hydroxy)methyl)piperidin-1-carboxylate

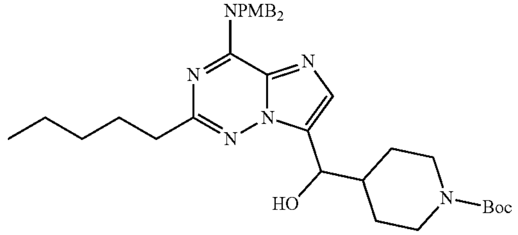

A mixture of tert-butyl (E)-4-((4-(bis(4-methoxybenzyl)amino)-2-(pent-1-en-1-yl)imidazo[2,1-f][1,2,4]triazin-7-yl)(hydroxy)methyl)piperidin-1-carboxylate (0.65 g, 0.99 mmol) and Pd/C (0.1 g) in MeOH (15 ml) was stirred at room temperature under $H_2$ atmosphere overnight. After completion of the reaction, the mixture was filtered through diatomite, and then evaporated under reduced pressure to obtain the product (0.6 g, 92%) as white oil. MS: M/e 659 $(M+1)^+$.

Step D: 2-pentyl-7-(piperidin-4-ylmethyl)imidazo[2,1-f][1,2,4]triazin-4-amine

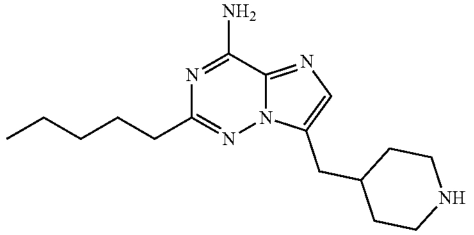 [SMILES: CCCCCc1nc(N)c2ncc(CC3CCNCC3)n2n1]

A mixture of tert-butyl 4-((4-(bis(4-methoxybenzyl)amino)-2-pentylimidazolo[2,1-f][1,2,4]triazin-7-yl)(hydroxy)methyl)piperidin-1-carboxylate (0.6 g, 0.91 mmol) in TFA (8 ml) and triethylsilane (2 ml) was stirred at 80° C. for 2 d, and then stirred at 100° C. for 2 d. The mixture was concentrated under reduced pressure. The residue was diluted with an aqueous $NaHCO_3$ solution (20 ml) and then extracted with EA (20 ml×3). The organic lay was dried and concentrated. The resulting residue was purified by preparative TLC and then by preparative HPLC to obtain the product (28 mg). $^1H$ NMR (400 MHz, DMSO-d6) δ 8.59 (s, 1H), 8.35-7.98 (m, 3H), 7.50-7.38 (m, 1H), 3.24 (d, J=12.7 Hz, 2H), 2.90-2.75 (m, 4H), 2.57 (t, J=7.5 Hz, 2H), 2.06-1.92 (m, 1H), 1.81-1.65 (m, 4H), 1.44-1.25 (m, 6H), 0.87 (t, J=6.8 Hz, 3H) ppm. MS: M/e 303 $(M+1)^+$.

Compound B12: (S)-7-((1-(2-(methylamino)ethyl)piperidin-4-yl)methyl)-2-(pent-2-yloxy)imidazo[2,1-f][1,2,4]triazin-4-amine

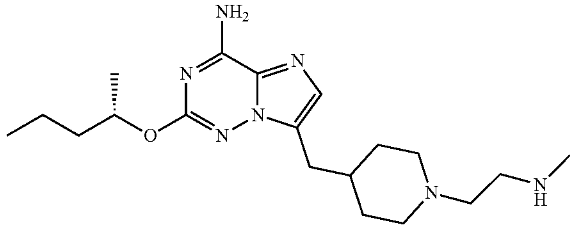

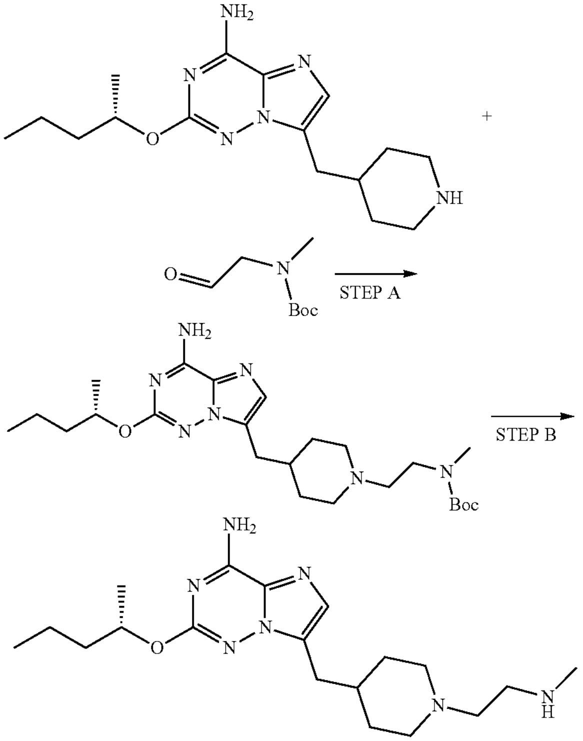

Step A: Tert-butyl(S)-(2-(4-((4-amino-2-(pent-2-yloxy)imidazo[2,1-f][1,2,4]triazin-7-yl)methyl)piperidin-1-yl)ethyl)(methyl)carbamate

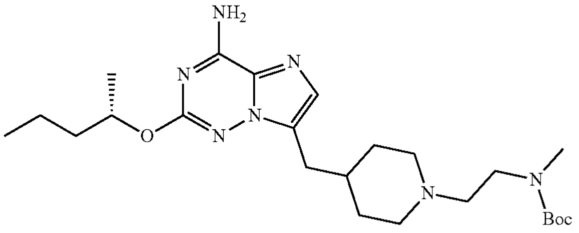 [SMILES: CCC[C@H](C)Oc1nc(N)c2ncc(CC3CCN(CCN(C)C(=O)OC(C)(C)C)CC3)n2n1]

At room temperature, to a mixture of (S)-2-(pent-2-yloxy)-7-(piperidin-4-ylmethyl)imidazo[2,1-f][1,2,4]triazin-4-amine (20 mg, 0.063 mmol) and tert-butyl (2-oxoethyl) carbamate (20 mg, 0.116 mmol) in THF (1 mL), AcOH (20 mg, 0.33 mmol) was added, then NaBH(OAc)$_3$ (40 mg, 0.189 mmol) was added, and the mixture was stirred for 16 h. 2 mL of brine was added and the mixture was extracted with EA (2 mL×3). The combined extracts were washed with brine (5 mL×3), dried over $Na_2SO_4$ and concentrated. The resulting residue was purified by preparative TLC (CH2Cl2/MeOH ($NH_3$ solution)=15:1) to obtain the title product (15 mg, 50%). MS: M/e 476 (M+1)$^+$.

Step B: (S)-7-((1-(2-(methylamino)ethyl)piperidin-4-yl)methyl)-2-(pent-2-yloxy)imidazo[2,1-f][1,2,4]triazin-4-amine

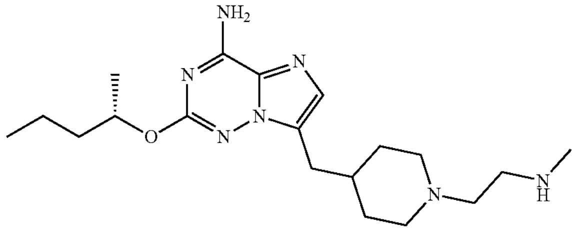 [SMILES: CCC[C@H](C)Oc1nc(N)c2ncc(CC3CCN(CCNC)CC3)n2n1]

The product of step A (15 mg, 0.032 mmol) in HCl/EA solution (4 M, 5 mL) was stirred at room temperature for 5 h. The mixture was concentrated, alkalized with NaOH (4 M, aqueous solution) and extracted with CH2Cl2 (2 mL×3). The combined extracts were washed with brine (5 mL×3), dried over $Na_2SO_4$ and concentrated. The resulting residue was purified by preparative TLC ($CH_2Cl_2$/MeOH ($NH_3$ solution)=15:1) to obtain the title product (4.5 mg, 38%). $^1$H NMR (400 MHz, CD3OD) δ 7.38 (s, 1H), 5.19-5.04 (m, 1H), 3.69-3.54 (m, 2H), 3.54-3.35 (m, 4H), 3.09-2.85 (m, 4H), 2.78 (s, 3H), 2.20-2.06 (m, 1H), 2.00-1.89 (m, 2H), 1.84-1.66 (m, 3H), 1.67-1.41 (m, 3H), 1.36 (d, J=6.4 Hz, 3H), 0.97 (t, J=7.2 Hz, 3H) ppm. MS: M/e 376 (M+1)$^+$.

Compound B13: 2—(((S)-pent-2-yl)oxy)-7-((1-(pyrrolidin-3-yl)piperidin-4-yl)methyl)imidazo[2,1-f][1,2,4]triazin-4-amine

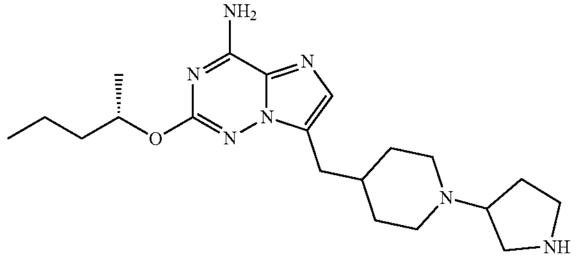

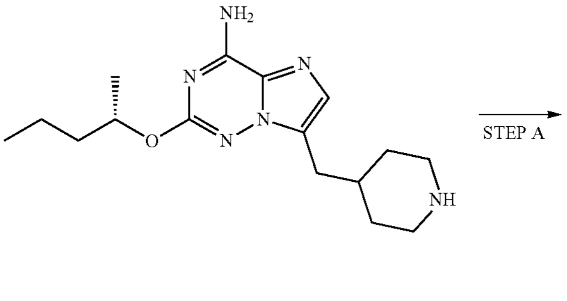

-continued

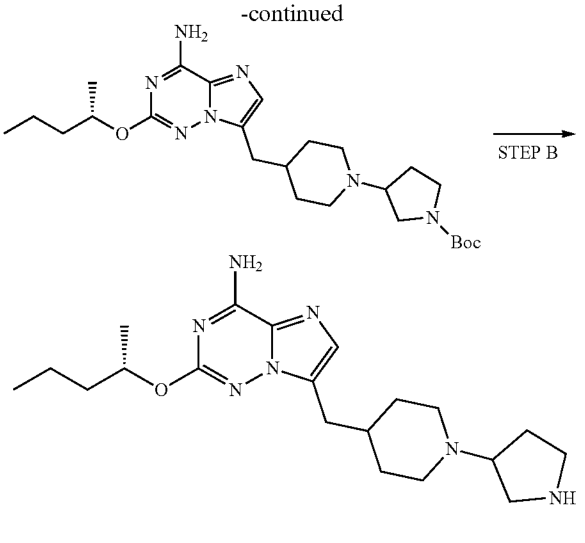

Step A: Tert-butyl 3-(4-((4-amino-2-(((S)-pent-2-yl)oxy)imidazo[2,1-f][1,2,4]triazin-7-yl)methyl)piperidin-1-yl)pyrrolidin-1-carboxylate

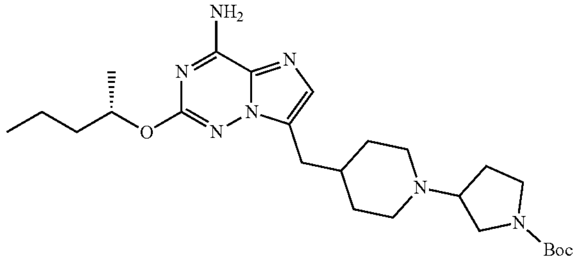 [SMILES: CCC[C@H](C)Oc1nc(N)c2ncc(CC3CCN(C4CCN(C(=O)OC(C)(C)C)C4)CC3)n2n1]

To a stirred solution of (S)-2-(pent-2-yloxy)-7-(piperidin-4-ylmethyl)imidazo[2,1-f][1,2,4]triazin-4-amine (20 mg, 0.063 mmol) and tert-butyl 3-oxopyrrolidin-1-carboxylate (23 mg, 0.126 mmol) in THF (5 mL), AcOH (2 droplets) was added. The mixture was then stirred at room temperature for half an hour, and then $NaBH(OAc)_3$ (27 mg, 0.126 mmol) was added. Thereafter, the reaction mixture was stirred for two days. The reaction mixture was concentrated to obtain a residue, and the residue was purified by preparative TLC ($CH_2Cl_2$/MeOH=10:1) to obtain the target compound (22 mg, 71.7%). MS: M/e 488 $(M+1)^+$.

Step B: 2-(((S)-pent-2-yl)oxy)-7-((1-(pyrrolidin-3-yl)piperidin-4-yl)methyl)imidazo[2,1-f][1,2,4]triazin-4-amine

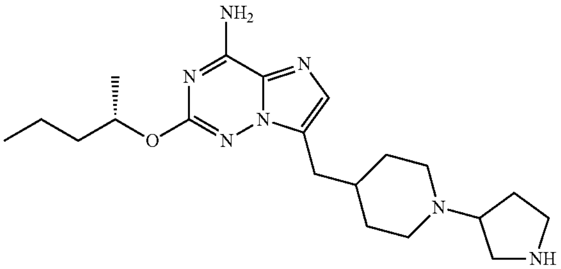 [SMILES: CCC[C@H](C)Oc1nc(N)c2ncc(CC3CCN(C4CCNC4)CC3)n2n1]

A mixture of the product of step A (22 mg, 0.045 mmol) in EtOAc/HCl (4.0 M, 5 mL) was stirred overnight. The reaction mixture was concentrated to obtain a residue, and the residue was purified by preparative HPLC to obtain the target compound (5 mg). $^1H$ NMR (400 MHz, DMSO-d6) δ 9.83 (s, 1H), 9.22 (s, 1H), 9.06 (s, 1H), 8.12 (s, 1H) 8.05 (s, 1H), 7.36 (s, 1H), 5.02-4.93 (m, 1H), 3.94-3.89 (m, 1H), 3.65-3.58 (m, 1H), 3.55-3.28 (m, 4H), 3.27-2.86 (m, 4H), 2.79 (d, J=6.4 Hz, 2H), 2.38-2.31 (m, 1H), 2.16-1.92 (m, 2H), 1.86-1.77 (m, 2H), 1.73-1.49 (m, 2H), 1.48-1.35 (m, 4H), 1.28 (d, J=6.0 Hz, 3H), 0.91 (t, J=7.2 Hz, 3H) ppm. MS: M/e 388 $(M+1)^+$.

Compound B14: (S)-2-(pent-2-yloxy)-7-((1-(piperidin-4-ylmethyl)piperidin-4-yl)methyl)imidazo[2,1-f][1,2,4]triazin-4-amine

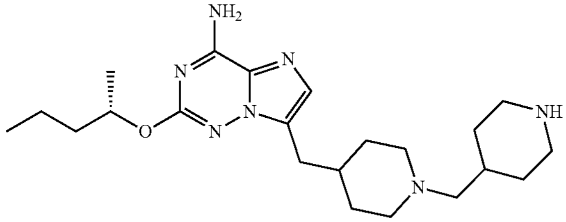

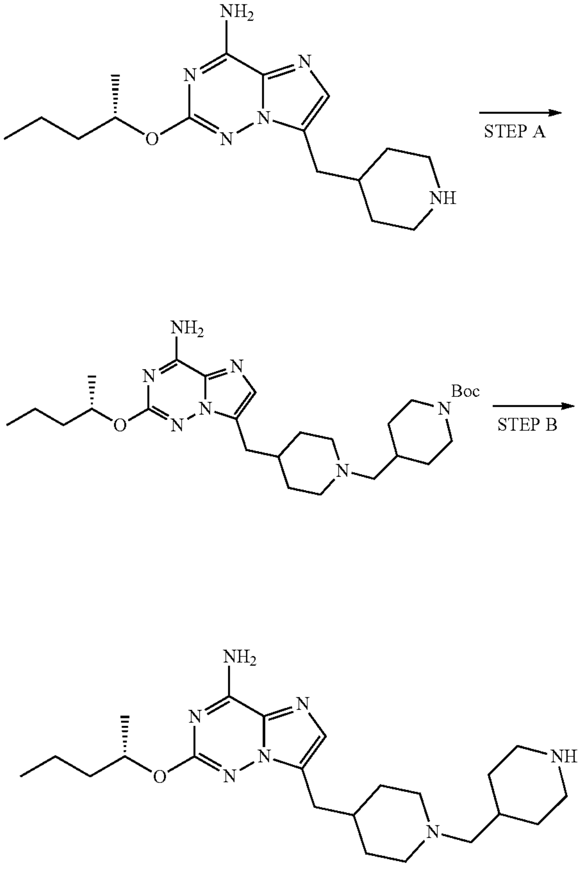

Step A: Tert-butyl(S)-4-((4-((4-amino-2-(pent-2-yloxy)imidazo[2,1-f][1,2,4]triazin-7-yl)methyl)piperidin-1-yl)methyl)piperidin-1-carboxylate

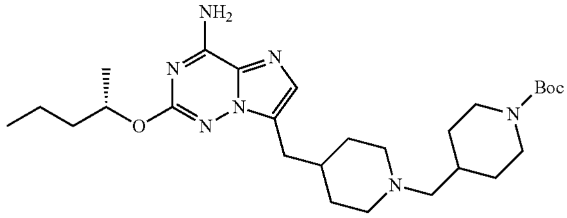 [SMILES: CCC[C@H](C)Oc1nc(N)c2ncc(CC3CCN(CC4CCN(C(=O)OC(C)(C)C)CC4)CC3)n2n1]

A mixture of (S)-2-(pent-2-yloxy)-7-(piperidin-4-ylmethyl)imidazo[2,1-f][1,2,4]triazin-4-amine (20 mg, 0.06 mmol), tert-butyl 4-formylpiperidin-1-carboxylate (27 mg, 0.12 mmol) and sodium triacetoxy borohydride (27 mg, 0.12 mmol) in THF (5 mL) was stirred at room temperature for 3 h. The mixture was extracted with DCM (20 mL), washed with water (5 ml), concentrated and purified by column chromatography (DCM/MeOH=20:1-3:1) to obtain the title product (30 mg, 92.62%). MS: M/e 516 $(M+1)^+$.

Step B: (S)-2-(pent-2-yloxy)-7-((1-(piperidin-4-ylmethyl)piperidin-4-yl)methyl)imidazo[2,1-f][1,2,4]triazin-4-amine

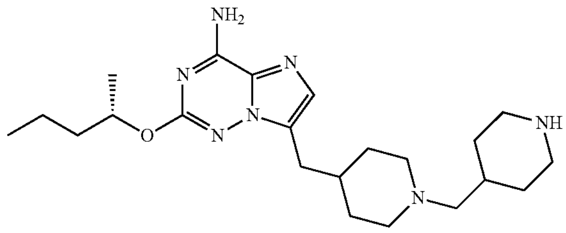 [SMILES: CCC[C@H](C)Oc1nc(N)c2ncc(CC3CCN(CC4CCNCC4)CC3)n2n1]

A mixture of tert-butyl(S)-4-((4-((4-amino-2-(pent-2-yloxy)imidazo[2,1-f][1,2,4]triazin-7-yl)methyl)piperidin-1-methyl)piperidin-1-carboxylate (30 mg, 0.06 mmol) and TFA (0.5 mL) in DCM (3 mL) was stirred at room temperature for 2 h. The mixture was concentrated and purified by preparative HPLC to obtain the product (18 mg, 74.46%). $^1$H NMR (400 MHz, DMSO-6) δ 8.93 (s, 1H), 8.55 (s, 1H), 8.31 (s, 1H), 8.14 (s, 1H), 8.06 (s, 1H), 7.37 (s, 1H), 5.01-4.97 (m, 1H), 3.48 (d, J=11.8 Hz, 2H), 3.38-3.18 (m, 3H), 2.96 (t, J=5.9 Hz, 2H), 2.92-2.81 (m, 4H), 2.79 (d, J=6.3 Hz, 2H), 2.07 (s, 1H), 1.95 (s, 1H), 1.83 (t, J=14.5 Hz, 4H), 1.70-1.63 (m, 1H), 1.58-1.42 (m, 3H), 1.42-1.31 (m, 3H), 1.28 (d, J=6.1 Hz, 3H), 0.91 (t, J=7.3 Hz, 3H) ppm. MS: M/e 416 $(M+1)^+$.

Compound B15: 7—(((R)-3-methylpiperazin-1-yl)methyl)-2-(pent-2-yloxy)imidazo[2,1-f][1,2,4]triazin-4-amine

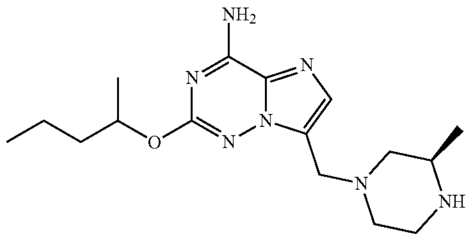

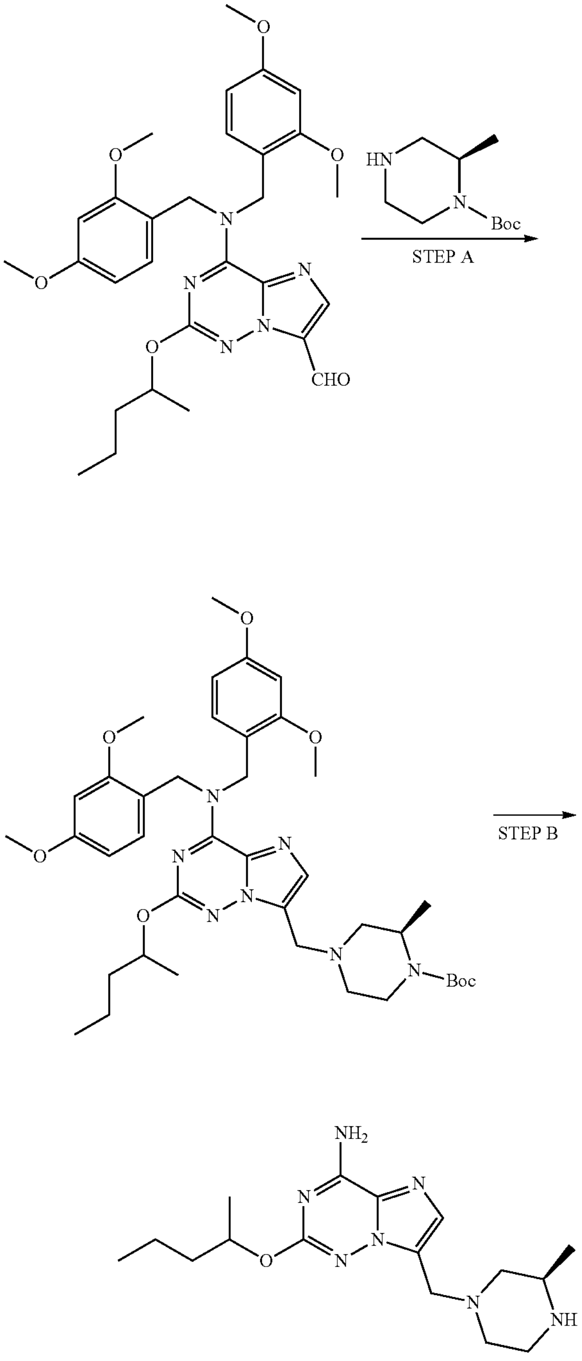

Step A: Tert-butyl (2R)-4-((4-(bis(2,4-dimethoxybenzyl)amino)-2-(pent-2-yloxy)imidazo[2,1-f][1,2,4]triazin-7-yl)methyl)-2-methylpiperazin-1-carboxylate

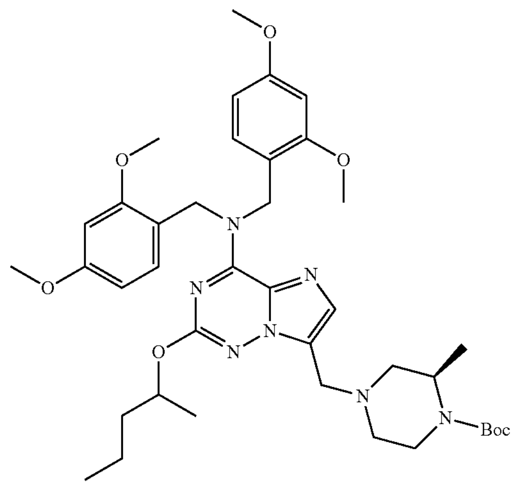 [SMILES: CCCC(C)Oc1nc(N(Cc2ccc(OC)cc2OC)Cc2ccc(OC)cc2OC)c2ncc(CN3CCN(C(=O)OC(C)(C)C)[C@H](C)C3)n2n1]

At room temperature, to a mixture of 4-(bis(2,4-dimethoxybenzyl)amino)-2-(pent-2-yloxy)imidazo[2,1-f][1,2,4]triazin-7-formaldehyde (100 mg, 0.18 mmol) and tert-butyl (R)-2-methylpiperazin-1-carboxylate (72 mg, 0.36 mmol) in THF (2 mL), AcOH (25 mg, 0.42 mmol) and then NaBH$(OAc)_3$ (115 mg, 0.54 mmol) were added, and the resulting mixture was stirred for 16 h. 2 mL of brine was added and the mixture was extracted with EA (2 mL×3). The combined extracts were washed with brine (2 mL×3), dried over $Na_2SO_4$ and concentrated. The resulting residue was purified by preparative TLC (PE/EA=1:1) to obtain the title product (85 mg, 64%). MS: M/e 734 $(M+1)^+$.

Step B: 7-(((R)-3-methylpiperazin-1-yl)methyl)-2-(pent-2-yloxy)imidazo[2,1-f][1,2,4]triazin-4-amine

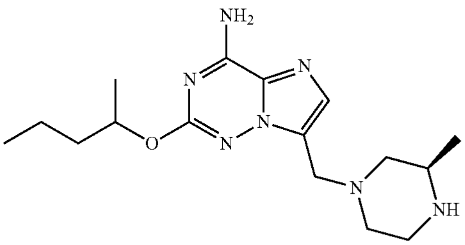 [SMILES: CCCC(C)Oc1nc(N)c2ncc(CN3CCN[C@H](C)C3)n2n1]

The product of step A (85 mg, 0.12 mmol) in HCl/EA solution (4 M, 5 mL) was stirred at room temperature for 16 h. The mixture was concentrated to dryness, 5 mL of TFA was added, and the resulting mixture was stirred at room temperature for 2 h and then at 60° C. for 5 h. The mixture was concentrated to dryness under high vacuum. 2 mL of NaOH (aqueous solution, 4 M) was added and the mixture was extracted with $CH_2Cl_2$ (5 mL×5). The combined extracts were washed with brine (10 mL×3), dried over $Na_2SO_4$ and concentrated. The resulting residue was purified by preparative TLC ($CH_2Cl_2$/MeOH ($NH_3$ solution)=10:1) to obtain the title product (25 mg, 65%). $^1H$ NMR (400 MHz, CD3OD) δ 7.49 (s, 1H), 5.22-5.06 (m, 1H), 4.05-3.87 (m, 2H), 3.17-2.91 (m, 5H), 2.38-2.22 (m, 1H), 2.08-1.96 (m, 1H), 1.83-1.69 (m, 1H), 1.69-1.56 (m, 1H), 1.55-1.40 (m, 2H), 1.40-1.30 (m, 3H), 1.20-1.07 (m, 3H), 1.00-0.91 (m, 3H) ppm. MS: M/e 334 $(M+1)^+$.

Compound B16: 7—(((S)-3-methylpiperazin-1-yl)methyl)-2-(pent-2-yloxy)imidazo[2,1-f][1,2,4]triazin-4-amine

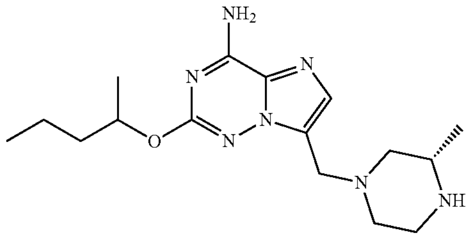

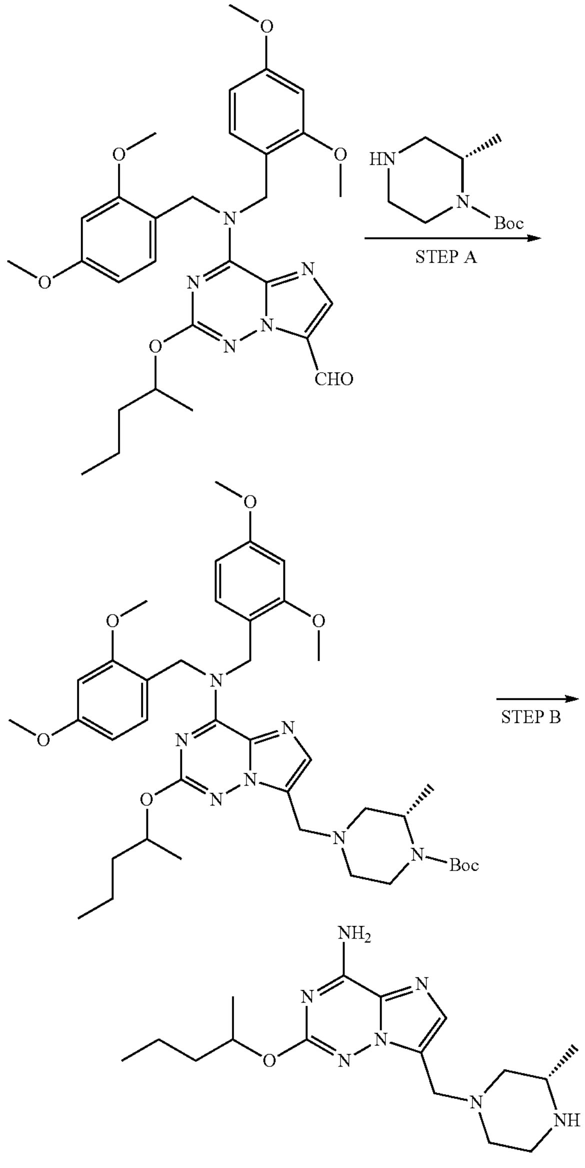

Step A: Tert-butyl (2S)-4-((4-(bis(2,4-dimethoxybenzyl)amino)-2-(pent-2-yloxy)imidazo[2,1-f][1,2,4]triazin-7-yl)methyl)-2-methylpiperazin-1-carboxylate

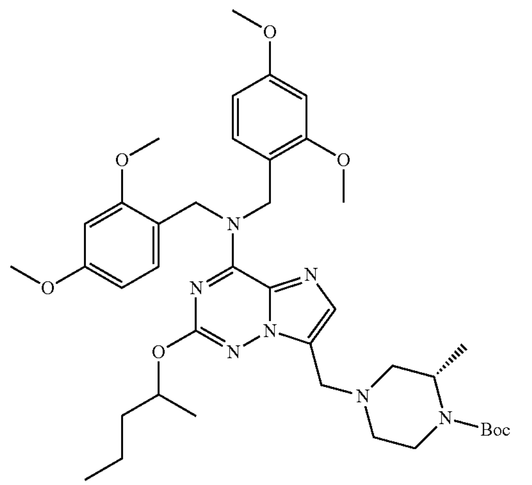 [SMILES: CCCC(C)Oc1nc(N(Cc2ccc(OC)cc2OC)Cc2ccc(OC)cc2OC)c2ncc(CN3CCN(C(=O)OC(C)(C)C)[C@@H](C)C3)n2n1]

At room temperature, to a mixture of 4-(bis(2,4-dimethoxybenzyl)amino)-2-(pent-2-yloxy)imidazo[2,1-f][1,2,4]triazin-7-formaldehyde (100 mg, 0.18 mmol) and tert-butyl (S)-2-methylpiperazin-1-carboxylate (72 mg, 0.36 mmol) in THF (2 mL), AcOH (25 mg, 0.42 mmol) and then NaBH$(OAc)_3$ (115 mg, 0.54 mmol) were added, and the resulting mixture was stirred for 16 h. 2 mL of brine was added and the mixture was extracted with EA (2 mL×3). The combined extracts were washed with brine (2 mL×3), dried over $Na_2SO_4$ and concentrated. The resulting residue was purified by preparative TLC (PE/EA=1:1) to obtain the title product (92 mg, 68%). MS: M/e 734 $(M+1)^+$.

Step B: 7-(((S)-3-methylpiperazin-1-yl)methyl)-2-(pent-2-yloxy)imidazo[2,1-f][1,2,4]triazin-4-amine

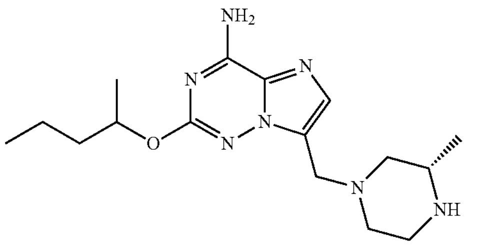 [SMILES: CCCC(C)Oc1nc(N)c2ncc(CN3CCN[C@@H](C)C3)n2n1]

The product of step A (92 mg, 0.12 mmol) in HCl/EA solution (4 M, 5 mL) was stirred at room temperature for 16 h. The mixture was concentrated to dryness, 5 mL of TFA was added, and the resulting mixture was stirred at room temperature for 2 h and then at 60° C. for 5 h. The mixture was concentrated to dryness under high vacuum. 2 mL of NaOH (aqueous solution, 4 M) was added and the mixture was extracted with $CH_2Cl_2$ (5 mL×5). The combined extracts were washed with brine (10 mL×3), dried over $Na_2SO_4$ and concentrated. The resulting residue was purified by preparative TLC ($CH_2Cl_2$/MeOH ($NH_3$ solution)=10:1) to obtain the title product (21 mg, 50%). $^1H$ NMR (400 MHz, CD3OD) δ 7.48 (s, 1H), 5.17-5.06 (m, 1H), 3.93 (s, 2H), 3.12-2.90 (m, 5H), 2.35-2.22 (m, 1H), 1.99 (t, J=10.8 Hz, 1H), 1.85-1.69 (m, 1H), 1.69-1.55 (m, 1H), 1.53-1.39 (m, 2H), 1.36 (d, J=6.0 Hz, 3H), 1.12 (d, J=6.4 Hz, 3H), 0.96 (t, J=7.2 Hz, 3H) ppm. MS: M/e 334 $(M+1)^+$.

Compound B17: 7—(((S)-2-methylpiperazin-1-yl)methyl)-2-(pent-2-yloxy)imidazo[2,1-f][1,2,4]triazin-4-amine

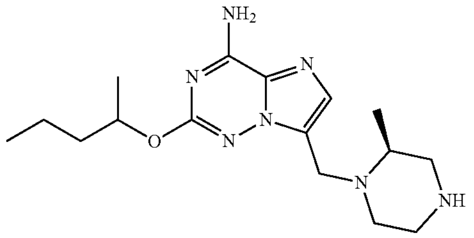

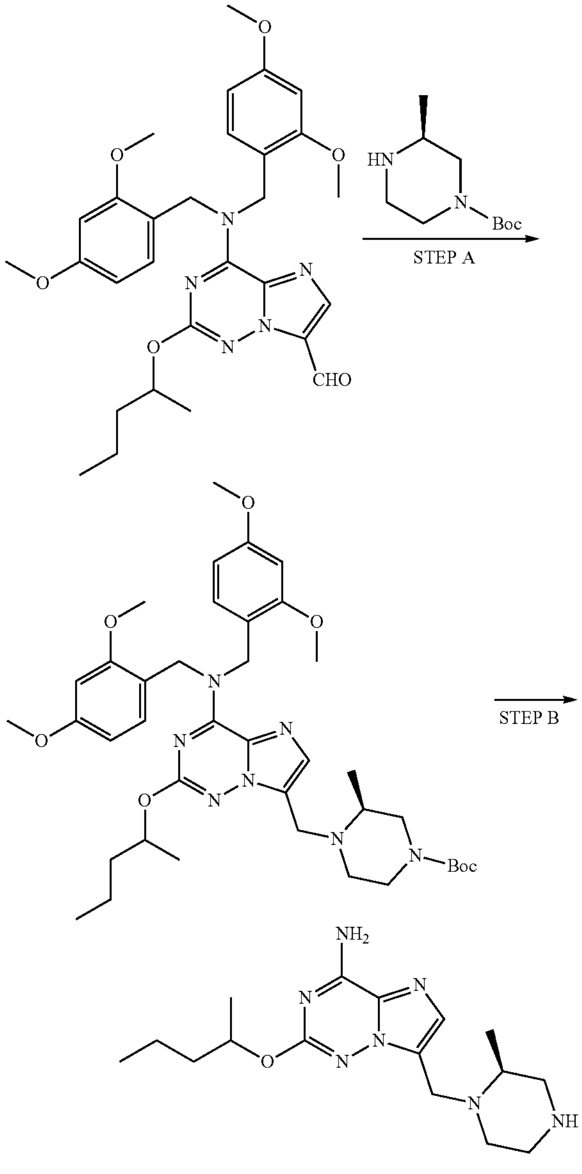

Step A: Tert-butyl (3S)-4-((4-(bis(2,4-dimethoxybenzyl)amino)-2-(pent-2-yloxy)imidazo[2,1-f][1,2,4]triazin-7-yl)methyl)-3-methylpiperazin-1-carboxylate

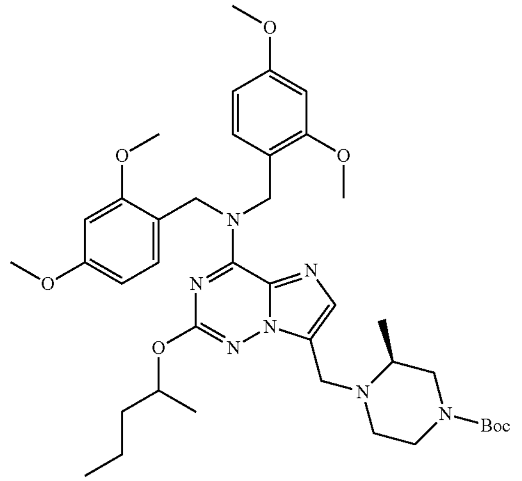 [SMILES: CCCC(C)Oc1nc(N(Cc2ccc(OC)cc2OC)Cc2ccc(OC)cc2OC)c2ncc(CN3CCN(C(=O)OC(C)(C)C)C[C@@H]3C)n2n1]

At room temperature, to a mixture of 4-(bis(2,4-dimethoxybenzyl)amino)-2-(pent-2-yloxy)imidazo[2,1-f][1,2,4]triazin-7-formaldehyde (100 mg, 0.18 mmol) and tert-butyl(S)-3-methylpiperazin-1-carboxylate (72 mg, 0.36 mmol) in THF (2 mL), AcOH (25 mg, 0.42 mmol) and then $NaBH(OAc)_3$ (115 mg, 0.54 mmol) were added, and the resulting mixture was stirred for 16 h. 2 mL of brine was added and the mixture was extracted with EA (2 mL×3). The combined extracts were washed with brine (2 mL×3), dried over $Na_2SO_4$ and concentrated. The resulting residue was purified by preparative TLC (PE/EA=1:1) to obtain the title product (86 mg, 64%). MS: M/e 734 $(M+1)^+$.

Step B: 7-(((S)-2-methylpiperazin-1-yl)methyl)-2-(pent-2-yloxy)imidazo[2,1-f][1,2,4]triazin-4-amine

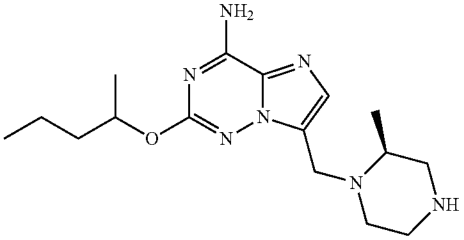 [SMILES: CCCC(C)Oc1nc(N)c2ncc(CN3CCNC[C@@H]3C)n2n1]

Tert-butyl (3S)-4-((4-(bis(2,4-dimethoxybenzyl)amino)-2-(pent-2-yloxy)imidazo[2,1-f][1,2,4]triazin-7-yl)methyl)-3-methylpiperazin-1-carboxylate (86 mg, 0.12 mmol) in HCl/EA (4 M, 5 mL) solution was stirred at room temperature for 16 h. The mixture was concentrated to dryness, 5 mL of TFA was added, the resulting mixture was stirred at room temperature for 2 h and then at 60° C. for 5 h. The mixture was concentrated to dryness under high vacuum. 2 mL of NaOH (aqueous solution, 4 M) was added and the mixture was extracted with $CH_2Cl_2$ (5 mL×5).

The combined extracts were washed with brine (10 mL×3), dried over $Na_2SO_4$ and concentrated. The resulting residue was purified by preparative TLC (CH2Cl/MeOH ($NH_3$ solution)=10:1) to obtain the title product (15 mg, 38%). $^1H$ NMR (400 MHz, CD3OD) δ 7.49 (s, 1H), 5.17-5.02 (m, 1H), 4.26 (d, J=14.8 Hz, 1H), 3.92 (dd, J=14.8, 5.2 Hz, 1H), 3.11-3.04 (m, 2H), 3.03-2.97 (m, 1H), 2.96-2.86 (m, 1H), 2.70-2.51 (m, 2H), 2.46-2.34 (m, 1H), 1.83-1.70 (m, 1H), 1.67-1.55 (m, 1H), 1.55-1.39 (m, 2H), 1.36 (dd, J=6.0, 0.8 Hz, 3H), 1.31 (d, J=6.0 Hz, 3H), 0.96 (t, J=7.2 Hz, 3H) ppm. MS: M/e 334 $(M+1)^+$.

Compound B18: 7—(((R)-2-methylpiperazin-1-yl)methyl)-2-(pent-2-yloxy)imidazo[2,1-f][1,2,4]triazin-4-amine

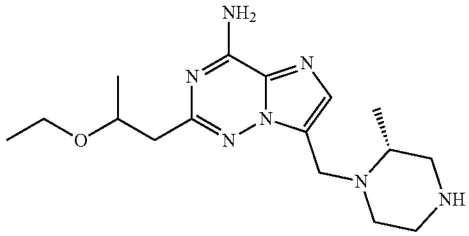

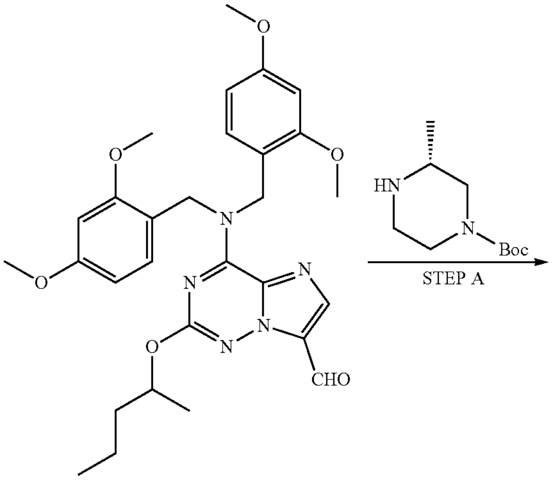

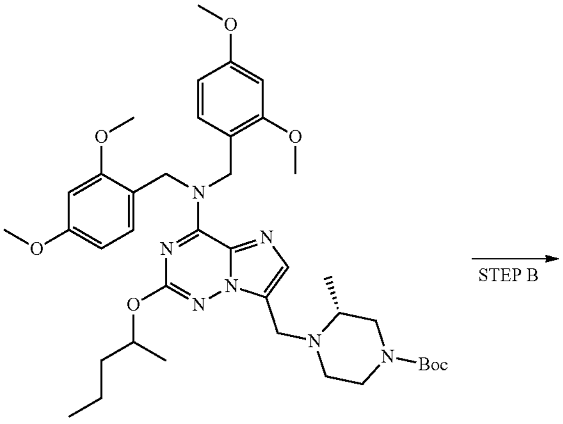

-continued

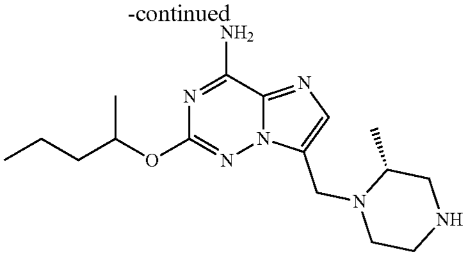

Step A: Tert-butyl (3R)-4-((4-(bis(2,4-dimethoxy-benzyl)amino)-2-(pent-2-yloxy)imidazo[2,1-f][1,2,4]triazin-7-yl)methyl)-3-methylpiperazin-1-carboxylate

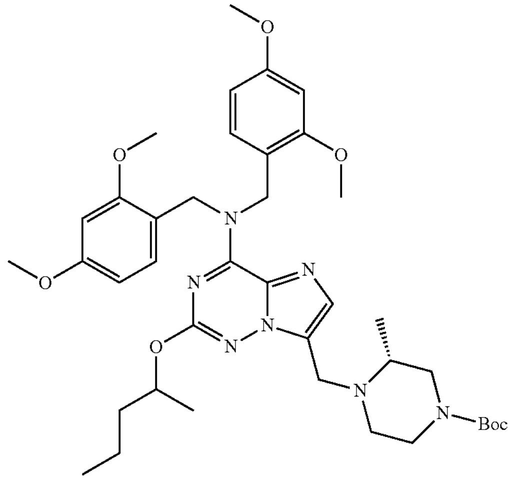 [SMILES: CCCC(C)Oc1nc(N(Cc2ccc(OC)cc2OC)Cc2ccc(OC)cc2OC)c2ncc(CN3CCN(C(=O)OC(C)(C)C)C[C@H]3C)n2n1]

At room temperature, to a mixture of 4-(bis(2,4-dimethoxybenzyl)amino)-2-(pent-2-yloxy)imidazo[2,1-f][1,2,4]triazin-7-formaldehyde (100 mg, 0.18 mmol) and tert-butyl (R)-3-methylpiperazin-1-carboxylate (72 mg, 0.36 mmol) in THF (2 mL), AcOH (25 mg, 0.42 mmol) and then NaBH$(OAc)_3$ (115 mg, 0.54 mmol) were added, and the resulting mixture was stirred for 16 h. 2 mL of brine was added and the mixture was extracted with EA (2 mL×3). The combined extracts were washed with brine (2 mL×3), dried over $Na_2SO_4$ and concentrated. The resulting residue was purified by preparative TLC (PE/EA=1:1) to obtain the title product (82 mg, 62%). MS: M/e 734 $(M+1)^+$.

Step B: 7-(((R)-2-methylpiperazin-1-yl)methyl)-2-(pent-2-yloxy)imidazo[2,1-f][1,2,4]triazin-4-amine

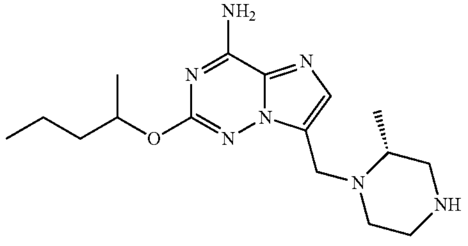 [SMILES: CCCC(C)Oc1nc(N)c2ncc(CN3CCNC[C@H]3C)n2n1]

Tert-butyl (3R)-4-((4-(bis(2,4-dimethoxybenzyl)amino)-2-(pent-2-yloxy)imidazo[2,1-f][1,2,4]triazin-7-yl)methyl)-3-methylpiperazin-1-carboxylate (82 mg, 0.11 mmol) in HCl/EA (4 M, 5 mL) solution was stirred at room temperature for 16 h. The mixture was concentrated to dryness, 5 mL of TFA was added, the resulting mixture was stirred at room temperature for 2 h and then at 60° C. for 5 h. The mixture was concentrated to dryness under high vacuum. 2 mL of NaOH (aqueous solution, 4 M) was added and the mixture was extracted with $CH_2Cl_2$ (5 mL×5). The combined extracts were washed with brine (10 mL×3), dried over $Na_2SO_4$ and concentrated. The resulting residue was purified by preparative TLC (CH2Ch/MeOH ($NH_3$ solution)=10:1) to obtain the title product (13 mg, 35%). $^1$H NMR (400 MHz, CD3OD) δ 7.49 (s, 1H), 5.21-5.01 (m, 1H), 4.25 (d, J=14.8 Hz, 1H), 3.92 (dd, J=14.8, 5.6 Hz, 1H), 3.06-2.93 (m, 3H), 2.92-2.81 (m, 1H), 2.64-2.45 (m, 2H), 2.43-2.31 (m, 1H), 1.82-1.70 (m, 1H), 1.67-1.55 (m, 1H), 1.54-1.40 (m, 2H), 1.36 (d, J=6.0 Hz, 3H), 1.30 (d, J=5.6 Hz, 3H), 0.96 (t, J=7.2 Hz, 3H) ppm. MS: M/e 334 $(M+1)^+$.

Compound B19: (S)-7-((1-(3-(methylamino)propyl)piperidin-4-yl)methyl)-2-(pent-2-yloxy)imidazo[2,1-f][1,2,4]triazin-4-amine

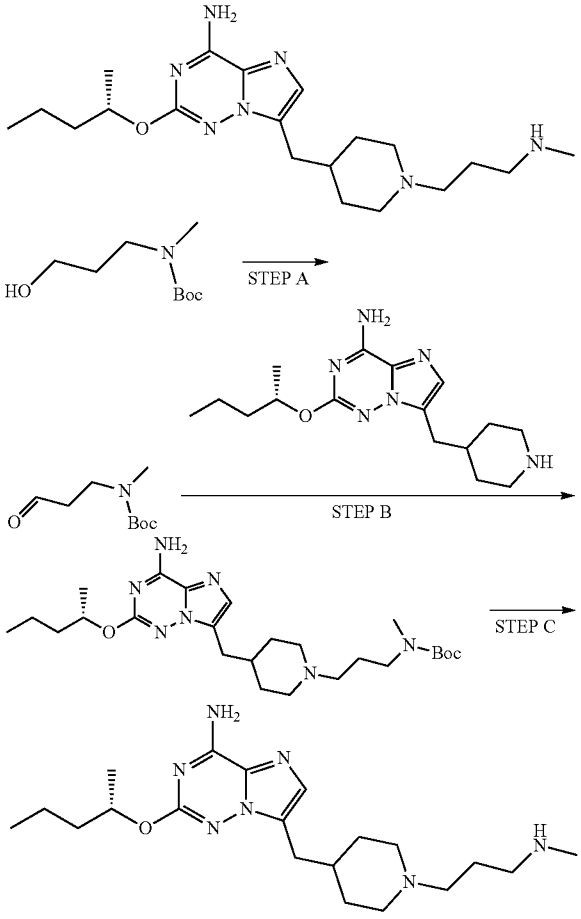

Step A: Tert-butyl (3-oxopropyl)methyl carbamate

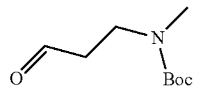

At −78° C. under N2, to a solution of oxalyl chloride (510 mg, 4.0 mmol) in $CH_2Cl_2$ (5 mL), a solution of DMSO (624 mg, 8.0 mmol) in $CH_2Cl_2$ (5 mL) was added. The mixture was stirred for 20 min. A solution of tert-butyl (3-hydroxypropyl)(methyl)carbamate (500 mg, 2.64 mmol) in $CH_2Cl_2$ (5 mL) was added at a temperature below −55° C. The resulting mixture was stirred at −78° C. for 30 min and then at −50° C. for 30 min. A solution of $Et_3N$ (1.54 g, 15.2 mmol) in $CH_2Cl_2$ (5 mL) was added, and the mixture was stirred at room temperature for 16 h. The mixture was diluted with 20 mL of $CH_2Cl_2$ and washed with brine (5 mL×3), dried over $Na_2SO_4$ and concentrated. The resulting residue was purified by column chromatography (PE/EA=5:1) to obtain the title product (180 mg, crude). MS: M/e 188 $(M+1)^+$.

Step B: Tert-butyl(S)-(3-(4-((4-amino-2-(pent-2-yloxy)imidazo[2,1-f][1,2,4]triazin-7-yl)methyl)piperidin-1-yl) propyl)(methyl)carbamate

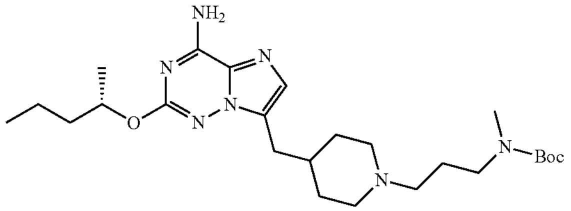 [SMILES: CCC[C@H](C)Oc1nc(N)c2ncc(CC3CCN(CCCN(C)C(=O)OC(C)(C)C)CC3)n2n1]

At room temperature, to a mixture of (S)-2-(pent-2-yloxy)-7-(piperidin-4-ylmethyl)imidazo[2,1-f][1,2,4]triazin-4-amine (20 mg, 0.063 mmol) and tert-butyl (3-oxopropyl) carbamate (26 mg, crude) in THF (1 mL), AcOH (20 mg, 0.33 mmol) and then $NaBH(OAc)_3$ (40 mg, 0.189 mmol) were added, and the resulting mixture was stirred for 16 h. 2 mL of brine was added and the mixture was extracted with EA (2 mL×3). The combined extracts were washed with brine (2 mL×3), dried over $Na_2SO_4$ and concentrated. The resulting residue was purified by preparative TLC ($CH2C_{12}$/MeOH ($NH_3$ solution)=15:1) to obtain the title product (17 mg, 55%). MS: M/e 490 $(M+1)^+$.

Step C: (S)-7-((1-(3-(methylamino)propyl)piperidin-4-yl)methyl)-2-(pent-2-yloxy)imidazo[2,1-f][1,2,4]triazin-4-amine

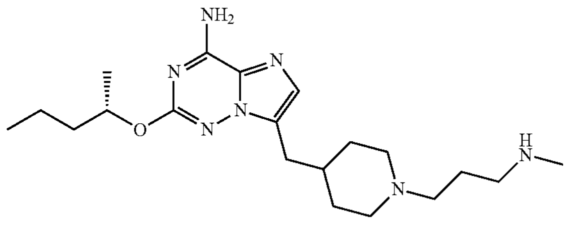 [SMILES: CCC[C@H](C)Oc1nc(N)c2ncc(CC3CCN(CCCNC)CC3)n2n1]

The product of step B (17 mg, 0.035 mmol) in HCl/EA solution (4 M, 5 mL) was stirred at room temperature for 5 h. The mixture was concentrated, alkalized with NaOH (4 M, aqueous solution) and extracted with $CH_2Cl_2$ (2 mL×5). The combined extracts were washed with brine (5 mL×3), dried over $Na_2SO_4$ and concentrated. The resulting residue was purified by preparative TLC ($CH_2Cl_2MeOH$ ($NH_3$ solution)=10:1) to obtain the title product (3.5 mg, 26%). $^1H$ NMR (400 MHz, CD3OD) δ 7.35 (d, J=5.2 Hz, 1H), 5.18-5.05 (m, 1H), 3.46-3.34 (m, 2H), 3.11-3.04 (m, 2H), 3.03-2.85 (m, 4H), 2.72 (s, 3H), 2.14-1.99 (m, 3H), 1.97-1.84 (m, 2H), 1.82-1.68 (m, 1H), 1.67-1.41 (m, 5H), 1.36 (d, J=6.0 Hz, 1H), 0.97 (t, J=7.2 Hz, 3H) ppm. MS: M/e 390 $(M+1)^+$.

Compound B20: 2—(((S)-pent-2-yl)oxy)-7-((1-(pyrrolidin-2-ylmethyl)piperidin-4-yl)methyl)imidazo[2,1-f][1,2,4]triazin-4-amine

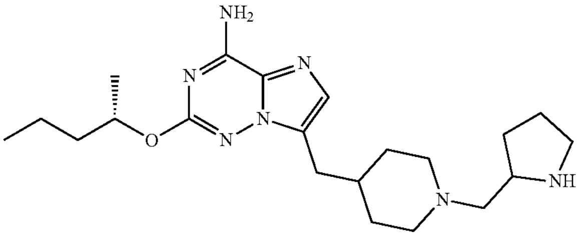

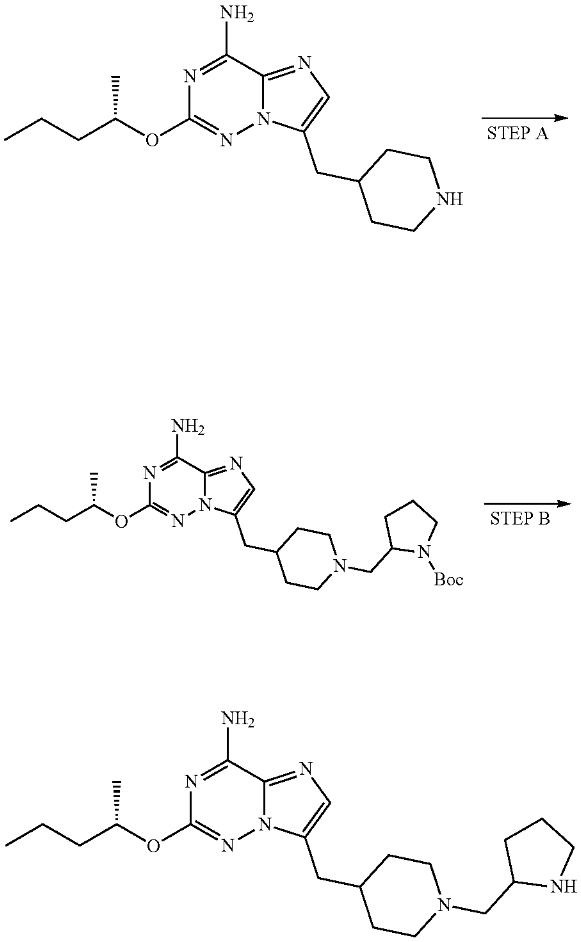

Step A: Tert-butyl 2-((4-(4-amino-2-(((S)-pent-2-yl)oxy)imidazo[2,1-f][1,2,4]triazin-7-yl)methyl)piperidin-1-yl)methyl)pyrrolidin-1-carboxylate

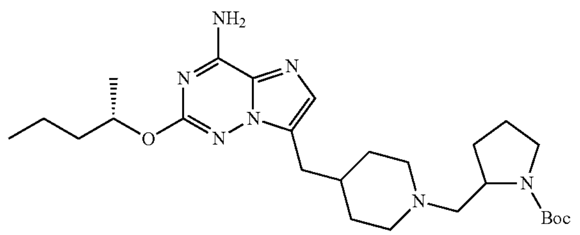 [SMILES: CCC[C@H](C)Oc1nc(N)c2ncc(CC3CCN(CC4CCCN4C(=O)OC(C)(C)C)CC3)n2n1]

To a stirred solution of (S)-2-(pent-2-yloxy)-7-(piperidin-4-ylmethyl)imidazo[2,1-f][1,2,4]triazin-4-amine (20 mg, 0.063 mmol) and tert-butyl 2-formylpyrrolidin-1-carboxylate (25 mg, 0.126 mmol) in THF (5 mL), AcOH (2 droplets) was added. The mixture was then stirred at room temperature for half an hour, and then $NaBH(OAc)_3$ (27 mg, 0.126 mmol) was added. Thereafter, the reaction mixture was stirred overnight. The reaction mixture was concentrated to obtain a residue, and the residue was purified by preparative TLC ($CH_2Cl_2$/MeOH=10:1) to obtain the target compound (23 mg, 72.8%). MS: M/e 502 $(M+1)^+$.

Step B: 2-(((S)-pent-2-yl)oxy)-7-((1-(pyrrolidin-2-ylmethyl)piperidin-4-yl)methyl)imidazo[2,1-f][1,2,4]triazin-4-amine

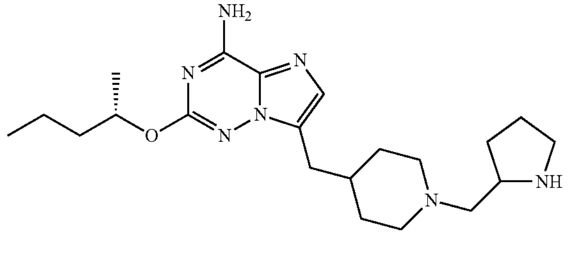 [SMILES: CCC[C@H](C)Oc1nc(N)c2ncc(CC3CCN(CC4CCCN4)CC3)n2n1]

A mixture of the product of step A (22 mg, 0.045 mmol) in EtOAc/HCl (4.0 M, 5 mL) was stirred overnight. The reaction mixture was concentrated to obtain a residue, and the residue was purified by preparative HPLC to obtain the target compound (10 mg). $^1$H NMR (400 MHz, DMSO-d6) & 9.33 (s, 1H), 9.08 (s, 1H), 8.84 (s, 1H), 8.14 (s, 1H), 8.06 (s, 1H), 7.37 (s, 1H), 5.06-4.94 (m, 1H), 3.94 (s, 1H), 3.66-3.30 (m, 4H), 3.24 (s, 2H), 3.08-2.71 (m, 4H), 2.22-2.10 (m, 1H), 2.09-1.74 (m, 5H), 1.73-1.60 (m, 2H), 1.61-1.34 (m, 5H), 1.28 (d, J=6.0 Hz, 3H), 0.91 (t, J=7.2 Hz, 3H) ppm. MS: M/e 402 $(M+1)^+$.

Compound B21: 7-((4-(methylamino)piperidin-1-yl)methyl)-2-(pent-2-yloxy)imidazo[2,1-f][1,2,4]triazin-4-amine

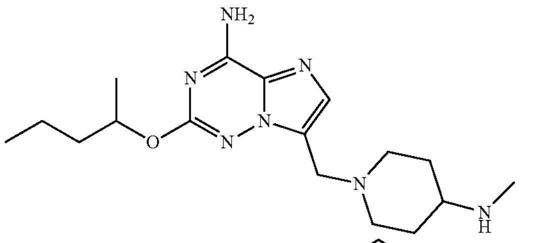

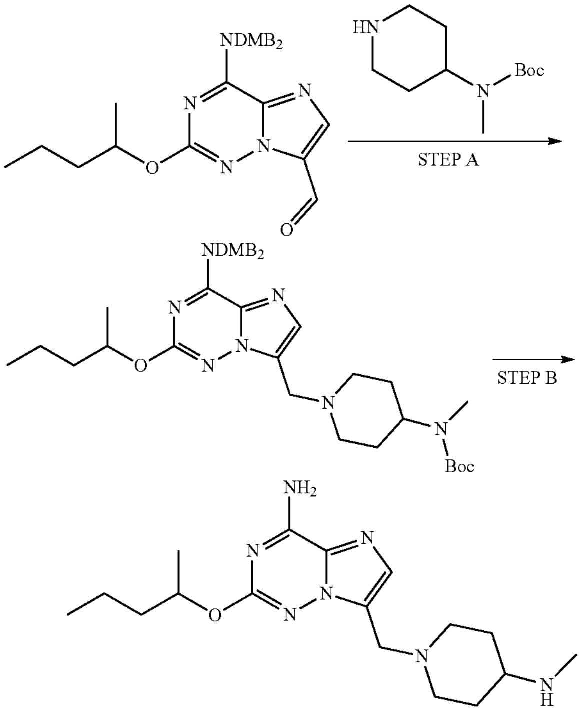

Step A: Tert-butyl (1-((4-(bis(2,4-dimethoxybenzyl)amino)-2-(pent-2-yloxy)imidazo[2,1-f][1,2,4]triazin-7-yl)methyl)piperidin-4-yl)(methyl)carbamate

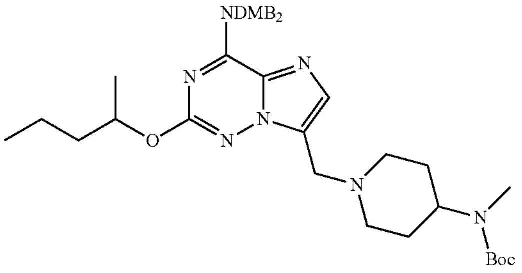

To a solution of 4-(bis(2,4-dimethoxybenzyl)amino)-2-(pent-2-yloxy)imidazo[2,1-f][1,2,4]triazin-7-formaldehyde (200 mg, 0.364 mmol) and tert-butyl methyl(piperidin-4-yl)carbamate (136 mg, 0.732 mmol) in THF (5 mL), AcOH (44 mg, 0.733 mmol) and $NaBH(AcO)_3$ (233 mg, 1.09 mmol) were added. The reaction mixture was stirred at 25° C. for 3 h. After completion of the reaction, the reaction mixture was quenched with water (20 mL) and extracted with EtOAc (3×30 mL). The combined organic layers were dried over $Na_2SO_4$ and concentrated under vacuum to obtain a residue. The residue was purified by column chromatography on silica gel eluted with ethyl acetate (80%) in petroleum ether to obtain the title compound (230 mg, 85%). MS: M/e 748 $(M+1)^+$.

Step B: 7-((4-(methylamino)piperidin-1-yl)methyl)-2-(pent-2-yloxy)imidazo[2,1-f][1,2,4]triazin-4-amine

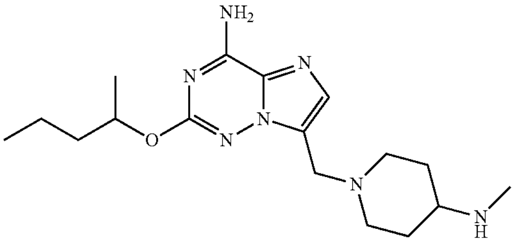 [SMILES: CCCC(C)Oc1nc(N)c2ncc(CN3CCC(NC)CC3)n2n1]

The product of step A (230 mg, 0.307 mmol) was dissolved in TFA (5 mL) under $N_2$. The reaction mixture was stirred at 70° C. for 12 h. After completion of the reaction, the reaction mixture was quenched with an aqueous $NaHCO_3$ solution (30 mL) and extracted with EtOAc (3×30 mL). The combined organic layers were dried over $Na_2SO_4$ and concentrated under vacuum to obtain a residue. The residue was purified by preparative HPLC under the following conditions: column: XBridge Prep C18 OBD column 19×150 mm 5 um; mobile phase A: water (0.1% TFA), mobile phase B: ACN; flow rate: 17 mL/min; gradient: 5% B to 30% B in 11 min; 214/254 nm, thereby obtaining the title compound (64 mg, 30%). $^1$H NMR (400 MHz, DMSO-$d_6$) δ 8.93 (br.s, 2H), 8.39 (s, 1H), 8.29 (s, 1H), 7.66 (s, 1H), 5.05 (dd, J=12.4, 6.4 Hz, 1H), 4.57 (s, 2H), 3.57 (s, 3H), 3.20-3.03 (m, 3H), 2.55 (s, 3H), 2.19 (d, J=12.4 Hz, 2H), 1.88-1.60 (m, 3H), 1.59-1.47 (m, 1H), 1.46-1.31 (m, 2H), 1.28 (d, J=6.4 Hz, 3H), 0.91 (t, J=7.2 Hz, 3H) ppm. MS: M/e 348 $(M+1)^+$.

Compound B22: 7-((4-((methylamino)methyl)piperidin-1-yl)methyl)-2-(pent-2-yloxy)imidazo[2,1-f][1,2,4]triazin-4-amine

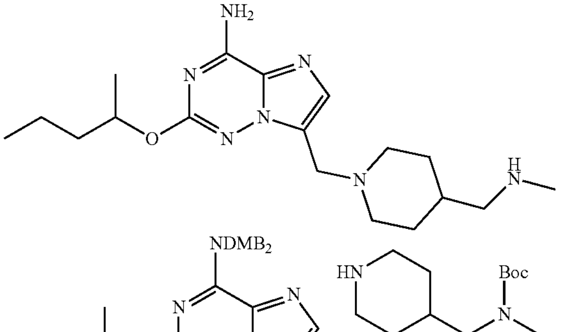

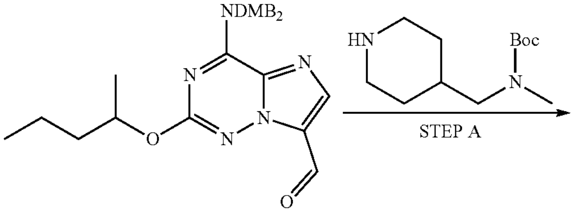

-continued

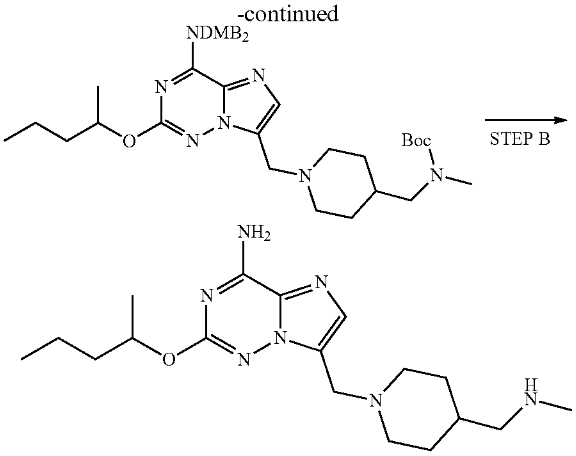

Step A: Tert-butyl ((1-(4-(bis(2,4-dimethoxybenzyl)amino)-2-(pent-2-yloxy)imidazo[2,1-f][1,2,4]triazin-7-yl)methyl)piperidin-4-yl)methyl)(methyl)carbamate

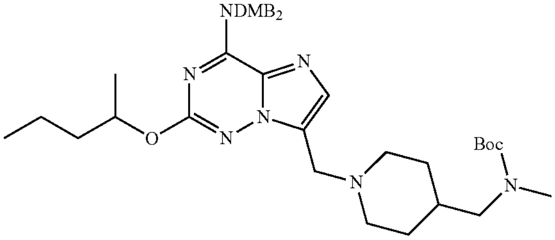

To a solution of 4-(bis(2,4-dimethoxybenzyl)amino)-2-(pent-2-yloxy)imidazo[2,1-f][1,2,4]triazin-7-formaldehyde (200 mg, 0.364 mmol) and tert-butyl methyl(piperidin-4-yl) carbamate (166 mg, 0.728 mmol) in THF (5 mL), AcOH (44 mg, 0.733 mmol) and $NaBH(AcO)_3$ (233 mg, 1.09 mmol) were added. The reaction mixture was stirred at 25° C. for 3 h. After completion of the reaction, the reaction mixture was quenched with water (20 mL) and extracted with EtOAc (3×30 mL). The combined organic layers were dried over $Na_2SO_4$ and concentrated under vacuum to obtain a residue. The residue was purified by column chromatography on silica gel eluted with ethyl acetate (80%) in petroleum ether to obtain the title compound (210 mg, 76%). MS: M/e 762 $(M+1)^+$.

Step B: 7-((4-((methylamino)methyl)piperidin-1-yl)methyl)-2-(pent-2-yloxy)imidazo[2,1-f][1,2,4]triazin-4-amine

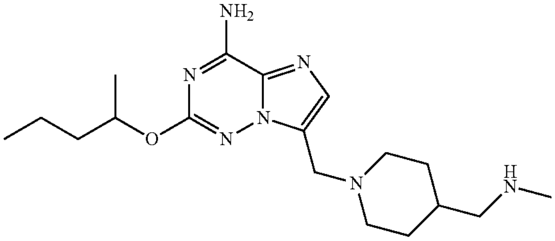 [SMILES: CCCC(C)Oc1nc(N)c2ncc(CN3CCC(CNC)CC3)n2n1]

Tert-butyl ((1-((4-(bis(2,4-dimethoxybenzyl)amino)-2-(pent-2-yloxy)imidazo[2,1-f][1,2,4]triazin-7-yl)methyl)piperidin-4-yl)methyl)(methyl)carbamate (210 mg, 0.276 mmol) was dissolved in TFA (5 mL) under N2. The reaction mixture was stirred at 70° C. for 12 h. After completion of the reaction, the reaction mixture was quenched with an aqueous $NaHCO_3$ solution (30 mL) and extracted with EtOAc (3×30 mL). The combined organic layers were dried over $Na_2SO_4$ and concentrated under vacuum to obtain a residue. The residue was purified by preparative HPLC under the following conditions: column: XBridge Prep C18 OBD column 19×150 mm 5 um; mobile phase A: water (0.1% TFA), mobile phase B: ACN; flow rate: 17 mL/min; gradient: 5% B to 30% B in 11 min; 214/254 nm, thereby obtaining the title compound (15 mg, 15%). $^1$H NMR (400 MHz, DMSO-d6) δ 10.05 (br.s, 1H), 8.56 (br.s, 2H), 8.40-8.25 (m, 2H), 7.67 (s, 1H), 5.06 (dd, J=12.4, 6.4 Hz, 1H), 4.54 (s, 2H), 3.45-3.35 (m, 2H), 3.02 (s, 3H), 2.82 (d, J=4.4 Hz, 2H), 2.55 (t, J=5.2 Hz, 3H), 1.90 (d, J=13.2 Hz, 3H), 1.73-1.49 (m, 2H), 1.49-1.31 (m, 4H), 1.28 (d, J=6.4 Hz, 3H), 0.91 (t, J=7.2 Hz, 3H) ppm. MS: M/e 362 $(M+1)^+$.

Compound B23: (S)-7-([1,4'-bipiperidin]-4-ylmethyl)-2-(pent-2-yloxy)imidazo[2,1-f][1,2,4]triazin-4-amine

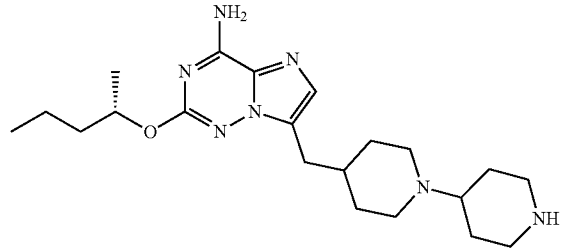

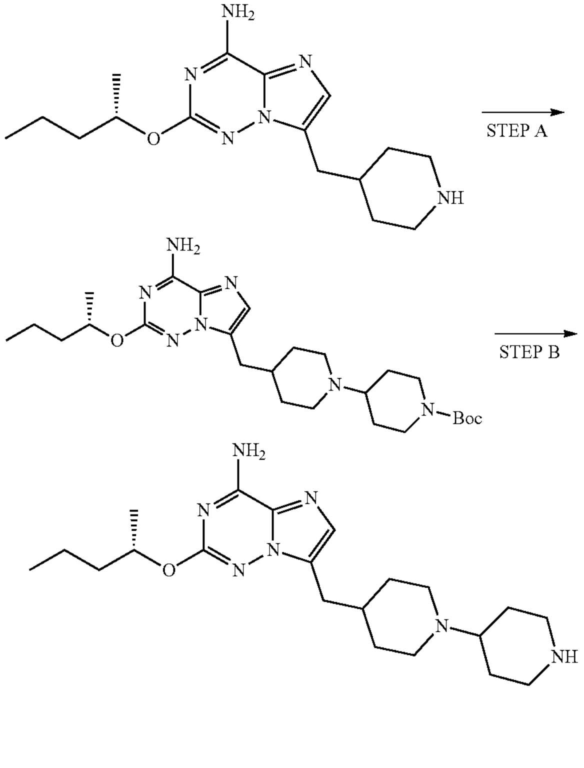

Step A: Tert-butyl(S)-4-((4-amino-2-(pent-2-yloxy)imidazo[2,1-f][1,2,4]triazin-7-yl)methyl) tert-butyl-[1,4'-bipiperidin]-1'-carboxylate

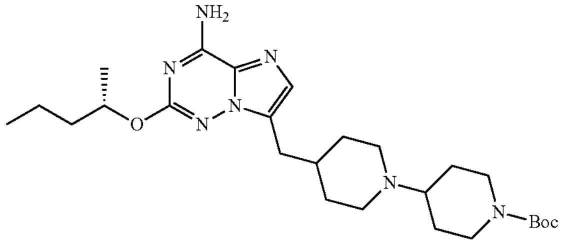 [SMILES: CCC[C@H](C)Oc1nc(N)c2ncc(CC3CCN(C4CCN(C(=O)OC(C)(C)C)CC4)CC3)n2n1]

A mixture of (S)-2-(pent-2-yloxy)-7-(piperidin-4-ylmethyl)imidazo[2,1-f][1,2,4]triazin-4-amine (20 mg, 0.06 mmol), tert-butyl 4-oxopiperidin-1-carboxylate (19 mg, 0.09 mmol) and titanium tetraisopropoxide (54 mg, 0.19 mmol) in EtOH (5 mL) was stirred at room temperature for 3 h. Then, sodium borohydride (27 mg, 0.12 mmol) was added and the mixture was stirred at room temperature for 1 h. The mixture was quenched with water (0.5 mL), extracted with DCM (20 mL), washed with water (5 ml), concentrated and purified by column chromatography (DCM/MeOH=20:1-3:1) to obtain the product (29 mg, 92.04%). MS: M/e 502 $(M+1)^+$.

Step B: (S)-7-([1,4'-bipiperidin]-4-ylmethyl)-2-(pent-2-yloxy)imidazo[2,1-f][1,2,4]triazin-4-amine

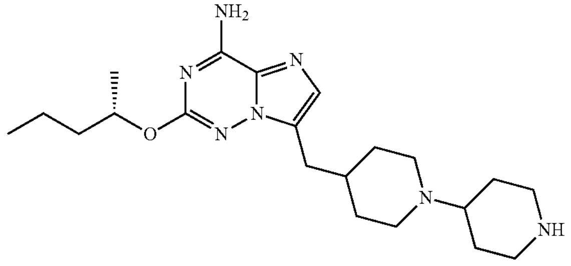 [SMILES: CCC[C@H](C)Oc1nc(N)c2ncc(CC3CCN(C4CCNCC4)CC3)n2n1]

A mixture of the product of step A (29 mg, 0.06 mmol) and TFA (0.5 mL) in DCM (3 mL) was stirred at room temperature for 2 h. The mixture was concentrated and purified by preparative HPLC to obtain the product (18 mg, 74.5%). $^1$H NMR (400 MHz, DMSO-d6) δ 9.40 (br.s, 1H), 8.73 (d, J=9.1 Hz, 1H), 8.43 (d, J=10.1 Hz, 1H), 8.11 (s, 1H), 8.03 (s, 1H), 7.35 (s, 1H), 5.01-4.99 (m, 1H), 3.48-3.35 (m, 5H), 2.98-2.86 (m, 4H), 2.79 (d, J=6.5 Hz, 2H), 2.15 (d, J=12.1 Hz, 2H), 1.98 (s, 1H), 1.86 (d, J=13.5 Hz, 2H), 1.79-1.69 (m, 2H), 1.69-1.62 (m, 1H), 1.60-1.42 (m, 3H), 1.42-1.32 (m, 2H), 1.28 (d, J=6.1 Hz, 3H), 0.91 (t, J=7.3 Hz, 3H) ppm. MS: M/e 402 $(M+1)^+$.

Compound B24: 2-(4-amino-2-(pent-2-yloxy)imidazo[2,1-f][1,2,4]triazin-7-yl)-7-azaspiro[3.5]nona-2-ol

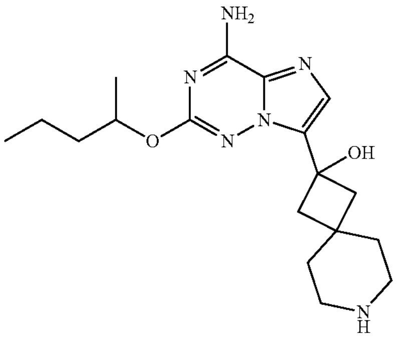

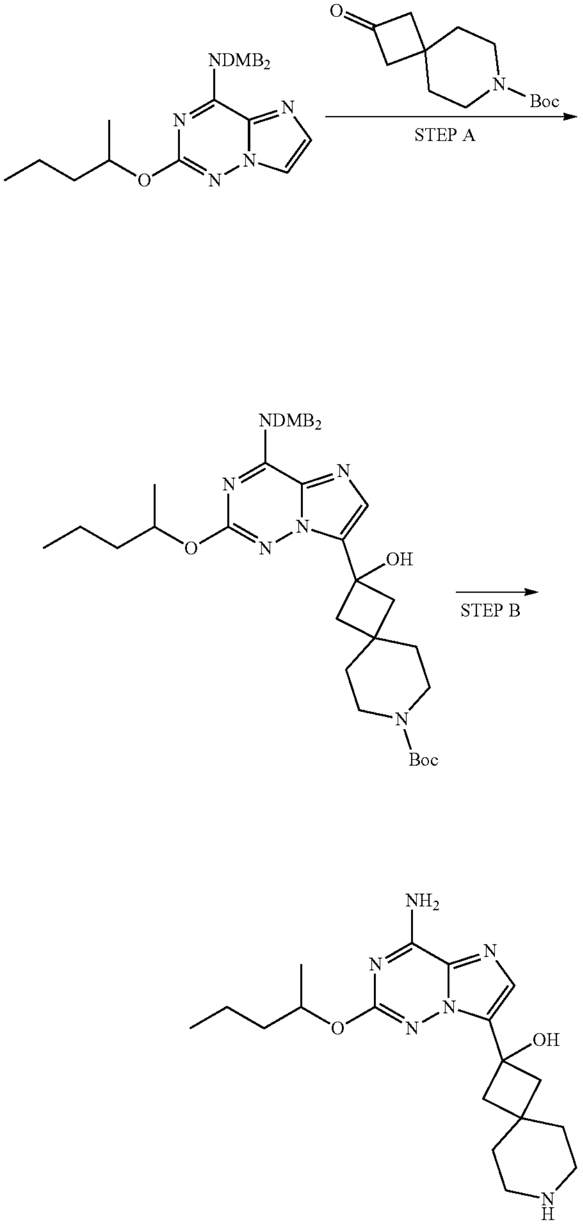

Step A: Tert-butyl 2-(4-(bis(2,4-dimethoxybenzyl)amino)-2-(pent-2-yloxy)imidazo[2,1-f][1,2,4]triazin-7-yl)-2-hydroxy-7-azaspiro[3.5]nonan-7-carboxylate

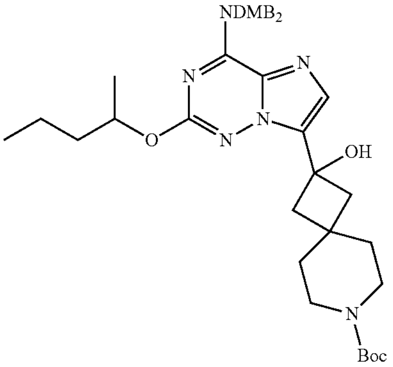

At −78° C. under N2, to a solution of N,N-bis(2,4-dimethoxybenzyl)-2-(pent-2-yloxy)imidazo[2,1-f][1,2,4]triazin-4-amine (300 mg, 0.576 mmol) in THF (8 mL), n-BuLi (1.8 mL, 2.88 mmol) was added. After the mixture was stirred at −78° C. for 0.5 h, tert-butyl 2-oxo-7-azaspiro[3.5]nonan-7-carboxylate (165 mg, 0.691 mmol) was added. The reaction mixture was warmed to −78° C. and stirred for 2.5 h. After completion of the reaction, the reaction mixture was quenched with an aqueous $NH_4Cl$ solution (20 mL) and extracted with EtOAc (3x30 mL). The combined organic layers were dried over $Na_2SO_4$ and concentrated under vacuum to obtain a residue. The residue was purified by column chromatography on silica gel eluted with ethyl acetate (40%) in petroleum ether to obtain the title compound (210 mg, 48%). MS: M/e 761 $(M+1)^+$.

Step B: 2-(4-amino-2-(pent-2-yloxy)imidazo[2,1-f][1,2,4]triazin-7-yl)-7-azaspiro[3.5]nona-2-ol

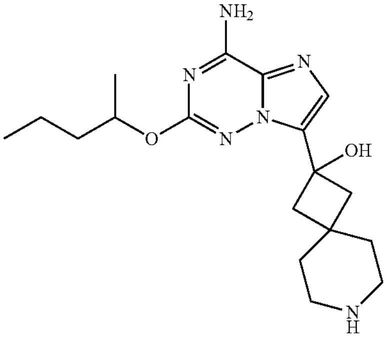 [SMILES: CCCC(C)Oc1nc(N)c2ncc(C3(O)CC4(CCNCC4)C3)n2n1]

Tert-butyl 2-(4-(bis(2,4-dimethoxybenzyl)amino)-2-(pent-2-yloxy)imidazo[2,1-f][1,2,4]triazin-7-yl)-2-hydroxy-7-azaspiro[3.5]nonan-7-carboxylate (210 mg, 0.276 mmol) was dissolved in TFA (5 mL) and $H_2O$ (0.5 mL) under N2. The reaction mixture was stirred at 35° C. for 12 h. After completion of the reaction, the reaction mixture was quenched with an aqueous $NaHCO_3$ solution (30 mL) and extracted with EtOAc (3x80 mL). The combined organic layers were dried over $Na_2SO_4$ and concentrated under vacuum to obtain a residue. The residue was purified by preparative HPLC under the following conditions: column:

XBridge Prep C18 OBD column 19×150 mm 5 um; mobile phase A: water (0.1% TFA), mobile phase B: ACN; flow rate: 17 mL/min; gradient: 5% B to 45% B in 11 min; 214/254 nm, thereby obtaining the title compound (51 mg, 51%). $^1H$ NMR (400 MHz, DMSO-d6) δ 8.27 (br.s, 2H), 8.20-7.98 (m, 2H), 7.43 (s, 1H), 5.45 (s, 1H), 4.96 (dd, J=12.4, 6.4 Hz, 1H), 3.15-2.80 (m, 5H), 2.74-2.64 (m, 2H), 2.18 (d, J=12.6 Hz, 2H), 1.90 (s, 2H), 1.72-1.46 (m, 4H), 1.45-1.32 (m, 2H), 1.28 (t, J=6.4 Hz, 3H), 0.90 (t, J=7.2 Hz, 3H) ppm. MS: M/e 361 $(M+1)^+$.

Compound B25:7-(azepan-4-ylmethyl)-2-(((S)-pent-2-yl)oxy)imidazo[2,1-f][1,2,4]triazin-4-amine

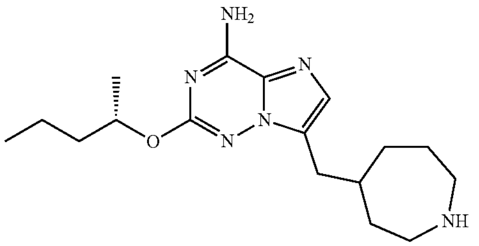

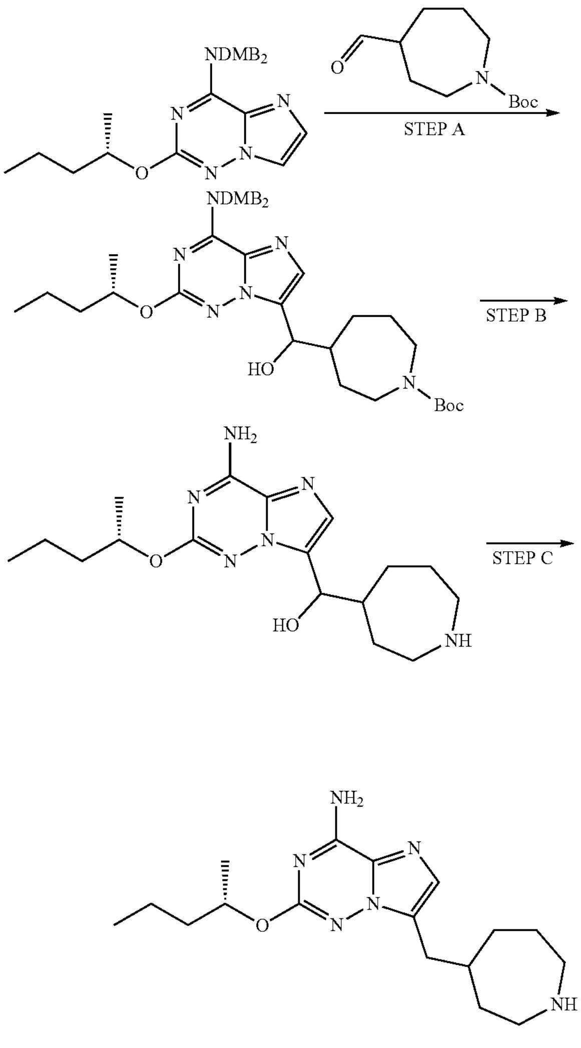

Step A: Tert-butyl 4-((4-(bis(2,4-dimethoxybenzyl)amino)-2-(((S)-pent-2-yl)oxy)imidazo[2,1-f][1,2,4]triazin-7-yl)(hydroxy)methyl) azepan-1-carboxylate

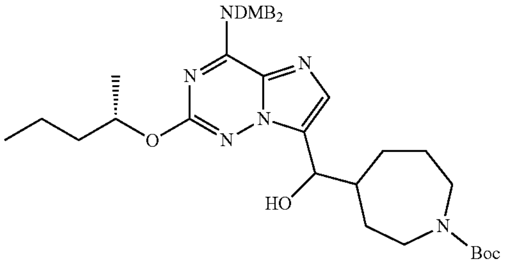

To a stirred solution of (S)—N,N-bis(2,4-dimethoxybenzyl)-2-(pent-2-yloxy)imidazo[2,1-f][1,2,4]triazin-4-amine (200 mg, 0.383 mmol) in THF (8 mL) cooled to −78° C. under nitrogen atmosphere, n-BuLi (1.6 M in hexane, 0.78 mmol, 0.48 mL) was added dropwise. After the mixture was stirred for 30 min, a solution of tert-butyl 4-formylazepan-1-carboxylate (150 mg, 0.66 mmol) in THF (2 mL) was slowly added. The reaction mixture was slowly warmed to room temperature and stirred overnight. The reaction mixture was poured into a saturated ammonium chloride solution and extracted with EtOAc (15 mL×3). The combined organic phases were washed with brine, dried over $Na_2SO_4$ and concentrated under vacuum. The crude product was purified by column chromatography to obtain the title product (120 mg, 41.3%). MS: M/e 748.9 $(M+1)^+$.

Step B: (4-amino-2-(((S)-pent-2-yl)oxy)imidazo[2,1-f][1,2,4]triazin-7-yl)(azepan-4-yl)methanol

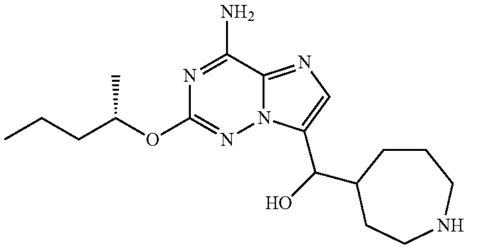 [SMILES: CCC[C@H](C)Oc1nc(N)c2ncc(C(O)C3CCCNCC3)n2n1]

$H_2O$ (2 ml) was added to a stirred mixture of the product of step A (120 mg, 0.16 mmol) in TFA (8 ml). Thereafter, the reaction mixture was stirred at 30° C. overnight. The reaction mixture was cooled to room temperature and concentrated under vacuum. 1 M HCl solution (20 ml) was added to the residue and the mixture was filtered. The filtrate was extracted with DCM (20 ml). The aqueous phase was adjusted to a pH of 12-13 with 2 M aqueous NaOH solution and extracted with DCM (20 mL×3). The organic phase was washed with brine, dried over $Na_2SO_4$ and concentrated under vacuum to obtain the product (35 mg, 62.5%), which was directly used in the next step. MS: Me 349 $(M+1)^+$.

Step C: 7-(azepan-4-ylmethyl)-2-(((S)-pent-2-yl)oxy)imidazo[2,1-f][1,2,4]triazin-4-amine

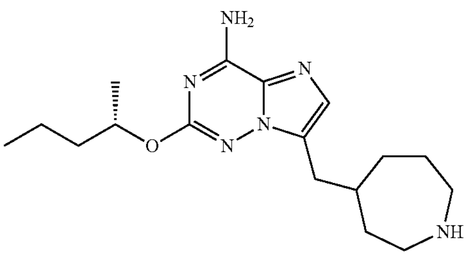 [SMILES: CCC[C@H](C)Oc1nc(N)c2ncc(CC3CCCNCC3)n2n1]

$Et_3SiH$ (5 ml) was added to a stirred mixture of (4-amino-2-(((S)-pent-2-yl)oxy)imidazo[2,1-f][1,2,4]triazin-7-yl)(azepan-4-yl)methanol (35 mg, 0.1 mmol) in TFA (5 ml). Thereafter, the reaction mixture was stirred at 80° C. for 2 d. The mixture was cooled to room temperature and concentrated under vacuum. The residue was purified by preparative HPLC to obtain the target compound (10 mg, 22.4%). $^1H$ NMR (400 MHz, MeOH-d6) δ 7.59 (s, 1H), 5.18-5.13 (m, 1H), 3.44-3.36 (m, 2H), 3.28 (s, 1H), 3.14 (m, 2H), 2.96 (dd, J=16.6, 7.0 Hz, 2H), 2.10-1.95 (m, 2H), 1.83-1.75 (m, 2H), 1.72-1.61 (m, 2H), 1.53-1.44 (m, 4H), 1.39 (d, J=6.1 Hz, 3H), 1.09-1.04 (m, 1H), 0.99 (t, J=7.3 Hz, 3H) ppm. MS: M/e 333 $(M+1)^+$.

Compound B26: 2—(((S)-pent-2-yl)oxy)-7-(pyrrolidin-3-ylmethyl)imidazo[2,1-f][1,2,4]triazin-4-amine

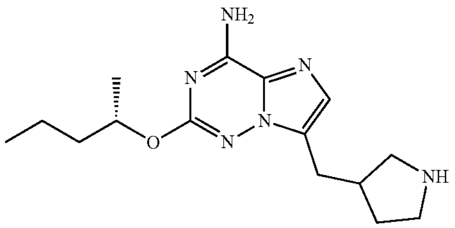

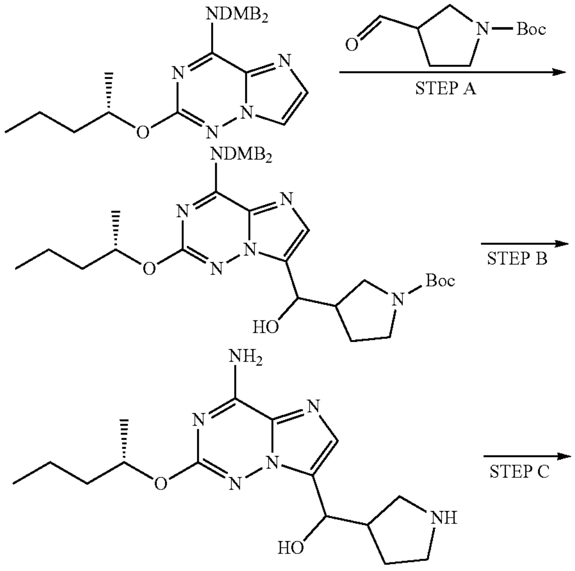

-continued

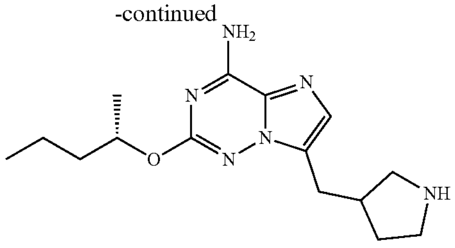

Step A: Tert-butyl 3-((4-(bis(2,4-dimethoxybenzyl)amino)-2-(((S)-pent-2-yl)oxy)imidazo[2,1-f][1,2,4]triazin-7-yl)(hydroxy)methyl)pyrrolidin-1-carboxylate

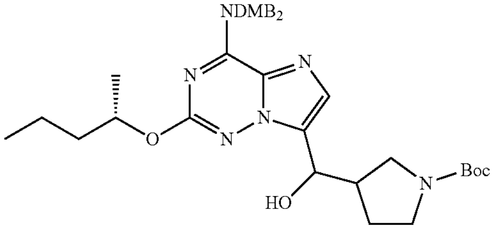

To a stirred solution of (S)-N,N-bis(2,4-dimethoxybenzyl)-2-(pent-2-yloxy)imidazo[2,1-f][1,2,4]triazin-4-amine (200 mg, 0.383 mmol) in THF (8 mL) cooled to −78° C. under nitrogen atmosphere, n-BuLi (1.6 M in hexane, 0.78 mmol, 0.48 mL) was added dropwise. After the mixture was stirred for 30 min, a solution of tert-butyl 3-formylpyrrolidin-1-carboxylate (150 mg, 0.75 mmol) in THF (2 mL) was slowly added. The reaction mixture was slowly warmed to room temperature and stirred overnight. The reaction mixture was poured into a saturated ammonium chloride solution and extracted with EtOAc (15 mL×3). The combined organic phases were washed with brine, dried over $Na_2SO_4$ and concentrated under vacuum. The crude product was purified by column chromatography to obtain the title product (110 mg, 40%). MS: M/e 721 $(M+1)^+$.

Step B: (4-amino-2-(((S)-pent-2-yl)oxy)imidazo[2,1-f][1,2,4]triazin-7-yl)(pyrrolidin-3-yl)methanol

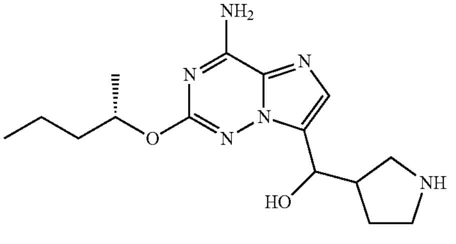 [SMILES: CCC[C@H](C)Oc1nc(N)c2ncc(C(O)C3CCNC3)n2n1]

$H_2O$ (2 ml) was added to a stirred mixture of the product of step A (110 mg, 0.152 mmol) in TFA (8 ml). Thereafter, the reaction mixture was stirred at 30° C. overnight. The reaction mixture was cooled to room temperature and concentrated under vacuum. 1 M HCl solution (20 ml) was added to the residue and the mixture was filtered. The filtrate was extracted with DCM (20 ml). The aqueous phase was adjusted to a pH of 12-13 with 2 M aqueous NaOH solution and extracted with DCM (20 mL×3). The organic phase was washed with brine, dried over $Na_2SO_4$ and concentrated under vacuum to obtain the product (30 mg, 61.4%), which was directly used in the next step. MS: M/e 321 $(M+1)^+$.

Step C: 2-(((S)-pent-2-yl)oxy)-7-(pyrrolidin-3-ylmethyl)imidazo[2,1-f][1,2,4]triazin-4-amine

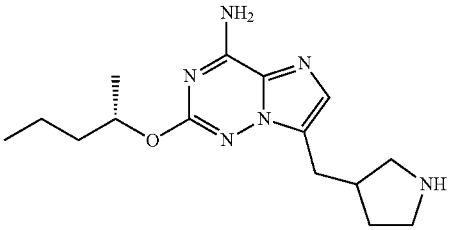 [SMILES: CCC[C@H](C)Oc1nc(N)c2ncc(CC3CCNC3)n2n1]

$Et_3SiH$ (5 ml) was added to a stirred mixture of the product of step B (30 mg, 0.093 mmol) in TFA (5 ml). Thereafter, the reaction mixture was stirred at 80° C. for 3 d. The mixture was cooled to room temperature and concentrated under vacuum. The residue was purified by preparative HPLC to obtain the target compound (12 mg, 32%). $^1H$ NMR (400 MHz, MeOH-d6) δ 7.90 (s, 1H), 5.44-5.40 (m, 1H), 3.78-3.66 (m, 2H), 3.56-5.53 (m, 2H), 3.37 (d, J=7.1 Hz, 2H), 3.34-3.25 (m, 1H), 3.16-3.13 (m, 1H), 2.50-2.47 (m, 1H), 2.11-2.03 (m, 2H), 1.89-1.85 (m, 1H), 1.82-1.68 (m, 2H), 1.64 (d, J=6.0 Hz, 3H), 1.23 (t, J=7.2 Hz, 3H) ppm. MS: M/e 305 $(M+1)^+$.

Compound B27: 7-((2-methylpiperidin-4-yl)methyl)-2-(((S)-pent-2-yl)oxy)imidazo[2,1-f][1,2,4]triazin-4-amine

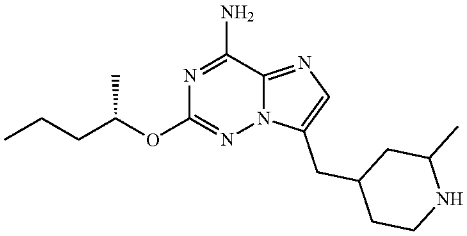

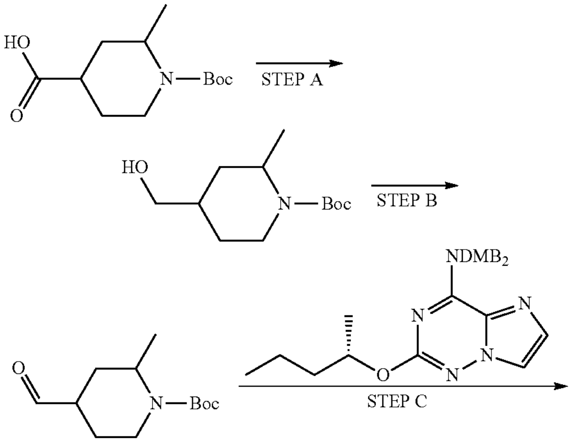

-continued

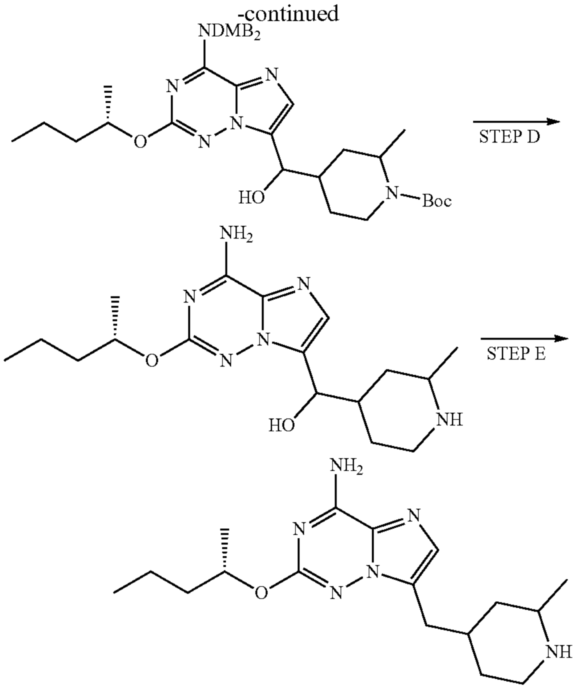

100

Step A: Tert-butyl 4-(hydroxymethyl)-2-methylpiperidin-1-carboxylate

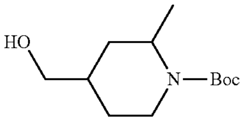 [SMILES: CC1CC(CO)CCN1C(=O)OC(C)(C)C]

$BH_3$-THF (1 M, 3 mL, 3 mmol) was added to a solution of 1-(tert-butoxycarbonyl)-2-methylpiperidin-4-carboxylic acid (243 mg, 1 mmol) in THF (10 mL) at 0° C. The reaction mixture was stirred at room temperature overnight. An aqueous ammonium chloride solution was added and the mixture was extracted with ethyl acetate. The combined organic extracts were dried over sodium sulfate, filtered and evaporated to obtain the product (220 mg, 100%), which was directly used in the next step. MS: m/e 230 $(M+1)^+$.

Step B: Tert-butyl 4-formyl-2-methylpiperidin-1-carboxylate

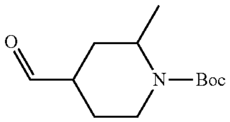 [SMILES: CC1CC(C=O)CCN1C(=O)OC(C)(C)C]

To a solution of tert-butyl 4-(hydroxymethyl)-2-methylpiperidin-1-carboxylate (220 mg, 1 mmol) in DCM (10 mL) at 0° C., Dess-Martin periodinane (636 mg, 1.5 mmol) was added. The reaction mixture was stirred at room temperature for 2 h. An aqueous $NaHCO_3$ solution was added and the mixture was extracted with ethyl acetate. The combined organic extracts were dried over sodium sulfate, filtered and evaporated. The crude product was purified by column chromatography to obtain the title product (140 mg, 61.7%). $^1$H NMR (400 MHz, $CDCl_3$) δ 9.83 (s, 1H), 4.28 (td, J=6.6, 4.5 Hz, 1H), 3.85 (ddd, J=13.9, 5.5, 2.5 Hz, 1H), 2.91 (ddd, J=13.9, 12.7, 3.8 Hz, 1H), 2.50 (t, J=4.7 Hz, 1H), 2.15-2.09 (m, 1H), 2.08-2.03 (m, 1H), 1.91 (ddd, J=14.1, 6.4, 2.5 Hz, 1H), 1.71 (dt, J=13.3, 6.4 Hz, 1H), 1.50-1.40 (m, 9H), 1.06 (d, J=6.9 Hz, 3H). MS: m/e228 $(M+1)^+$.

Step C: Tert-butyl 4-((4-(bis(2,4-dimethoxybenzyl) amino)-2-(((S)-pent-2-yl)oxy)imidazo[2,1-f][1,2,4] triazin-7-yl)(hydroxy)methyl)piperidin-2-methylpiperidin-1-carboxylate

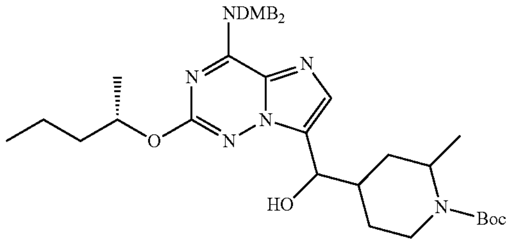

To a solution of (S)—N,N-bis(2,4-dimethoxybenzyl)-2-(pent-2-yloxy)imidazo[2,1-f][1,2,4]triazin-4-amine (200 mg, 0.38 mmol) in THF (8 mL), a solution of n-BuLi (1.6 M, 0.48 mL, 0.76 mmol) was added dropwise at a temperature of −75° C. to −65° C. One hour later, a suspension of tert-butyl 4-formyl-2-methylpiperidin-1-carboxylate (140 mg, 0.63 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (110 mg, crude yellow oil). MS: M/e 749 $(M+1)^+$.

Step D: (4-amino-2-(((S)-pent-2-yl)oxy)imidazo[2,1-f][1,2,4]triazin-7-yl)(2-methylpiperidin-4-yl) methanol

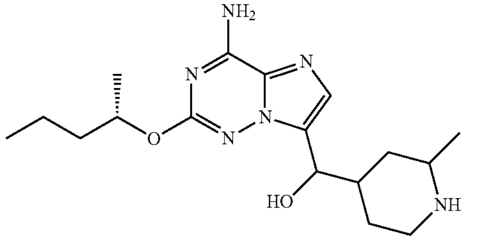 [SMILES: CCC[C@H](C)Oc1nc(N)c2ncc(C(O)C3CCNC(C)C3)n2n1]

$H_2O$ (4 mL) was added to a mixture of the product of step C (110 mg, crude) in TFA (8 mL), and the resulting mixture was stirred at room temperature for 2 d. The mixture was concentrated to dryness. $H_2O$ was added to the residue and the mixture was filtered. The filtrate was washed with DCM, and adjusted to a pH of 12-13 with 2 M NaOH solution. The solution was extracted with DCM (20 mL×3). The organic phase was washed with brine, dried over $Na_2SO_4$, filtered and concentrated to obtain the target compound (35 mg), which was directly used in the next step. MS: M/e 349 $(M+1)^+$.

Step E: 7-((2-methylpiperidin-4-yl)methyl)-2-(((S)-pent-2-yl)oxy)imidazo[2,1-f][1,2,4]triazin-4-amine

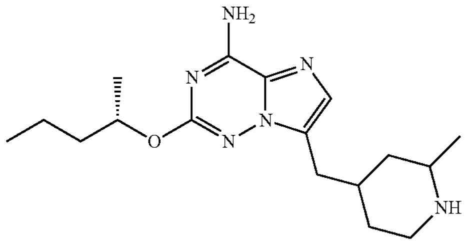 [SMILES: CCC[C@H](C)Oc1nc(N)c2ncc(CC3CCNC(C)C3)n2n1]

$Et_3SiH$ (4 mL) was added to a mixture of the product of step D (35 mg, crude) in TFA (4 mL), and the resulting mixture was stirred at 85° C. for 2 h. The mixture was cooled to room temperature and concentrated to dryness. The residue was purified by preparative HPLC to obtain the target compound (17 mg, 34.8% for three steps). $^1$H NMR (400 MHz, DMSO-d6) δ 8.73 (s, 1H), 8.13 (br.s, 3H), 7.46 (s, 1H), 5.00 (m, 1H), 3.27 (s, 2H), 3.09 (s, 1H), 2.87 (s, 2H), 2.77 (s, 1H), 2.00 (s, 1H), 1.78 (s, 2H), 1.66 (s, 1H), 1.57 (s, 1H), 1.38 (s, 3H), 1.28 (d, J=6.0 Hz, 3H), 1.16 (d, J=6.2 Hz, 3H), 1.11 (d, J=10.9 Hz, 1H), 0.91 (t, J=7.3 Hz, 3H) ppm. MS: M/e 333 $(M+1)^+$.

Compound B28: 3-((4-amino-7-(piperidin-4-ylmethyl)imidazo[2,1-f][1,2,4]triazin-2-yl)oxy)hexan-1-ol

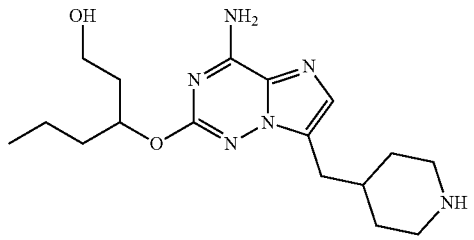

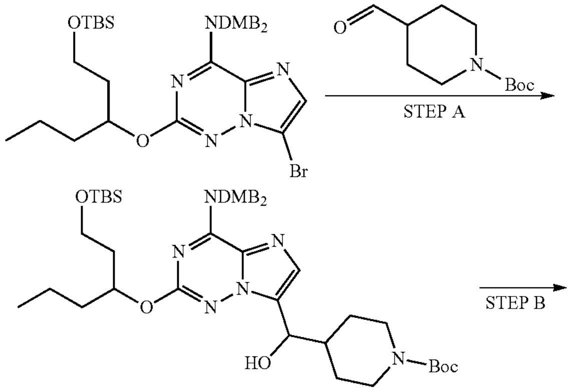

-continued

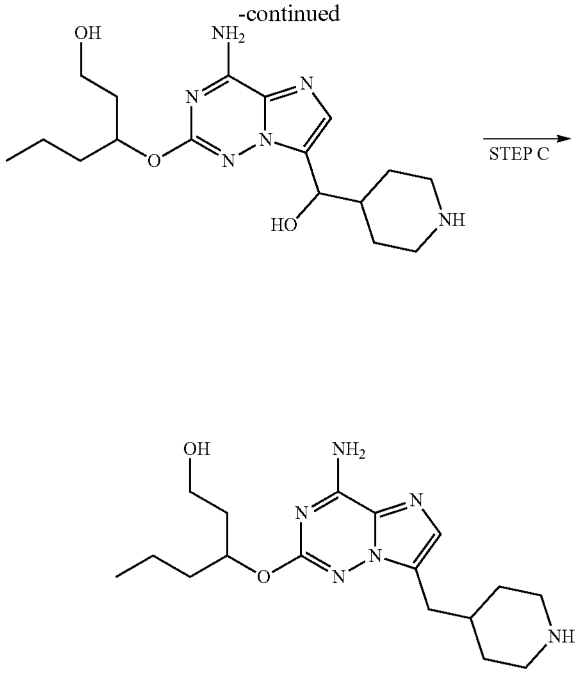

Step A: Tert-butyl 4-((4-(bis(2,4-dimethoxybenzyl) amino)-2-((1-(tert-butyldimethylsilyl)oxy) hex-3-yl) oxy)imidazo[2,1-f][1,2,4]triazin-7-yl)(hydroxy) methyl)piperidin-1-carboxylate

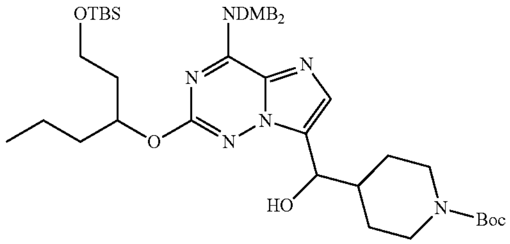

To a solution of 7-bromo-2-((1-((tert-butyldimethylsilyl) oxy) hex-3-yl)oxy)-N,N-bis(2,4-dimethoxybenzyl)imidazo [2,1-f][1,2,4]triazin-4-amine (500 mg, 0.671 mmol) in THF (10 mL), n-BuLi (0.9 mL, 1.44 mmol) was added at −78° C. under N2. After the mixture was stirred at −78° C. for 0.5 h, tert-butyl 4-formylpiperidin-1-carboxylate (215 mg, 1.01 mmol) was added. The reaction mixture was stirred at −78° C. for 3.5 h. After completion of the reaction, the reaction mixture was quenched with an aqueous $NH_4Cl$ solution (20 mL) and extracted with DCM (3×30 mL). The combined organic layers were dried over $Na_2SO_4$ and concentrated under vacuum to obtain a residue. The residue was purified by column chromatography on silica gel eluted with ethyl acetate (50%) in petroleum ether to obtain the title compound (310 mg, 53%). MS: M/e 879 $(M+1)^+$.

Step B: 3-((4-amino-7-(hydroxy (piperidin-4-yl) methyl)imidazo[2,1-f][1,2,4]triazin-2-yl)oxy) hexan-1-ol

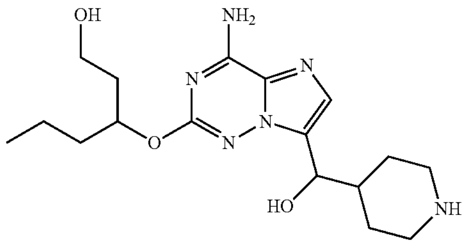 [SMILES: CCCC(CCO)Oc1nc(N)c2ncc(C(O)C3CCNCC3)n2n1]

Tert-butyl 4-((4-(bis(2,4-dimethoxy benzyl)amino)-2-((1-(tert-butyldimethylsilyl)oxy)hex-3-yl)oxy)imidazo[2,1-f][1,2,4]triazin-7-yl)(hydroxy)methyl)piperidin-1-carboxylate (290 mg, 0.329 mmol) was dissolved in TFA (8 mL) and $H_2O$ (0.8 mL) under $N_2$. The reaction mixture was stirred at 40° C. for 12 h. After completion of the reaction, the solvent was removed under vacuum. The residue was diluted with water (10 mL) and DCM (20 mL), and the aqueous phase was acidified with 1 N HCl to adjust PH=2-3. The aqueous phase was washed with DCM (3×50 mL), alkalized with 2 N NaOH to adjust PH=13-14, and extracted with DCM/i-PrOH (5/1, 3×60 mL). The combined organic layers were dried over $Na_2SO_4$ and concentrated under vacuum to obtain the title compound (110 mg, 92%). MS: M/e 365 $(M+1)^+$.

Step C: 3-((4-amino-7-(piperidin-4-ylmethyl)imidazo[2,1-f][1,2,4]triazin-2-yl)oxy)hexan-1-ol

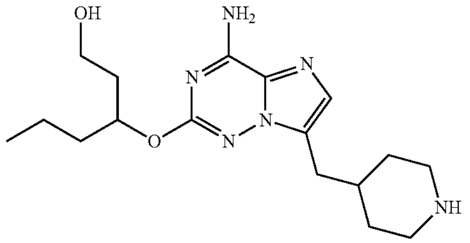 [SMILES: CCCC(CCO)Oc1nc(N)c2ncc(CC3CCNCC3)n2n1]

3-((4-amino-7-(hydroxy(piperidin-4-yl)methyl)imidazo [2,1-f][1,2,4]triazin-2-yl)oxy)hexan-1-ol (110 mg, 0.301 mmol) was dissolved in TFA (4 mL) and $Et_3SiH$ (4 mL) under $N_2$. The reaction mixture was stirred at 90° C. for 12 h. After completion of the reaction, the solvent was removed under vacuum. The residue was diluted with water (10 mL) and DCM (20 mL), and the aqueous phase was acidified with 1 N HCl to adjust pH=2-3. The aqueous phase was washed with DCM (3×50 mL), alkalized with 2 N LiOH to adjust PH=13-14, and extracted with DCM/i-PrOH (5/1, 3×60 mL). The combined organic layers were dried over $Na_2SO_4$ and concentrated under vacuum to obtain a residue. The residue was purified by preparative HPLC under the following conditions; column: XBridge Prep C18 OBD column 19×150 mm 5 um: mobile phase A: water (0.1% TFA), mobile phase B: ACN; flow rate: 17 mL/min; gradient: 10% B to 30% B in 12 min: 214/254 nm, thereby obtaining the title compound (20 mg, 19%). $^1H$ NMR (400 MHz, CD3OD) δ 7.42 (s, 1H), 5.30-5.10 (m, 1H), 3.75-3.59 (m, 2H), 3.39 (d, J=12.4 Hz, 2H), 3.05-2.85 (m, 4H), 2.64 (s, 1H), 2.16 (s, 1H), 2.05-1.85 (m, 4H), 1.83-1.65 (m, 2H), 1.63-1.40 (m, 4H), 0.97 (t, J=7.2 Hz, 3H) ppm. MS: M/e 349 $(M+1)^+$.

Compound B29: 7-(cyclohexylmethyl)-2-(pent-2-yloxy)imidazo[2,1-f][1,2,4]triazin-4-amine

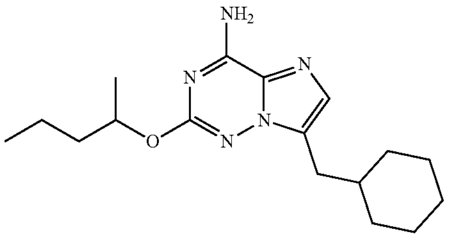

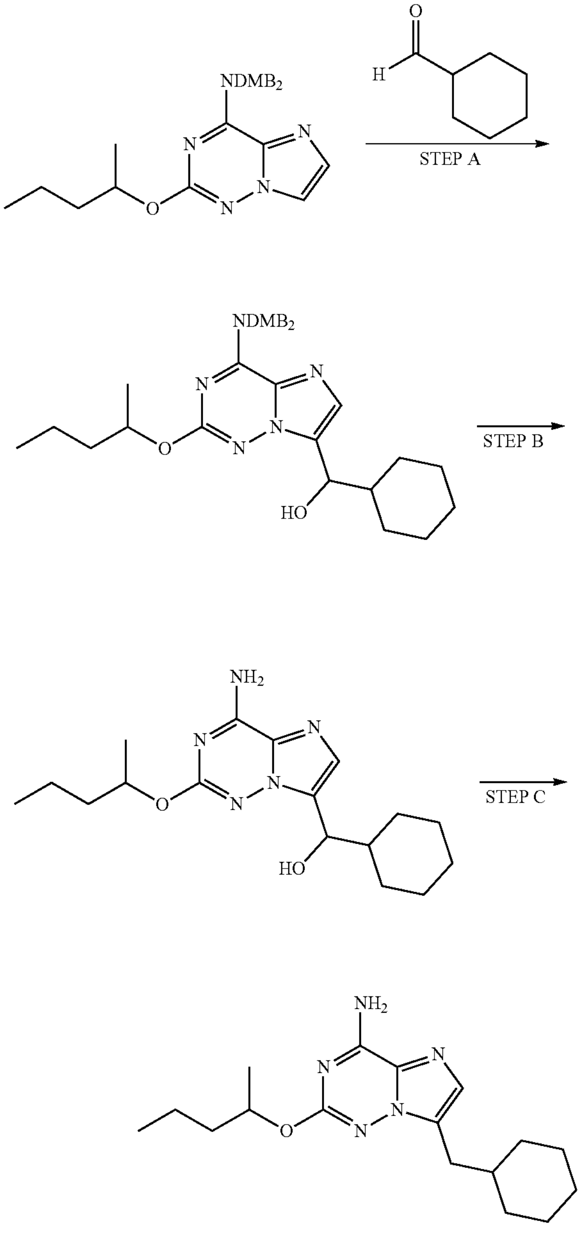

Step A: (4-(bis(2,4-dimethoxybenzyl)amino)-2-(pent-2-yloxy)imidazo[2,1-f][1,2,4]triazin-7-yl)(cyclohexyl)methanol

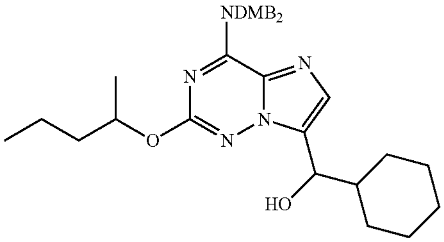

At −78° C. under N2, to a solution of N,N-bis(2,4-dimethoxybenzyl)-2-(pent-2-yloxy)imidazo[2,1-f][1,2,4]triazin-4-amine (500 mg, 0.959 mmol) in THF (10 mL), n-BuLi (1.8 mL, 2.88 mmol) was added. After the mixture was stirred at −78° C. for 0.5 h, cyclohexyl formaldehyde (161 mg, 1.438 mmol) was added. The reaction mixture was stirred at −78° C. for 2.5 h. After completion of the reaction, the reaction mixture was quenched with an aqueous $NH_4Cl$ solution (30 mL) and extracted with DCM (3×30 mL). The combined organic layers were dried over $Na_2SO_4$ and concentrated under vacuum to obtain a residue. The residue was purified by column chromatography on silica gel eluted with ethyl acetate (40%) in petroleum ether to obtain the title compound (560 mg, 92%). MS: M/e 634 $(M+1)^+$.

Step B: (4-amino-2-(pent-2-yloxy)imidazo[2,1-f][1,2,4]triazin-7-yl)(cyclohexyl)methanol

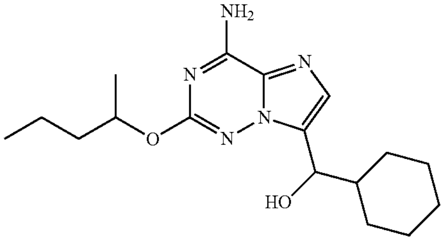 [SMILES: CCCC(C)Oc1nc(N)c2ncc(C(O)C3CCCCC3)n2n1]

(4-(bis(2,4-dimethoxybenzyl)amino)-2-(pent-2-yloxy)imidazo[2,1-f][1,2,4]triazin-7-yl)(cyclohexyl)methanol (560 mg, 0.883 mmol) was dissolved in TFA (8 mL) and $H_2O$ (0.8 mL) under $N_2$. The reaction mixture was stirred at 35° C. for 12 h. After completion of the reaction, the solvent was removed under vacuum. The residue was diluted with water (20 mL) and DCM (20 mL), and the aqueous phase was extracted with DCM (3×20 mL). The combined organic layers were dried over $Na_2SO_4$ and concentrated under vacuum to obtain a residue. The residue was purified by column chromatography on silica gel eluted with methanol ($NH_3$) in dichloromethane (20%) to obtain the title compound (190 mg, 65%). MS. M/e 334 $(M+1)^+$.

Step C: 7-(cyclohexylmethyl)-2-(pent-2-yloxy)imidazo[2,1-f][1,2,4]triazin-4-amine

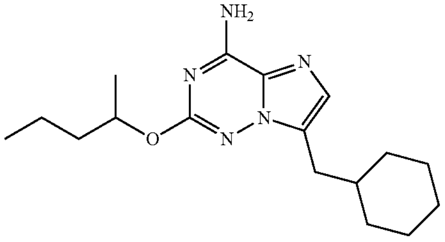 [SMILES: CCCC(C)Oc1nc(N)c2ncc(CC3CCCCC3)n2n1]

(4-amino-2-(pent-2-yloxy)imidazo[2,1-f][1,2,4]triazin-7-yl)(cyclohexyl)methanol (190 mg, 0.569 mmol) was dissolved in TFA (5 mL) and $Et_3SiH$ (5 mL) under $N_2$. The reaction mixture was stirred at 90° C. for 12 h. After completion of the reaction, the solvent was removed under vacuum. The residue was diluted with an aqueous $NaHCO_3$ solution (20 mL) and DCM (20 mL), and the aqueous phase was extracted with DCM (3×20 mL). The combined organic layers were dried over $Na_2SO_4$ and concentrated under vacuum to obtain a residue. The residue was purified by column chromatography on silica gel eluted with ethyl acetate (66%) in petroleum ether to obtain the title compound (20 mg, 11%). $^1H$ NMR (400 MHz, $CD_3OD$) δ 7.41 (s, 1H), 5.15-5.05 (m, 1H), 2.77 (d, J=6.8 Hz, 2H), 1.88-1.56 (m, 9H), 1.55-1.40 (m, 2H), 1.37 (d, J=6.4 Hz, 3H), 1.35-1.19 (m, 4H), 1.05 (t, J=10.8 Hz, 2H), 0.98 (t, J=7.2 Hz, 3H) ppm. MS: M/e 318 $(M+1)^+$.

Compound B30: 7-(((1s,3S)-3-aminocyclobutyl)methyl)-2-(((S)-pent-2-yl)oxy)imidazo[2,1-f][1,2,4]triazin-4-amine

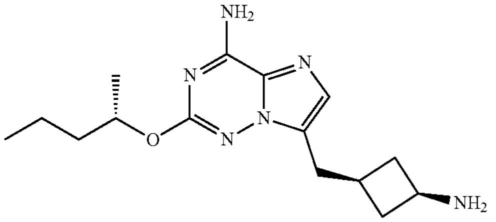

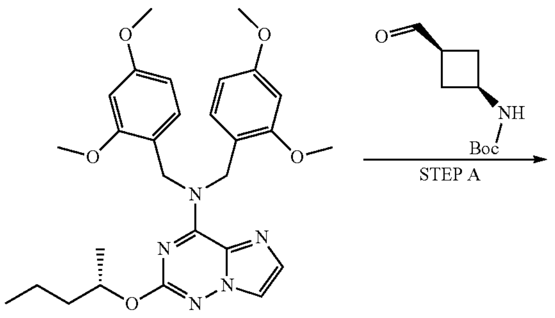

-continued

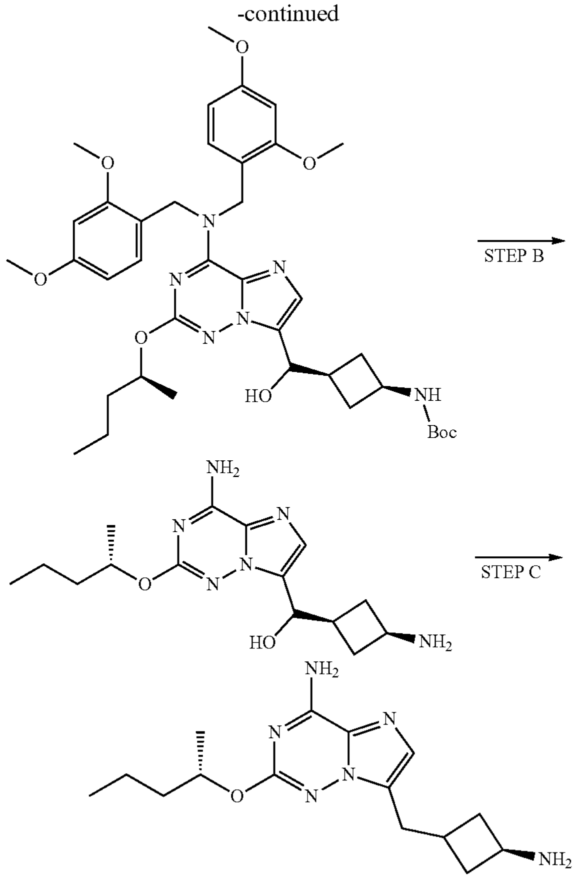

Step A: Tert-butyl ((1R,3s)-3-((S)-(4-(bis(2,4-dimethoxybenzyl)amino)-2-(((S)-pent-2-yl)oxy)imidazo[2,1-f][1,2,4]triazin-7-yl)(hydroxy)methyl)cyclobutyl)carbamate

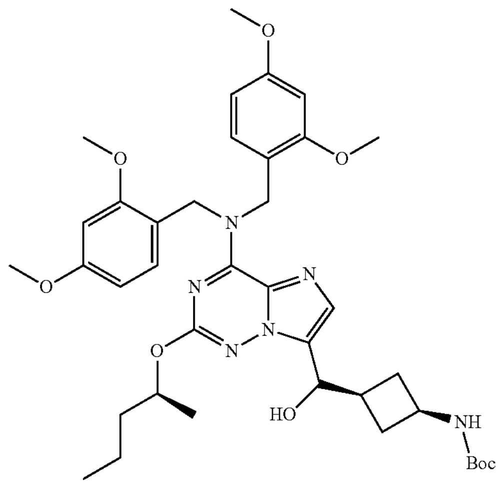 [SMILES: CCC[C@H](C)Oc1nc(N(Cc2ccc(OC)cc2OC)Cc2ccc(OC)cc2OC)c2ncc(C(O)[C@H]3C[C@@H](NC(=O)OC(C)(C)C)C3)n2n1]

At −78° C. under N2 atmosphere, to a solution of (S)-N,N-bis(2,4-dimethoxybenzyl)-2-(pent-2-yloxy)imidazo[2,1-f][1,2,4]triazin-4-amine (300 mg, 0.57 mmol) in THF (3 mL), n-BuLi (1.6 M, 0.55 mL, 0.88 mmol) was added. The mixture was stirred at −78° C. for 30 min. Then, a solution of tert-butyl ((1s,3s)-3-formylcyclobutyl)carbamate (204 mg, 1.02 mmol) in THF (2 mL) was added to the system at −78° C. The reaction was warmed to room temperature and stirred for 30 min. The reaction was quenched with a saturated aqueous $NH_4Cl$ solution at room temperature and extracted with EA (10 mL×2). The combined organic phases were washed with brine (10 mL×2), dried over $Na_2SO_4$ and concentrated under reduced pressure. The residue was purified by column chromatography to obtain the title compound (240 mg, yield: 58%). MS: M/e 721 $(M+1)^+$.

Step B: (S)-(4-amino-2-(((S)-pent-2-yl)oxy)imidazo[2,1-f][1,2,4]triazin-7-yl)((1s,3R)-3-aminocyclobutyl)methanol

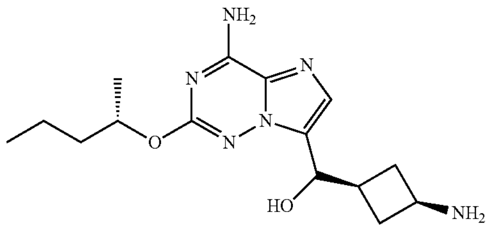 [SMILES: CCC[C@H](C)Oc1nc(N)c2ncc(C(O)[C@H]3C[C@@H](N)C3)n2n1]

Tert-butyl ((1R,3s)-3-((S)-(4-(bis(2,4-dimethoxybenzyl)amino)-2-(((S)-pent-2-yl)oxy)imidazo[2,1-f][1,2,4]triazin-7-yl)(hydroxy)methyl)cyclobutyl)carbamate (240 mg, 0.33 mmol) in TFA/$H_2O$ (9:1, 5 mL) was stirred at room temperature for 20 h. The reaction mixture was concentrated under reduced pressure. 10 mL of $H_2O$ was added. The mixture was stirred at room temperature for 10 min and then filtered. The filtrate was extracted with DCM (5 mL×2) to remove impurities. The aqueous layer was alkalized with an aqueous NaOH (4 M) solution to pH>10, and extracted with DCM/IPA (5:1, 5 mL×3). The combined extracts were washed with brine (5 mL×3), dried over $Na_2SO_4$ and concentrated to obtain the title product (55 mg, yield: 51%). MS: M/e 321 $(M+1)^+$.

Step C: 7-(((1s,3S)-3-aminocyclobutyl)methyl)-2-(((S)-pent-2-yl)oxy)imidazo[2,1-f][1,2,4]triazin-4-amine

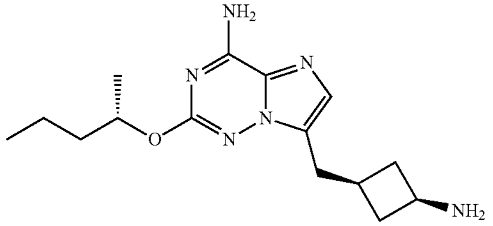 [SMILES: CCC[C@H](C)Oc1nc(N)c2ncc(C[C@H]3C[C@@H](N)C3)n2n1]

A mixture of (S)-(4-amino-2-(((S)-pent-2-yl)oxy)imidazo[2,1-f][1,2,4]triazin-7-yl)((1S,3R)-3-aminocyclobutyl)methanol (55 mg, 0.17 mmol), TFA (5 mL) and $Et_3SiH$ (5 mL) was stirred at 60° C. for 16 h. The reaction mixture was concentrated under reduced pressure. The residue was dissolved in $H_2O$ (2.5 mL) and extracted with DCM (2 mL×3). The organic phase was discarded. The inorganic phase was alkalinized with an aqueous NaOH (4 M) solution to pH>10. The mixture was extracted with DCM/iPrOH (5:1, 2 mL×5). The combined organic phases were washed with brine (5 mL×2), dried over $Na_2SO_4$ and concentrated. The residue was purified by preparative TLC (DCM/MeOH $(NH_3)$=10:1) to obtain the title compound (8 mg, yield: 15%). $^1H$ NMR (400 MHz, CD3OD) δ 7.28 (s, 1H), 5.20-5.01 (m, 1H), 3.51-3.35 (m, 1H), 2.96 (d, J=6.0 Hz, 2H), 2.58-2.32 (m, 3H), 1.83-1.55 (m, 4H), 1.54-1.39 (m, 2H), 1.36 (d, J=6.0 Hz, 3H), 0.96 (t, J=7.2 Hz, 3H) ppm. MS: M/e 305 $(M+1)^+$.

Compound B31: (S)-7-((4-(methylamino)cyclohexyl)methyl)-2-(pent-2-yloxy)imidazo[2,1-f][1,2,4]triazin-4-amine

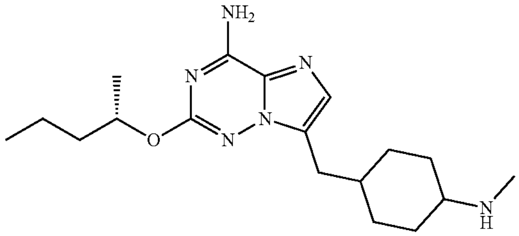

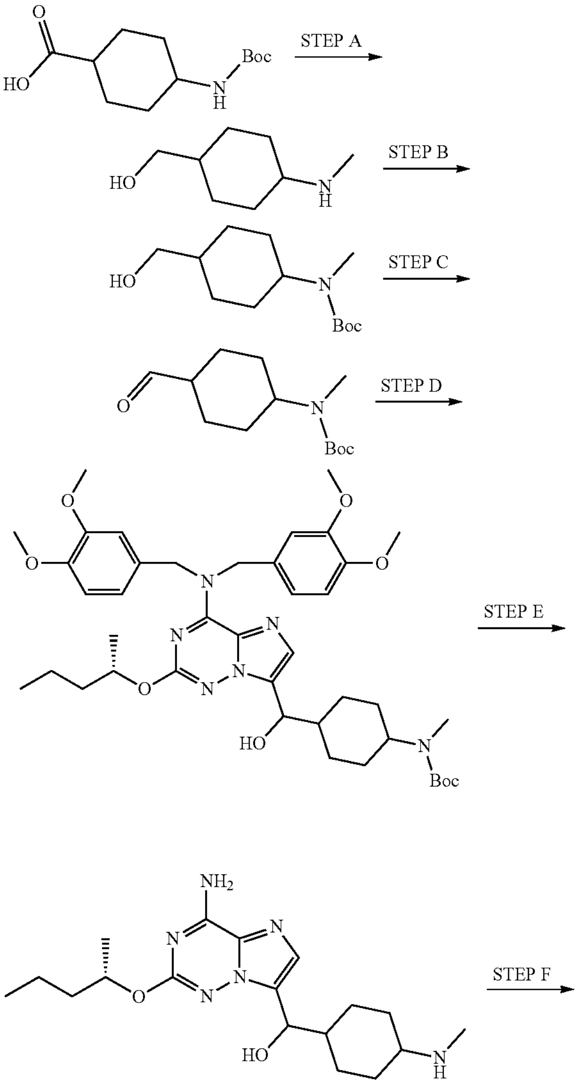

-continued

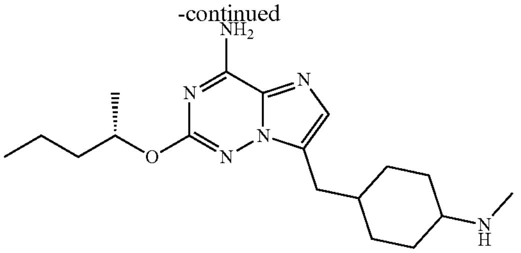

Step A: (4-(methylamino)cyclohexyl)methanol

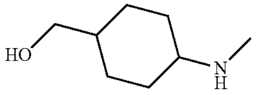

At 0° C., To a mixture of 4-((tert-butoxycarbonyl)amino)cyclohexan-1-carboxylic acid (5 g, 20.57 mmol) in THF (10 mL), LAH (2.35 g, 61.73 mmol) was added in batches and the resulting mixture was stirred at room temperature for 1 h. Then, the mixture was warmed to 60° C. and stirred overnight. The mixture was quenched with a solution of NaOH (10 mL) and extracted with DCM (50 mL×3). The combined organic layers were washed with brine, dried over $Na_2SO_4$ and concentrated to obtain the target compound (2.20 g, 74.77%) as colorless oil. MS: M/e 144 $(M+1)^+$.

Step B: Tert-butyl (4-(hydroxymethyl)cyclohexyl)(methyl)carbamate

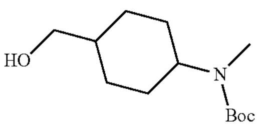 [SMILES: CN(C(=O)OC(C)(C)C)C1CCC(CO)CC1]

A mixture of (4-(methylamino)cyclohexyl)methanol (2 g, 13.99 mmol), di-tert-butyl dicarbonate (3.66 g, 16.78 mmol) and DIPEA (3.61 g, 27.97 mmol) in DCM (30 mL) was stirred at room temperature for 2 h. The mixture was quenched with water (10 mL) and extracted with DCM (30 mL×3). The combined organic layers were washed with water and brine, dried over $Na_2SO_4$, and concentrated to obtain tert-butyl (4-(hydroxymethyl)cyclohexyl)(methyl)carbamate (3.26 g, 95.92%) as colorless oil. MS: M/e 244 $(M+1)^+$.

Step C: Tert-butyl (4-formylcyclohexyl)(methyl)carbamate

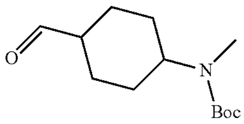 [SMILES: CN(C(=O)OC(C)(C)C)C1CCC(C=O)CC1]

A mixture of tert-butyl (4-(hydroxymethyl)cyclohexyl)(methyl)carbamate (3 g, 12.35 mmol) and DMP (6.28 g, 14.82 mmol) in DCM (30 mL) was stirred at room temperature for 2 h. The mixture was filtered, diluted with PE, filtered and concentrated to obtain the target compound (2.32 g, 77.98%) as yellow oil. MS: M/e 242 $(M+1)^+$.

Step D: Tert-butyl (4-((4-(bis(3,4-dimethoxybenzyl)amino)-2-(((S)-pent-2-yl)oxy)imidazo[2,1-f][1,2,4]triazin-7-yl)(hydroxy)methyl)cyclobutyl)(methyl)carbamate

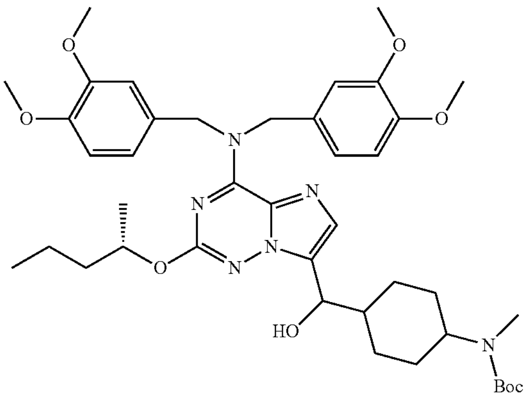

At −78° C., to a solution of (S)—N,N-bis(3,4-dimethoxybenzyl)-2-(pent-2-yloxy)imidazo[2,1-f][1,2,4]triazin-4-amine (200 mg, 0.3839 mmol) in THF (5 mL), n-butyl lithium (0.29 ml, 0.4607 mmol) was added, and the mixture was stirred for 1 h. Then, a solution of tert-butyl (4-formylcyclohexyl)(methyl)carbamate (139 mg, 0.5758 mmol) in THF (1 mL) was added dropwise at −78° C. Thereafter, the mixture was warmed to room temperature and stirred for 3 h. The mixture was quenched with a saturated ammonium chloride solution (5 mL) and extracted with DCM (20 mL×3). The combined organic layers were washed with brine, dried over $Na_2SO_4$, concentrated and purified by column chromatography (DCM/MeOH=20:1-5:1) to obtain the target compound (198 mg, 67.60%) as yellow oil. MS: M/e 763 $(M+1)^+$.

Step E: (4-amino-2-(((S)-pent-2-yl)oxy)imidazo[2,1-f][1,2,4]triazin-7-yl)(4-(methylamino)cyclohexyl)methanol

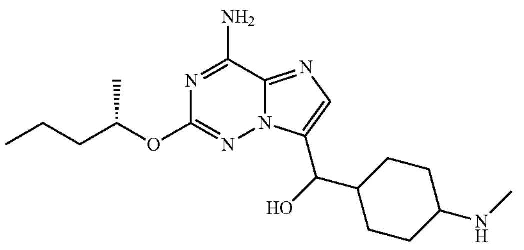 [SMILES: CCC[C@H](C)Oc1nc(N)c2ncc(C(O)C3CCC(NC)CC3)n2n1]

A solution of tert-butyl (4-((4-(bis(3,4-dimethoxybenzyl)amino)-2-(((S)-pent-2-yl)oxy)imidazo[2,1-f][1,2,4]triazin-7-yl)(hydroxy)methyl)cyclohexyl)(methyl)carbamate (198 mg, 0.2595 mmol) in TFA (2 mL) was stirred at room temperature overnight. The mixture was concentrated and purified by preparative TLC to obtain (4-amino-2-(((S)- pent-2-yl)oxy)imidazo[2,1-f][1,2,4]triazin-7-yl)(4-(methylamino)cyclohexyl)methanol (70 mg, 74.52%) as a white solid. MS: M/e 363 (M+1).

Step F: (S)-7-((4-(methylamino)cyclohexyl)methyl)-2-(pent-2-yloxy)imidazo[2,1-f][1,2,4]triazin-4-amine

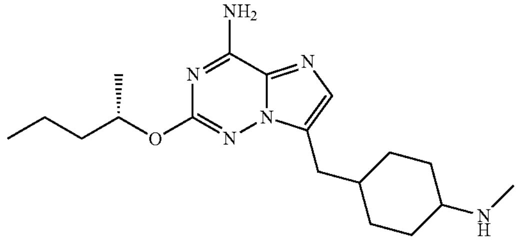 [SMILES: CCC[C@H](C)Oc1nc(N)c2ncc(CC3CCC(NC)CC3)n2n1]

A mixture of (4-amino-2-(((S)-pent-2-yl)oxy)imidazo[2,1-f][1,2,4]triazin-7-yl)(4-(methylamino)cyclohexyl)methanol (70 mg, 0.1934 mmol) and triethylsilane (1 mL) in TFA (2 mL) was stirred at 90° C. overnight. The mixture was concentrated and purified by preparative HPLC to obtain the target compound (35 mg, 52.31%). $^1$H NMR (400 MHz, DMSO-d6) δ 8.35 (br. s, 2H), 8.08 (s, 1H), 8.01 (s, 1H), 7.32 (s, 1H), 4.97 (dd, J=12.5, 6.5 Hz, 1H), 2.89 (s, 1H), 2.70 (d, J=6.2 Hz, 2H), 2.53 (d, J=5.5 Hz, 2H), 2.00 (d, J=10.4 Hz, 2H), 1.71 (m, 4H), 1.58-1.50 (m, 1H), 1.42-1.32 (m, 2H), 1.28 (d, J=6.1 Hz, 3H), 1.26-1.13 (m, 3H), 1.13-0.98 (m, 2H), 0.91 (t, J=7.2 Hz, 3H) ppm. MS: M/e 347 $(M+1)^+$.

Compound B32: (S)-7-((1-methylpiperidin-4-yl)methyl)-2-(pent-2-yloxy)imidazo[2,1-f][1,2,4]triazin-4-amine

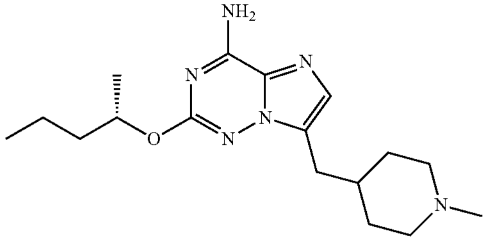 [SMILES: CCC[C@H](C)Oc1nc(N)c2ncc(CC3CCN(C)CC3)n2n1]

At room temperature, to a mixture of (S)-2-(pent-2-yloxy)-7-(piperidin-4-ylmethyl)imidazo[2,1-f][1,2,4]triazin-4-amine (65 mg, 0.2 mmol), formaldehyde (30%, 0.5 mL) in MeOH (2 mL), $NaBH_3CN$ (40 mg, 0.63 mmol) was added, and the mixture was stirred for 16 h. The mixture was concentrated and diluted with EA (10 mL), washed with brine (10 mL×3), dried over $Na_2SO_4$ and concentrated under reduced pressure. The residue was purified by preparative TLC to obtain the title compound (18 mg, yield: 27%). $^1$H NMR (400 MHz, $CD_3OD$) δ 7.32 (s, 1H), 5.18-5.01 (m, 1H), 3.02 (d, J=12.0 Hz, 2H), 2.85 (d, J=6.8 Hz, 2H), 2.40 (s, 3H), 2.24 (t, J=12.0 Hz, 2H), 1.98-1.82 (m, 1H), 1.82-1.70 (m, 3H), 1.65-1.55 (m, 1H), 1.54-1.38 (m, 4H), 1.36 (d, J=6.0 Hz, 3H), 0.97 (t, J=7.2 Hz, 3H) ppm. MS: M/e 333 $(M+1)^+$.

Compound B33: 7-(((1R,5S,6s)-3-azabicyclo[3.1.0]hex-6-yl)methyl)-2-(((S)-pent-2-yl)oxy)imidazo[2,1-f][1,2,4]triazin-4-amine

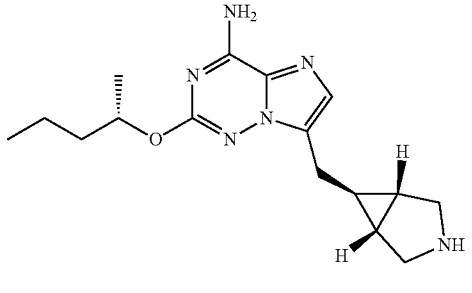 [SMILES: CCC[C@H](C)Oc1nc(N)c2ncc(C[C@H]3[C@@H]4CNC[C@@H]43)n2n1]

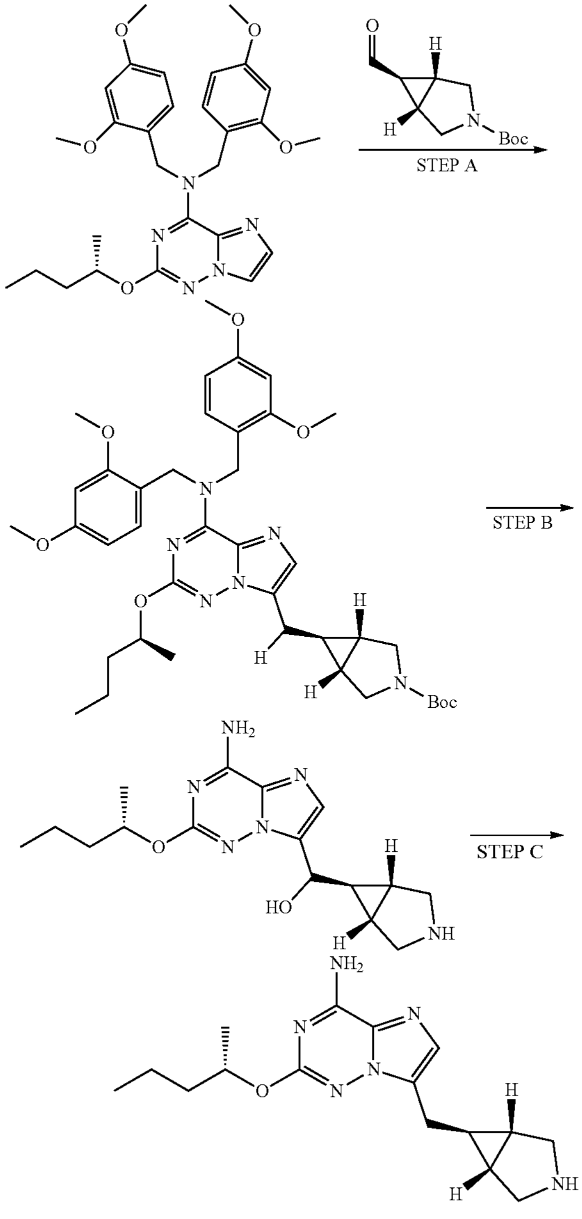

Step A: Tert-butyl (1R,5S,6r)-6-((S)-(4-(bis(2,4-dimethoxybenzyl)amino)-2-(((S)-pent-2-yl)oxy)imidazo[2,1-f][1,2,4]triazin-7-yl)(hydroxy)methyl)-3-azabicyclo[3.1.0]hexan-3-carboxylate

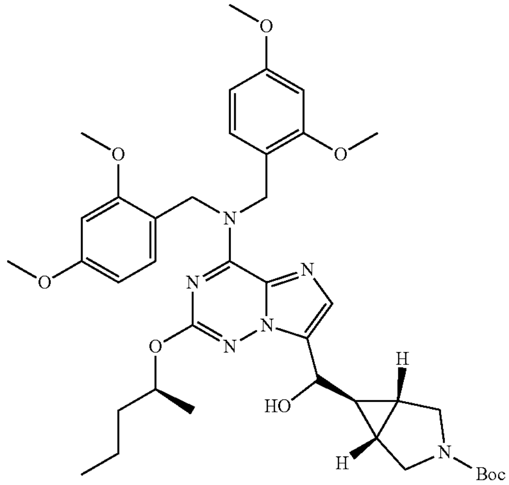 [SMILES: CCC[C@H](C)Oc1nc(N(Cc2ccc(OC)cc2OC)Cc2ccc(OC)cc2OC)c2ncc(C(O)[C@H]3[C@@H]4CN(C(=O)OC(C)(C)C)C[C@@H]43)n2n1]

At −78° C. under N2 atmosphere, to a solution of (S)-N,N-bis(2,4-dimethoxybenzyl)-2-(pent-2-yloxy)imidazo[2,1-f][1,2,4]triazin-4-amine (300 mg, 0.57 mmol) in THF (3 mL), n-BuLi (1.6 M, 0.55 mL, 0.88 mmol) was added. The mixture was stirred at −78° C. for 30 min. Then, a solution of tert-butyl (1R,5S,6r)-6-formyl-3-azabicyclo[3.1.0]hexan-3-carboxylate (218 mg, 1.03 mmol) in THF (2 mL) was added to the system at −78° C. The reaction was warmed to room temperature and stirred for 30 min. The reaction was quenched with a saturated aqueous $NH_4Cl$ solution at room temperature and extracted with EA (10 mL×2). The combined organic phases were washed with brine (10 mL×2), dried over $Na_2SO_4$ and concentrated under reduced pressure. The residue was purified by column chromatography to obtain the title compound (270 mg, yield: 65%). MS: M/e 733 $(M+1)^+$.

Step B: (S)-(4-amino-2-(((S)-pent-2-yl)oxy)imidazo[2,1-f][1,2,4]triazin-7-yl) ((1R,5S,6r)-3-azabicyclo[3.1.0]hex-6-yl)methanol

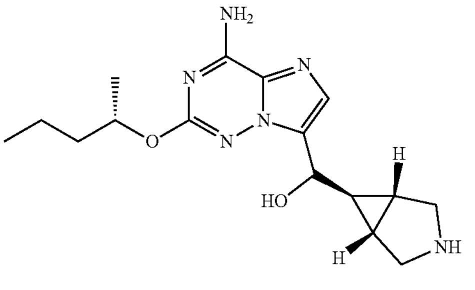 [SMILES: CCC[C@H](C)Oc1nc(N)c2ncc(C(O)[C@H]3[C@@H]4CNC[C@@H]43)n2n1]

Tert-butyl (1R,5S,6r)-6-((S)-(4-(bis(2,4-dimethoxybenzyl)amino)-2-(((S)-pent-2-yl)oxy)imidazo[2,1-f][1,2,4]triazin-7-yl)(hydroxy)methyl)-3-azabicyclo[3.1.0]hexan-3-carboxylate (270 mg, 0.37 mmol) in TFA/$H_2O$ (9:1, 5 mL) was stirred at room temperature for 20 h. The reaction mixture was concentrated under reduced pressure. 10 mL of $H_2O$ was added. The mixture was stirred at room temperature for 10 min and then filtered. The filtrate was extracted with DCM (5 mL×2) to remove impurities. The aqueous layer was alkalized with an aqueous NaOH (4 M) solution to pH>10, and extracted with DCM/IPA (5:1, 5 mL×3). The combined extracts were washed with brine (5 mL×3), dried over $Na_2SO_4$ and concentrated to obtain the title product (35 mg, yield: 26%). MS. M/e 333 $(M+1)^+$.

Step C: 7-(((1R,5S,6s)-3-azabicyclo[3.1.0]hex-6-yl)methyl)-2-(((S)-pent-2-yl)oxy)imidazo[2,1-f][1,2,4]triazin-4-amine

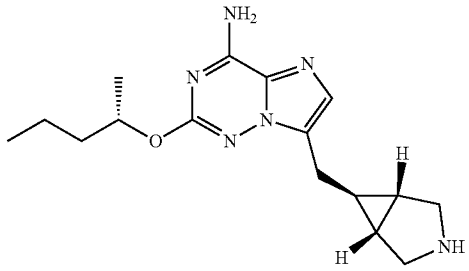 [SMILES: CCC[C@H](C)Oc1nc(N)c2ncc(C[C@H]3[C@@H]4CNC[C@@H]43)n2n1]

A mixture of (S)-(4-amino-2-(((S)-pent-2-yl)oxy)imidazo[2,1-f][1,2,4]triazin-7-yl)((1R,5S,6r)-3-azabicyclo[3.1.0]hex-6-yl)methanol (35 mg, 0.1 mmol), TFA (5 mL) and $Et_3SiH$ (5 mL) was stirred at 60° C. for 16 h. The reaction mixture was concentrated under reduced pressure. The residue was dissolved in $H_2O$ (2.5 mL) and extracted with DCM (2 mL×3). The organic phase was discarded. The inorganic phase was alkalinized with an aqueous NaOH (4 M) solution to pH>10. The mixture was extracted with DCM/iPrOH (5:1, 2 mL×5). The combined organic phases were washed with brine (5 mL×2), dried over $Na_2SO_4$ and concentrated. The residue was purified by preparative TLC (DCM/MeOH $(NH_3)$=10:1) to obtain the title compound (12 mg, yield: 36%). $^1H$ NMR (400 MHz, CD3OD) δ 7.36 (s, 1H), 5.19-5.01 (m, 1H), 3.22 (d, J=11.6 Hz, 2H), 3.13 (d, J=11.6 Hz, 2H), 2.85 (d, J=6.8 Hz, 2H), 1.86-1.66 (m, 3H), 1.65-1.54 (m, 1H), 1.54-1.38 (m, 2H), 1.35 (d, J=6.0 Hz, 3H), 1.18-1.05 (m, 1H), 0.96 (t, J=7.2 Hz, 3H) ppm. MS: M/e 317 $(M+1)^+$.

Step B34: 2-((4-amino-7-(piperidin-4-ylmethyl) imidazo[2,1f][1,2,4]triazin-2-yl)oxy) pentan-1-ol

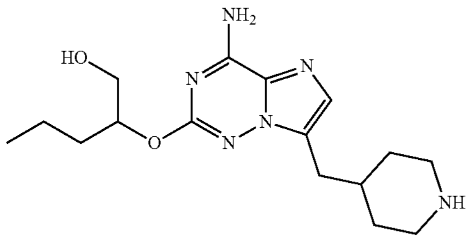

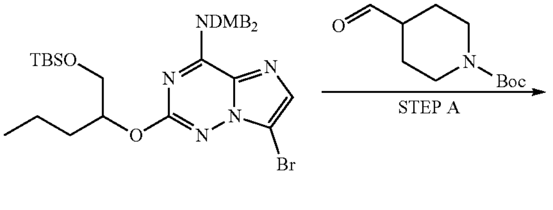

-continued

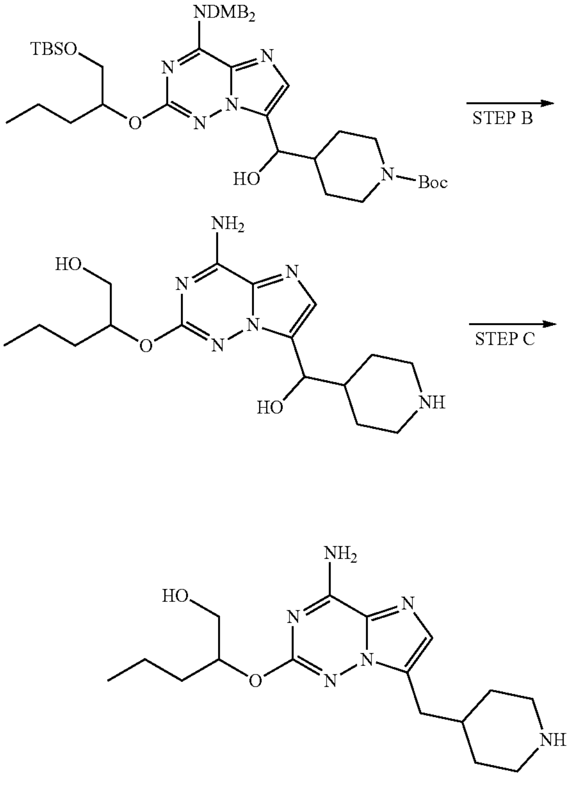

Step A: Tert-butyl 4-((4-(bis(2,4-dimethoxybenzyl)amino)-2-((1-(tert-butyldimethylsilyl)oxy) pent-2-yl)oxy)imidazo[2,1-f][1,2,4]triazin-7-yl)(hydroxy)methyl)piperidin-1-carboxylate

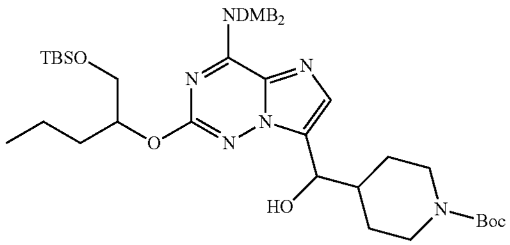

At −78° C. under N2, to a solution of 7-bromo-2-((1-((tert-butyldimethylsilyl)oxy) pent-2-yl)oxy)-N,N-bis(2,4-dimethoxybenzyl)imidazo[2,1-f][1,2,4]triazin-4-amine (980 mg, 1.34 mmol) in THF (20 mL), n-BuLi (2.5 mL, 4.0 mmol) was added. After the mixture was stirred at −78° C. for 0.5 h, tert-butyl 4-formylpiperidin-1-carboxylate (428 mg, 2.01 mmol) was added. The reaction 1 mixture was stirred at −78° C. for 2.5 h. After completion of the reaction, the reaction mixture was quenched with an aqueous $NH_4Cl$ solution (30 mL) and extracted with DCM (3×50 mL). The combined organic layers were dried over $Na_2SO_4$ and concentrated under vacuum to obtain a residue. The residue was purified by column chromatography on silica gel eluted with ethyl acetate (60%) in petroleum ether to obtain the title compound (1 g, 86%). MS: M/e 865 $(M+1)^+$.

Step B: 2-((4-amino-7-(hydroxy(piperidin-4-yl)methyl)imidazo[2,1-f][1,2,4]triazin-2-yl)oxy)pentan-1-ol

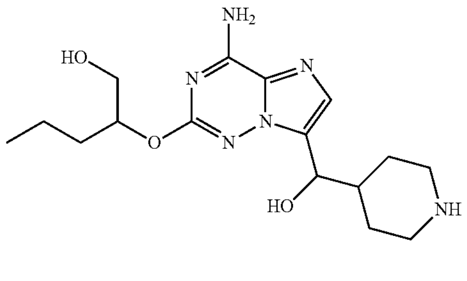 [SMILES: CCCC(CO)Oc1nc(N)c2ncc(C(O)C3CCNCC3)n2n1]

Tert-butyl 4-((4-(bis(2,4-dimethoxybenzyl)amino)-2-((1-(tert-butyldimethylsilyl)oxy)pent-2-yl)oxy)imidazo[2,1-f][1,2,4]triazin-7-yl)(hydroxy)methyl)piperidin-1-carboxylate (1 g, 1.156 mmol) was dissolved in TFA (9 mL) and $H_2O$ (1 mL) under $N_2$. The reaction mixture was stirred at 40° C. for 12 h. After completion of the reaction, the solvent was removed under vacuum. The residue was diluted with water (20 mL) and DCM (20 mL), and the aqueous phase was acidified with 1 N HCl to adjust pH=2-3. The aqueous phase was washed with DCM (3×50 mL), alkalized with 2 N NaOH to adjust pH=13-14, and extracted with DCM/i-PrOH (5/1, 3×100 mL). The combined organic layers were dried over $Na_2SO_4$ and concentrated under vacuum to obtain the title compound (350 mg, 86%). MS: M/e 351 $(M+1)^+$.

Step C: 2-((4-amino-7-(piperidin-4-ylmethyl)imidazo[2,1-f][1,2,4]triazin-2-yl)oxy) pentan-1-ol

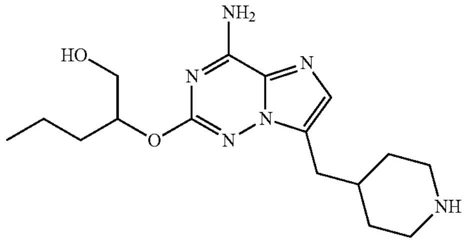 [SMILES: CCCC(CO)Oc1nc(N)c2ncc(CC3CCNCC3)n2n1]

2-((4-amino-7-(hydroxy(piperidin-4-yl)methyl)imidazo[2,1-f][1,2,4]triazin-2-yl)oxy)pentan-1-ol (350 mg, 1.0 mmol) was dissolved in TFA (5 mL) and $Et_3SiH$ (5 mL) under $N_2$. The reaction mixture was stirred at 90° C. for 12 h. After completion of the reaction, the solvent was removed under vacuum. The residue was diluted with water (10 mL) and DCM (20 mL), and the aqueous phase was acidified with 1 N HCl to adjust pH=2-3. The aqueous phase was washed with DCM 3×60 mL). The combined organic layers were dried over $Na_2SO_4$ and concentrated under vacuum to obtain a residue. The residue was purified by preparative TLC (DCM/CH3OH($NH_3$)=10/1) to obtain the title compound (10 mg). $^1$H NMR (400 MHz, CD3OD) & 7.43 (s, 1H), 5.15-5.08 (m, 1H), 3.75-3.71 (m, 2H), 3.38 (d, J=12.0 Hz, 2H), 3.00-2.85 (m, 4H), 2.22-2.09 (m, 1H), 1.98-1.85 (m, 2H), 1.78-1.65 (m, 2H), 1.55-1.38 (m, 4H), 0.97 (t, J=7.2 Hz, 3H) ppm. MS: M/e 335 $(M+1)^+$.

Compound B35: (S)-2-(pent-2-yloxy)-7-(piperidin-4-ylidenemethyl)imidazo[2,1-f][1,2,4]triazin-4-amine

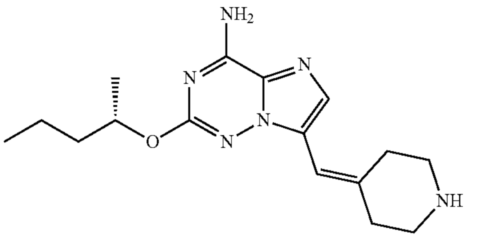

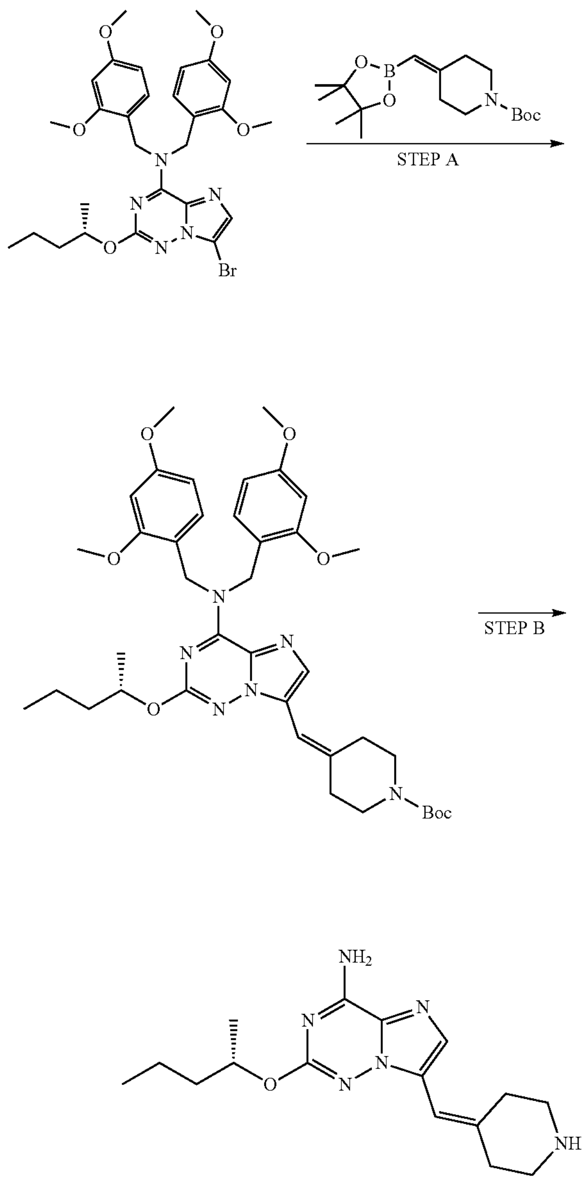

Step A: Tert-butyl(S)-4-((4-(bis(2,4-dimethoxybenzyl)amino)-2-(pent-2-yloxy)imidazo[2,1-f][1,2,4]triazin-7-yl)methylene)piperidin-1-carboxylate

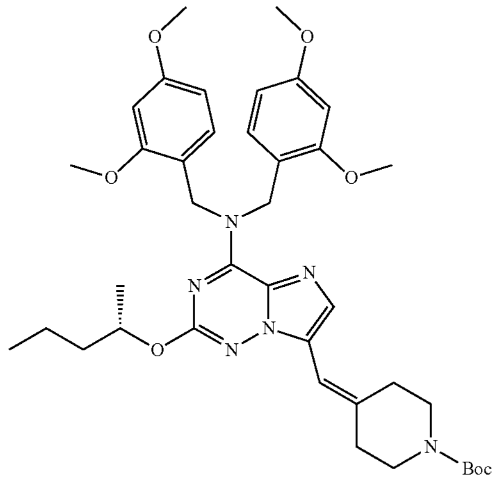 [SMILES: CCC[C@H](C)Oc1nc(N(Cc2ccc(OC)cc2OC)Cc2ccc(OC)cc2OC)c2ncc(C=C3CCN(C(=O)OC(C)(C)C)CC3)n2n1]

A mixture of (S)-7-bromo-N,N-bis(2,4-dimethoxybenzyl)-2-(pent-2-yloxy)imidazo[2,1-f][1,2,4]triazin-4-amine (200 mg, 0.33 mmol), tert-butyl 4-((4,4,5,5-tetramethyl-1,3,2-dioxboran-2-yl)methylene)piperidin-1-carboxylate (215 mg, 0.67 mmol), $Pd(PPh_3)$ 4 (38 mg, 0.03 mmol), $K_2CO_3$ (93 mg, 0.67 mmol) and $H_2O$ (0.5 mL) in dioxane (2 mL) was stirred at 100° C. for 16 h. The mixture was diluted with EA (10 mL), washed with brine (10 mL×3), dried over $Na_2SO_4$ and concentrated. The residue was purified by preparative TLC to obtain the title compound (100 mg, yield: 42%). MS: M/e 717 $(M+1)^+$.

Step B: (S)-2-(pent-2-yloxy)-7-(piperidin-4-ylidenemethyl)imidazo[2,1-f][1,2,4]triazin-4-amine

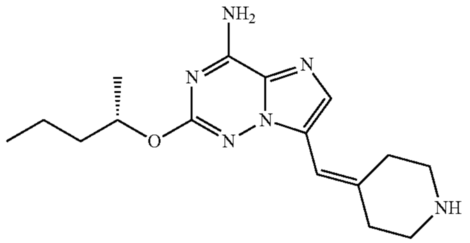 [SMILES: CCC[C@H](C)Oc1nc(N)c2ncc(C=C3CCNCC3)n2n1]

Tert-butyl (S)-4-((4-(bis(2,4-dimethoxybenzyl)amino)-2-(pent-2-yloxy)imidazo[2,1-f][1,2,4]triazin-7-yl)methylene) piperidin-1-carboxylate (100 mg, 0.14 mmol) in TFA/$H_2O$ (9:1, 5 mL) was stirred at room temperature for 16 h. The reaction mixture was concentrated under reduced pressure. 5 mL of $H_2O$ was added. The mixture was stirred at room temperature for 2 h and then filtered. The filtrate was alkalized with an aqueous NaOH (4 M) solution to pH>10, and extracted with DCM/IPA (5.1, 5 mL×5). The combined extracts were washed with brine (10 mL×3), dried over $Na_2SO_4$ and concentrated. The crude product was purified by preparative TLC (DCM/MeOH $(NH_3)$=10:1) to obtain the title product (12 mg, yield: 27%). $^1H$ NMR (400 MHz, $CD_3OD$) δ 7.55 (s, 1H), 6.48 (s, 1H), 5.23-5.04 (m, 1H), 3.11 (t, J=6.0 Hz, 2H), 3.06 (t, J=6.0 Hz, 2H), 2.72 (t, J=5.6 Hz, 2H), 2.58 (t, J=5.6 Hz, 2H), 1.85-1.67 (m, 1H), 1.67-1.54 (m, 1H), 1.54-1.38 (m, 2H), 1.35 (d, J=6.0 Hz, 3H), 0.96 (t, J=7.2 Hz, 3H) ppm. MS: M/e 317 $(M+1)^+$.

Step B36: 2-(pent-2-yloxy)-7-((tetrahydro-2H-pyran-4-yl)methyl)imidazo[2,1-f][1,2,4]triazin-4-amine

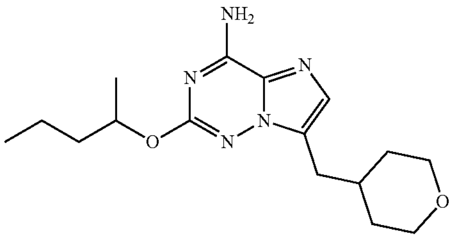 [SMILES: CCCC(C)Oc1nc(N)c2ncc(CC3CCOCC3)n2n1]

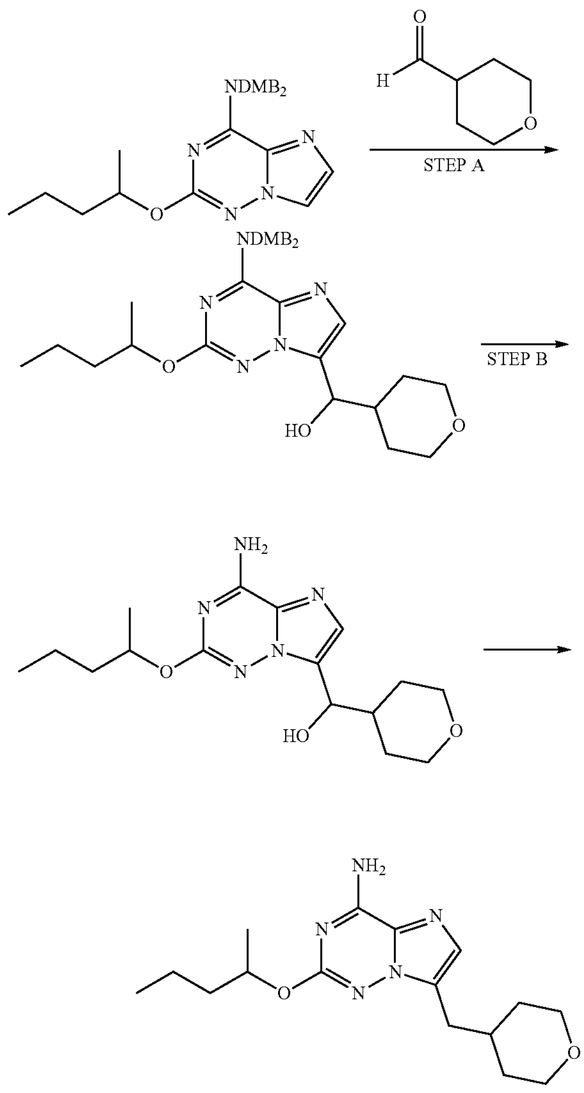

Step A: (4-(bis(2,4-dimethoxybenzyl)amino)-2-(pent-2-yloxy)imidazo[2,1-f][1,2,4]triazin-7-yl) (tetrahydro-2H-pyran-4-yl)methanol

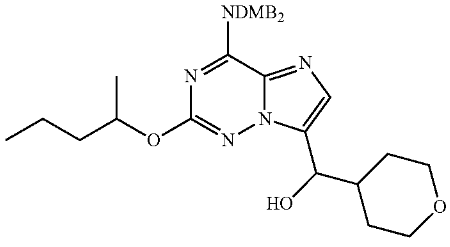

At −78° C. under N2, to a solution of N,N-bis(2,4-dimethoxybenzyl)-2-(pent-2-yloxy)imidazo[2,1-f][1,2,4]triazin-4-amine (500 mg, 0.959 mmol) in THF (10 mL), n-BuLi (1.8 mL, 2.88 mmol) was added. After the mixture was stirred at −78° C. for 0.5 h, tetrahydro-2H-pyran-4-formaldehyde (164 mg, 1.439 mmol) was added. The reaction mixture was stirred at −78° C. for 2.5 h. After completion of the reaction, the reaction mixture was quenched with an aqueous $NH_4Cl$ solution (30 mL) and extracted with DCM (3×30 mL). The combined organic layers were dried over $Na_2SO_4$ and concentrated under vacuum to obtain a residue. The residue was purified by column chromatography on silica gel eluted with ethyl acetate (60%) in petroleum ether to obtain the title compound (400 mg, 66%). MS: M/e 636 $(M+1)^+$.

Step B: (4-amino-2-(pent-2-yloxy)imidazo[2,1-f][1,2,4]triazin-7-yl) (tetrahydro-2H-pyran-4-yl)methanol

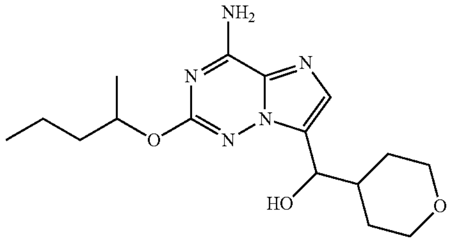 [SMILES: CCCC(C)Oc1nc(N)c2ncc(C(O)C3CCOCC3)n2n1]

(4-(bis(2,4-dimethoxybenzyl)amino)-2-(pent-2-yloxy)imidazo[2,1-f][1,2,4]triazin-7-yl) (tetrahydro-2H-pyran-4-yl) methanol (400 mg, 0.629 mmol) was dissolved in TFA (8 mL) and $H_2O$ (0.8 mL) under $N_2$. The reaction mixture was stirred at 35° C. for 12 h. After completion of the reaction, the solvent was removed under vacuum. The residue was diluted with water (20 mL) and DCM (20 mL), and the aqueous phase was extracted with DCM (3×20 mL). The combined organic layers were dried over $Na_2SO_4$ and concentrated under vacuum to obtain a residue. The residue was purified by column chromatography on silica gel eluted with methanol ($NH_3$) in dichloromethane (10%) to obtain the title compound (180 mg, 85%). MS: M/e 335 $(M+1)^+$.

Step C: 2-(pent-2-yloxy)-7-((tetrahydro-2H-pyran-4-yl)methyl)imidazo[2,1-f][1,2,4]triazin-4-amine

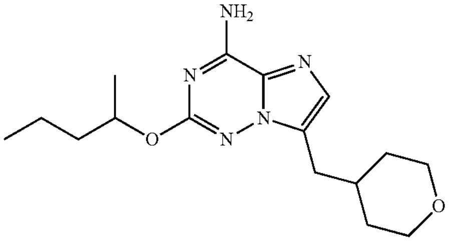 [SMILES: CCCC(C)Oc1nc(N)c2ncc(CC3CCOCC3)n2n1]

(4-amino-2-(pent-2-yloxy)imidazo[2,1-f][1,2,4]triazin-7-yl)(tetrahydro-2H-pyran-4-yl)methanol (180 mg, 0.537) was dissolved in TFA (5 mL) and $Et_3SiH$ (5 mL) under $N_2$. The reaction mixture was stirred at 90° C. for 12 h. After completion of the reaction, the solvent was removed under vacuum. The residue was diluted with an aqueous $NaHCO_3$ solution (20 mL) and DCM (20 mL), and the aqueous phase was extracted with DCM (3×20 mL). The combined organic layers were dried over $Na_2SO_4$ and concentrated under vacuum to obtain a residue. The residue was purified by preparative TLC (PE/EtOAc=2/1) to obtain the title compound (70 mg, 41%). $^1H$ NMR (400 MHz, DMSO-$d_6$) δ 8.17-7.89 (m, 2H), 7.30 (s, 1H), 5.04-4.98 (m, 1H), 3.81 (d, J=9.2 Hz, 2H), 3.23 (t, J=11.6 Hz, 2H), 2.73 (d, J=6.8 Hz, 2H), 1.94 (s, 1H), 1.76-1.61 (m, 1H), 1.59-1.44 (m, 3H), 1.42-1.31 (m, 2H), 1.31-1.16 (m, 5H), 0.91 (t, J=7.2 Hz, 3H) ppm. MS: Me 320 $(M+1)^+$.

Compound B37: (S)-2-(pent-2-yloxy)-N7-(piperidin-4-yl)imidazo[2,1-f][1,2,4]triazin-4,7-diamine

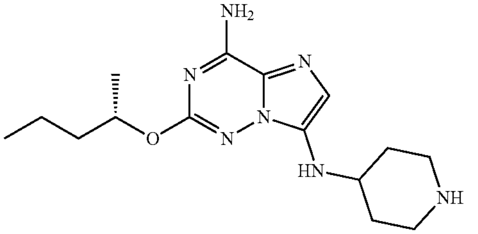

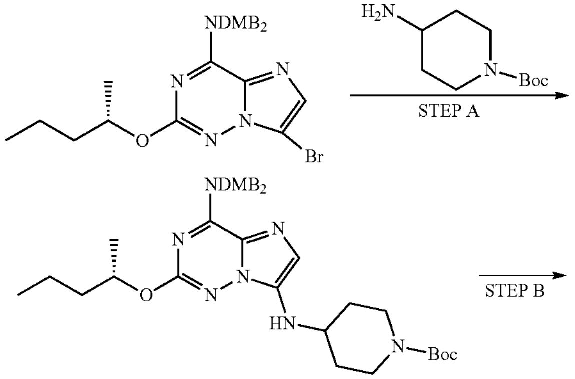

-continued

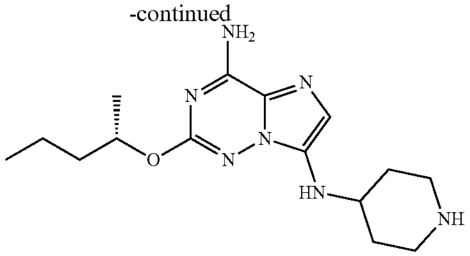

Step A: Tert-butyl(S)-4-((4-(bis(2,4-dimethoxybenzyl)amino)-2-(pent-2-yloxy)imidazo[2,1-f][1,2,4]triazin-7-yl)amino) piperidin-1-carboxylate

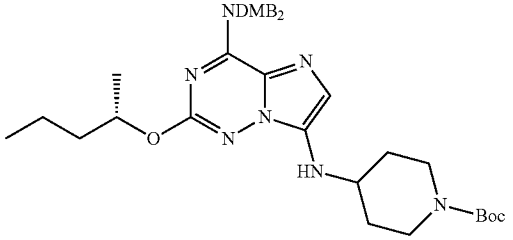

To a solution of (S)-7-bromo-N,N-bis(2,4-dimethoxybenzyl)-2-(pent-2-yloxy)imidazo[2,1-f][1,2,4]triazin-4-amine (300 mg, 0.5 mmol) in toluene (10 mL), tert-butyl 4-aminopiperidin-1-carboxylate (200 mg, 1 mmol), $Pd_2(dba)_3$ (23 mg, 0.025 mmol), t-BuONa (96 mg, 1 mmol) and BINAP (600 mg, 1 mmol) were added. The reaction mixture was stirred at 100° C. overnight under the protection of N2 atmosphere. $H_2O$ was added, and the mixture was extracted with ethyl acetate. The combined organic extracts were dried over sodium sulfate, filtered and evaporated. The crude product was purified by column chromatography to obtain the title product (160 mg, 44.4%). MS: m/e: 720 $(M+1)^+$.

Step B: (S)-2-(pent-2-yloxy)-N7-(piperidin-4-yl)imidazo[2,1-f][1,2,4]triazin-4,7-diamine

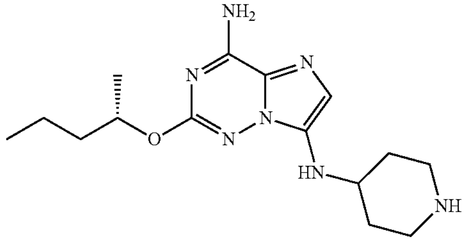 [SMILES: CCC[C@H](C)Oc1nc(N)c2ncc(NC3CCNCC3)n2n1]

$H_2O$ (2 mL) was added to a mixture of tert-butyl(S)-4-((4-(bis(2,4-dimethoxybenzyl)amino)-2-(pent-2-yloxy)imidazo[2,1-f][1,2,4]triazin-7-yl)amino) piperidin-1-carboxylate (160 mg, 0.22 mmol) in TFA (8 mL). The resulting mixture was stirred at room temperature for 2 d, and concentrated to dryness. The residue was purified by preparative HPLC to obtain the target compound (17 mg, 34.8%). $^1H$ NMR (400 MHz, DMSO-d6) δ 8.72 (s, 1H), 8.49 (s, 1H), 7.88 (s, 2H), 6.90 (s, 1H), 5.45 (s, 1H), 5.05 (dd, J=12.3, 5.9 Hz, 1H), 3.48 (s, 2H), 2.95 (m, 2H), 2.06 (d, J=13.4 Hz, 2H), 1.70 (m, 2H), 1.63-1.48 (m, 2H), 1.37 (dt, J=15.6, 7.7 Hz, 2H), 1.25 (d, J=6.1 Hz, 3H), 0.90 (t, J=7.2 Hz, 3H) ppm. MS: M/e 320 $(M+1)^+$.

Compound B38: (S)-7-((1-(2-aminomethyl)piperidin-4-yl)methyl)-2-(pent-2-yloxy)imidazo[2,1-f][1,2,4]triazin-4-amine

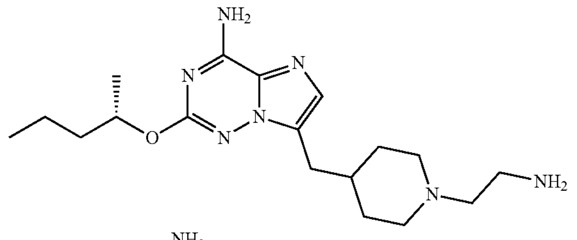

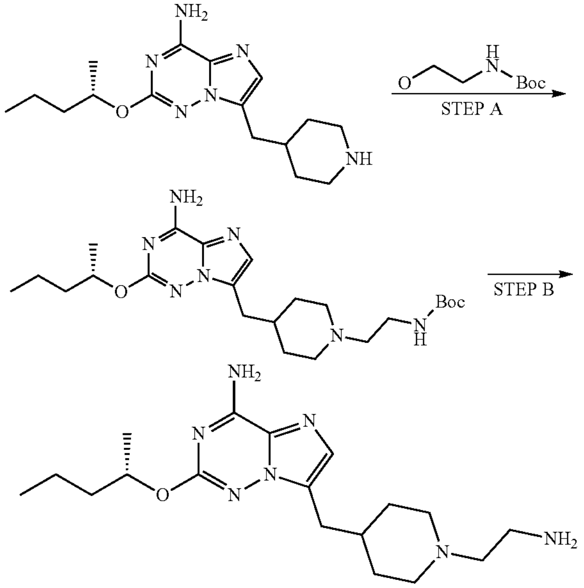

Step A: Tert-butyl(S)-(2-(4-((4-amino-2-(pent-2-yloxy)imidazo[2,1-f][1,2,4]triazin-7-yl)methyl)piperidin-1-yl)ethyl) carbamate

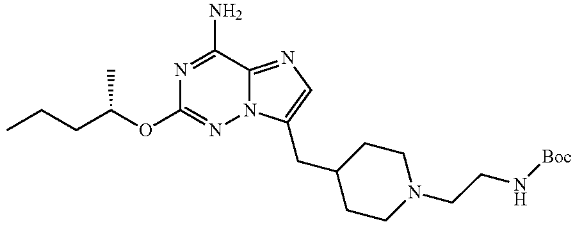 [SMILES: CCC[C@H](C)Oc1nc(N)c2ncc(CC3CCN(CCNC(=O)OC(C)(C)C)CC3)n2n1]

At room temperature, to a mixture of (S)-2-(pent-2-yloxy)-7-(piperidin-4-ylmethyl)imidazo[2,1-f][1,2,4]triazin-4-amine (50 mg, 0.16 mmol), tert-butyl (2-oxoethyl) carbamate (50 mg, 0.31 mmol) in MeOH (2 mL), $NaBH_3CN$ (20 mg, 0.31 mmol) was added, and the mixture was stirred for 16 h. The mixture was concentrated and diluted with DCM (10 mL), washed with brine (10 mL×3), dried over $Na_2SO_4$ and concentrated under reduced pressure. The residue was purified by preparative TLC (DCM/MeOH $(NH_3)$=10:1) to obtain the title compound (45 mg, yield: 63%). MS: M/e 462 $(M+1)^+$ Step B: (S)-7-((1-(2-aminomethyl)piperidin-4-yl)methyl)-2-(pent-2-yloxy)imidazo[2,1-f][1,2,4]triazin-4-amine

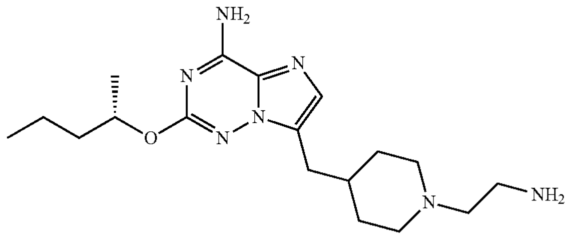 [SMILES: CCC[C@H](C)Oc1nc(N)c2ncc(CC3CCN(CCN)CC3)n2n1]

TFA (2 mL) was added to a solution of tert-butyl(S)-2-(4-((4-amino-2-(pent-2-yloxy)imidazo[2,1-f][1,2,4]triazin-7-yl)methyl)piperidin-1-yl)ethyl) carbamate (45 mg, 0.1 mmol) in DCM (5 mL), and the solution was stirred at room temperature for 16 h. The reaction mixture was concentrated under reduced pressure. The resulting residue was treated with 5 mL of $NaHCO_3$ solution. The resulting mixture was extracted with DCM/IPA (5:1, 5 mL×3). The combined extracts were washed with brine (5 mL×2), dried over $Na_2SO_4$ and concentrated. The crude product was purified by preparative TLC (DCM/MeOH $(NH_3)$=7:1) to obtain the title product (8 mg, yield: 22%). $^1H$ NMR (400 MHz, $CD_3OD$) δ 7.32 (s, 1H), 5.18-5.03 (m, 1H), 3.28-2.97 (m, 4H), 3.00-2.76 (m, 4H), 2.63-2.13 (m, 2H), 2.04-1.88 (m, 1H), 1.88-1.68 (m, 3H), 1.66-1.40 (m, 5H), 1.36 (d, J=6.0 Hz, 3H), 0.97 (t, J=7.2 Hz, 3H) ppm. MS: M/e 362 $(M+1)^+$.

Compound B39: (S)-7-(azetidin-3-ylmethyl)-2-(pent-2-yloxy)imidazo[2,1-f][1,2,4]triazin-4-amine

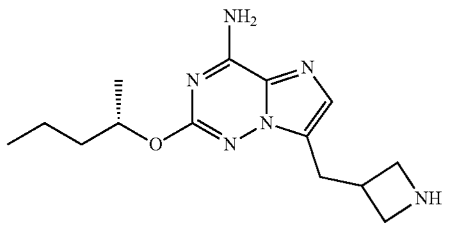

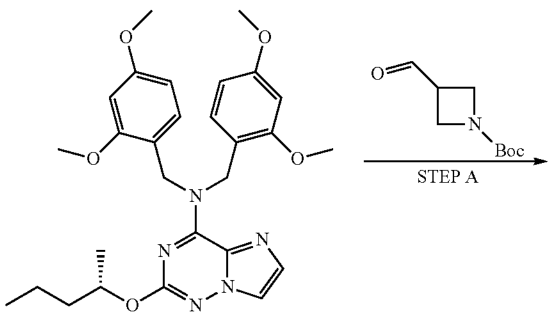

-continued

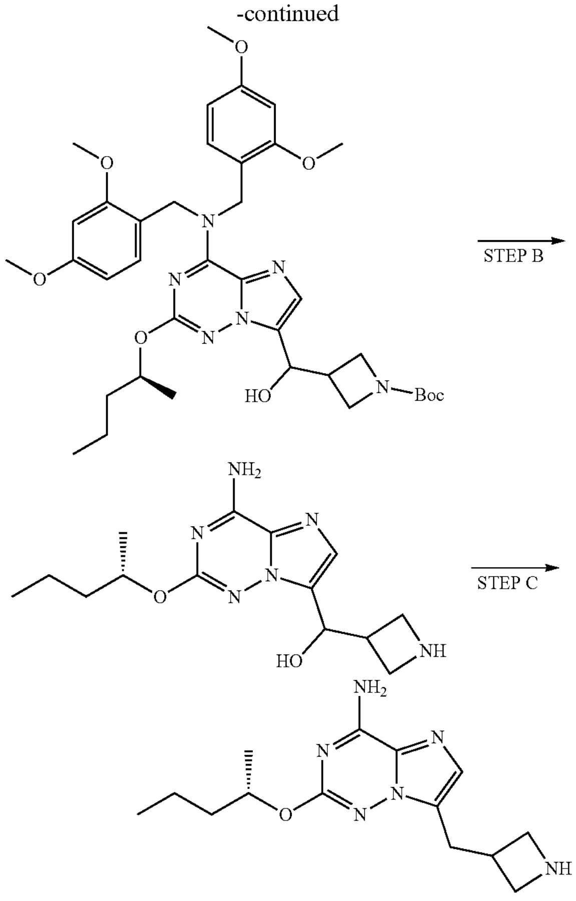

Step A: Tert-butyl 3-((4-(bis(2,4-dimethoxybenzyl) amino)-2-(((S)-pent-2-yl)oxy)imidazo[2,1-f][1,2,4] triazin-7-yl)(hydroxy)methyl) azetidin-1-carboxylate

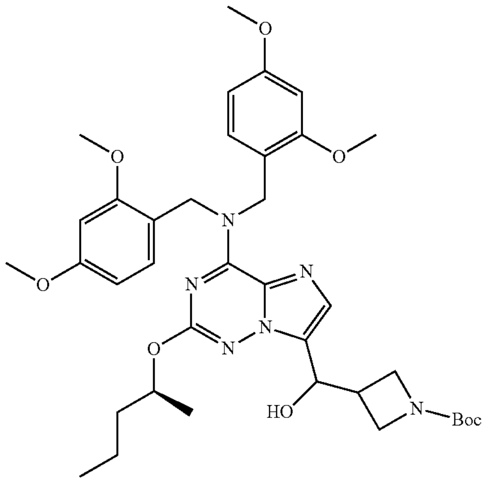 [SMILES: CCC[C@H](C)Oc1nc(N(Cc2ccc(OC)cc2OC)Cc2ccc(OC)cc2OC)c2ncc(C(O)C3CN(C(=O)OC(C)(C)C)C3)n2n1]

At −78° C. under $N_2$ atmosphere, to a solution of (S)—N,N-bis(2,4-dimethoxybenzyl)-2-(pent-2-yloxy)imidazo[2,1-f][1,2,4]triazin-4-amine (300 mg, 0.57 mmol) in THF (3 mL). n-BuLi (1.6 M, 1.1 mL, 1.72 mmol) was added. The mixture was stirred at −78° C. for 30 min. Then, a solution of tert-butyl 3-formylpiperidin-1-carboxylate (320 mg, 1.72 mmol) in THF (3 mL) was added to the system at −78° C. The reaction was warmed to room temperature and stirred for 30 min. The reaction was quenched with a saturated aqueous $NH_4Cl$ solution at room temperature and extracted with EA (10 mL×2). The combined organic phases were washed with brine (10 mL×3), dried over $Na_2SO_4$ and concentrated under reduced pressure. The residue was purified by column chromatography to obtain the title compound (420 mg, yield: >90%). MS: M/e 707 $(M+1)^+$.

Step B: (4-amino-2-(((S)-pent-2-yl)oxy)imidazo[2,1-f][1,2,4]triazin-7-yl)(azetidin-3-yl)methanol

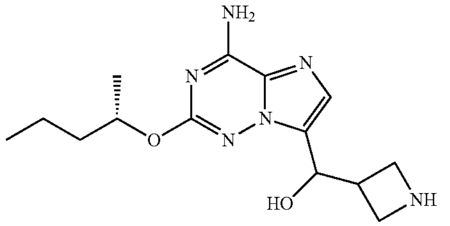 [SMILES: CCC[C@H](C)Oc1nc(N)c2ncc(C(O)C3CNC3)n2n1]

Tert-butyl 3-((4-(bis(2,4-dimethoxybenzyl)amino)-2-(((S)-pent-2-yl)oxy)imidazo[2,1-f][1,2,4]triazin-7-yl)(hydroxy)methyl)azetidin-1-carboxylate (420 mg, 0.57 mmol) in TFA/$H_2O$ (9:1, 5 mL) was stirred at 40° C. for 20 h. The reaction mixture was concentrated under reduced pressure. 10 mL of $H_2O$ was added. The mixture was stirred at room temperature for 10 min and then filtered. The filtrate was extracted with DCM (5 mL×2) to remove impurities. The aqueous layer was alkalized with an aqueous NaOH (4 M) solution to pH>10, and extracted with DCM/IPA (5:1, 5 mL×3). The combined extracts were washed with brine (10 mL×2), dried over $Na_2SO_4$ and concentrated to obtain the title product (160 mg, yield: 88%). MS: M/e 307 $(M+1)^+$.

Step C: (S)-7-(azetidin-3-ylmethyl)-2-(pent-2-yloxy)imidazo[2,1-f][1,2,4]triazin-4-amine

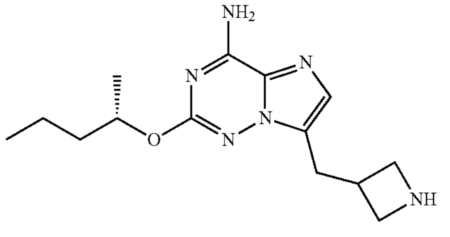 [SMILES: CCC[C@H](C)Oc1nc(N)c2ncc(CC3CNC3)n2n1]

A mixture of (4-amino-2-(((S)-pent-2-yl)oxy)imidazo[2,1-f][1,2,4]triazin-7-yl)(azetidin-3-yl)methanol (160 mg, 0.52 mmol), TFA (5 mL) and $Et_3SiH$ (5 mL) was stirred at 70° C. for 16 h. Additional TFA (5 mL) and $Et_3SiH$ (5 mL) were added, and the resulting mixture was stirred at 70° C. for 2 d. The reaction mixture was concentrated under reduced pressure. The residue was treated with $H_2O$ (10 mL) and alkalized with an aqueous NaOH solution (4 M) to pH>10. The mixture was extracted with DCM/iPrOH (5:1, 10 mL×3). The combined organic phases were washed with brine (10 mL×2), dried over $Na_2SO_4$ and concentrated. The residue was purified by preparative TLC (DCM/MeOH $(NH_3)$=10:1) to obtain the title compound (12 mg, yield: 8%). $^1H$ NMR (400 MHz, $CD_3OD$) δ 7.37 (s, 1H), 5.20-5.04 (m, 1H), 4.15 (t, J=9.6 Hz, 2H), 4.02-3.90 (m, 2H), 3.48-3.35 (m, 1H), 3.22 (d, J=7.2 Hz, 2H), 1.87-1.67 (m, 1H), 1.67-1.56 (m, 1H), 1.55-1.40 (m, 2H), 1.36 (d, J=6.0 Hz, 3H), 0.96 (t, J=7.2 Hz, 3H) ppm. MS: M/e 291 $(M+1)^+$.

Compound B40: (S)-7-((3-aminobicyclo[1.1.1]pent-1-yl)methyl)-2-(pent-2-yloxy)imidazo[2,1-f][1,2,4]triazin-4-amine

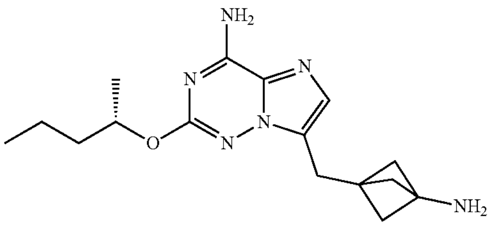

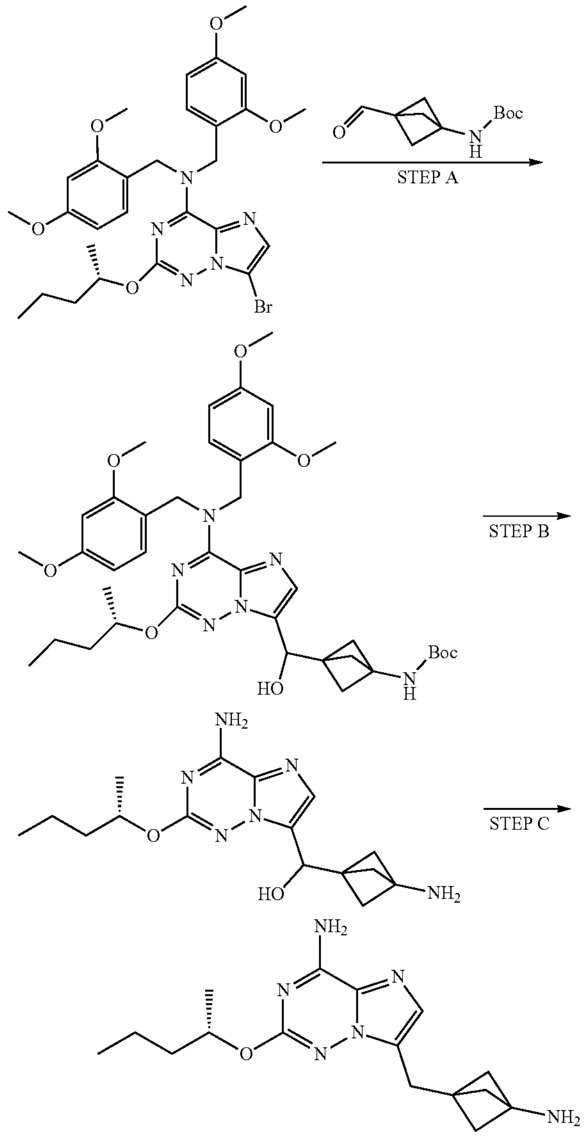

Step A: Tert-butyl (3-((4-(bis(2,4-dimethoxybenzyl)amino)-2-(((S)-pent-2-yl)oxy)imidazo[2,1-f][1,2,4]triazin-7-yl)(hydroxy)methyl) bicyclo[1.1.1]pent-1-yl) carbamate

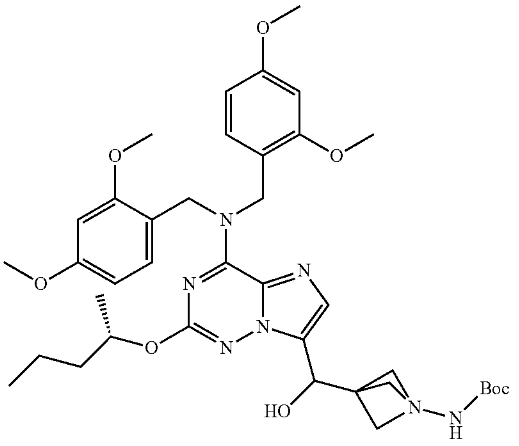

To a solution of (S)-7-bromo-N,N-bis(2,4-dimethoxybenzyl)-2-(pent-2-yloxy)imidazo[2,1-f][1,2,4]triazin-4-amine (450 mg, 0.75 mmol) in THF (10 mL), a solution of n-BuLi (1.6 M, 0.94 mL, 1.5 mmol) was added dropwise at a temperature of −75° C. to −65° C. One hour later, a suspension of tert-butyl (3-formylbicyclo[1.1.1]pent-1-yl) carbamate (317 mg, 1.5 mmol) in THE (3 mL) was added dropwise. The resulting mixture was stirred at −70° C. for 3 h and then warmed to room temperature. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (130 mg, yellow oil, yield 23.6%). MS: M/e 733 $(M+1)^+$.

Step B: (4-amino-2-(((S)-pent-2-yl)oxy)imidazo[2,1-f][1,2,4]triazin-7-yl) (3-aminobicyclo[1.1.1]pent-1-yl)methanol

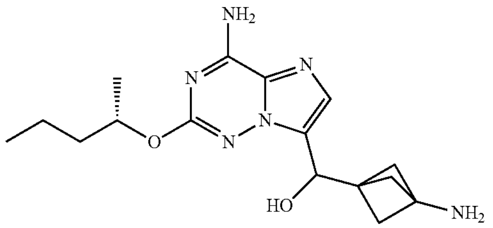 [SMILES: CCC[C@H](C)Oc1nc(N)c2ncc(C(O)C34CC(N)(C3)C4)n2n1]

$H_2O$ (1 mL) was added to a mixture of the product of step A (130 mg, crude) in TFA (4.5 mL), and the resulting mixture was stirred at 40° C. for 12 h. The mixture was cooled to room temperature and concentrated to dryness. $H_2O$ (15 mL) was added to the residue, and the mixture was extracted with DCM (15 mL×2). The aqueous phase was alkalized with 2 N NaOH to pH=12-13, extracted with a DCM/iPrOH (4:1) mixture (20 mL×2), dried over $Na_2SO_4$, filtered and concentrated. The residue (30 mg) was used directly without further purification. MS: M/e 333 $(M+1)^+$.

Step C: (S)-7-((3-aminobicyclo[1.1.1]pent-1-yl)methyl)-2-(pent-2-yloxy)imidazo[2,1-f][1,2,4]triazin-4-amine

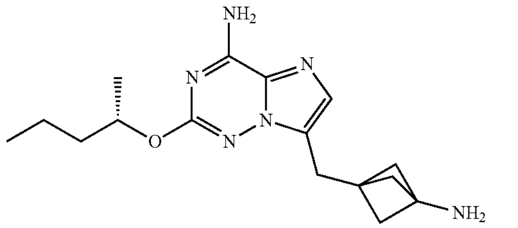 [SMILES: CCC[C@H](C)Oc1nc(N)c2ncc(CC34CC(N)(C3)C4)n2n1]

$Et_3SiH$ (3 mL) was added to a mixture of the product of step B (30 mg, crude) in TFA (3 mL), and the resulting mixture was stirred at 70° C. for 12 h. The mixture was cooled to room temperature and concentrated to dryness. $H_2O$ (15 mL) was added to the residue and the mixture was extracted with DCM (15 mL×2). The aqueous phase was alkalized with 2 N NaOH to pH=12-13, extracted with a DCM/iPrOH (4:1) mixture (20 mL×2), dried over $Na_2SO_4$, filtered and concentrated. The residue was purified by preparative TLC to obtain the target compound (13.5 mg, 24% for two steps). $^1H$ NMR (400 MHz, DMSO-d6) δ 8.13 (s, 1H), 8.04 (s, 1H), 7.33 (s, 1H), 5.02 (dd, J=12.2, 6.1 Hz, 1H), 3.10 (s, 2H), 1.69 (d, J=11.8 Hz, 8H), 1.59 (dt, J=13.4, 6.3 Hz, 1H), 1.44 (dt, J=14.8, 6.9 Hz, 2H), 1.33 (d, J=6.1 Hz, 3H), 0.96 (t, J=7.3 Hz, 3H) ppm. MS: M/e 317 $(M+1)^+$.

Compound B41: 2-((5-methylisoxazol-3-yl)methoxy)-7-(piperidin-4-ylmethyl)imidazo[2,1-f][1,2,4]triazin-4-amine

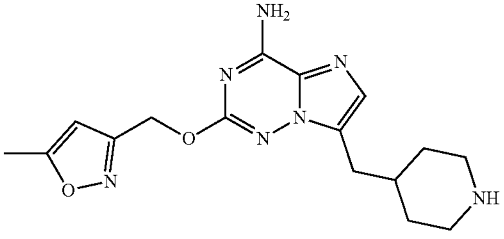

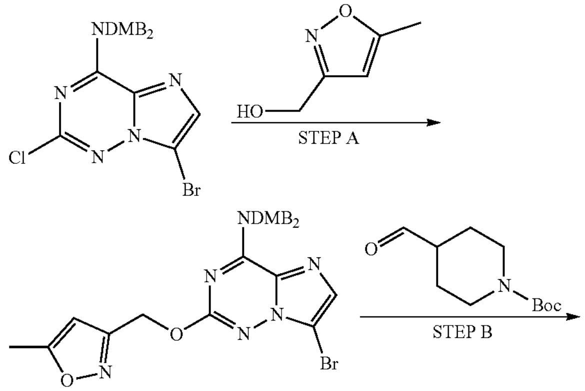

-continued

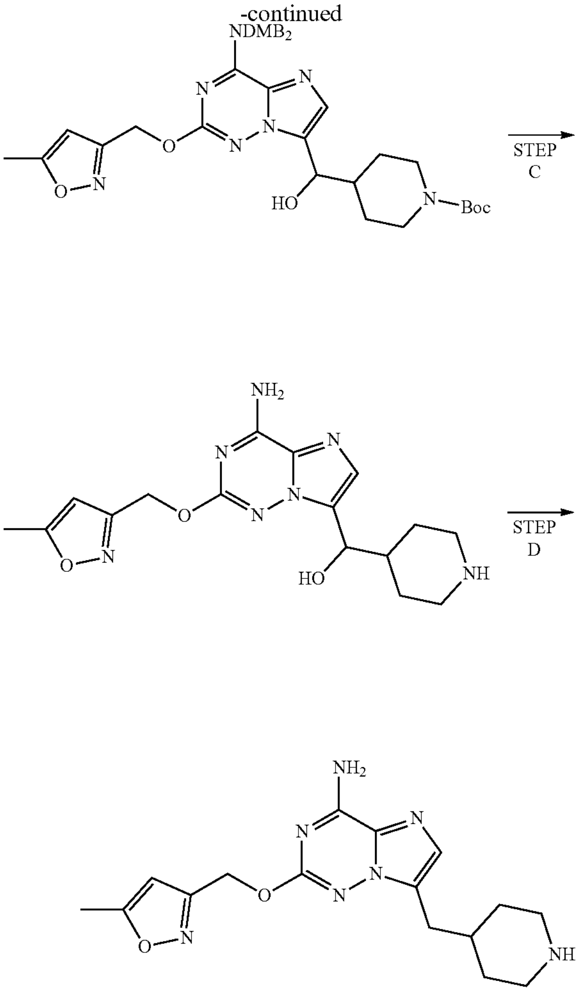

Step A: 7-bromo-N,N-bis(2,4-dimethoxybenzyl)-2-((5-methylisoxazol-3-yl)methoxy)imidazo[2,1-f][1,2,4]triazin-4-amine

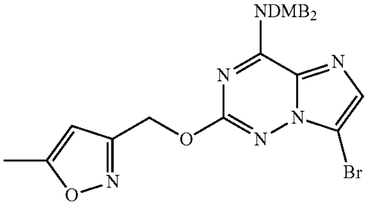

NaH (60%, 80 mg, 2 mmol) was added to a solution of (5-methylisoxazol-3-yl)methanol (113 mg, 1 mmol) in THF (10 mL) at 0° C. The reaction mixture was stirred at room temperature for 20 min. 7-bromo-2-chloro-N,N-bis(2,4-dimethoxybenzyl)imidazo[2,1-f][1,2,4]triazin-4-amine (300 mg, 0.5 mmol) was added to the mixture. The reaction mixture was stirred at room temperature for 20 min. An aqueous ammonium chloride solution was added and the mixture was extracted with ethyl acetate. The combined organic extracts were dried over sodium sulfate, filtered and evaporated. The crude product was purified by column chromatography to obtain the title product (200 mg, 64.1%). MS: M/e: 624.7 $(M+1)^+$.

Step B: Tert-butyl 4-((4-(bis(2,4-dimethoxybenzyl) amino)-2-((5-methylisoxazol-3-yl) methoxy)imidazo [2,1-f][1,2,4]triazin-7-yl)(hydroxy)methyl)piperidin-1-carboxylate

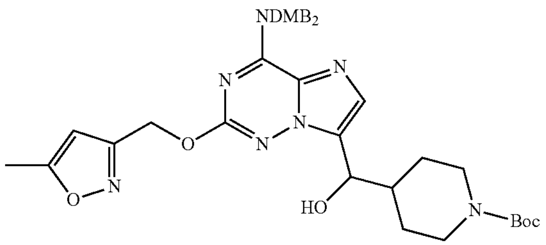

To a solution of 7-bromo-N,N-bis(2,4-dimethoxybenzyl)-2-((5-methylisoxazol-3-yl)methoxy)imidazo[2,1-f][1,2,4] triazin-4-amine (200 mg, 0.32 mmol) in THF (8 mL), a solution of n-BuLi (1.6 M, 0.3 mL, 0.48 mmol) was added dropwise at a temperature of −75° C. to −65° C. One hour later, a suspension of tert-butyl 4-formyl-2-methylpiperidin-1-carboxylate (82 mg, 0.38 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (100 mg, 41.3%). MS: M/e 760 $(M+1)^+$.

Step C: (4-amino-2-((5-methylisoxazol-3-yl) methoxy)imidazo[2,1-f][1,2,4]triazin-7-yl)(piperidin-4-yl)methanol

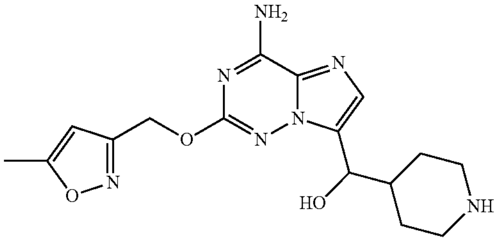 [SMILES: Cc1cc(COc2nc(N)c3ncc(C(O)C4CCNCC4)n3n2)no1]

To a mixture of the product of step B (100 mg, 0.131 mmol) in TFA (8 mL), $H_2O$ (2 mL) was added, and the resulting mixture was stirred at room temperature for 2 d. The mixture was concentrated to dryness. $H_2O$ was added to the residue and the mixture was filtered. The filtrate was washed with DCM, and adjusted to pH 12-13 with a 2 M NaOH solution. The solution was extracted with DCM (20 mL×3). The organic phase was washed with brine, dried over $Na_2SO_4$, filtered and concentrated to obtain the target compound (30 mg), which was directly used in the next step. MS: M/e 360 $(M+1)^+$.

Step D: 2-((5-methylisoxazol-3-yl)methoxy)-7-(piperidin-4-ylmethyl)imidazo[2,1-f][1,2,4]triazin-4-amine

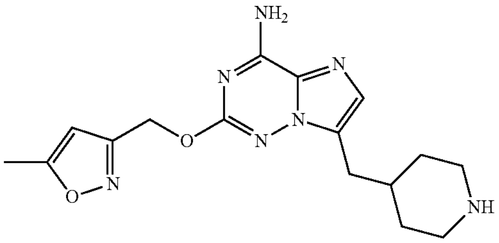 [SMILES: Cc1cc(COc2nc(N)c3ncc(CC4CCNCC4)n3n2)no1]

$Et_3SiH$ (4 mL) was added to a mixture of the product of step C (30 mg, crude) in TFA (4 mL), and the resulting mixture was stirred at 85° C. for 2 h. The mixture was cooled to room temperature and concentrated to dryness. The residue was purified by preparative HPLC to obtain the target compound (5 mg, 11.1% for two steps). $^1H$ NMR (400 MHz, DMSO-d6) δ 8.49 (s, 1H), 8.27 (s, 1H), 8.19 (s, 1H), 7.36 (s, 1H), 6.33 (s, 1H), 5.33 (s, 2H), 3.23 (d, J=11.7 Hz, 2H), 2.77 (d, J=6.3 Hz, 2H), 2.41 (s, 3H), 1.96 (s, 1H), 1.73 (m, 2H), 1.34 (m, 2H) ppm. MS: M/e 333 $(M+1)^+$.

Compound B42: 2—(((S)-pent-2-yl)oxy)-7-(pyrrolidin-2-ylmethyl)imidazo[2,1-f][1,2,4]triazin-4-amine

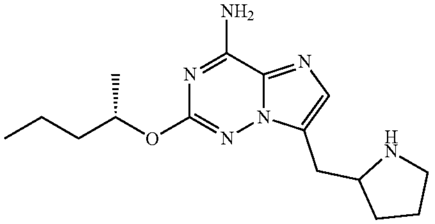

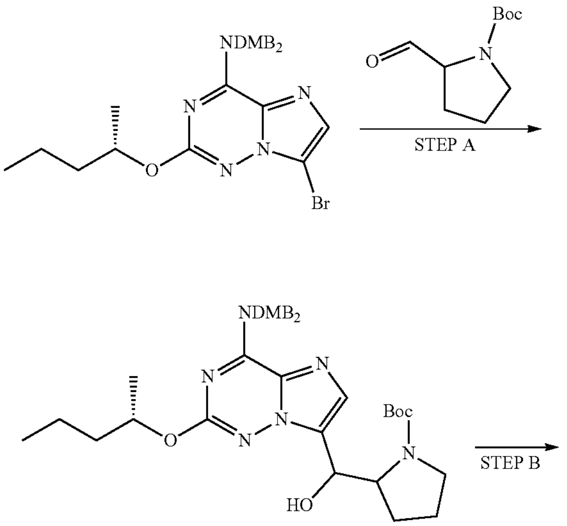

-continued

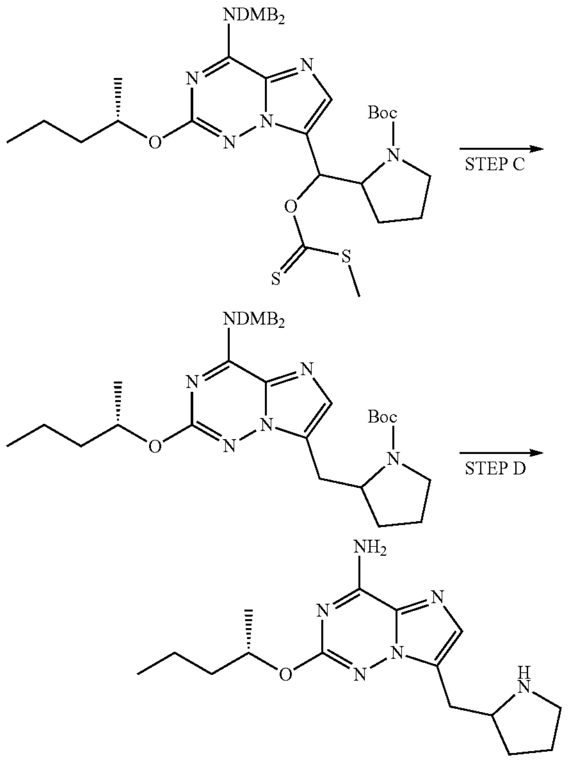

Step A: Tert-butyl 2-((4-(bis(2,4-dimethoxybenzyl)amino)-2-(((S)-pent-2-yl)oxy)imidazo[2,1-f][1,2,4]triazin-7-yl)(hydroxy)methyl)pyrrolidin-1-carboxylate

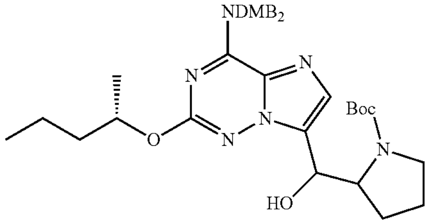

To a solution of (S)-7-bromo-N,N-bis(2,4-dimethoxybenzyl)-2-(pent-2-yloxy)imidazo[2,1-f][1,2,4]triazin-4-amine (600 mg, 1 mmol) in THF (8 mL), a solution of n-BuLi (1.6 M, 1.25 mL, 2 mmol) was added dropwise at a temperature of −75° C. to −65° C. One hour later, a suspension of tert-butyl 2-formylpyrrolidin-1-carboxylate (298 mg, 1.5 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (600 mg, 83.4%). MS: M/e 721 $(M+1)^+$.

Step B: Tert-butyl 2-((4-(bis(2,4-dimethoxybenzyl)amino)-2-(((S)-pent-2-yl)oxy)imidazo[2,1-f][1,2,4]triazin-7-v)(((methylthio)thiocarbonyl)oxy)methyl)pyrrolidin-1-carboxylate

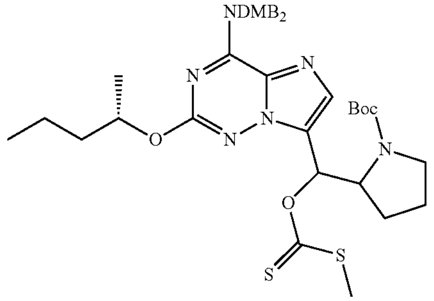

At 0° C., to a solution of tert-butyl 2-((4-(bis(2,4-dimethoxybenzyl)amino)-2-(((S)-pent-2-yl)oxy)imidazo[2,1-f][1,2,4]triazin-7-yl)(hydroxy)methyl)pyrrolidin-1-carboxylate (200 mg, 0.28 mmol), carbon disulfide (32 mg, 0.42 mmol) and imidazole (20 mg, 0.3 mmol) in THF (8 mL), NaH (6(0%, 23 mg, 0.56 mmol) was added, and the mixture was stirred for 30 min. To this mixture, methyl iodide (80 mg, 0.56 mmol) was added, and then the mixture was stirred at 0° C. for 1.5 h and at room temperature for 3.5 h. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (160 mg, 70.7%). MS: M/e 811 $(M+1)^+$.

Step C: Tert-butyl 2-((4-(bis(2,4-dimethoxybenzyl)amino)-2-(((S)-pent-2-yl)oxy)imidazo[2,1-f][1,2,4]triazin-7-yl)methyl)pyrrolidin-1-carboxylate

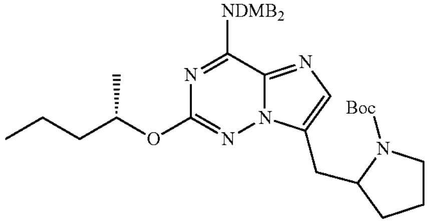

To a mixture of tert-butyl 2-((4-(bis(2,4-dimethoxybenzyl)amino)-2-(((S)-pent-2-yl)oxy)imidazo[2,1-f][1,2,4]triazin-7-yl)(((methylthio)thiocarbonyl)oxy)methyl)pyrrolidin-1-carboxylate (90 mg, 0.111 mmol) in toluene (10 mL), tributyltin hydride (65 mg, 0.22 mmol) and AIBN (18 mg, 0.11 mmol) were added. The resulting mixture was stirred at 100° C. overnight under the protection of nitrogen atmosphere, and then concentrated and dried. The residue was added to water, extracted with EtOAc (20 mL×3), washed with brine, dried over $Na_2SO_4$, filtered and concentrated. The residue was purified by preparative TLC to obtain the target compound (60 mg, 77.9%). MS: M/e 705 $(M+1)^+$.

Step D: 2-(((S)-pent-2-yl)oxy)-7-(pyrrolidin-2-ylmethyl)imidazo[2,1-f][1,2,4]triazin-4-amine

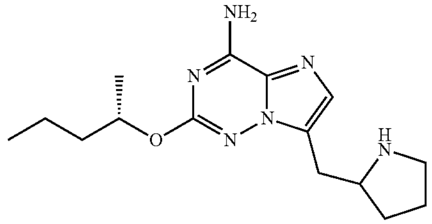 [SMILES: CCC[C@H](C)Oc1nc(N)c2ncc(CC3CCCN3)n2n1]

To a mixture of the product of step C (60 mg, 0.085 mmol) in TFA (8 mL), $H_2O$ (2 mL) was added, and then the mixture was stirred at room temperature for 2 d. The mixture was concentrated to dryness. The residue was purified by preparative HPLC to obtain the target compound (9 mg, 34.6%). $^1$H NMR (400 MHz, DMSO-d6) δ 8.74 (s, 1H), 8.21 (s, 1H), 8.10 (s, 1H), 7.44 (s, 1H), 5.02 (dd, J=12.0, 6.0 Hz, 1H), 3.85 (s, 1H), 3.28-3.18 (m, 3H), 3.16 (d, J=6.6 Hz, 1H), 2.08 (d, J=6.7 Hz, 1H), 1.97 (d, J=5.4 Hz, 1H), 1.89 (d, J=7.1 Hz, 1H), 1.73-1.61 (m, 2H), 1.54 (d, J=6.3 Hz, 1H), 1.38 (dt, J=15.5, 7.9 Hz, 2H), 1.28 (d, J=6.0 Hz, 3H), 0.90 (dd, J=15.4, 8.0 Hz, 3H) ppm. MS: M/e 305 $(M+1)^+$.

Compound B43: (S)-7-((2-azaspiro[3.5]non-7-yl)methyl)-2-(pent-2-yloxy)imidazo[2,1-f][1,2,4]triazin-4-amine

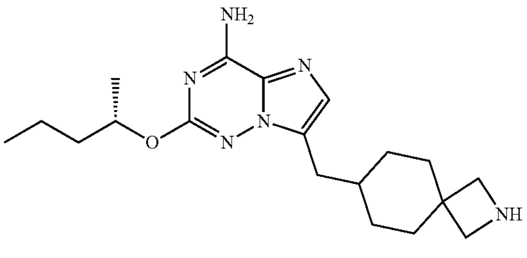

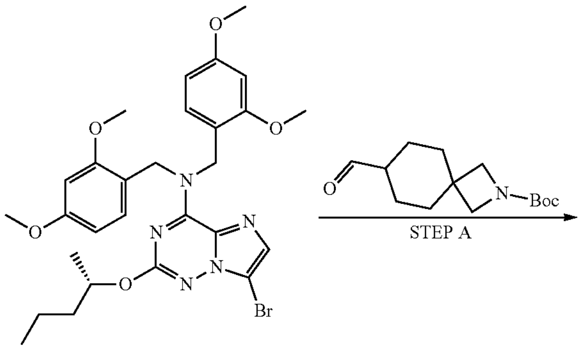

-continued

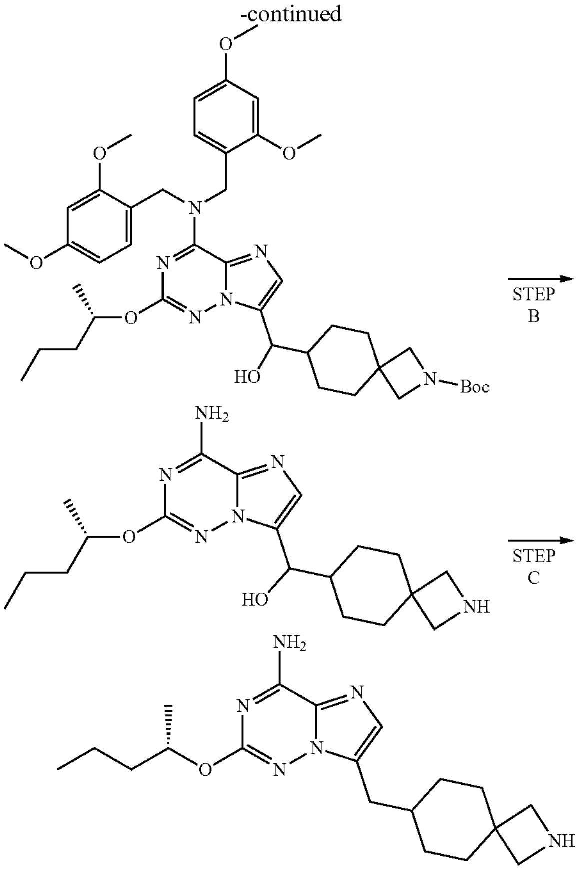

Step A: Tert-butyl 7-((4-(bis(2,4-dimethoxybenzyl)amino)-2-(((S)-pent-2-yl)oxy)imidazo[2,1-f][1,2,4]triazin-7-yl)(hydroxy)methyl)piperidin-2-azaspiro[3.5]nonan-2-carboxylate

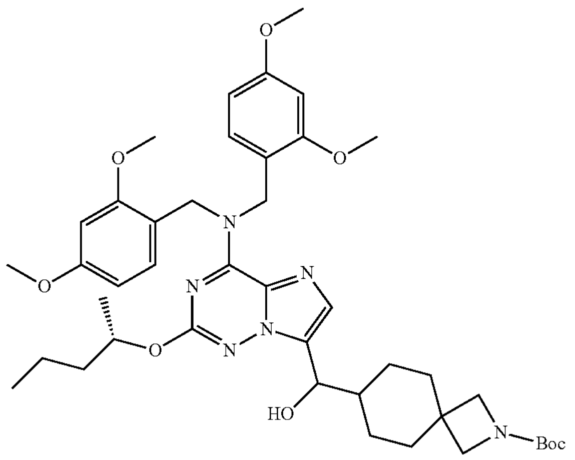 [SMILES: CCC[C@H](C)Oc1nc(N(Cc2ccc(OC)cc2OC)Cc2ccc(OC)cc2OC)c2ncc(C(O)C3CCC4(CC3)CN(C(=O)OC(C)(C)C)C4)n2n1]

To a solution of (S)-7-bromo-N,N-bis(2,4-dimethoxybenzyl)-2-(pent-2-yloxy)imidazo[2,1-f][1,2,4]triazin-4-amine (330 mg, 0.55 mmol) in THF (10 mL), a solution of n-BuLi (1.6 M, 0.69 mL, 1.1 mmol) was added dropwise at a temperature of −75° C. to −65° C. One hour later, a suspension of tert-butyl 7-formyl-2-azaspiro[3.5]nonan-2- carboxylate (209 mg, 0.82 mmol) in THF (3 mL) was added dropwise. The resulting mixture was stirred at −70° C. for 3 h and then warmed to room temperature. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (200 mg, yellow oil, yield 47%). MS: M/e 775 $(M+1)^+$.

Step B: (4-amino-2-(((S)-pent-2-yl)oxy)imidazo[2,1-f][1,2,4]triazin-7-yl) (2-azaspiro[3.5]non-7-yl) methanol

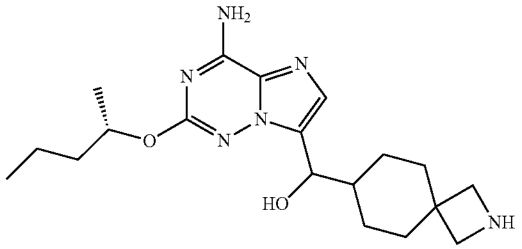 [SMILES: CCC[C@H](C)Oc1nc(N)c2ncc(C(O)C3CCC4(CC3)CNC4)n2n1]

$H_2O$ (1 mL) was added to a mixture of the product of step A (200 mg, crude) in TFA (4.5 mL), and the resulting mixture was stirred at 40° C. for 12 h. The mixture was cooled to room temperature and concentrated to dryness. $H_2O$ (15 mL) was added to the residue and the mixture was extracted with DCM (15 mL×2). The aqueous phase was alkalized to pH 12-13 with 2 N NaOH, extracted with DCM/iPrOH=4:1 (20 mL×2), dried over $Na_2SO_4$, filtered and concentrated. The residue (65 mg) was used directly without further purification. MS: M/e 375 $(M+1)^+$.

Step C: (S)-7-((2-azaspiro[3.5]non7-yl)methyl)-2-(pent-2-yloxy)imidazo[2,1-f][1,2,4]triazin-4-amine

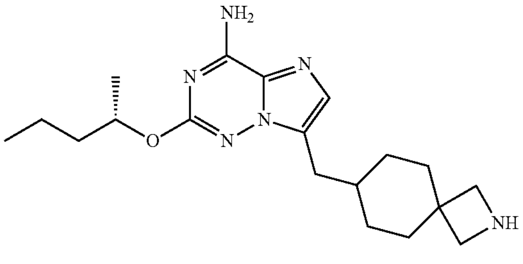 [SMILES: CCC[C@H](C)Oc1nc(N)c2ncc(CC3CCC4(CC3)CNC4)n2n1]

$Et_3SiH$ (4 mL) was added to a mixture of the product of step B (65 mg, crude) in TFA (4 mL), and the residue was stirred at 70° C. for 12 h. The mixture was cooled to room temperature and concentrated to dryness. $H_2O$ (15 mL) was added to the residue and the mixture was extracted with DCM (15 mL×2). The aqueous phase was alkalized to pH 12-13 with 2 N NaOH, extracted with DCM/iPrOH=4:1 (20 mL×2), dried over $Na_2SO_4$, filtered and concentrated. The residue was purified by preparative HPLC to obtain the target compound (8.3 mg, 10% for two steps). $^1H$ NMR (400 MHz, DMSO-d6) δ 8.38 (s, 1H), 8.05 (s, 1H), 7.96 (s, 1H), 7.27 (s, 1H), 4.96 (m, 1H), 3.58 (s, 2H), 3.50 (s, 3H), 2.65 (d, J=6.8 Hz, 2H), 1.95 (d, J=12.7 Hz, 2H), 1.66 (d, J=6.2 Hz, 2H), 1.55 (d, J=9.3 Hz, 3H), 1.35 (d, J=12.8 Hz, 4H), 1.27 (d, J=6.0 Hz, 3H), 0.99 (m, 2H), 0.90 (t, J=7.2 Hz, 3H) ppm. MS: M/e 359 $(M+1)^+$.

Compound B44: 2-((5-methylthiazol-2-yl)methoxy)-7-(piperidin-4-ylmethyl)imidazo[2,1-f][1,2,4]triazin-4-amine

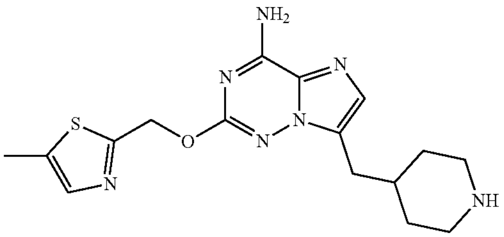

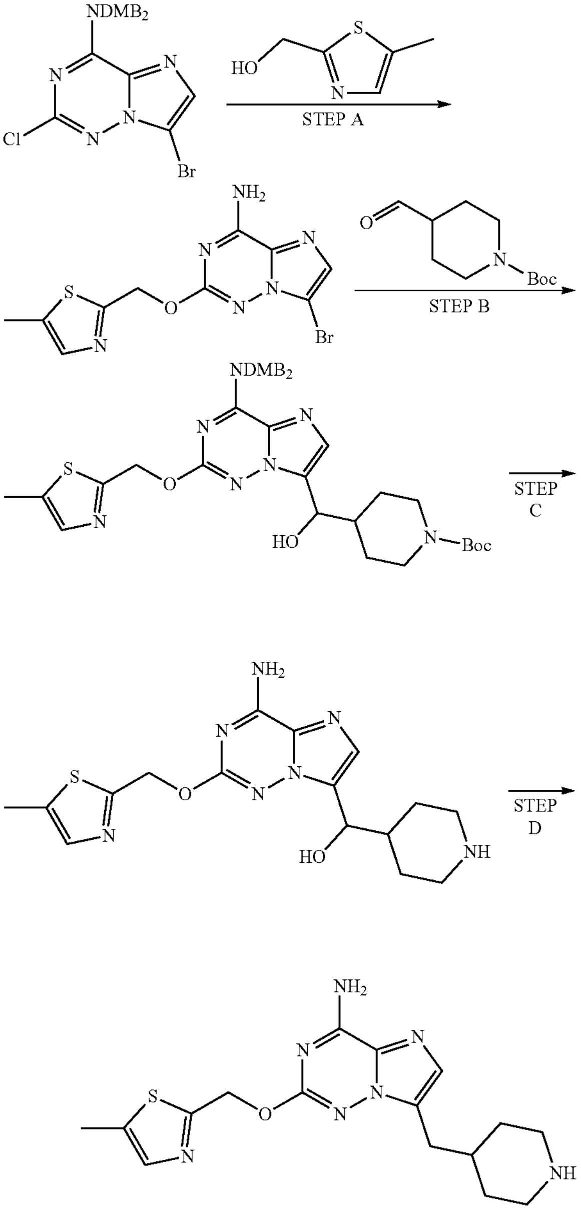

Step A: 7-bromo-N,N-bis(2,4-dimethoxybenzyl)-2-((5-methylthiazol-2-yl) methoxy)imidazo[2,1-f][1,2,4]triazin-4-amine

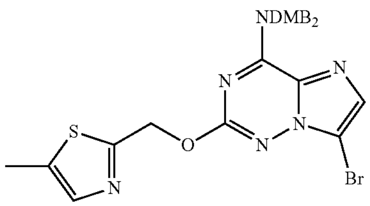

NaH (60%, 80 mg, 2 mmol) was added to a solution of (5-methylthiazol-2-yl)methanol (129 mg, 1 mmol) in THF (10 mL) at 0° C. The reaction mixture was stirred at room temperature for 20 min. 7-bromo-2-chloro-N,N-bis(2,4-dimethoxybenzyl)imidazo[2,1-f][1,2,4]triazin-4-amine (300 mg, 0.5 mmol) was added to the mixture. The reaction mixture was stirred at 70° C. overnight. An aqueous ammonium chloride solution was added and the mixture was extracted with ethyl acetate. The combined organic extracts were dried over sodium sulfate, filtered and evaporated. The crude product was purified by column chromatography to obtain the title product (240 mg, 75%). MS: M/e: 642 $(M+1)^+$.

Step B: Tert-butyl 4-((4-(bis(2,4-dimethoxybenzyl) amino)-2-((5-methylthiazol-2-yl)oxy)imidazo[2,1-f][1,2,4]triazin-7-yl)(hydroxy)methyl)piperidin-1-carboxylate

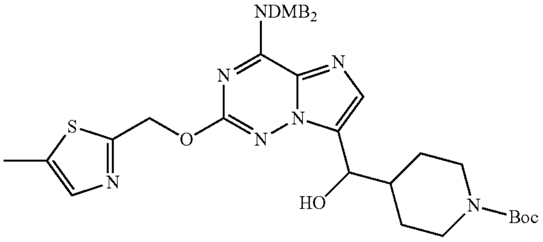

To a solution of 7-bromo-N,N-bis(2,4-dimethoxybenzyl)-2-((5-methylthiazol-2-yl)methoxy)imidazo[2,1-f][1,2,4]triazin-4-amine (240 mg, 0.38 mmol) in THF (8 mL), a solution of n-BuLi (1.6 M, 0.35 mL, 0.56 mmol) was added dropwise at a temperature of −75° C. to −65° C. One hour later, a suspension of tert-butyl 4-formyl-2-methylpiperidin-1-carboxylate (95 mg, 0.45 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (110 mg, 37.8%). MS: M/e 777 $(M+1)^+$.

Step C: (4-amino-2-((5-methylthiazol-2-yl)methoxy) imidazo[2,1-f][1,2,4]triazin-7-yl)(piperidin-4-yl) methanol

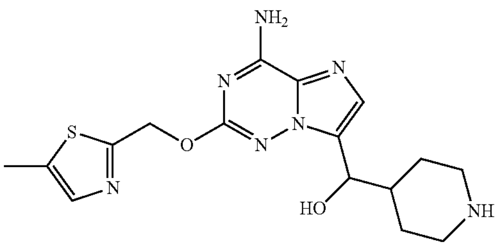 [SMILES: Cc1cnc(COc2nc(N)c3ncc(C(O)C4CCNCC4)n3n2)s1]

$H_2O$ (2 mL) was added to a mixture of the product of step B (110 mg, 0.141 mmol) in TFA (8 mL), and the resulting mixture was stirred at room temperature for 2 d. The mixture was concentrated to dryness. $H_2O$ was added to the residue and the mixture was filtered. The filtrate was washed with DCM, and adjusted to pH 12-13 with 2 M NaOH solution. The solution was extracted with DCM (20 mL×3). The organic phase was washed with brine, dried over $Na_2SO_4$, filtered and concentrated to obtain the target compound (30 mg), which was directly used in the next step. MS: M/e 376 $(M+1)^+$.

Step D: 2-((5-methylthiazol-2-yl)methoxy)-7-(piperidin-4-ylmethyl)imidazo[2,1-f][1,2,4]triazin-4-amine

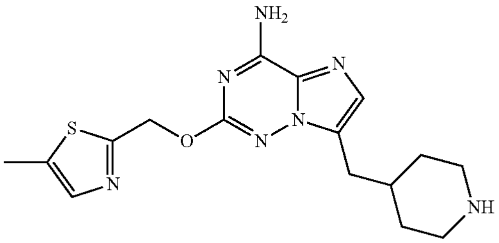 [SMILES: Cc1cnc(COc2nc(N)c3ncc(CC4CCNCC4)n3n2)s1]

$Et_3SiH$ (4 mL) was added to a mixture of the product of step C (30 mg, crude) in TFA (4 mL), and the resulting mixture was stirred at 80° C. for 2 h. The mixture was cooled to room temperature and concentrated to dryness. The residue was purified by preparative HPLC to obtain the target compound (5 mg, 9.8% for two steps). $^1H$ NMR (400 MHz, DMSO-d6)) δ 8.34 (s, 1H), 8.28 (s, 1H), 7.50 (s, 1H), 7.39 (d, J=5.6 Hz, 1H), 7.23 (s, 1H), 5.52 (s, 2H), 3.21 (d, J=12.5 Hz, 2H), 2.79 (d, J=6.4 Hz, 4H), 2.43 (s, 3H), 1.99 (s, 1H), 1.75 (d, J=5.3 Hz, 1H), 1.71 (s, 1H), 1.39 (s, 2H) ppm. MS: M/e 360 $(M+1)^+$.

Compound B45: 2-((1-phenylpent-2-yl)oxy)-7-(piperidin-4-ylmethyl)imidazo[2,1-f][1,2,4]triazin-4-amine

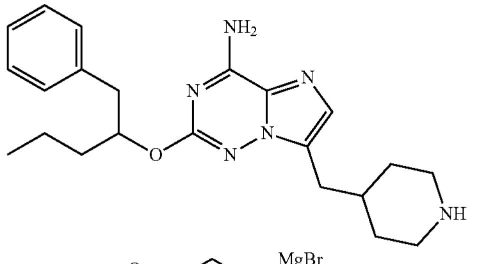

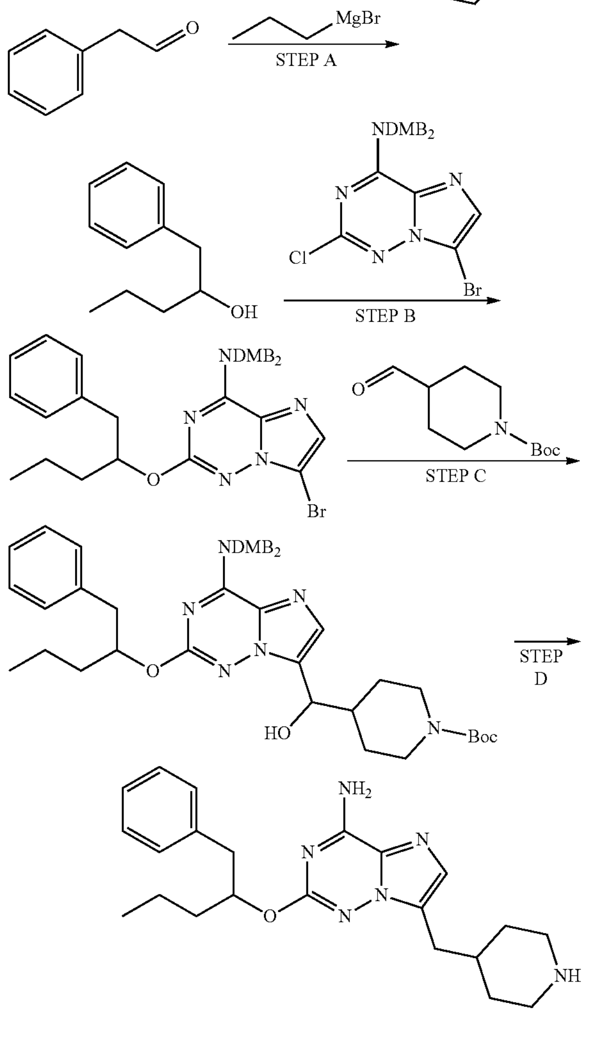

Step A: 1-phenylpentan-2-ol

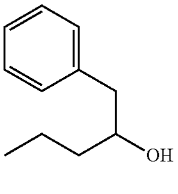

Ethyl magnesium bromide (2 M, 7 mL, 14 mmol) was added to a solution of 2-phenylacetaldehyde (1.2 g, 10 mmol) in THF (10 mL) at 0° C. The reaction mixture was stirred at room temperature for 2 h. Water was added to the mixture and the resulting mixture was extracted with ethyl acetate. The combined organic extracts were dried over sodium sulfate, filtered and evaporated. The crude product was purified by column chromatography to obtain the title product (520 mg, 31.7%). MS: M/e: 165 $(M+1)^+$.

Step B: 7-bromo-N,N-bis(4-methoxybenzyl)-2-((1-phenylpent-2-yl)oxy)imidazo[2,1-f][1,2,4]triazin-4-amine

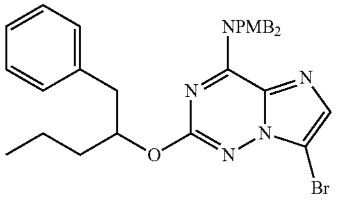

NaH (60%, 80 mg, 2 mmol) was added to a solution of 1-phenylpentan-2-ol (169 mg, 1 mmol) in THF (10 mL) at 0° C., and the reaction mixture was stirred at room temperature for 20 min. 7-bromo-2-chloro-N,N-bis(4-methoxybenzyl)imidazo[2,1-f][1,2,4]triazin-4-amine (243 mg, 0.5 mmol) was added to the mixture. The reaction mixture was stirred at 70° C. overnight. An aqueous ammonium chloride solution was added and the mixture was extracted with ethyl acetate. The combined organic extracts were dried over sodium sulfate, filtered and evaporated. The crude product was purified by column chromatography to obtain the title product (220 mg, 81.9%). MS: M/e: 616 $(M+1)^+$.

Step C: Tert-butyl 4-((4-(bis(4-methoxybenzyl)amino)-2-((1-phenylpent-2-yl)oxy)imidazo[2,1-f][1,2,4]triazin-7-yl)(hydroxy)methyl)piperidin-1-carboxylate

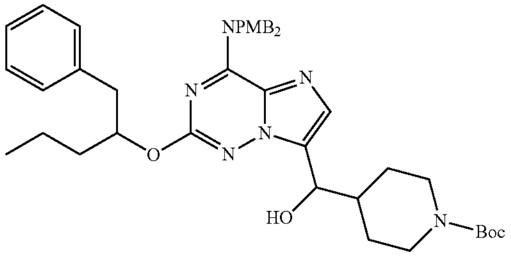

To a solution of 7-bromo-N,N-bis(4-methoxybenzyl)-2-((1-phenylpent-2-yl)oxy)imidazo[2,1-f][1,2,4]triazin-4-amine (220 mg, 0.36 mmol) in THF (8 mL), a solution of n-BuLi (1.6 M, 0.45 mL, 0.72 mmol) was added dropwise at a temperature of −75° C. to −65° C. One hour later, a suspension of tert-butyl 4-formyl-2-methylpiperidin-1-carboxylate (115 mg, 0.54 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (140 mg, 51.8%). MS: M/e 752 $(M+1)^+$.

Step D: 2-((1-phenylpent-2-yl)oxy)-7-(piperidin-4-ylmethyl)imidazo[2,1-f][1,2,4]triazin-4-amine

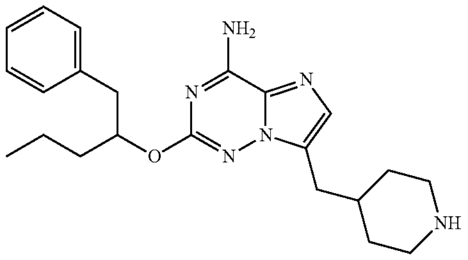 [SMILES: CCCC(Cc1ccccc1)Oc1nc(N)c2ncc(CC3CCNCC3)n2n1]

$Et_3SiH$ (4 mL) was added to a mixture of the product of step C (140 mg, 0.186 mmol) in TFA (4 mL), and the resulting mixture was stirred at 85° C. for 4 h. The mixture was cooled to room temperature and concentrated to dryness. TFA (5 mL) was added to the residue, and then the reaction mixture was heated at 80° C. overnight. The mixture was concentrated and the residue was purified by preparative HPLC to obtain the target compound (4 mg, 15% for two steps). $^1H$ NMR (400 MHz, DMSO-d6) δ 8.09 (s, 1H), 8.02 (s, 1H), 7.33-7.25 (m, 5H), 7.20 (d, J=3.2 Hz, 1H), 5.11 (s, 1H), 3.06 (d, J=12.3 Hz, 3H), 2.89-2.83 (m, 1H), 2.75 (d, J=6.3 Hz, 2H), 2.57 (s, 2H), 1.90 (s, 1H), 1.68-1.53 (m, 4H), 1.46-1.31 (m, 2H), 1.24 (s, 2H), 0.86 (t, J=7.0 Hz, 3H) ppm. MS: Me 395 $(M+1)^+$.

Compound B46: 7-(piperidin-4-ylmethyl)-2-((tetrahydrofuran-3-yl)methoxy)imidazo[2,1-f][1,2,4]triazin-4-amine

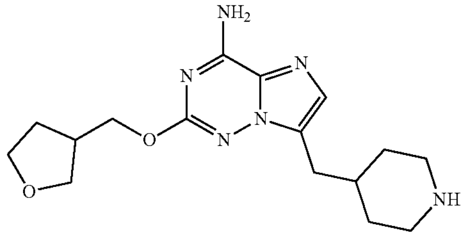 [SMILES: Nc1nc(OCC2CCOC2)nn2c(CC3CCNCC3)cnc12]

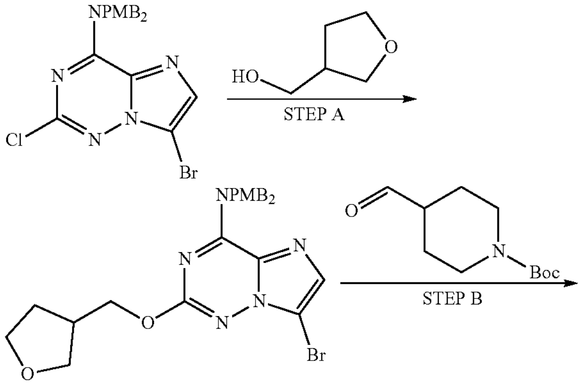

-continued

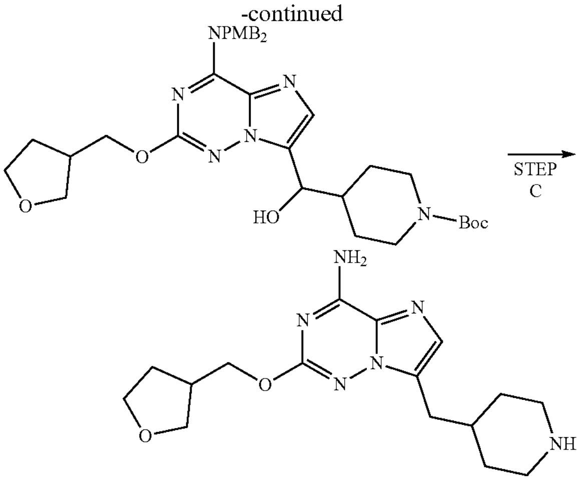

Step A: 7-bromo-N,N-bis(4-methoxybenzyl)-2-((tetrahydrofuran-3-yl) methoxy)imidazo[2,1-f][1,2,4]triazin-4-amine

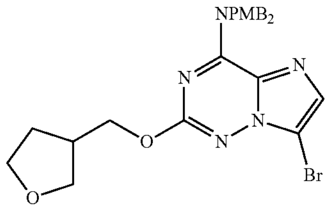

NaH (60%, 160 mg, 4 mmol) was added to a solution of (tetrahydrofuran-3-yl)methanol (204 mg, 2 mmol) in THF (10 mL) at 0° C. The reaction mixture was stirred at room temperature for 20 min. 7-bromo-2-chloro-N,N-bis(4-methoxybenzyl)imidazo[2,1-f][1,2,4]triazin-4-amine (487 mg, 1 mmol) was added to the mixture. The reaction mixture was stirred at 70° C. overnight. An aqueous ammonium chloride solution was added and the mixture was extracted with ethyl acetate. The combined organic extracts were dried over sodium sulfate, filtered and evaporated. The crude product was purified by column chromatography to obtain the title product (500 mg, 90%). MS: M/e: 554 $(M+1)^+$.

Step B: Tert-butyl 4-((4-(bis(4-methoxybenzyl) amino)-2-((tetrahydrofuran-3-yl) methoxy)imidazo [2,1-f][1,2,4]triazin-7-yl)(hydroxy)methyl)piperidin-1-carboxylate

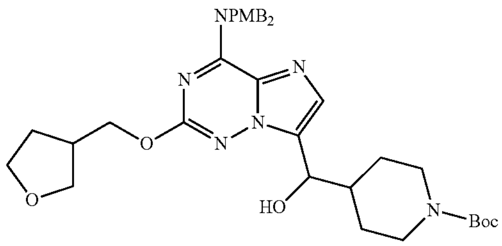

To a solution of 7-bromo-N,N-bis(4-methoxybenzyl)-2-((tetrahydrofuran-3-yl) methoxy)imidazo[2,1-f][1,2,4]triazin-4-amine (220 mg, 0.39 mmol) in THF (8 mL), a solution of n-BuLi (1.6 M, 0.45 mL, 0.72 mmol) was added dropwise at a temperature of −75° C. to −65° C. One hour later, a suspension of tert-butyl 4-formyl-2-methylpiperidin-1-carboxylate (115 mg, 0.54 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (130 mg, 47.6%). MS: M/e 689 (M+1).

Step C: 7-(piperidin-4-ylmethyl)-2-((tetrahydrofuran-3-yl)methoxy)imidazo[2,1-f][1,2,4]triazin-4-amine

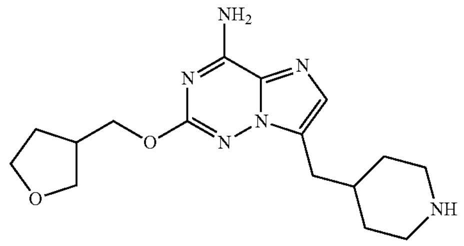 [SMILES: Nc1nc(OCC2CCOC2)nn2c(CC3CCNCC3)cnc12]

$Et_3SiH$ (4 mL) was added to a mixture of the product of step B (130 mg, 0.33 mmol) in TFA (4 mL), and the resulting mixture was stirred at 85° C. for 4 h. The mixture was cooled to room temperature and concentrated to dryness. TFA (5 mL) was added to the residue, and the reaction mixture was heated at 80° C. overnight. The mixture was concentrated, and the residue was purified by preparative HPLC to obtain the target compound (18 mg, 16.3%). $^1H$ NMR (400 MHz, DMSO-d6) δ 8.13 (s, 1H), 8.03 (s, 1H), 7.30 (s, 1H), 4.19 (d, J=6.8 Hz, 1H), 4.15-4.07 (m, 1H), 3.77 (dd, J=16.7, 8.5 Hz, 2H), 3.65 (d, J=7.6 Hz, 1H), 3.55-3.48 (m, 1H), 2.96 (d, J=12.1 Hz, 2H), 2.71 (d, J=6.6 Hz, 2H), 2.69-2.63 (m, 1H), 2.45 (s, 2H), 2.00 (s, 1H), 1.80 (s, 1H), 1.65 (dd, J=12.1, 6.1 Hz, 1H), 1.56 (d, J=12.6 Hz, 2H), 1.13 (d, J=11.4 Hz, 2H) ppm. MS: M/e 333 $(M+1)^+$.

Compound B47: 2-(hept-4-yloxy)-7-(piperidin-4-ylmethyl)imidazo[2,1-f][1,2,4]triazin-4-amine

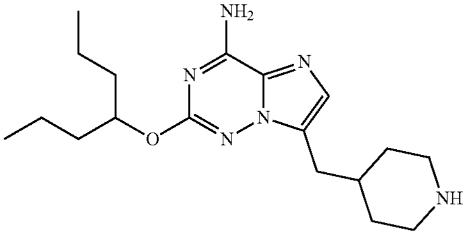 [SMILES: CCCC(CCC)Oc1nc(N)c2ncc(CC3CCNCC3)n2n1]

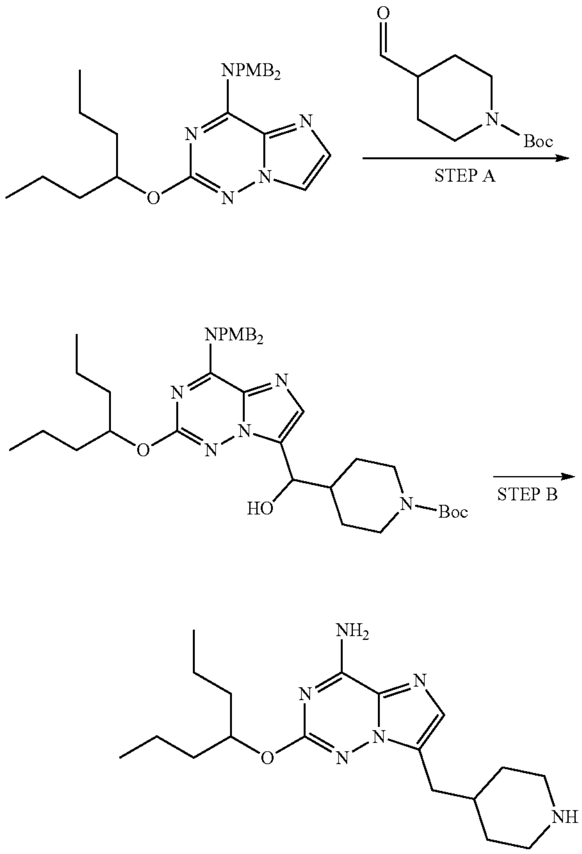

Step A: Tert-butyl 4-((4-(bis(4-methoxybenzyl)amino)-2-(hept-4-yloxy)imidazo[2,1-f][1,2,4]triazin-7-yl)(hydroxy)methyl)piperidin-1-carboxylate

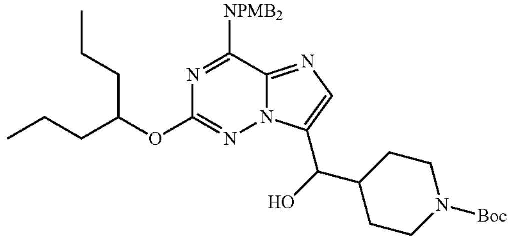

To a solution of 2-(hept-4-yloxy)-N,N-bis(4-methoxybenzyl)imidazo[2,1-f][1,2,4]triazin-4-amine (160 mg, 0.327 mmol) in THF (8 mL), a solution of n-BuLi (1.6 M, 0.31 mL, 0.5 mmol) was added dropwise at a temperature of −75° C. to −65° C. One hour later, a suspension of tert-butyl 4-formylpiperidin-1-carboxylate (98 mg, 0.46 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (120 mg, 52.4%). MS: M/e 703 $(M+1)^+$.

Step B: 2-(hept-4-yloxy)-7-(piperidin-4-ylmethyl)imidazo[2,1-f][1,2,4]triazin-4-amine

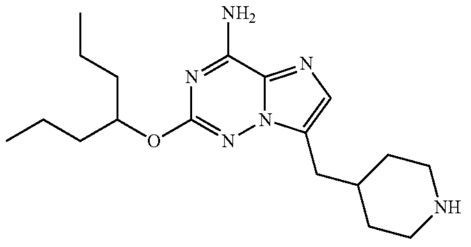 [SMILES: CCCC(CCC)Oc1nc(N)c2ncc(CC3CCNCC3)n2n1]

$Et_3SiH$ (4 mL) was added to a mixture of the product of step A (120 mg, 0.17 mmol) in TFA (4 mL), and the resulting mixture was stirred at 85° C. for 4 h. The mixture was cooled to room temperature and concentrated to dryness. TFA (5 mL) was added to the residue, and the reaction mixture was stirred at 80° C. overnight. The mixture was concentrated under vacuum, and the residue was purified by preparative HPLC to obtain the target compound (6 mg, 10.2%). $^1H$ NMR (400 MHz, DMSO-d6) δ 8.07 (s, 1H), 7.97 (s, 1H), 7.31 (s, 1H), 5.02-4.90 (m, 1H), 3.12 (d, J=12.3 Hz, 2H), 2.74 (d, J=6.7 Hz, 2H), 2.65 (t, J=11.6 Hz, 2H), 1.89 (s, 1H), 1.70-1.54 (m, 6H), 1.42-1.23 (m, 7H), 0.90 (t, J=7.3 Hz, 6H) ppm. MS: M/e 347 $(M+1)^+$.

Step B48:2-(pent-3-yloxy)-7-(piperidin-4-ylmethyl)imidazo[2,1-f][1,2,4]triazin-4-amine

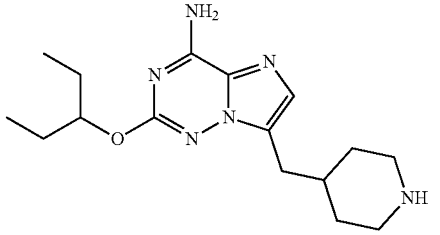

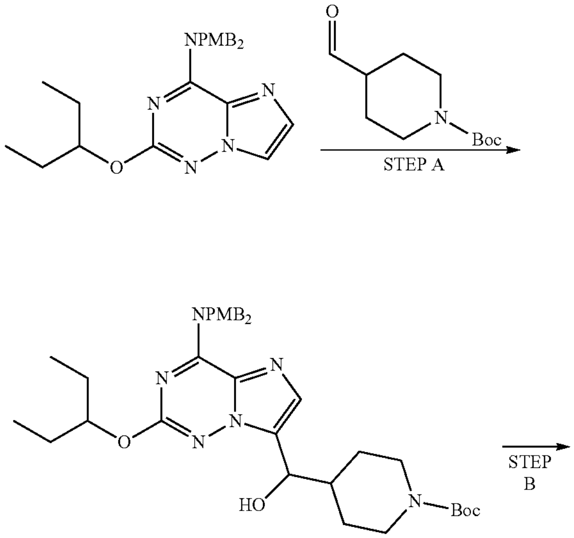

-continued

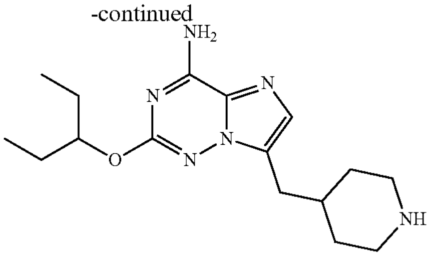

Step A: Tert-butyl 4-((4-(bis(4-methoxybenzyl)amino)-2-(pent-3-yloxy)imidazo[2,1-f][1,2,4]triazin-7-yl)(hydroxy)methyl)piperidin-1-carboxylate

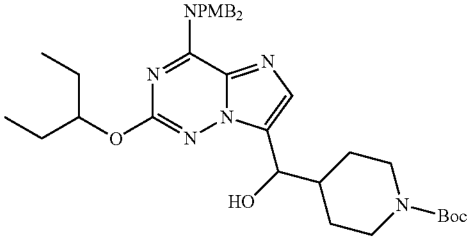

To a solution of N,N-bis(4-methoxybenzyl)-2-(pent-3-yloxy)imidazo[2,1-f][1,2,4]triazin-4-amine (110 mg, 0.23 mmol) in THF (8 mL), a solution of n-BuLi (1.6 M, 0.3 mL, 0.48 mmol) was added dropwise at a temperature of −75° C. to −65° C. One hour later, a suspension of tert-butyl 4-formylpiperidin-1-carboxylate (60 mg, 0.3 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (70 mg, 45.2%). MS: M/e 675 $(M+1)^+$.

Step B: 2-(pent-3-yloxy)-7-(piperidin-4-ylmethyl)imidazo[2,1-f][1,2,4]triazin-4-amine

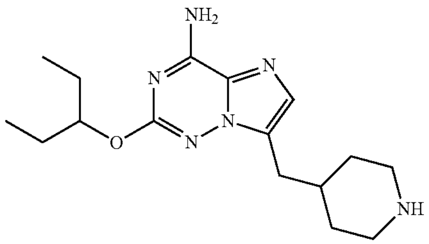 [SMILES: CCC(CC)Oc1nc(N)c2ncc(CC3CCNCC3)n2n1]

$Et_3SiH$ (4 mL) was added to a mixture of the product of step A (70 mg, 0.103 mmol) in TFA (4 mL), and the resulting mixture was stirred at 85° C. for 4 h. The mixture was cooled to room temperature and concentrated to dryness. TFA (5 mL) was added to the residue and the reaction mixture was stirred at 80° C. overnight. The mixture was concentrated, and the residue was purified by preparative HPLC to obtain the target compound (7 mg, 21.2%). $^1H$ NMR (400 MHz, DMSO-d6) δ 8.06 (s, 1H), 7.96 (s, 1H), 7.29 (s, 1H), 4.82-4.73 (m, 1H), 3.00 (d, J=12.0 Hz, 2H), 2.71 (d, J=6.7 Hz, 2H), 2.54 (s, 2H), 1.84 (s, 1H), 1.69-1.53 (m, 6H), 1.23-1.11 (m, 2H), 0.90 (t, J=7.3 Hz, 6H) ppm. MS: M/e 319 $(M+1)^+$.

Compound B49: (S)-2-(hex-3-yloxy)-7-(piperidin-4-ylmethyl)imidazo[2,1-f][1,2,4]triazin-4-amine

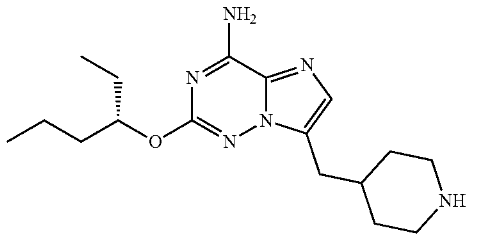

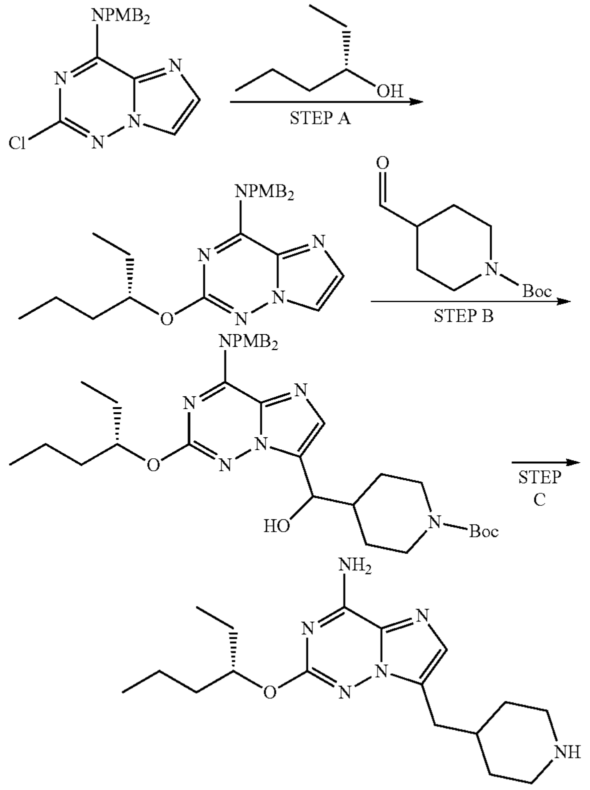

Step A: (S)-2-(hex-3-yloxy)-N,N-bis(4-methoxybenzyl)imidazo[2,1-f][1,2,4]triazin-4-amine

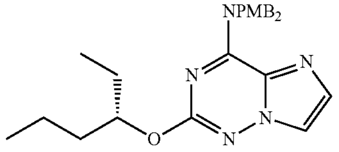

NaH (60%, 80 mg, 2 mmol) was added to a solution of (S)-hexan-3-ol (102 mg, 1 mmol) in THF (10 mL) at 0° C. The reaction mixture was stirred at room temperature for 20 min. 2-chloro-N,N-bis(4-methoxybenzyl)imidazo[2,1-f][1,2,4]triazin-4-amine (204 mg, 0.5 mmol) was added to the reaction mixture. The reaction mixture was stirred at 70° C. overnight. An aqueous ammonium chloride solution was added and the mixture was extracted with ethyl acetate. The combined organic extracts were dried over sodium sulfate, filtered and evaporated. The crude product was purified by column chromatography to obtain the title product (190 mg, 80%). MS: M/e: 476 $(M+1)^+$.

Step B: Tert-butyl 4-((4-(bis(4-methoxybenzyl)amino)-2-(((S)-hex-3-yl)oxy)imidazo[2,1-f][1,2,4]triazin-7-yl)(hydroxy)methyl)piperidin-1-carboxylate

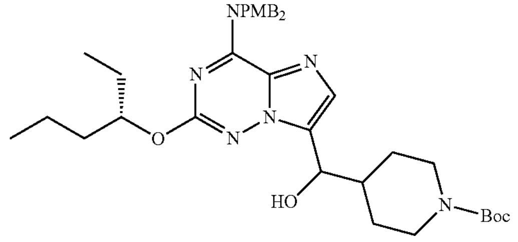

To a solution of (S)-2-(hexan-3-yloxy)-N,N-bis(4-methoxybenzyl)imidazo[2,1-f][1,2,4]triazin-4-amine (190 mg, 0.4 mmol) in THF (8 mL), a solution of n-BuLi (1.6 M, 0.44 mL, 0.72 mmol) was added dropwise at a temperature of −75° C. to −65° C. One hour later, a suspension of tert-butyl 4-formylpiperidin-1-carboxylate (122 mg, 0.6 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (90 mg, 32.7%). MS: M/e 689 $(M+1)^+$.

Step C: (S)-2-(hex-3-yloxy)-7-(piperidin-4-ylmethyl)imidazo[2,1-f][1,2,4]triazin-4-amine

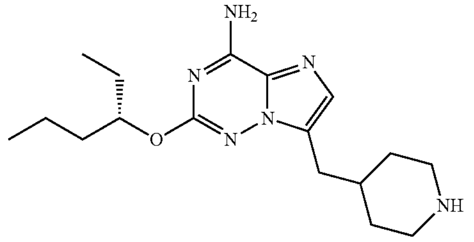 [SMILES: CCC[C@H](CC)Oc1nc(N)c2ncc(CC3CCNCC3)n2n1]

$Et_3SiH$ (4 mL) was added to a mixture of the product of step B (90 mg, 0.130 mmol) in TFA (4 mL), and the resulting mixture was stirred at 85° C. for 4 h. The mixture was cooled to room temperature and concentrated to dryness. TFA (5 mL) was added to the residue and the reaction mixture was stirred at 80° C. overnight. The mixture was concentrated under vacuum, and the residue was purified by preparative HPLC to obtain the target compound (9 mg, 20.8%). $^1H$ NMR (400 MHz, DMSO-d6) δ 8.06 (br.s, 1H), 7.96 (s, 1H), 7.29 (s, 1H), 4.91-4.81 (m, 1H), 3.00 (d, J=11.8 Hz, 2H), 2.71 (d, J=6.7 Hz, 2H), 2.54 (s, 2H), 1.83 (s, 1H), 1.72-1.51 (m, 6H), 1.42-1.33 (m, 2H), 1.25-1.07 (m, 2H), 0.90 (t, J=7.3 Hz, 6H) ppm. MS: M/e 333 $(M+1)^+$. Compound B50: (S)-7-((7-azaspiro[3.5]non-2-yl)methyl)-2-(pent-2-yloxy)imidazo[2,1-f][1,2,4]triazin-4-amine

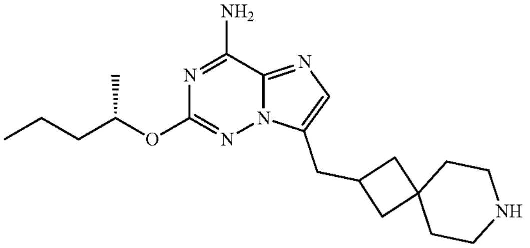

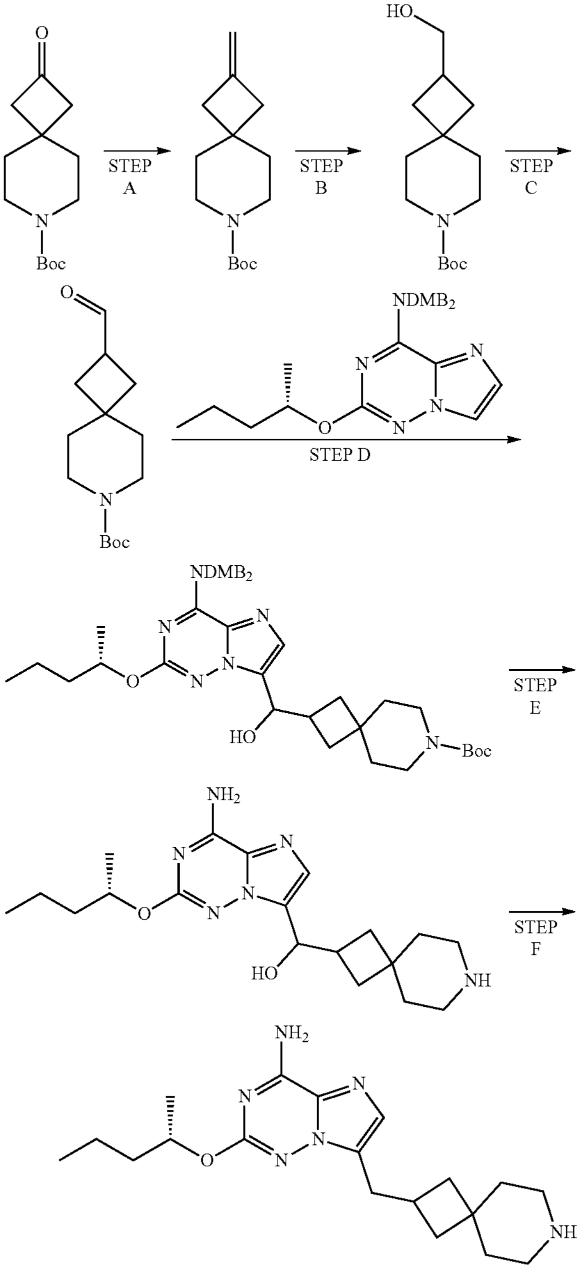

Step A: Tert-butyl 2-methylene-7-azaspiro[3.5]nonan-7-carboxylate

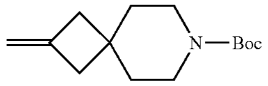 [SMILES: C=C1CC2(CCN(C(=O)OC(C)(C)C)CC2)C1]

NaHMDS (8.4 mL, 16.8 mmol) was added to a solution of Ph3PCH3Br (5.98 g, 16.74 mmol) in THF (30 mL) at −78° C. under N2. After the mixture was stirred at −78° C. for 10 min, the reaction was warmed to 25° C. and stirred for 2 h. Tert-butyl 2-oxo-7-azaspiro[3.5]nonan-7-carboxylate (2 g, 8.37 mmol) in, THF (10 mL) was added dropwise at 0° C. The reaction mixture was stirred at 70° C. for 5 h. After completion of the reaction, the reaction mixture was quenched with water (50 mL) and extracted with EtOAc (3×50 mL). The combined organic layers were dried over $Na_2SO_4$ and concentrated under vacuum to obtain a residue. The residue was purified by column chromatography on silica gel eluted with ethyl acetate (25%) in petroleum ether to obtain the title compound (1.2 g, 61%). $^1H$ NMR (400 MHz, DMSO-d6) δ 4.84 (s, 2H), 3.26 (s, 4H), 2.41 (s, 4H), 1.53-1.43 (m, 4H), 1.41 (s, 9H) ppm.

Step B: Tert-butyl 2-(hydroxymethyl)-7-azaspiro[3.5]nonan-7-carboxylate

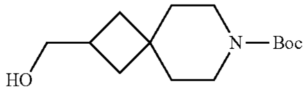

Under $N_2$, 9—BBN (15 mL, 7.5 mmol) was added to a solution of tert-butyl 2-methylene-7-azaspiro[3.5]nonan-7-carboxylate (1.2 g, 5.06 mmol) in THF (20 mL). After the mixture was stirred at 70° C. for 6 h, the reaction was cooled to 0° C. and NaOH (3 N, 8 mL) and $H_2O_2$ (8 mL) were added. The reaction mixture was stirred at 25° C. for 12 h. After completion of the reaction, the reaction mixture was quenched with ice water (20 mL) and extracted with DCM (3×50 mL). The combined organic layers were dried over $Na_2SO_4$ and concentrated under vacuum to obtain a residue. The residue was purified by column chromatography on silica gel eluted with ethyl acetate (70%) in petroleum ether to obtain the title compound (1 g, 78%). $^1H$ NMR (400 MHz, DMSO-$d_6$) δ 4.44 (t, J=5.2 Hz, 1H), 3.35 (s, 2H), 3.24 (s, 2H), 3.15 (s, 2H), 2.36-2.24 (m, 1H), 1.76 (t, J=10.4 Hz, 2H), 1.50-1.40 (m, 4H), 1.41-1.30 (m, 11H) ppm.

Step C: Tert-butyl 2-formyl-7-azaspiro[3.5]nonan-7-carboxylate

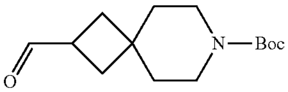 [SMILES: CC(C)(C)OC(=O)N1CCC2(CC1)CC(C=O)C2]

DMP (2 g, 4.72 mmol) was added to a solution of tert-butyl 2-(hydroxymethyl)-7-azaspiro[3.5]nonan-7-carboxylate (1 g, 3.92 mmol) in DCM (20 mL) at 0° C. under $N_2$. The mixture was stirred at 25° C. for 3 h. After completion of the reaction, the reaction mixture was quenched with an aqueous $Na_2S_2O_3$ solution (30 mL) and extracted with DCM (3×50 mL). The combined organic layers were washed with an aqueous $NaHCO_3$ solution (50 mL), dried over $Na_2SO_4$ and concentrated under vacuum to obtain a residue. The residue was purified by column chromatography on silica gel eluted with ethyl acetate (50%) in petroleum ether to obtain the title compound (660 mg, 67%). $^1$H NMR (400 MHz, DMSO-$d_6$) δ 9.67 (s, 1H), 3.25 (s, 2H), 3.17 (s, 3H), 1.98-1.85 (m, 4H), 1.56-1.46 (m, 2H), 1.38 (s, 9H), 1.36-1.29 (m, 2H) ppm.

Step D: Tert-butyl 2-((4-(bis(2,4-dimethoxybenzyl) amino)-2-(((S)-pent-2-yl)oxy)imidazo[2,1-f][1,2,4] triazin-7-yl)(hydroxy)methyl)-7-azaspiro[3.5]nonan-7-carboxylate

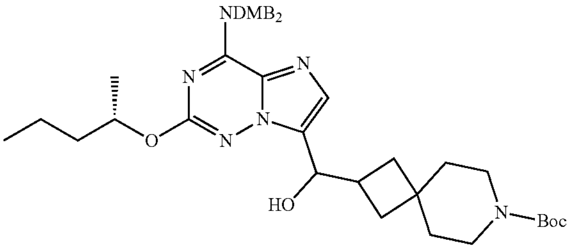

At −78° C. under $N_2$, to a solution of (S)—N,N-bis(2,4-dimethoxybenzyl)-2-(pent-2-yloxy)imidazo[2,1-f][1,2,4]triazin-4-amine (500 mg, 0.959 mmol) in THF (10 mL), n-BuLi (1.2 mL, 1.920 mmol) was added. After the mixture was stirred at −78° C. for 0.5 h, tert-butyl 2-formyl-7-azaspiro[3.5]nonan-7-carboxylate (340 mg, 1.344 mmol) in THF (5 mL) was added. The reaction mixture was stirred at −78° C. for 2.5 h. After completion of the reaction, the reaction mixture was quenched with an aqueous $NH_4Cl$ solution (30 mL) and extracted with DCM (3×50 mL). The combined organic layers were dried over $Na_2SO_4$ and concentrated under vacuum to obtain a residue. The residue was purified by column chromatography on silica gel eluted with ethyl acetate (40%) in petroleum ether to obtain the title compound (560 mg, 75%). MS: M/e 775 $(M+1)^+$.

Step E: (4-amino-2-(((S)-pent-2-yl)oxy)imidazo[2,1-f][1,2,4]triazin-7-yl)(7-azaspiro[3.5]non-2-yl) methanol

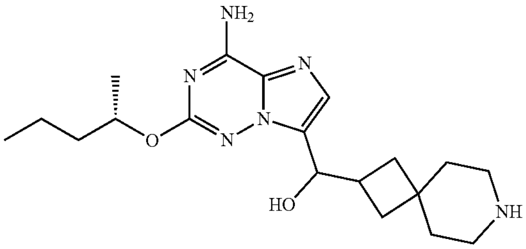 [SMILES: CCC[C@H](C)Oc1nc(N)c2ncc(C(O)C3CC4(CCNCC4)C3)n2n1]

Tert-butyl 2-((4-(bis(2,4-dimethoxybenzyl)amino)-2-(((S)-pent-2-yl)oxy)imidazo[2,1-f][1,2,4]triazin-7-yl)(hydroxy)methyl)-7-azaspiro[3.5]nonan-7-carboxylate (560 mg, 0.722 mmol) was dissolved in TFA (9 mL) and $H_2O$ (1 mL) under $N_2$. The reaction mixture was stirred at 40° C. for 12 h. After completion of the reaction, the solvent was removed under vacuum. The residue was diluted with water (20 mL) and DCM (20 mL), and the aqueous phase was acidified with 1 N HCl to adjust pH=1-2. The aqueous phase was washed with DCM (3×20 ML), alkalized with 2 N NaOH to adjust PH=13-14, and extracted with DCM/i-PrOH (5/1, 3×100 mL). The combined organic layers were dried over $Na_2SO_4$ and concentrated under vacuum to obtain a crude compound (280 mg, crude). MS: M/e 375 $(M+1)^+$.

Step F. (S)-7-((7-azaspiro[3.5]non-2-yl)methyl)-2-(pent-2-yloxy)imidazo[2,1-f][1,2,4]triazin-4-amine

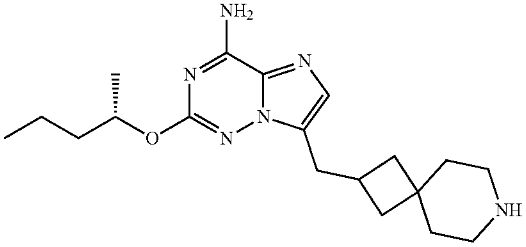 [SMILES: CCC[C@H](C)Oc1nc(N)c2ncc(CC3CC4(CCNCC4)C3)n2n1]

(4-amino-2-(((S)-pent-2-yl)oxy)imidazo[2,1-f][1,2,4]triazin-7-yl)(7-azaspiro[3.5]non-2-yl)methanol (280 mg, crude) was dissolved in TFA (6 mL) and $Et_3SiH$ (6 mL) under $N_2$. The reaction mixture was stirred at 90° C. for 12 h. After completion of the reaction, the solvent was removed under vacuum. The residue was diluted with water (20 mL) and DCM (20 mL), and the aqueous phase was acidified with 1 N HCl to adjust pH=1-2. The aqueous phase was washed with DCM (3×20 mL), alkalized with 2 N NaOH to adjust pH=13-14, and extracted with DCM/i-PrOH (5/1, 3×60 mL). The combined organic layers were dried over $Na_2SO_4$ and concentrated under vacuum to obtain a residue. The residue was purified by preparative TLC (DCM/MeOH $(NH_3)$=15/1) to obtain the title compound (80 mg, 31% for two steps). $^1$H NMR (400 MHz, $CD_3OD$) δ 7.30 (s, 1H), 5.10 (d, J=6.0 Hz, 1H), 3.17-3.08 (m, 2H), 3.05 (d, J=5.2 Hz, 2H), 2.98 (d, J=7.6 Hz, 2H), 2.88-2.68 (m, 1H), 2.08 (t, J=10.4 Hz, 2H), 1.86 (d, J=5.2 Hz, 2H), 1.88-1.70 (m, 3H), 1.71-1.54 (m, 3H), 1.53-1.40 (m, 2H), 1.36 (d, J=6.0 Hz, 3H), 0.96 (t, J=7.2 Hz, 3H) ppm. MS: M/e 359 $(M+1)^+$.

Compound B51: 2—(((S)-pent-2-yl)oxy)-7-(piperidin-2-ylmethyl)imidazo[2,1-f][1,2,4]triazin-4-amine

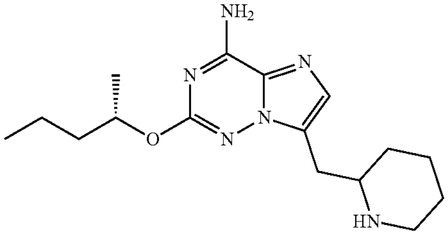 [SMILES: CCC[C@H](C)Oc1nc(N)c2ncc(CC3CCCCN3)n2n1]

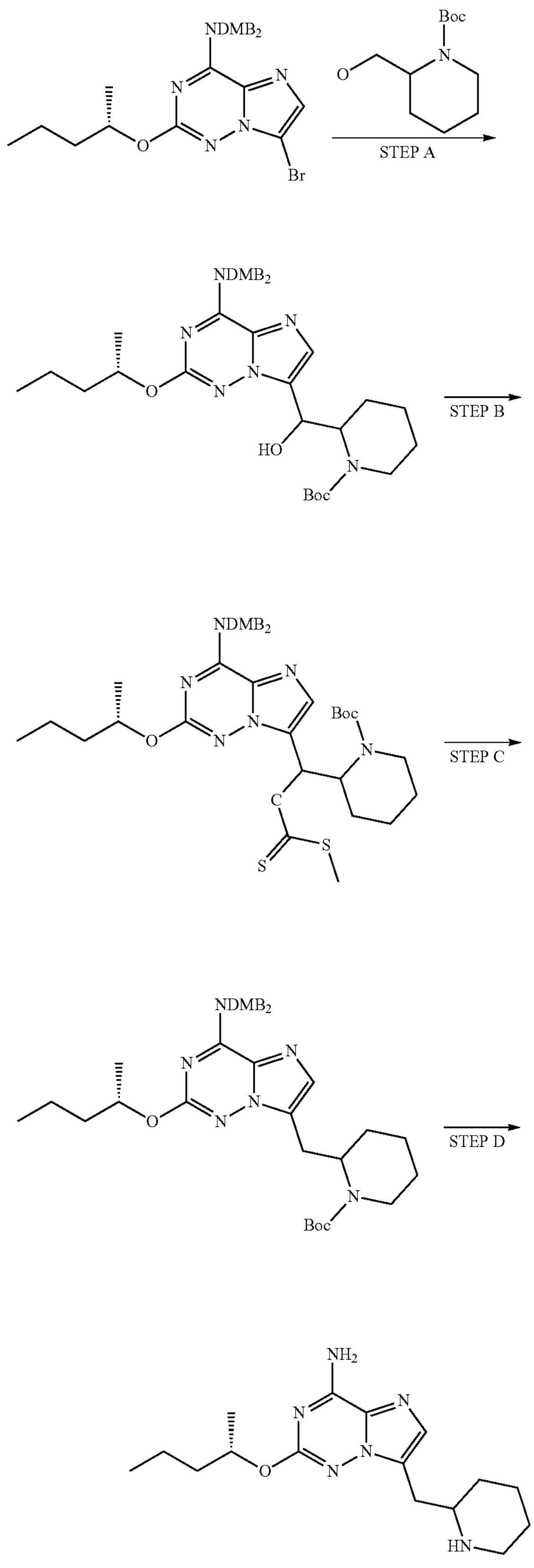

Step A: Tert-butyl 2-((4-(bis(2,4-dimethoxybenzyl) amino)-2-(((S)-pent-2-yl)oxy)imidazo[2,1-f][1,2,4] triazin-7-yl)(hydroxy)methyl)piperidin-1-carboxylate

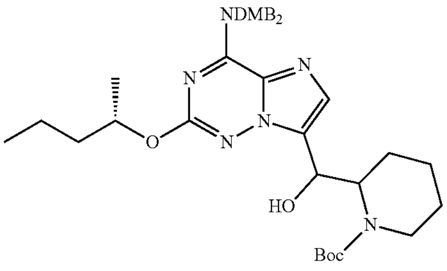

To a solution of (S)-7-bromo-N,N-bis(2,4-dimethoxybenzyl)-2-(pent-2-yloxy)imidazo[2,1-f][1,2,4]triazin-4-amine (600 mg, 1 mmol) in THF (8 mL), a solution of n-BuLi (1.6 M, 1.25 mL, 2 mmol) was added dropwise at a temperature of −75° C. to −65° C. One hour later, a suspension of tert-butyl 2-formylpiperidin-1-carboxylate (319 mg, 1.5 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (590 mg, 80.3%). MS: M/e 735 $(M+1)^+$.

Step B: Tert-butyl 2-((4-(bis(2,4-dimethoxybenzyl) amino)-2-(((S)-pent-2-yl)oxy)imidazo[2,1-f][1,2,4] triazin-7-yl) (((methylthio)thiocarbonyl)oxy) methyl)piperidin-1-carboxylate

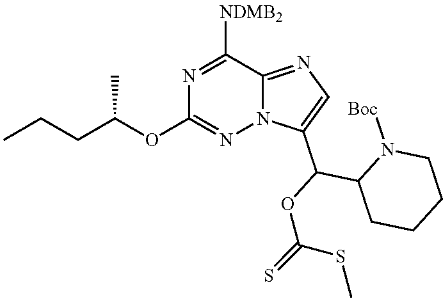

To a mixture of tert-butyl 2-((4-(bis(2,4-dimethoxybenzyl)amino)-2-(((S)-pent-2-yl)oxy)imidazol[2,1-f][1,2,4]triazin-7-yl)(hydroxy)methyl)piperidin-1-carboxylate (130 mg, 0.18 mmol), carbon disulfide (70 mg, 0.9 mmol) and imidazole (20 mg, 0.3 mmol) in THF (8 mL), NaH (60%, 23 mg, 0.56 mmol) was added at 0° C., and the mixture was stirred 30 min. Methyl iodide (126 mg, 0.9 mmol) was added to the mixture, and the mixture was stirred at 0° C. for 1.5 h and at room temperature for 3.5 h. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (50 mg, 33.7%). MS: Me 825 $(M+1)^+$.

Step C: Tert-butyl 2-((4-(bis(2,4-dimethoxybenzyl)amino)-2-(((S)-pent-2-yl)oxy)imidazo[2,1-f][1,2,4]triazin-7-yl)methyl)piperidin-1-carboxylate

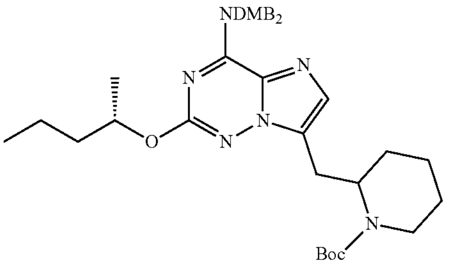

To a mixture of tert-butyl 2-((4-(bis(2,4-dimethoxybenzyl)amino)-2-(((S)-pent-2-yl)oxy)imidazo[2,1-f][1,2,4]triazin-7-yl)(((methylthio)thiocarbonyl)oxy)methyl)piperidin-1-carboxylate (50 mg, 0.06 mmol) in toluene (10 mL), tri-n-butyl tin hydride (65 mg, 0.22 mmol) and AIBN (18 mg, 0.11 mmol) were added. The resulting reaction mixture was stirred at 100° C. overnight under the protection of $N_2$ atmosphere. The mixture was concentrated to dryness. $H_2O$ was added to the residue, the mixture was extracted with EtOAc (20 mL×3), washed with brine, dried over $Na_2SO_4$, filtered and concentrated. The residue was purified by preparative TLC to obtain the target compound (20 mg, 45.9%). MS: M/e 719 $(M+1)^+$.

Step D: 2-(((S)-pent-2-yl)oxy)-7-(piperidin-2-ylmethyl)imidazo[2,1-f][1,2,4]triazin-4-amine

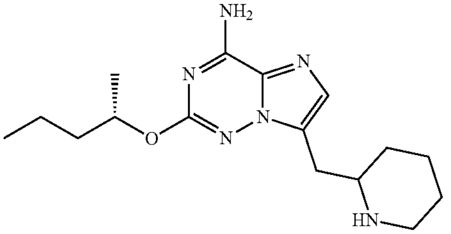 [SMILES: CCC[C@H](C)Oc1nc(N)c2ncc(CC3CCCCN3)n2n1]

$H_2O$ (2 mL) was added to a mixture of the product of step C (20 mg, 0.027 mmol) in TFA (8 mL), and the resulting mixture was stirred at room temperature for 2 d. The mixture was concentrated to dryness. The residue was purified by preparative HPLC to obtain the target compound (1 mg, 11.2%). $^1$H NMR (400 MHz, CD3OD) ô 7.45 (s, 1H), 5.34 (s, 1H), 5.15 (s, 1H), 3.23 (d, J=5.6 Hz, 2H), 2.18 (d, J=6.6 Hz, 1H), 2.02 (s, 2H), 1.88 (d, J=13.6 Hz, 2H), 1.57 (d, J=12.1 Hz, 4H), 1.37-1.26 (M, 3H), 0.96 (t, J=6.6 Hz, 3H), 0.90 (s, 3H) ppm.MS: M/e 319 $(M+1)^+$.

Compound B52 and compound B53: (S)-7-((3,3-dimethylpiperidin-4-ylidene)methyl)-2-(pent-2-yloxy)imidazo[2,1-f][1,2,4]triazin-4-amine and 7-((3,3-dimethylpiperidin-4-yl)methyl)-2-(((S)-pent-2-yl)oxy)imidazol[2,1-f][1,2,4]triazin-4-amine

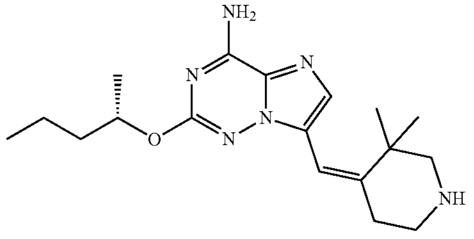

COMPOUND B52

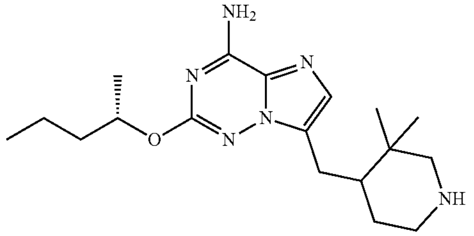

COMPOUND B53

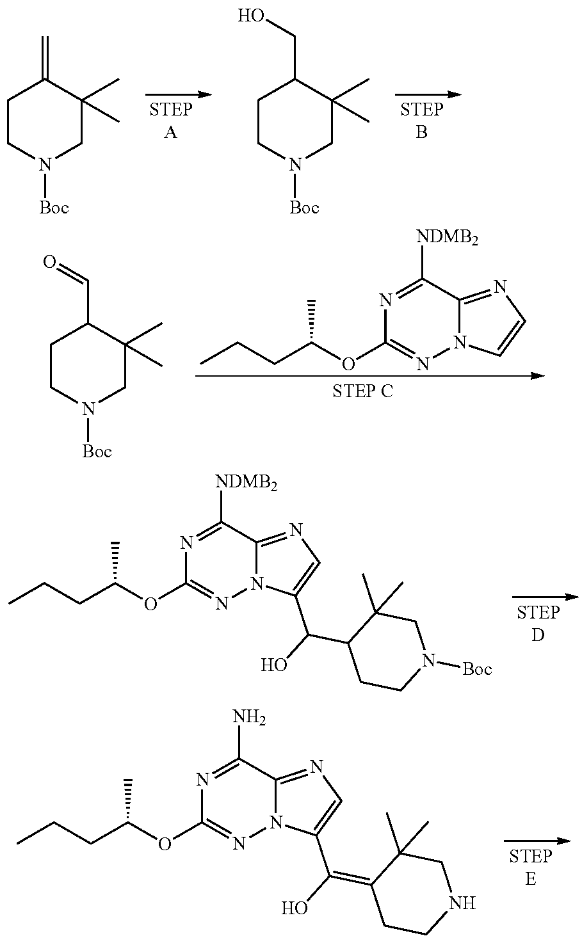

-continued

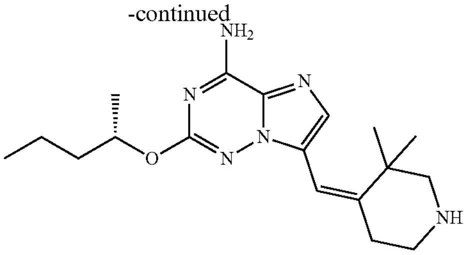

COMPOUND B52

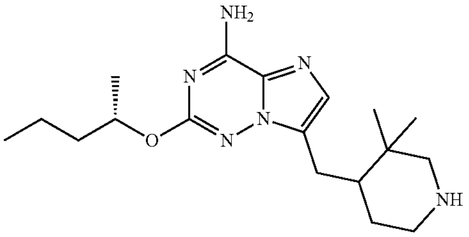

COMPOUND B53

Step A: Tert-butyl 4-(hydroxymethyl)-3,3-dimethylpiperidin-1-carboxylate

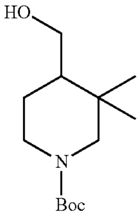 [SMILES: CC(C)(C)OC(=O)N1CCC(CO)C(C)(C)C1]

Under $N_2$, 9—BBN (26 mL, 13.0 mmol) was added to a solution of tert-butyl 3,3-dimethyl-4-methylenepiperidin-1-carboxylate (2 g, 8.88 mmol) in THF (20 mL). After the mixture was stirred at 70° C. for 8 h, the reaction was cooled to 0° C. and NaOH (3 N, 15 mL) and $H_2O_2$ (15 mL) were added. The reaction mixture was stirred at 25° C. for 12 h. After completion of the reaction, the reaction mixture was quenched with ice water (50 mL) and extracted with DCM (3×80 mL). The combined organic layers were dried over $Na_2SO_4$ and concentrated under vacuum to obtain a residue. The residue was purified by column chromatography on silica gel eluted with ethyl acetate (80%) in petroleum ether to obtain the title compound (1.7 g, 79%). $^1H$ NMR (400 MHz, DMSO-$d_6$) δ 4.37 (t, J=5.2 Hz, 1H), 3.96 (s, 1H), 3.64-3.37 (m, 2H), 3.06 (d, J=5.6 Hz, 1H), 2.79-2.54 (m, 2H), 1.67 (d, J=13.2 Hz, 1H), 1.38 (s, 9H), 1.32-1.07 (m, 2H), 0.90 (s, 3H), 0.70 (s, 3H) ppm.

Step B: Tert-butyl 4-formyl-3,3-dimethylpiperidin-1-carboxylate

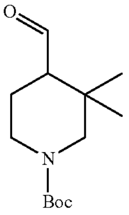 [SMILES: CC(C)(C)OC(=O)N1CCC(C=O)C(C)(C)C1]

DMP (3.6 g, 8.49 mmol) was added to a solution of tert-butyl 4-(hydroxymethyl)-3,3-dimethylpiperidin-1-carboxylate (1.7 g, 6.99 mmol) in DCM (30 mL) at 0° C. under $N_2$. The reaction was stirred at 25° C. for 3 h. After completion of the reaction, the reaction mixture was quenched with an aqueous $Na_2S_2O_3$ solution (50 mL) and extracted with DCM (3×50 mL). The combined organic layers were washed with an aqueous $NaHCO_3$ solution (50 mL) and brine (2×30 mL), dried over $Na_2SO_4$ and concentrated under vacuum to obtain a residue. The residue was purified by column chromatography on silica gel eluted with ethyl acetate (40%) in petroleum ether to obtain the title compound (840 mg, 50%). $^1H$ NMR (400 MHz, DMSO-d6) δ 9.76 (s, 1H), 4.02 (s, 1H), 3.61-3.39 (m, 1H), 2.85-2.57 (m, 2H), 2.31 (t, J=7.6 Hz, 1H), 1.59-1.49 (m, 2H), 1.39 (s, 9H), 1.11 (s, 3H), 0.83 (s, 3H) ppm.

Step C: Tert-butyl 4-((4-(bis(2,4-dimethoxybenzyl)amino)-2-(((S)-pent-2-yl)oxy)imidazo[2,1-f][1,2,4]triazin-7-yl)(hydroxy)methyl)-3,3-dimethylpiperidin-1-carboxylate

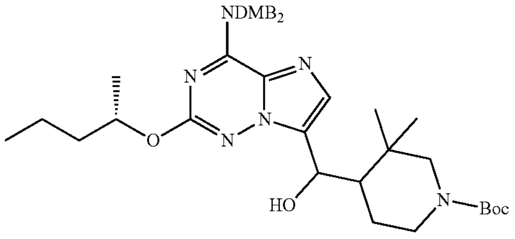

At −78° C. under $N_2$, to a solution of (S)—N,N-bis(2,4-dimethoxybenzyl)-2-(pent-2-yloxy)imidazo[2,1-f][1,2,4]triazin-4-amine (500 mg, 0.959 mmol) in THF (10 mL), n-BuLi (0.9 mL, 1.44 mmol) was added. After the mixture was stirred at −78° C. for 0.5 h, tert-butyl 4-formyl-3,3-dimethylpiperidin-1-carboxylate (340 mg, 1.41 mmol) in THF (4 mL) was added. The reaction mixture was stirred at −78° C. for 2.5 h. After completion of the reaction, the reaction mixture was quenched with an aqueous $NH_4Cl$ solution (50 mL) and extracted with DCM (3×50 mL). The combined organic layers were dried over $Na_2SO_4$ and concentrated under vacuum to obtain a residue. The residue was purified by column chromatography on silica gel eluted with ethyl acetate (40%) in petroleum ether to obtain the title compound (600 mg, 82%). MS: M/e 763 $(M+1)^+$.

Step D: (4-amino-2-(((S)-pent-2-yl)oxy)imidazo[2,1-f][1,2,4]triazin-7-yl)(3,3-dimethylpiperidin-4-yl)methanol

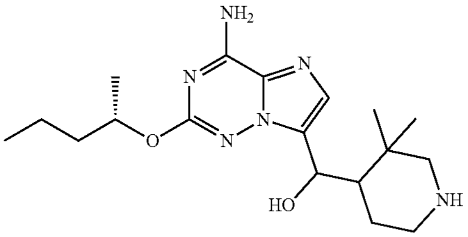 [SMILES: CCC[C@H](C)Oc1nc(N)c2ncc(C(O)C3CCNCC3(C)C)n2n1]

Under $N_2$, tert-butyl 4-((4-(bis(2,4-dimethoxybenzyl)amino)-2-(((S)-pent-2-yl)oxy)imidazo[2,1-f][1,2,4]triazin-7-yl)(hydroxy)methyl)-3,3-dimethylpiperidin-1-carboxylate (600 mg, 0.786 mmol) was dissolved in TFA (9 mL) and $H_2O$ (1 mL). The reaction mixture was stirred at 40° C. for 12 h. After completion of the reaction, the solvent was removed under vacuum. The residue was diluted with water (20 mL) and DCM (20 mL), and the aqueous phase was acidified with 1 N HCl to adjust pH=1-2. The aqueous phase was washed with DCM (3×30 mL), alkalized with 2 N NaOH to adjust PH=13-14, and extracted with DCM/i-PrOH (5/1, 3×120 mL). The combined organic layers were dried over $Na_2SO_4$ and concentrated under vacuum to obtain the crude compound (240 mg, crude). MS: M/e 363 $(M+1)^+$.

Step E: (S)-7-((3,3-dimethylpiperidin-4-methylene)methyl)-2-(pent-2-yloxy)imidazo[2,1-f][1,2,4]triazine 4-amine and 7-(3,3-dimethylpiperidin-4-yl)methyl)-2-(((S)-pent-2-yl)oxy)imidazo[2,1-f][1,2,4]triazin-4-amine Compound B52

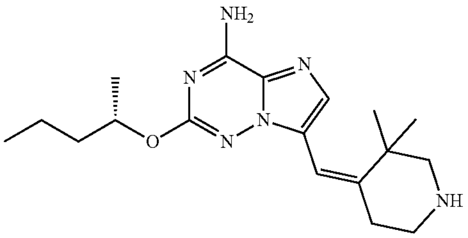

Compound B53

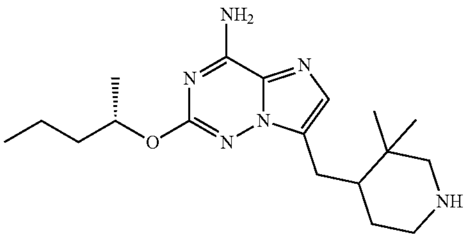

Under N2, (4-amino-2-(((S)-pent-2-yl)oxy)imidazo[2,1-f][1,2,4]triazin-7-yl) (3,3-dimethylpiperidin-4-yl)methanol (240 mg, crude) was dissolved in TFA (5 mL) and EtsSiH (5 mL). The reaction mixture was stirred at 90° C. for 12 h. After completion of the reaction, the solvent was removed under vacuum. The residue was diluted with water (20 mL) and DCM (20 mL), and the aqueous phase was acidified with 1N HCl to adjust pH=1-2. The aqueous phase was washed with DCM (3×20 mL), alkalized with 2 N NaOH to adjust PH=13-14, and extracted with DCM/i-PrOH (5/1, 3×120 mL). The combined organic layers were dried over $Na_2SO_4$ and concentrated under vacuum to obtain a residue. The residue was purified by preparative TLC (DCM/MeOH $(NH_3)$=40/1 to 20/1) to obtain the product compound B52 (3 mg) and compound B53 (25 mg, 9% for two steps).

Compound B52: $^1$H NMR (400 MHz, $CD_3OD$) & 7.55 (s, 1H), 6.62 (s, 1H), 5.17-5.05 (m, 1H), 3.16 (t, J=5.6 Hz, 2H), 3.02 (s, 2H), 2.88 (t, J=5.6 Hz, 2H), 1.84-1.66 (m, 1H), 1.67-1.52 (m, 1H), 1.53-1.39 (m, 2H), 1.36 (s, 9H), 0.97 (t, J=7.2 Hz, 3H) ppm.MS: M/e 345 $(M+1)^+$.

Compound B53: $^1$H NMR (400 MHz, CD3OD) δ 7.35 (s, 1H), 5.16-5.01 (m, 1H), 3.29-3.15 (m, 2H), 3.13-3.04 (m, 1H), 2.89-2.74 (m, 2H), 2.64-2.51 (m, 1H), 1.99-1.85 (m, 1H), 1.82-1.69 (m, 1H), 1.69-1.56 (m, 3H), 1.55-1.41 (m, 2H), 1.37 (d, J=6.0 Hz, 3H), 1.22 (s, 3H), 1.14 (s, 3H), 1.02-0.91 (m, 3H). MS: M/e 347 $(M+1)^+$.

Compound B54: 7-((1-(2-(methylamino)propyl)piperidin-4-yl)methyl)-2-(((S)-pent-2-yl)oxy)imidazo[2,1-f][1,2,4]triazin-4-amine

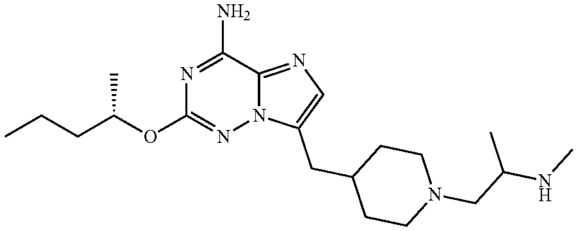

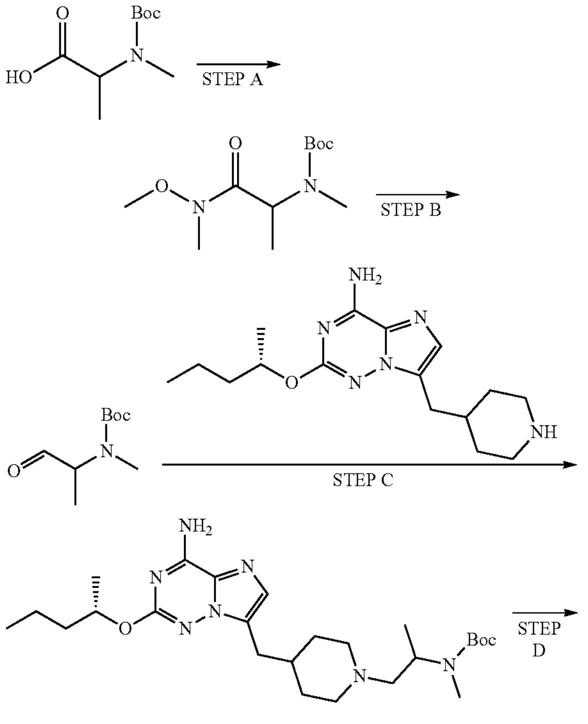

-continued

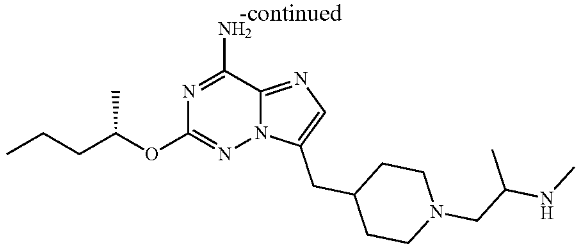

Step A: Tert-butyl (1-(methoxy(methyl)amino)-1-oxoprop-2-yl)(methyl)carbamate

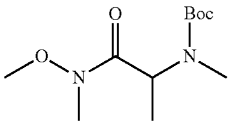

HATU (2 g, 5.26 mmol) and DIEA (1.7 mL, 9.62 mmol) were added to a solution of N-(tert-butoxycarbonyl)-N-methylalanine (1 g, 4.93 mmol) in DMF (10 mL) under N2. After the mixture was stirred for 10 min, the reaction was cooled to 0° C., and N,O-dimethylhydroxylamine hydrochloride (526 mg, 5.42 mmol) was added. The reaction mixture was stirred at 25° C. for 12 h. After completion of the reaction, the reaction mixture was quenched with ice water (30 mL) and extracted with DCM (3×60 mL). The combined organic layers were washed with brine (3×20 mL), dried over $Na_2SO_4$ and concentrated under vacuum to obtain a residue. The residue was purified by column chromatography on silica gel eluted with ethyl acetate (30%) in petroleum ether to obtain the title compound (1.1 g, 91%). $^1$H NMR (400 MHz, DMSO-d6) δ 5.05-4.67 (m, 1H), 3.67 (s, 3H), 3.10 (s, 3H), 2.74 (s, 3H), 1.39 (d, J=7.6 Hz, 9H), 1.21 (dd, J=11.6, 7.2 Hz, 3H) ppm.

Step B: Tert-butyl (1-oxoprop-2-yl)carbamate

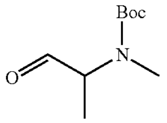

At 0° C. under $N_2$. LAH (620 mg, 16.32 mmol) was added to a solution of tert-butyl (1-(methoxy(methyl)amino)-1-oxoprop-2-yl)(methyl)carbamate (1 g, 4.07 mmol) in THF (20 mL). After the mixture was stirred for 0.5 h at 0° C., the reaction was further stirred for 2 h at 25° C. After completion of the reaction, the reaction mixture was quenched with 0° C. water (0.7 mL), 15% NaOH (0.7 mL) and water (2.1 mL), and $Na_2SO_4$ was added. The mixture was filtered, the filtrates were combined and concentrated under vacuum to obtain a residue. The residue was purified by column chromatography on silica gel eluted with ethyl acetate (30%) in petroleum ether to obtain the title compound (580 mg, 76%). $^1$H NMR (400 MHz, DMSO-$d_6$) δ 9.53-9.38 (m, 1H), 4.05-3.85 (m, 1H), 2.85 (s, 3H), 1.37 (s, 9H), 1.20 (t, J=7.6 Hz, 3H) ppm.

Step C: Tert-butyl (1-(4-((4-amino-2-(((S)-pent-2-yl)oxy)imidazo[2,1-f][1,2,4]triazin-7-yl)methyl)piperidin-1-yl)prop-2-yl)(methyl)carbamate

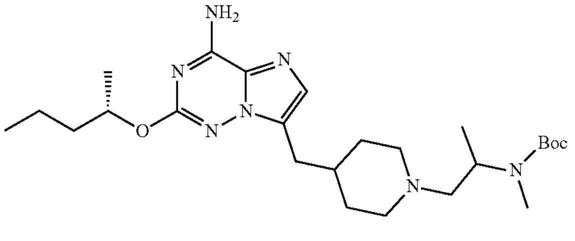 [SMILES: CCC[C@H](C)Oc1nc(N)c2ncc(CC3CCN(CC(C)N(C)C(=O)OC(C)(C)C)CC3)n2n1]

At 0° C. under $N_2$, to a solution of (S)-2-(pent-2-yloxy)-7-(piperidin-4-ylmethyl)imidazo[2,1-f][1,2,4]triazin-4-amine (50 mg, 0.157 mmol) and tert-butyl (1-oxoprop-2-yl) carbamate (44 mg, 0.235 mmol) in MeOH (3 mL), $NaBH_3CN$ (22 mg, 0.349 mmol) was added. The reaction mixture was stirred at 25° C. for 24 h. After completion of the reaction, the solvent was concentrated under vacuum to obtain a residue. The residue was purified by preparative TLC (DCM/MeOH ($NH_3$)=18/1) to obtain the title compound (30 mg, 39%). MS: M/e 490 $(M+1)^+$.

Step D: 7-((1-(2-(methylamino)propyl)piperidin-4-yl)methyl)-2-(((S)-pent-2-yl)oxy)imidazo[2,1-f][1,2,4]triazin-4-amine

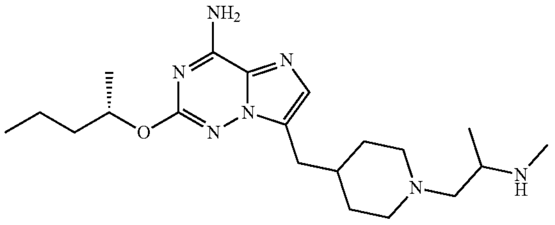 [SMILES: CCC[C@H](C)Oc1nc(N)c2ncc(CC3CCN(CC(C)NC)CC3)n2n1]

At 0° C. under $N_2$, to a solution of tert-butyl (1-(4-((4-amino-2-(((S)-pent-2-yl)oxy)imidazo[2,1-f][1,2,4]triazin-7-yl)methyl)piperidin-1-yl)prop-2-yl)(methyl)carbamate (30 mg, 0.061 mmol) in DCM (3 mL), TFA (2 mL) was added. The reaction mixture was stirred at 25° C. for 1 h. After completion of the reaction, the solvent was concentrated under vacuum to obtain a residue. The residue was diluted with DCM/MeOH=1/1 and alkalized with 2 N NaOH. The residue was purified by preparative TLC (DCM/MeOH ($NH_3$)=18/1) to obtain the title compound (15 mg, 63%). $^1$H NMR (400 MHz, $CD_3OD$) δ 7.30 (s, 1H), 5.14-5.05 (m, 1H), 3.36 (s, 1H), 3.04 (s, 1H), 2.84 (d, J=6.8 Hz, 3H), 2.69 (s, 3H), 2.50 (s, 2H), 2.29 (s, 1H), 2.05 (s, 1H), 1.91-1.65 (m, 4H), 1.64-1.53 (m, 1H), 1.50-1.39 (m, 4H), 1.36 (d, J=6.0 Hz, 3H), 1.25 (d, J=6.4 Hz, 3H), 0.97 (t, J=7.2 Hz, 3H) ppm. MS: M/e 390 $(M+1)^+$.

Compound B55 and compound B56: 7-((8-azabicyclo[3.2.1]oct-3-ylene)methyl)-2-(((S)-pent-2-yl)oxy)imidazo[2,1-f][1,2,4]triazin-4-amine and 7-((8-azabicyclo[3.2.1]oct-3-yl)methyl)-2-(((S)-pent-2-yl)oxy)imidazo[2,1-f][1,2,4]triazin-4-amine

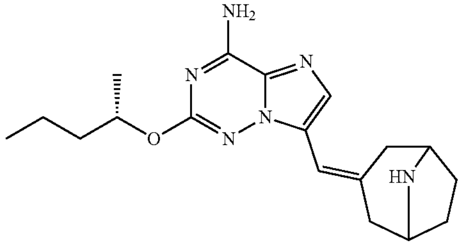

Compound B55

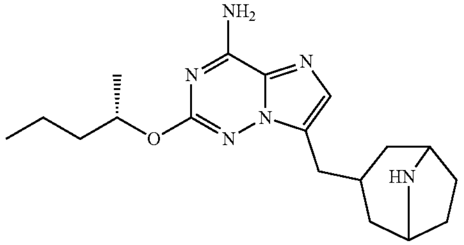

Compound B56

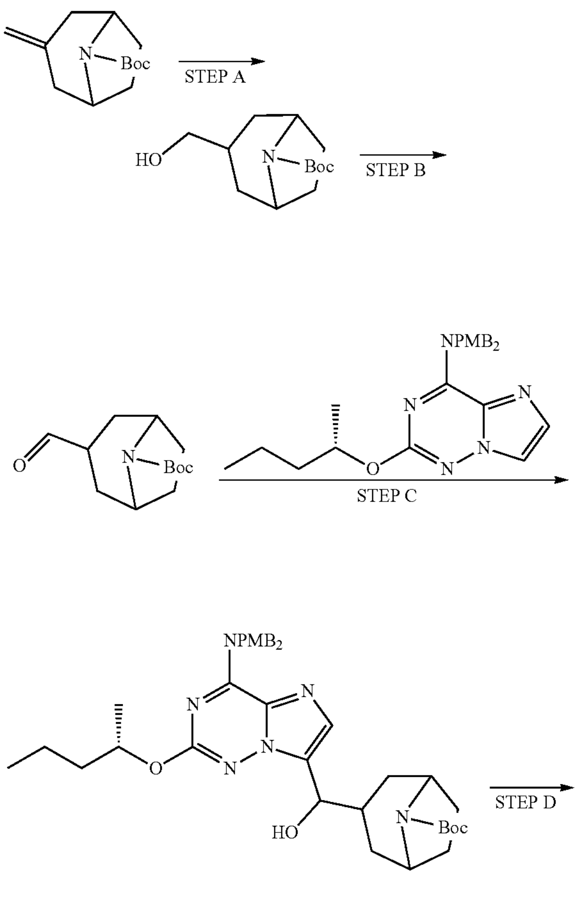

-continued

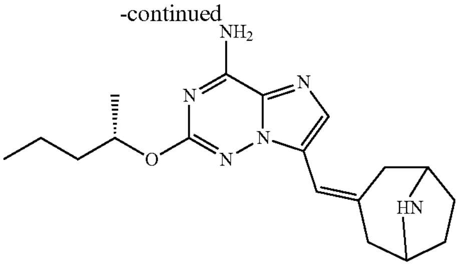

COMPOUND B55

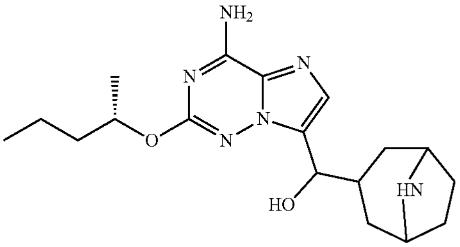

COMPOUND B56

Step A: Tert-butyl 3-(hydroxymethyl)-8-azabicyclo[3.2.1]octan-8-carboxylate

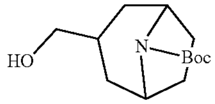 [SMILES: CC(C)(C)OC(=O)N1C2CCC1CC(CO)C2]

$BH_3$-THF (1 M, 2.5 mmol, 5 mL) was added to a solution of tert-butyl 3-methylene-8-azabicyclo[3.2.1]octan-8-carboxylate (448 mg, 2 mmol) in THF (5 mL) at 0° C. under the protection of N2 atmosphere. The reaction was stirred at room temperature overnight. Then, an aqueous NaOH solution (3 M, 3.3 mL) and $H_2O_2$ (30%, 3.3 mL) were added to the mixture, and the reaction was continuously stirred overnight. $H_2O$ was added to the mixture and the resulting mixture was extracted with ethyl acetate. The combined organic extracts were dried over sodium sulfate, filtered and evaporated, and purified by preparative TLC to obtain the title product (348 mg) as an oil. MS: M/e 242 $(M+1)^+$.

Step B: Tert-butyl 3-formyl-8-azabicyclo[3.2.1]octan-8-carboxylate

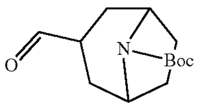 [SMILES: CC(C)(C)OC(=O)N1C2CCC1CC(C=O)C2]

To a solution of tert-butyl 3-(hydroxymethyl)-8-azabicyclo[3.2.1]octan-8-carboxylate (348 mg, 1.54 mmol) in DCM (10 mL), Dess-Martin periodinane (979 mg, 2.31 mmol) was added. The reaction was stirred at room temperature for 4 h. $H_2O$ was added to the mixture and the resulting mixture was extracted with ethyl acetate. The combined organic extracts were dried over sodium sulfate, filtered and evaporated, and purified by preparative TLC to obtain the title product (200 mg, 57.7%). MS: M/e 240 $(M+1)^+$.

Step C: Tert-butyl 3-((4-(bis(4-methoxybenzyl)amino)-2-(((S)-pent-2-yl)oxy)imidazo[2,1-f][1,2,4]triazin-7-yl)(hydroxy)methyl)-8-azabicyclo[3.2.1]octan-8-carboxylate

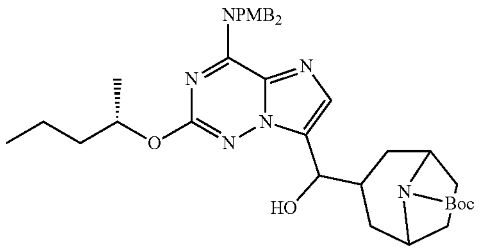

To a solution of (S)—N,N-bis(4-methoxybenzyl)-2-(pent-2-yloxy)imidazo[2,1-f][1,2,4]triazin-4-amine (290 mg, 0.6 mmol) in THF (4 mL), a solution of n-BuLi (1.6 M, 0.56 mL, 0.9 mmol) was added dropwise at a temperature of −75° C. to −65° C. One hour later, a suspension of tert-butyl 3-formyl-8-azabicyclo[3.2.1]octan-8-carboxylate (200 mg, 0.89 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (60 mg, crude, yellow oil). MS: M/e 701 $(M+1)^+$.

Step D: 7-((8-azabicyclo[3.2.1]oct-3-ylene)methyl)-2-(((S)-pent-2-yl)oxy)imidazo[2,1-f][1,2,4]triazin-4-amine and 7-((8-azabicyclo[3.2.1]oct-3-yl)methyl)-2-(((S)-pent-2-yl)oxy)imidazo[2,1-f][1,2,4]triazin-4-amine Compound B55

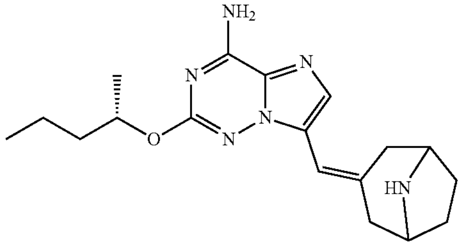

Compound B56

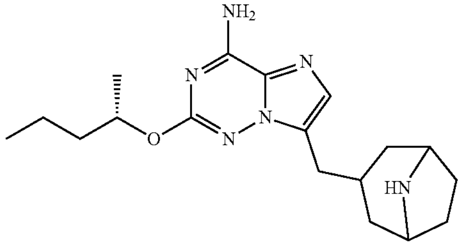

$Et_3SiH$ (4 mL) was added to a mixture of the product of step C (60 mg, crude) in TFA (4 mL), and the resulting mixture was stirred at 85° C. for 4 h. The mixture was cooled to room temperature and concentrated to dryness. TFA (5 mL) was added to the residue, and the reaction was heated at 80° C. overnight. The mixture was concentrated under vacuum. The residue was purified by preparative HPLC to obtain compound B55 (0.6 mg) and compound B56 (0.9 mg).

Compound B55: 1H NMR (400 MHz, CD3OD) δ 7.46 (s, 1H), 6.60 (s, 1H), 4.53 (s, 1H), 4.06 (s, 2H), 2.87 (t, J=14.7 Hz, 2H), 2.52 (d, J=14.5 Hz, 1H), 2.09 (s, 1H), 1.96 (d, J=19.5 Hz, 2H), 1.67 (s, 2H), 1.51 (s, 2H), 1.37 (s, 2H), 1.26 (d, J=6 Hz, 3H), 0.87 (s, 3H) ppm.MS: M/e 343 $(M+1)^+$.

Compound B56: 1H NMR (400 MHz, CD3OD) δ 7.30 (s, 1H), 4.53 (s, 1H), 3.91 (s, 2H), 3.0.7 (d, J=8.6 Hz, 2H), 2.29 (d, J=16.2 Hz, 2H), 2.09 (s, 4H), 1.94 (s, 1H), 1.69 (d, J=15.5 Hz, 2H), 1.51 (s, 2H), 1.36 (s, 2H), 1.27 (d, J=6 Hz, 3H), 0.87 (t, J=7.3 Hz, 3H) ppm.MS: M/e 345 $(M+1)^+$.

Compound B57: 7-((3,3-difluorpiperidin-4-yl)methyl)-2-(((S)-pent-2-yl)oxy)imidazo[2,1-f][1,2,4]triazin-4-amine

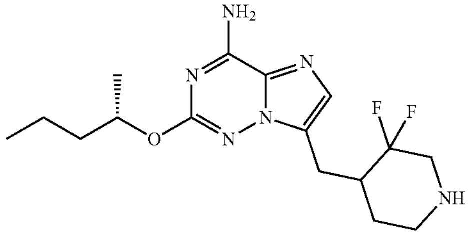

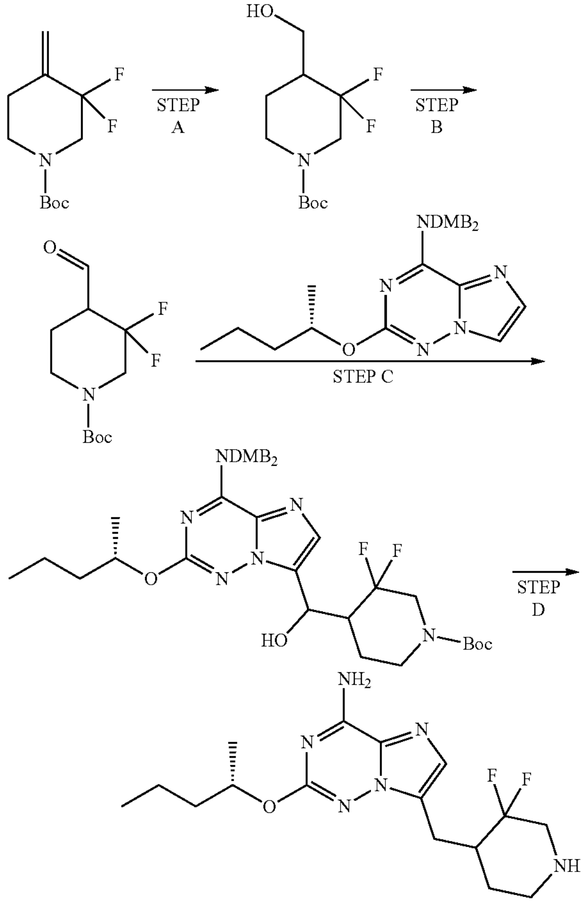

Step A: Tert-butyl 3,3-difluoro-4-(hydroxymethyl) piperidin-1-carboxylate

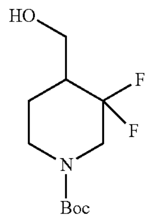 [SMILES: CC(C)(C)OC(=O)N1CCC(CO)C(F)(F)C1]

$BH_3$-THF (1 M, 2.5 mmol, 1.5 mL) was added to a solution of tert-butyl 3,3-difluoro-4-methylenepiperidin-1-carboxylate (223 mg, 1 mmol) in THF (5 mL) at 0° C. under the protection of $N_2$ atmosphere. The reaction was stirred at room temperature overnight. Then, an aqueous NaOH solution (3 M, 1.7 mL) and $H_2O_2$ (30%, 1.7 mL) were added to the mixture, and the reaction was continuously stirred overnight. $H_2O$ was added to the mixture and the resulting mixture was extracted with ethyl acetate. The combined organic extracts were dried over sodium sulfate, filtered and evaporated, and purified by preparative TLC to obtain the title product (100 mg) as an oil. MS: M/e 252 $(M+1)^+$.

Step B: Tert-butyl 3,3-difluoro-4-formylpiperidin-1-carboxylate

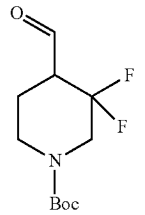 [SMILES: CC(C)(C)OC(=O)N1CCC(C=O)C(F)(F)C1]

To a solution of tert-butyl 3,3-difluoro-4-(hydroxymethyl)piperidin-1-carboxylate (100 mg, 0.41 mmol) in DCM (10 mL), Dess-Martin periodinane (265 mg, 0.2 mmol) was added. The reaction was stirred at room temperature for 4 h. $H_2O$ was added to the mixture and the resulting mixture was extracted with ethyl acetate. The combined organic extracts were dried over sodium sulfate, filtered and evaporated, and purified by preparative TLC to obtain the title product (48 mg, 48%). MS: M/e 250 $(M+1)^+$.

Step C: Tert-butyl 4-((4-(bis(4-methoxybenzyl) amino)-2-(((S)-pent-2-yl)oxy)imidazo[2,1-f][1,2,4] triazin-7-yl)(hydroxy)methyl)-3,3-difluorpiperidin-1-carboxylate

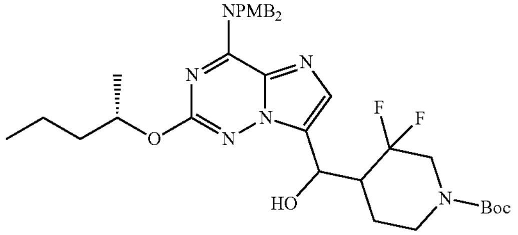

To a solution of (S)—N,N-bis(4-methoxybenzyl)-2-(pent-2-yloxy)imidazo[2,1-f][1,2,4]triazin-4-amine (97 mg, 0.2 mmol) in THF (4 mL), a solution of n-BuLi (1.6 M, 0.2 mL, 0.3 mmol) was added dropwise at a temperature of −75° C. to −65° C. One hour later, a suspension of tert-butyl 3,3-difluoro-4-formylpiperidin-1-carboxylate (48 mg, 0.2 mmol) in THF (2 mL) was added dropwise. The resulting mixture was stirred at −70° C. for 2 h, and then warmed to room temperature to react overnight. The reaction was quenched with a saturated $NH_4Cl$ solution, extracted with EtOAc (20 mL×3), washed with brine, dried over $Na_2SO_4$, filtered and concentrated. The residue was purified by preparative TLC to obtain the target compound (20 mg, 14.1%). MS: M/e 711 $(M+1)^+$.

Step D: 7-((3,3-difluorpiperidin-4-yl)methyl)-2-(((S)-pent-2-yl)oxy)imidazo[2,1-f][1,2,4]triazin-4-amine

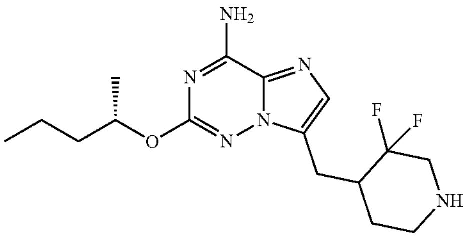

$Et_3SiH$ (4 mL) was added to a mixture of the product of step C (20 mg, 0.028 mmol) in TFA (4 mL), and the resulting mixture was stirred at 85° C. for 4 h. The mixture was cooled to room temperature and concentrated to dryness. TFA (5 mL) was added to the residue, and the reaction was heated at 80° C. overnight. The mixture was concentrated under vacuum. The residue was purified by preparative HPLC to obtain the product (1.1 mg, 11.1%). $^1H$ NMR (400 MHz, CD3OD) δ 7.28 (s, 1H), 5.00 (d, J=5.8 Hz, 1H), 2.76 (s, 2H), 2.58-2.40 (m, 2H), 2.09 (t, J=7.6 Hz, 1H), 1.94 (s, 1H), 1.74 (s, 1H), 1.65 (s, 1H), 1.62-1.55 (m, 1H), 1.51 (s, 2H), 1.37 (s, 2H), 1.27 (d, J=6.2 Hz, 3H), 0.87 (t, J=7.3 Hz, 3H) ppm.MS: M/e 355 $(M+1)^+$.

Compound B58 and B59: 7-((1-((R or S)-2-(methylamino)propyl)piperidin-4-yl)methyl)-2-(((S)-pent-2-yl)oxy)imidazo[2,1-f][1,2,4]triazin-4-amine and 7-((1-((S or R)-2-(methylamino)propyl)piperidin-4-yl)methyl)-2-(((S)-pent-2-yl)oxy)imidazo[2,1-f][1,2,4]triazin-4-amine

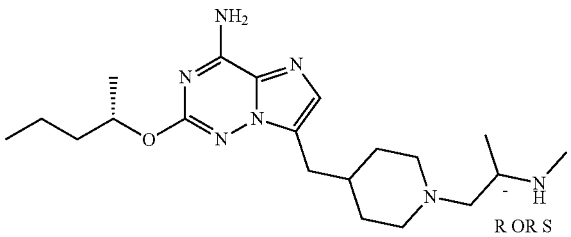

COMPOUND B58, OPTICAL ISOMER 1

-continued

AND

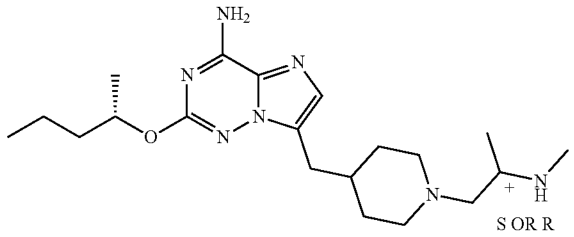

COMPOUND B59, OPTICAL ISOMER 2

Compound B54 7-((1-(2-(methylamino)propyl)piperidin-4-yl)methyl)-2-(((S)-pent-2-yl)oxy)imidazo[2,1-f][1,2,4]triazin-4-amine (150 mg, 0.386 mmol) was purified by preparative SFC (chiral PAK AD-H column, 3 cm*25 cm, 5 um, flow rate 20 mL/min, phase: hexane (2 mM $NH_3$-MeOH): IPA=90:10, UV: 220 nm, 25° C.), thereby obtaining compound B58 (55 mg) and compound B59 (53 mg).

Compound B58: 1H NMR (400 MHz, CD3OD) δ 7.29 (s, 1H), 5.14-5.02 (m, 1H), 2.94 (d, J=11.2 Hz, 1H), 2.85-2.71 (m, 4H), 2.40 (s, 3H), 2.32-2.14 (m, 2H), 2.10 (t, J=11.2 Hz, 1H), 1.91-1.70 (m, 3H), 1.70-1.54 (m, 3H), 1.54-1.25 (m, 7H), 1.02 (d, J=6.4 Hz, 3H), 0.97 (t, J=7.2 Hz, 3H) ppm. MS: M/e 390 $(M+1)^+$.

Compound B59: 1H NMR (400 MHz, CD3OD) δ 7.29 (s, 1H), 5.14-5.04 (m, 1H), 2.93 (d, J=11.2 Hz, 1H), 2.85-2.64 (m, 4H), 2.40 (s, 3H), 2.30-2.12 (m, 2H), 2.08 (t, J=11.6 Hz, 1H), 1.90-1.70 (m, 3H), 1.70-1.53 (m, 3H), 1.53-1.25 (m, 7H), 1.02-0.93 (m, 6H) ppm.MS: M/e 390 $(M+1)^+$.

Compound B60: 7-((3-methylpiperidin-4-yl)methyl)-2-(((S)-pent-2-yl)oxy)imidazo[2,1-f][1,2,4]triazin-4-amine

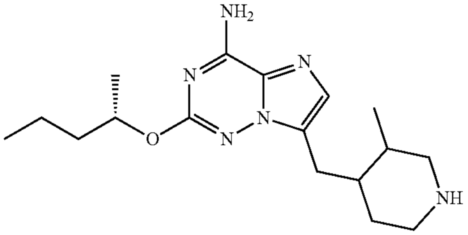

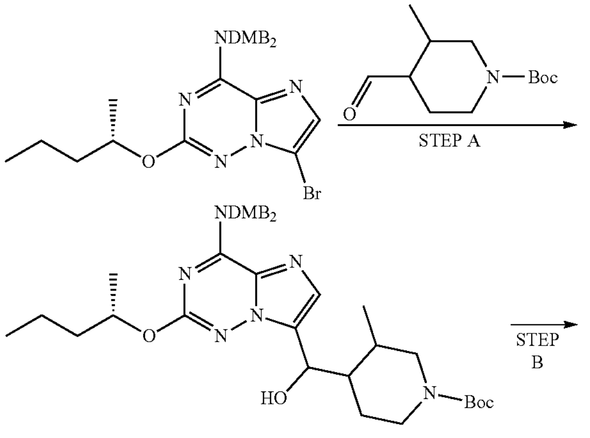

-continued

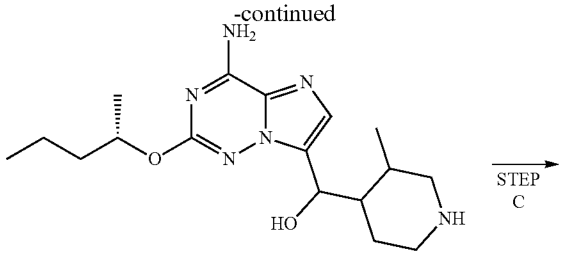

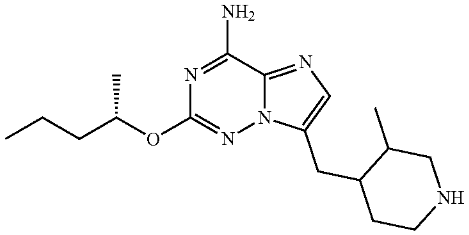

Step A: Methyl 4-((4-(bis(2,4-dimethoxybenzyl)amino)-2-(((S)-pent-2-yl)oxy)imidazo[2,1-f][1,2,4]triazin-7-yl)(hydroxy)methyl)-3-methylpiperidin-1-carboxylate

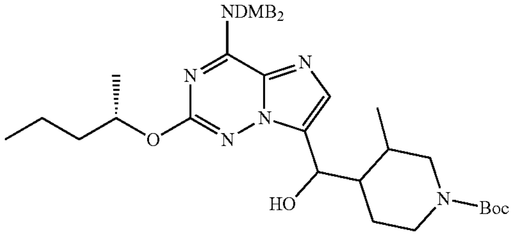

At −78° C. under $N_2$, to a solution of (S)-7-bromo-N,N-bis(2,4-dimethoxybenzyl)-2-(pent-2-yloxy)imidazo[2,1-f][1,2,4]triazin-4-amine (500 mg, 0.833 mmol) in THF (10 mL), n-BuLi (1.04 mL, 1.664 mmol) was added. After the mixture was stirred at −78° C. for 0.5 h, tert-butyl 4-formyl-3-methylpiperidin-1-carboxylate (284 mg, 1.251 mmol) was added. The reaction mixture was stirred at −78° C. for 2.5 h. After completion of the reaction, the reaction mixture was quenched with an aqueous $NH_4Cl$ solution (20 mL) and extracted with DCM (3×30 mL). The combined organic layers were dried over $Na_2SO_4$ and concentrated under vacuum to obtain a residue. The residue was purified by column chromatography on silica gel eluted with ethyl acetate (40%) in petroleum ether to obtain the title compound (400 mg, 64%). MS: M/e 749 $(M+1)^+$.

Step B: (4-amino-2-(((S)-pent-2-yl)oxy)imidazo[2,1-f][1,2,4]triazin-7-yl)(3-methylpiperidin-4-yl)methanol

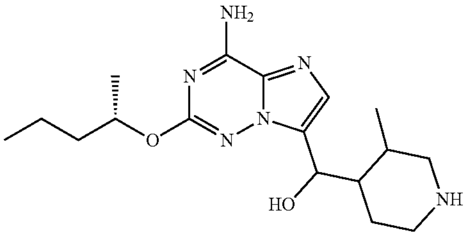 [SMILES: CCC[C@H](C)Oc1nc(N)c2ncc(C(O)C3CCNCC3C)n2n1]

Under $N_2$, tert-butyl 4-((4-(bis(2,4-dimethoxybenzyl)amino)-2-(((S)-pent-2-yl)oxy)imidazo[2,1-f][1,2,4]triazin-7-yl)(hydroxy)methyl)-3-methylpiperidin-1-carboxylate (400 mg, 0.534 mmol) was dissolved in TFA (9 mL) and $H_2O$ (1 mL). The reaction mixture was stirred at 40° C. for 12 h. After completion of the reaction, the solvent was removed under vacuum. The residue was diluted with water (20 mL) and DCM (20 mL), and the aqueous phase was acidified with 1 N HCl to adjust pH=1-2. The aqueous phase was washed with DCM (3' 20 mL), alkalized with 2 N NaOH to adjust PH=13-14, and extracted with DCM/i-PrOH (5/1, 3x60 mL). The combined organic layers were dried over $Na_2SO_4$ and concentrated under vacuum to obtain the crude compound (180 mg, crude). MS: M/e 349 $(M+1)^+$.

Step C: 7-((3-methylpiperidin-4-yl)methyl)-2-(((S)-pent-2-yl)oxy)imidazo[2,1-f][1,2,4]triazin-4-amine

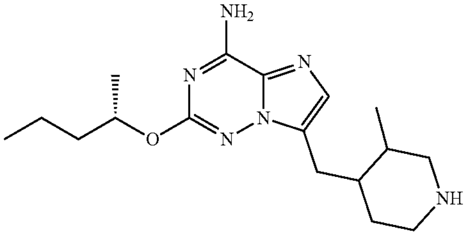 [SMILES: CCC[C@H](C)Oc1nc(N)c2ncc(CC3CCNCC3C)n2n1]

(4-amino-2-(((S)-pent-2-yl)oxy)imidazo[2,1-f][1,2,4]triazin-7-yl)(3-methylpiperidin-4-yl)methanol (180 mg, crude) was dissolved in TFA (5 mL) and $Et_3SiH$ (5 mL) under $N_2$. The reaction mixture was stirred at 90° C. for 12 h. After completion of the reaction, the solvent was removed under vacuum. The residue was diluted with water (20 mL) and DCM (20 mL), and the aqueous phase was acidified with 1 N HCl to adjust pH=1-2. The aqueous phase was washed with DCM (3x20 mL), alkalized with 2 N NaOH to adjust PH=13-14, and extracted with DCM/i-PrOH (5/1, 3x120 mL). The combined organic layers were dried over $Na_2SO_4$ and concentrated under vacuum to obtain a residue. The residue was purified by preparative HPLC to obtain the title compound (12 mg). $^1H$ NMR (400 MHz, $CD_3OD$) δ 7.58 (s, 1H), 5.13 (d, J=6.0 Hz, 1H), 3.34 (s, 1H), 3.15 (dd, J=10.4, 4.4 Hz, 2H), 3.07-2.86 (m, 3H), 2.36 (s, 1H), 2.15 (s, 1H), 1.84-1.68 (s, 3H), 1.67-1.55 (m, 1H), 1.55-1.40 (m, 2H), 1.37 (d, J=6.4 Hz, 3H), 1.16 (d, J=7.2 Hz, 3H), 0.97 (t, J=7.2 Hz, 3H) ppm. MS: M/e 333 $(M+1)^+$.

TLR8 Stimulation Determined by HEK-Blue Detection

This assay was designed to study the stimulation of human TLR 8 protein in HEK-blue hTLR 8 tool cell line by monitoring the activation of NF-κB. HEK-blue hTLR8 cells were obtained by co-transfection of hTLR8 gene and optimized secretory embryonic alkaline phosphatase (SEAP) reporter gene into HEK293 cells. SEAP reporter gene was put under the control of IFN-pi minimal promoter fused with five NF-κB and AP-1-binding sites. NF-κB and AP-1 were activated by stimulation with TLR 8 ligand, thus inducing the expression of SEAP. The level of SEAP can be easily determined by HEK-Blue Detection (a cell culture medium that allows real-time detection of SEAP). HEK-Blue Detection comprises all nutrients needed for cell growth and specific SEAP color substrates. The hydrolysis of substrate by SEAP produces purple/blue color which can be measured by spectrophotometer.

When growing to 50-80% confluence, HEK-Blue hTLR7/8 cells were plated into 96-well plates (costar 3599) at a density of 40,000 cells/well. Then, the compound serially diluted at 10 points with a final concentration ranging from 1 nM to 10 μm in 0.1% DMSO/HEK-Blue Detection was added. The plates were then incubated in 5% $CO_2$ at 37° C. for 16 h. Optical density at 620-655 nm was read on BMG PHERAstar FSX instrument. The EC50 of each compound was determined by calculating the maximum activation percentage identified using Resiquimod or motolimod.

The EC50 of the tested compound of the present invention is as follows.

TABLE 1

Compounds for HEK-Blue hTLR8 cells ("D" denotes E50 > 10 μmol)

| Compound No. | Structure | EC50 (nmol) |
|---|---|---|
| B1 | 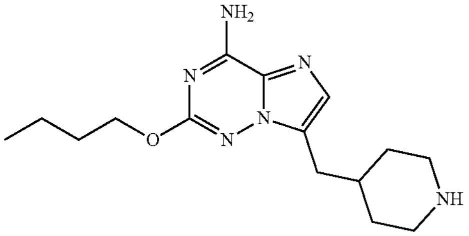 [SMILES: CCCCOc1nc(N)c2ncc(CC3CCNCC3)n2n1] | 51 |

TABLE 1-continued
| Compounds for HEK-Blue hTLR8 cells ("D" denotes E50 > 10 μmol) | | |
|---|---|---|
| Compound No. | Structure | EC50 (nmol) |
| B2 | 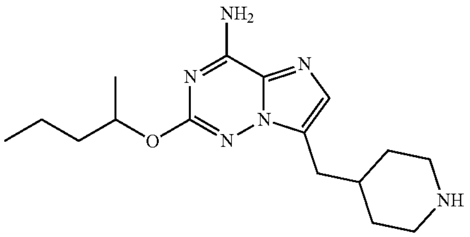 [SMILES: CCCC(C)Oc1nc(N)c2ncc(CC3CCNCC3)n2n1] | 15 |
| B3 | 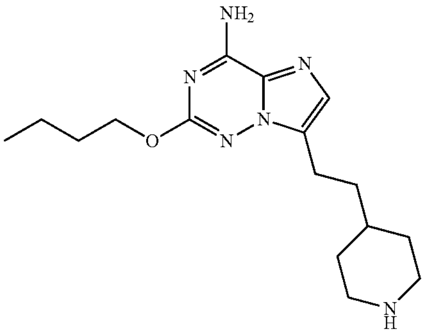 [SMILES: CCCCOc1nc(N)c2ncc(CCC3CCNCC3)n2n1] | 346 |
| B4 | 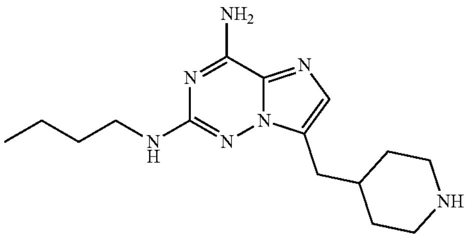 [SMILES: CCCCNc1nc(N)c2ncc(CC3CCNCC3)n2n1] | 347 |
| B5 | 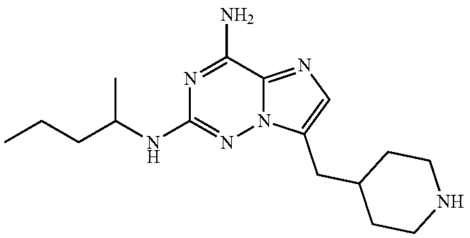 [SMILES: CCCC(C)Nc1nc(N)c2ncc(CC3CCNCC3)n2n1] | 917 |
| B6 | 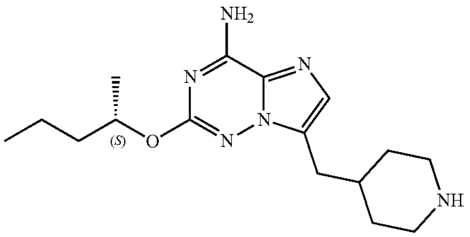 | 8.2 |

TABLE 1-continued
| Compounds for HEK-Blue hTLR8 cells ("D" denotes E50 > 10 μmol) | | |
|---|---|---|
| Compound No. | Structure | EC50 (nmol) |
| B7 | 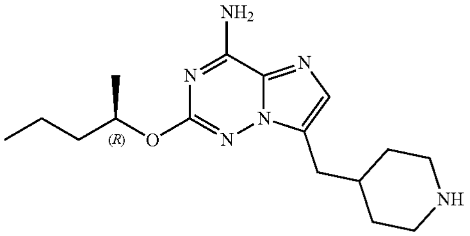 | 1288 |
| B8 | 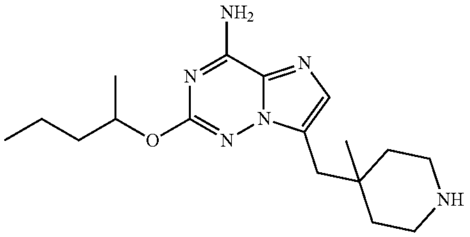 [SMILES: CCCC(C)Oc1nc(N)c2ncc(CC3(C)CCNCC3)n2n1] | 515 |
| B9 | 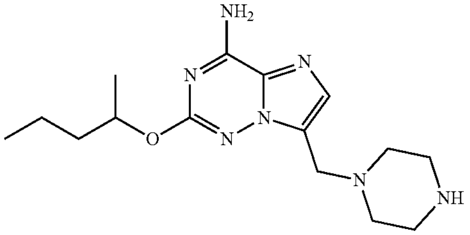 [SMILES: CCCC(C)Oc1nc(N)c2ncc(CN3CCNCC3)n2n1] | 529 |
| B10 | 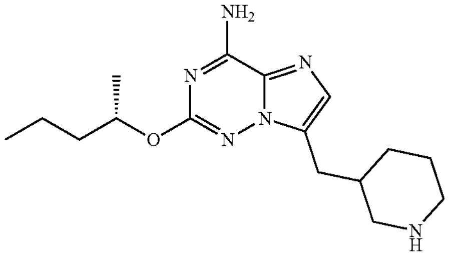 [SMILES: CCC[C@H](C)Oc1nc(N)c2ncc(CC3CCCNC3)n2n1] | 172 |
| B11 | 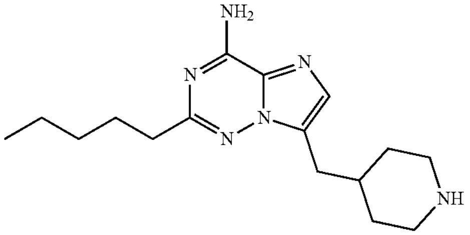 [SMILES: CCCCCc1nc(N)c2ncc(CC3CCNCC3)n2n1] | 1794 |
| B12 | 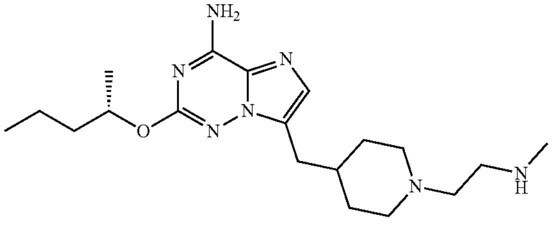 [SMILES: CCC[C@H](C)Oc1nc(N)c2ncc(CC3CCN(CCNC)CC3)n2n1] | 19 |

TABLE 1-continued
Compounds for HEK-Blue hTLR8 cells ("D" denotes E50 > 10 μmol)
| Compound No. | Structure | EC50 (nmol) |
|---|---|---|
| B13 | 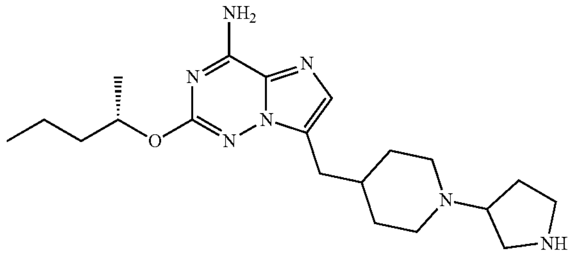 [SMILES: CCC[C@H](C)Oc1nc(N)c2ncc(CC3CCN(C4CCNC4)CC3)n2n1] | 387 |
| B14 | 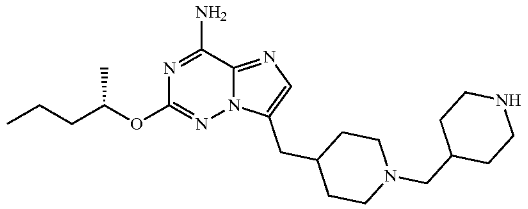 [SMILES: CCC[C@H](C)Oc1nc(N)c2ncc(CC3CCN(CC4CCNCC4)CC3)n2n1] | 138 |
| B15 | 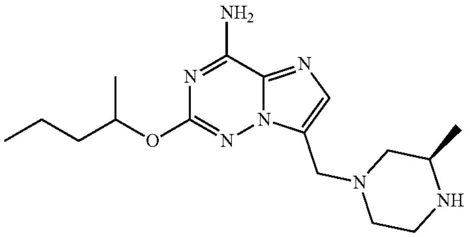 [SMILES: CCCC(C)Oc1nc(N)c2ncc(CN3CCN[C@H](C)C3)n2n1] | 1076 |
| B16 | 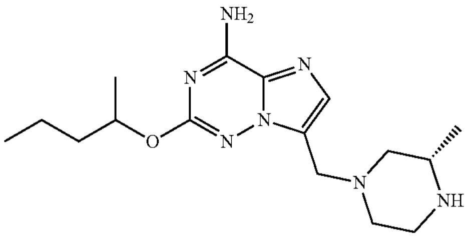 [SMILES: CCCC(C)Oc1nc(N)c2ncc(CN3CCN[C@@H](C)C3)n2n1] | 8493 |
| B17 | 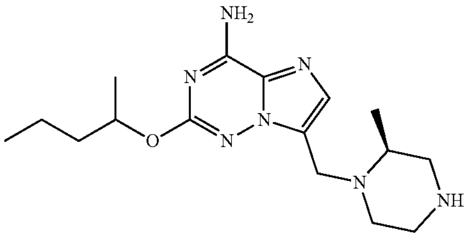 [SMILES: CCCC(C)Oc1nc(N)c2ncc(CN3CCNC[C@@H]3C)n2n1] | 3953 |
| B18 | 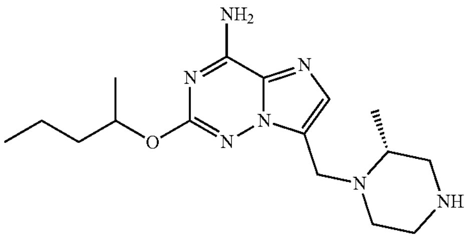 [SMILES: CCCC(C)Oc1nc(N)c2ncc(CN3CCNC[C@H]3C)n2n1] | 2719 |

TABLE 1-continued
| Compounds for HEK-Blue hTLR8 cells ("D" denotes E50 > 10 μmol) | | |
|---|---|---|
| Compound No. | Structure | EC50 (nmol) |
| B19 | 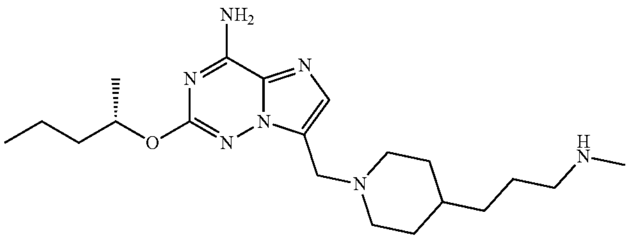 [SMILES: CCC[C@H](C)Oc1nc(N)c2ncc(CN3CCC(CCCNC)CC3)n2n1] | 66 |
| B20 | 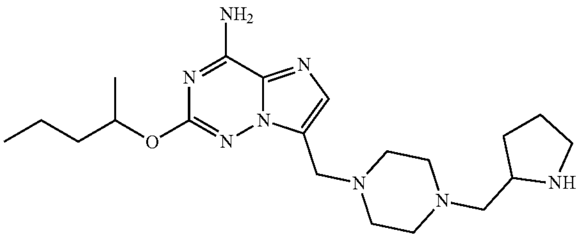 [SMILES: CCCC(C)Oc1nc(N)c2ncc(CN3CCN(CC4CCCN4)CC3)n2n1] | 558 |
| B21 | 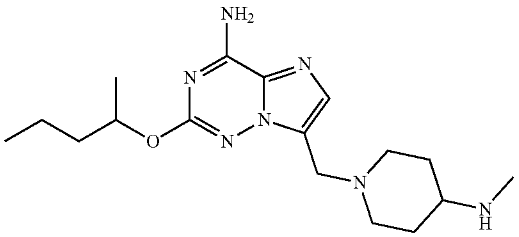 [SMILES: CCCC(C)Oc1nc(N)c2ncc(CN3CCC(NC)CC3)n2n1] | D |
| B22 | 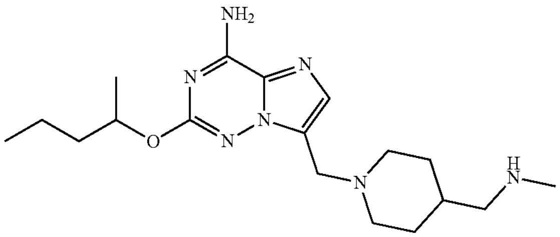 [SMILES: CCCC(C)Oc1nc(N)c2ncc(CN3CCC(CNC)CC3)n2n1] | D |
| B23 | 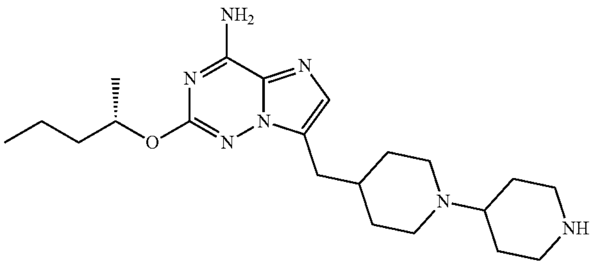 [SMILES: CCC[C@H](C)Oc1nc(N)c2ncc(CC3CCN(C4CCNCC4)CC3)n2n1] | 143 |

TABLE 1-continued
| Compounds for HEK-Blue hTLR8 cells ("D" denotes E50 > 10 μmol) | | |
|---|---|---|
| Compound No. | Structure | EC50 (nmol) |
| B24 | 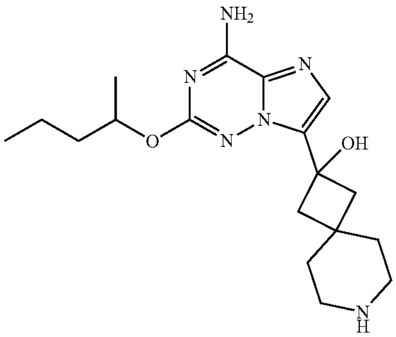 [SMILES: CCCC(C)Oc1nc(N)c2ncc(C3(O)CC4(CCNCC4)C3)n2n1] | D |
| B25 | 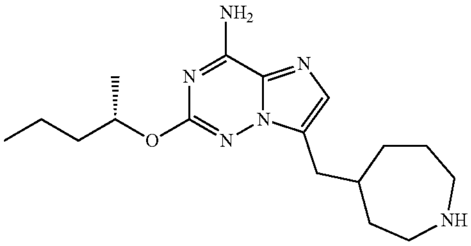 [SMILES: CCC[C@H](C)Oc1nc(N)c2ncc(CC3CCCNCC3)n2n1] | 63 |
| B26 | 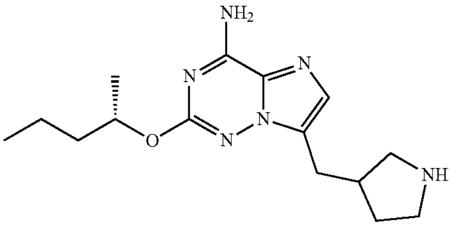 [SMILES: CCC[C@H](C)Oc1nc(N)c2ncc(CC3CCNC3)n2n1] | 99 |
| B27 | 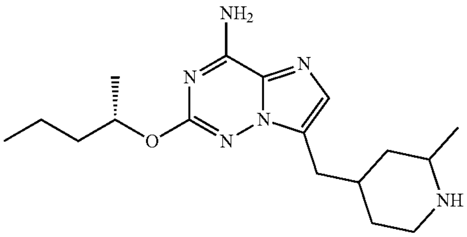 [SMILES: CCC[C@H](C)Oc1nc(N)c2ncc(CC3CCNC(C)C3)n2n1] | 20 |
| B28 | 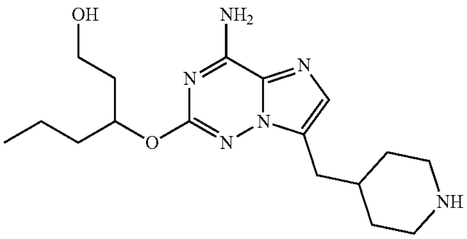 [SMILES: CCCC(CCO)Oc1nc(N)c2ncc(CC3CCNCC3)n2n1] | 308 |

TABLE 1-continued
| Compound No. | Structure | EC50 (nmol) |
|---|---|---|
| Compounds for HEK-Blue hTLR8 cells ("D" denotes E50 > 10 μmol) | | |
| B29 | 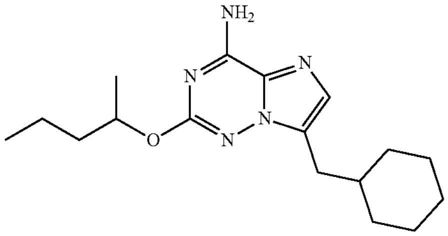 [SMILES: CCCC(C)Oc1nc(N)c2ncc(CC3CCCCC3)n2n1] | D |
| B30 | 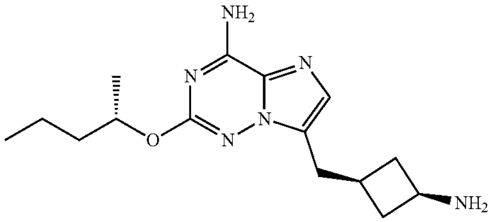 [SMILES: CCC[C@H](C)Oc1nc(N)c2ncc(C[C@H]3C[C@@H](N)C3)n2n1] | 26 |
| B31 | 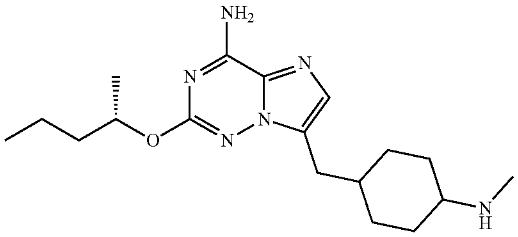 [SMILES: CCC[C@H](C)Oc1nc(N)c2ncc(CC3CCC(NC)CC3)n2n1] | 103 |
| B32 | 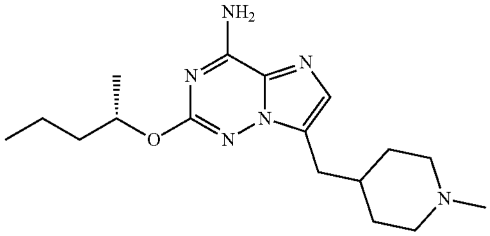 [SMILES: CCC[C@H](C)Oc1nc(N)c2ncc(CC3CCN(C)CC3)n2n1] | 22 |
| B33 | 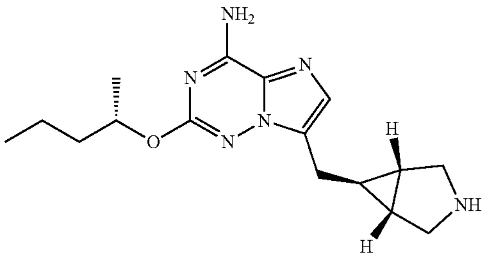 [SMILES: CCC[C@H](C)Oc1nc(N)c2ncc(C[C@H]3[C@@H]4CNC[C@@H]43)n2n1] | 766 |
| B34 | 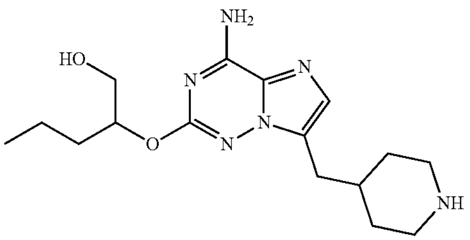 [SMILES: CCCC(CO)Oc1nc(N)c2ncc(CC3CCNCC3)n2n1] | 225 |

TABLE 1-continued
| Compound No. | Structure | EC50 (nmol) |
|---|---|---|
| Compounds for HEK-Blue hTLR8 cells ("D" denotes E50 > 10 μmol) | | |
| B35 | 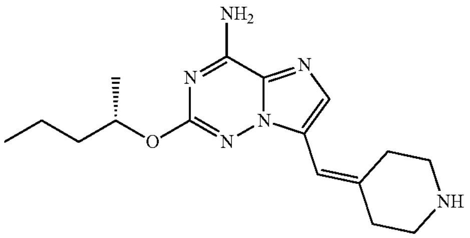 [SMILES: CCC[C@H](C)Oc1nc(N)c2ncc(C=C3CCNCC3)n2n1] | 921 |
| B36 | 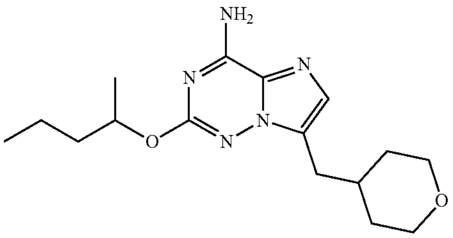 [SMILES: CCCC(C)Oc1nc(N)c2ncc(CC3CCOCC3)n2n1] | D |
| B37 | 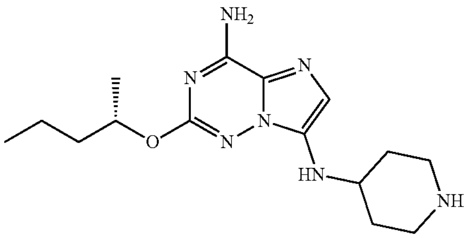 [SMILES: CCC[C@H](C)Oc1nc(N)c2ncc(NC3CCNCC3)n2n1] | D |
| B38 | 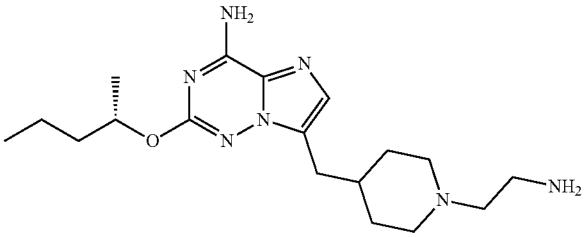 [SMILES: CCC[C@H](C)Oc1nc(N)c2ncc(CC3CCN(CCN)CC3)n2n1] | 47 |
| B39 | 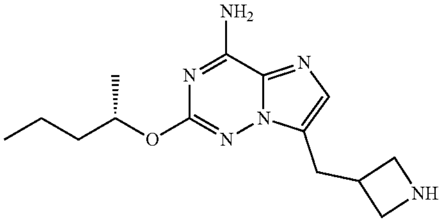 [SMILES: CCC[C@H](C)Oc1nc(N)c2ncc(CC3CNC3)n2n1] | 127 |
| B40 | 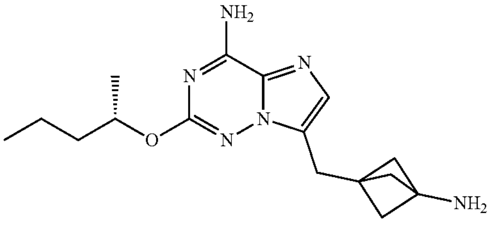 [SMILES: CCC[C@H](C)Oc1nc(N)c2ncc(CC34CC(N)(C3)C4)n2n1] | 1006 |

TABLE 1-continued
| Compound No. | Structure | EC50 (nmol) |
|---|---|---|
| B41 | 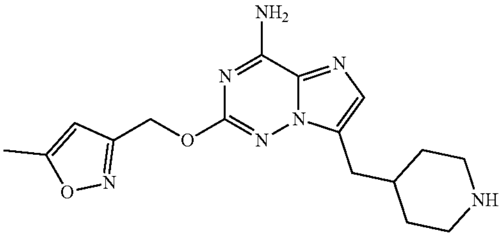 [SMILES: Cc1cc(COc2nc(N)c3ncc(CC4CCNCC4)n3n2)no1] | D |
| B42 | 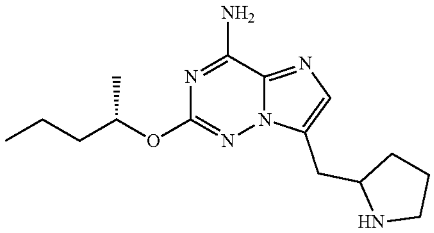 [SMILES: CCC[C@H](C)Oc1nc(N)c2ncc(CC3CCCN3)n2n1] | 36 |
| B43 | 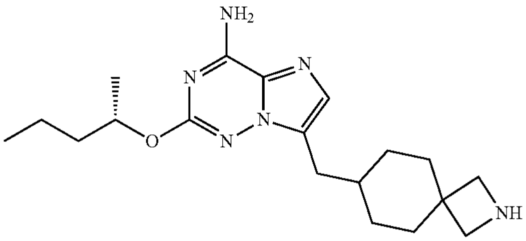 [SMILES: CCC[C@H](C)Oc1nc(N)c2ncc(CC3CCC4(CC3)CNC4)n2n1] | 24 |
| B44 | 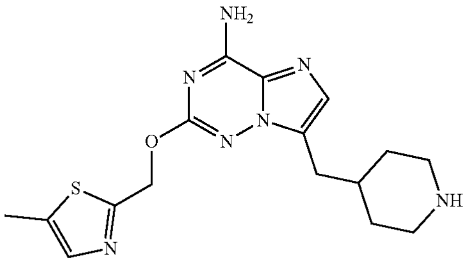 [SMILES: Cc1cnc(COc2nc(N)c3ncc(CC4CCNCC4)n3n2)s1] | D |
| B45 | 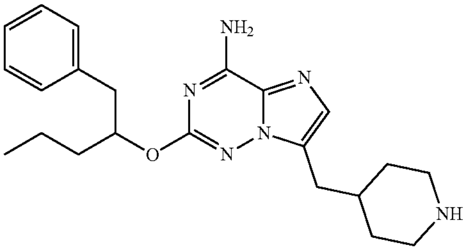 [SMILES: CCCC(Cc1ccccc1)Oc1nc(N)c2ncc(CC3CCNCC3)n2n1] | 531 |
| B46 | 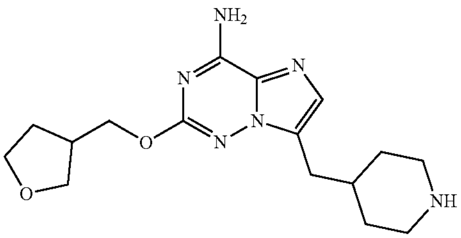 [SMILES: Nc1nc(OCC2CCOC2)nn2c(CC3CCNCC3)cnc12] | D |
Compounds for HEK-Blue hTLR8 cells ("D" denotes E50 > 10 μmol)

TABLE 1-continued
| Compound No. | Structure | EC50 (nmol) |
|---|---|---|
| Compounds for HEK-Blue hTLR8 cells ("D" denotes E50 > 10 μmol) | | |
| B47 | 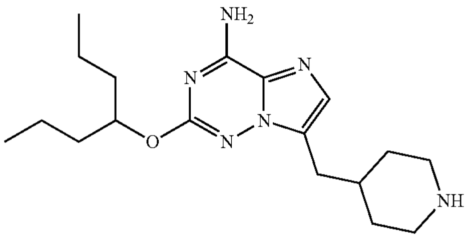 [SMILES: CCCC(CCC)Oc1nc(N)c2ncc(CC3CCNCC3)n2n1] | 84 |
| B48 | 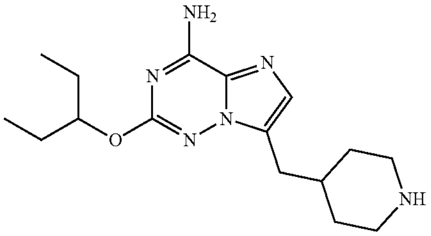 [SMILES: CCC(CC)Oc1nc(N)c2ncc(CC3CCNCC3)n2n1] | 14.7 |
| B49 | 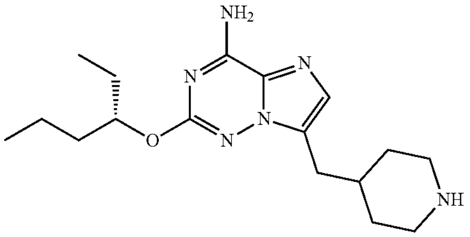 [SMILES: CCC[C@H](CC)Oc1nc(N)c2ncc(CC3CCNCC3)n2n1] | 7.5 |
| B50 | 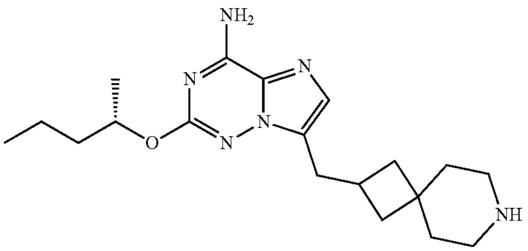 [SMILES: CCC[C@H](C)Oc1nc(N)c2ncc(CC3CC4(CCNCC4)C3)n2n1] | 209 |
| B51 | 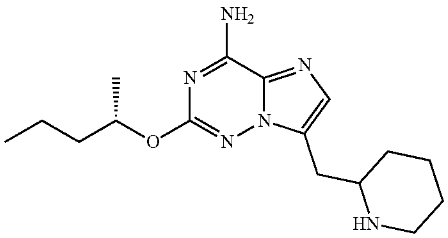 [SMILES: CCC[C@H](C)Oc1nc(N)c2ncc(CC3CCCCN3)n2n1] | 410 |
| B52 | 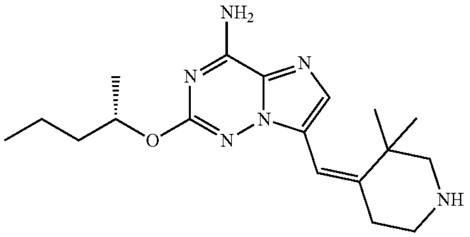 [SMILES: CCC[C@H](C)Oc1nc(N)c2ncc(/C=C3/CCNCC3(C)C)n2n1] | >10μM |

TABLE 1-continued
| Compounds for HEK-Blue hTLR8 cells ("D" denotes E50 > 10 μmol) | | |
|---|---|---|
| Compound No. | Structure | EC50 (nmol) |
| B53 | 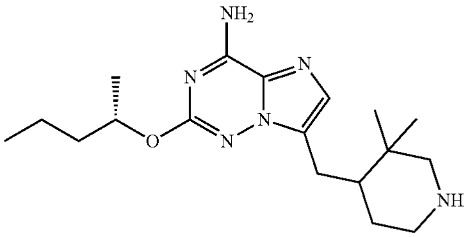 [SMILES: CCC[C@H](C)Oc1nc(N)c2ncc(CC3CCNCC3(C)C)n2n1] | 3863 |
| B54 | 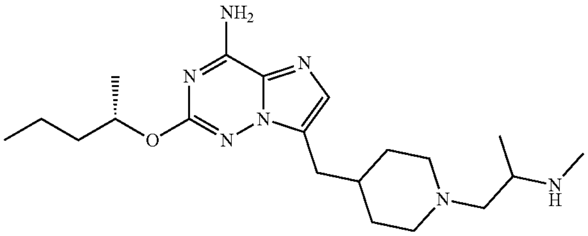 [SMILES: CCC[C@H](C)Oc1nc(N)c2ncc(CC3CCN(CC(C)NC)CC3)n2n1] | 22 |
| B55 | 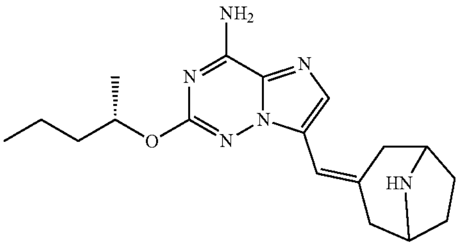 [SMILES: CCC[C@H](C)Oc1nc(N)c2ncc(C=C3CC4CCC(C3)N4)n2n1] | >10μM |
| B56 | 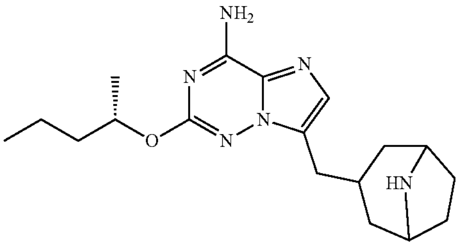 [SMILES: CCC[C@H](C)Oc1nc(N)c2ncc(CC3CC4CCC(C3)N4)n2n1] | 1925 |
| B57 | 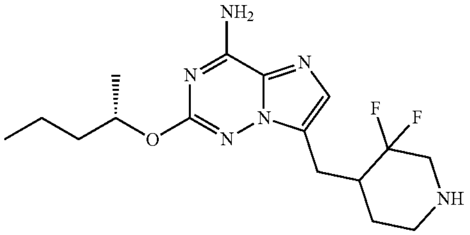 [SMILES: CCC[C@H](C)Oc1nc(N)c2ncc(CC3CCNCC3(F)F)n2n1] | >10μM |
| B58 | 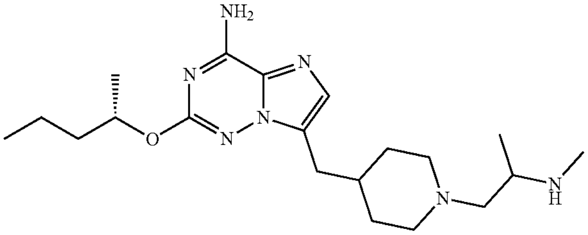 Optical isomer 1 | 24 |

TABLE 1-continued

| Compounds for HEK-Blue hTLR8 cells ("D" denotes E50 > 10 μmol) | | |
|---|---|---|
| Compound No. | Structure | EC50 (nmol) |
| B59 | 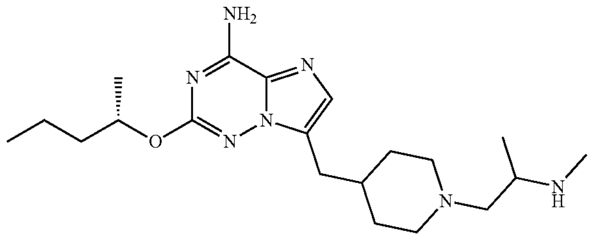 Optical isomer 2 | 21 |
| B60 | 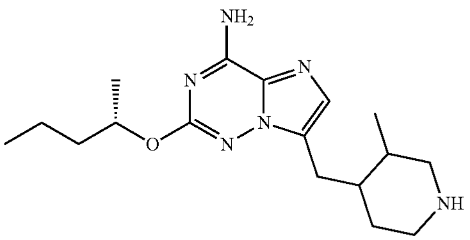 [SMILES: CCC[C@H](C)Oc1nc(N)c2ncc(CC3CCNCC3C)n2n1] | 917 |

Determination of PBMC (Peripheral Blood Monocyte) Cell Preparation, Separation and Culture Human whole blood was collected from healthy volunteers using BD Vacutainer® Lithium Heparin Tubes. PBMCs were prepared using Ficoll separation medium (GE Healthcare) by SopMate™ (STEMCELL). The cell survival rate was over 85% as monitored by Countstar. PBMCs were cultured in RPMI 1640 (Gibco) 10% (v/v) FBS (Gibco), 1×MEM NEAA (Gibco), 1× GlutaMAX (Gibco), 1 mM sodium pyruvate (Gibco), 50 uM 2-mercaptoethanol (sigma), and 100 U/ml penicillin-streptomycin (Thermo fisher Scientific).

Cell Stimulation

PBMCs were plated into 96-well plates (costar 3894) with a density of 2×10^5 cells/well. Then, TLR7/8 compound was added, and serial dilution was carried out at ten points. The final concentration in 0.1% DMSO/RPMI 1640 ranged from 1 nM to 10 μM. Then, the plates were incubated in 5% $CO_2$ at 37° C. for 24 h.

HTRF (Homogeneous Time-Resolved Fluorescence)

After the specified time point, according to the manufacturers recommendations, the cytokines in the cell culture supernatant were measured by Human IL6 kit (cisbio) and Human TNF alpha kit (cisbio). The EC50 of each compound was determined by calculating the maximum activation percentage identified using Resiquimod or Motolimod.

TABLE 2

| PBMC determination of compounds ("D" denotes EC 50 > 10 μmol) | | | | | |
|---|---|---|---|---|---|
| Compound No. | IL6 | TNF-alpha | Compound No. | IL6 | TNF-alpha |
| B6 | 162 | 115 | B7 | D | D |
| B12 | 14 | 10 | B19 | 247 | 430 |
| B25 | 236 | 456 | B27 | 228 | 326 |
| B30 | 85 | 153 | B38 | 28 | 39 |

Although the present invention has been described in connection with the specific embodiments set forth above, many alternatives, modifications and other variations thereof will be obvious to those skilled in the art. All such alternatives, modifications and variations are intended to fall within the spirit and scope of the present invention.

The invention claimed is:

1. A compound of formula (I), (I)

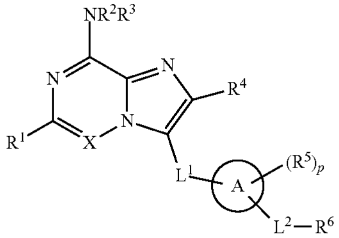

or a pharmaceutically acceptable salt thereof, or a stereoisomer thereof, wherein:

X is N or $CR^7$;

wherein $R^7$ is hydrogen, alkyl, alkenyl, alkynyl, cycloalkyl, cycloalkenyl, cycloalkynyl, heterocyclyl, aryl or heteroaryl;

$L^1$ is $-(CR^aR^b)_m-$, —O—, —S—, —S(O)—, $-SO_2-$, —C(O)—, —C(O)O—, —OC(O)—, $-NR^a-$, $-C(O)NR^a-$, $-NR^aC(O)-$, $-NR^aC(O)O-$, $-NR^aC(O)NR^b-$, $-SO_2NR^a-$, $-NR^aSO_2-$, $-NR^aS(O)_2NR^b-$, $-NR^aS(O)NR^b-$, $-C(O)NR^aSO_2-$, $-C(O)NR^aSO-$, or $-C(=NR^a)NR^b-$, wherein m is 0 to 8, and one or two $CR^aR^b$ moieties in $-(CR^aR^b)_m-$ are not replaced or replaced by one or more moieties selected from O, S, SO, $SO_2$, C(O) or $NR^a$;

$R^a$ and $R^b$ in each occurrence are independently hydrogen, halogen, alkyl, alkenyl, alkynyl, cycloalkyl, cycloalkenyl, cycloalkynyl, heterocyclyl, aryl, heteroaryl or —$OR^c$;

wherein $R^c$ is hydrogen, alkyl, alkoxy-alkyl-, alkenyl, alkynyl, cycloalkyl, aryl, heterocyclyl or heteroaryl;

$R^1$ is —$OR^{1a}$, —$SR^{1a}$, —$NR^{1a}R^{1b}$, —$COR^{1a}$, —$SO_2R^{1a}$, —C(═O) $OR^{1a}$, —C(═O)$NR^{1a}R^{1b}$, —C(═$NR^{1a}$) $NR^{1b}R^{1c}$, —N($R^{1a}$)C(═O)$R^{1b}$, —N($R^{1a}$) C(═O) $OR^{1b}$, —N($R^{1a}$)C(O)$NR^{1b}R^{1c}$, —N($R^{1a}$)S(O) $NR^{1b}R^{1c}$, —N($R^{1a}$)$S(O)_2NR^{1b}R^{1c}$, —$NR^{1a}SO_2R^{1b}$, alkyl, alkenyl, alkynyl, cycloalkyl, cycloalkenyl, cycloalkynyl, heterocyclyl, aryl, or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{1d}$, $R^{1a}$, $R^{1b}$ and $R^{1c}$ are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each optionally substituted with one or two or three substituents selected from: halogen, —$C_{1-8}$ alkyl optionally substituted with $R^{1e}$, cycloalkyl optionally substituted with $R^{1e}$, heterocyclyl optionally substituted with $R^{1e}$, aryl optionally substituted with $R^{1e}$, heteroaryl optionally substituted with $R^{1e}$, $CH_3$—$(OCH_2CH_2)_n$— where n is 3 to 10, or —$OR^{1f}$, wherein $R^{1e}$ is halogen, nitro, cyano, hydroxyl, —$NH_2$, alkylamino, dialkylamino, —$C_{1-6}$ alkyl optionally substituted with halogen, carboxyl, alkoxycarbonyl, aminocarbonyl, alkylaminocarbonyl, or dialkylaminocarbonyl;

wherein $R^{1f}$ is alkyl, cycloalkyl, heterocyclyl, aryl or heteroaryl, each being optionally substituted with —$C_{1-4}$ alkyl or halogen;

$R^{1d}$ in each occurrence is independently hydrogen, oxo, —CN, —$NO_2$, hydroxyl, —$NH_2$, alkylamino, dialkylamino, halogen, haloalkyl, alkyl, haloalkoxy, alkoxy, alkenyl, alkynyl, cycloalkyl, cycloalkenyl, cycloalkynyl, heterocyclyl, aryl or heteroaryl;

$R^2$ and $R^3$ in each occurrence are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are optionally substituted with 1-3 substituents selected from: oxo, —CN, —$NO_2$, —$NH_2$, alkylamino, dialkylamino, halogen, hydroxyl, haloalkyl, alkyl, haloalkoxy, alkoxy, alkenyl, alkynyl, cycloalkyl, cycloalkenyl, cycloalkynyl, heterocyclyl, aryl or heteroaryl;

$R^4$ is hydrogen, halogen, cyano, —$NO_2$, —$OR^{4a}$, —$SR^{4a}$, —$NR^{4a}R^{4b}$, —$COR^{4a}$, —$SO_2R^{4a}$, —C(═O)$OR^{4a}$, —C(═O)$NR^{4a}R^{4b}$, —C(═$NR^{4a}$)$NR^{4b}R^{4c}$, —N($R^{4a}$) C(═O)$R^{4b}$, —N($R^{4a}$)C(═O)$OR^{4b}$, —N($R^{4a}$)C(O) $NR^{4b}R^{4c}$, —N($R^{4a}$) S(O)$NR^{4b}R^{4c}$, —N($R^{4a}$) $S(O)_2NR^{4b}R^{4c}$, —$NR^{4a}SO_2R^{4b}$, alkyl, alkenyl, alkynyl, cycloalkyl, cycloalkenyl, cycloalkynyl, heterocyclyl, aryl, or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{4d}$, $R^{4a}$, $R^{4b}$ and $R^{4c}$ are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each optionally substituted with halogen, hydroxyl, —$NH_2$, alkylamino, dialkylamino or alkoxy;

$R^{4d}$ in each occurrence is independently hydrogen, oxo, —CN, —$NO_2$, halogen, hydroxyl, —$NH_2$, alkylamino, dialkylamino, alkyl, alkoxy, alkenyl, alkynyl, cycloalkyl, cycloalkenyl, cycloalkynyl, heterocyclyl, aryl or heteroaryl, wherein the alkyl, alkoxy, alkenyl, alkynyl, cycloalkyl, cycloalkenyl, cycloalkynyl, heterocyclyl, aryl or heteroaryl are each optionally substituted with halogen, hydroxyl, —$NH_2$, alkylamino, dialkylamino or alkoxy;

ring A is azetidin-3-yl, azepan-4-yl, piperidin-2-yl, piperidin-3-yl, piperidin-4-yl, pyrrolidin-1-yl, pyrrolidin-2-yl, pyrrolidin-3-yl, piperazin-1-yl, 7-azaspiro[3.5]non-2-yl, 2-azaspiro[3.3]hept-6-yl, 7-azaspiro[3.5]non-2-yl, 2-azaspiro[3.5]non-7-yl, 3-azabicyclo[3.1.0]hex-6-yl, 2-azabicyclo[2.2.1]hept-5-yl, 8-azabicyclo[3.2.1]oct-3-yl, 2-azabicyclo[4.1.0]hept-5-yl, cyclobutyl, bicyclo[1.1.1]pent-1-yl, bicyclo[1.1.1]pent-1-yl, or 1,2,3,6-tetrahydropyridin-4-yl;

$R^5$ is halogen, oxo, hydroxyl, alkyl, haloalkyl, alkoxy, haloalkoxy or —C(═O)$OR^{5a}$, wherein $R^{5a}$ is hydrogen, alkyl or haloalkyl;

p is 0, 1, 2 or 3;

$L^2$ is a direct bond, —$(CR^fR^g)_t$—, —O—, —S—, —S(O)—, —$SO_2$—, —C(O)—, —C(O)O—, —OC (O)—, or —$NR_d$— where $R^d$ is —$C_{1-6}$ alkyl, wherein t is 1 to 8, and one or two $CR^fR^g$ moieties in —$(CR^fR^g)_t$— are not replaced or are replaced by one or more moieties selected from O, S, SO, $SO_2$, C(O) or $NR^f$;

$R^f$ and $R^g$ are independently hydrogen, alkyl, alkenyl, alkynyl, cycloalkyl, cycloalkenyl, cycloalkynyl, heterocyclyl, aryl or heteroaryl;

$R^6$ is hydrogen, —$NR^{6a}R^{6b}$, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{6c}$;

$R^{6a}$ and $R^{6b}$ are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each optionally substituted with halogen, hydroxyl, —$NH_2$, alkylamino, dialkylamino or alkoxy;

$R^{6c}$ is independently hydrogen, halogen, cyano, —$NO_2$, —$OR^{6d}$, —$SR^{6d}$, —$NR^{6d}R^{6e}$, —$COR^{6d}$, —$SO_2R^{6d}$, —C(═O)$OR^{6d}$, —C(═O)$NR^{6d}R^{6e}$, —C(═$NR^{6d}$) $NR^{6e}R^{6f}$, —N($R^{6d}$)C(═O)$R^{6e}$, —N($R^{6d}$)C(═O)$OR^{6e}$, —N($R^{6d}$)C(O)$NR^{6e}R^{6f}$, —N($R^{6d}$)S(O)$NR^{6e}R^{6f}$, —N($R^{6d}$)$S(O)_2NR^{6e}R^{6f}$, —$NR^{6d}SO_2R^{6e}$, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each independently and optionally substituted with one or two or three substituents $R^{6g}$;

$R^{6d}$, $R^{6e}$ and $R^{6f}$ are independently hydrogen, alkyl, alkenyl, alkynyl, cycloalkyl, cycloalkenyl, cycloalkynyl, heterocyclyl, aryl or heteroaryl, wherein the alkyl, alkenyl, alkynyl, cycloalkyl, cycloalkenyl, cycloalkynyl, heterocyclyl, aryl or heteroaryl are each optionally substituted with one or two or three substituents $R^{6g}$;

$R^{6g}$ in each occurrence is independently hydrogen, halogen, cyano, $—NO_2$, $—OR^{6h}$, $—SR^{6h}$, $—NR^{6h}R^{6i}$, $—COR^{6h}$, $—SO_2R^{6h}$, $—C(=O)OR^{6h}$, $—C(=O)NR^{6h}R^{6i}$, $—C(=NR^{6h})NR^{6i}R^{6j}$, $—N(R^{6h})C(=O)R^{6i}$, $—N(R^{6h})C(=O)OR^{6i}$, $—N(R^{6h})C(O)NR^{6i}R^{6j}$, $—N(R^{6h})S(O)NR^{6i}R^{6j}$, $—N(R^{6h})S(O)_2NR^{6i}R^{6h}$, $—NR^{6h}SO_2R^{6i}$, alkyl, alkenyl, alkynyl, cycloalkyl, cycloalkenyl, cycloalkynyl, heterocyclyl, aryl or heteroaryl; and $R^{6h}$, $R^{6i}$ and $R^{6j}$ are independently hydrogen, alkyl, alkoxy, alkenyl, alkynyl, cycloalkyl, cycloalkenyl, cycloalkynyl, heterocyclyl, aryl or heteroaryl, wherein the alkyl, alkoxy, alkenyl, alkynyl, cycloalkyl, cycloalkenyl, cycloalkynyl, heterocyclyl, aryl or heteroaryl are each independently and optionally substituted with one or two or three substituents selected from:

halogen, $—C_{1-4}$ alkyl, $—C_{1-4}$ alkoxy, hydroxyl, nitro, $—NH_2$, alkylamino, dialkylamino or cyano.

2. The compound according to claim 1, wherein X is N.

3. The compound according to claim 1, wherein m is:

a) 1 to 5;

b) 1 to 3; or c) 1.

4. The compound according to claim 1, wherein $L^1$ is $—CR^aR^b—$, wherein $R^a$ and $R^b$ in each occurrence are independently hydrogen, halogen, $—C_{1-8}$ alkyl or —OH.

5. The compound according to claim 1, wherein $R^1$ is $—OR^{1a}$ or $—NR^{1a}R^{1b}$.

6. The compound according to claim 1, wherein:

$R^1$ is $—OR^{1a}$ or $—NR^{1a}R^{1b}$;

$R^{1a}$ and $R^{1b}$ are independently hydrogen, $—C_{1-8}$ alkyl or $—C_{2-8}$ alkenyl, wherein the $—C_{1-8}$ alkyl or $—C_{2-8}$ alkenyl are each optionally substituted with one or two or three substituents selected from: heterocyclyl optionally substituted with $R^{1e}$, aryl optionally substituted with $R^{1e}$, $CH_3—(OCH_2CH_2)_n—$ where n is 3 to 10, or $—OR^{1f}$, $R^{1e}$ is halogen, $—C_{1-6}$ alkyl optionally substituted with halogen, carboxyl, alkoxycarbonyl, aminocarbonyl, alkylaminocarbonyl, or dialkylaminocarbonyl; and $R^{1f}$ is $—C_{1-8}$ alkyl, aryl or heteroaryl, each being optionally substituted with $—C_{1-4}$ alkyl or halogen.

7. The compound according to claim 1, wherein $R^1$ is $—OR^{1a}$, and wherein $R^{1a}$ is $—C_{1-8}$ alkyl optionally substituted with one or two or three substituents selected from: halogen, $—C_{1-8}$ alkyl optionally substituted with $R^{1e}$, cycloalkyl optionally substituted with $R^{1e}$, heterocyclyl optionally substituted with $R^{1e}$, aryl optionally substituted with $R^{1e}$, heteroaryl optionally substituted with $R^{1e}$, $CH_3—(OCH_2CH_2)_n—$ where n is 3 to 10, or $—OR^{1f}$.

8. The compound according to claim 1, wherein $R^1$ is $—OR^{1a}$, and $R^{1a}$ is branched alkyl, wherein the branching is at the α position relative to the oxygen atom.

9. The compound according to claim 1, wherein $R^2$ and $R^3$ at each occurrence are each independently hydrogen or $C_{1-8}$ alkyl.

10. The compound according to claim 1, wherein $R^4$ is hydrogen.

11. The compound according to claim 1, wherein $R^5$ is halogen, oxo, hydroxyl, $C_{1-8}$ alkyl, halogenated $C_{1-8}$ alkyl, $C_{1-8}$ alkoxy, halogenated $C_{1-8}$ alkoxy or $—C(=O)OR^{5a}$; $R^{5a}$ is hydrogen, $C_{1-8}$ alkyl or halogenated $C_{1-8}$ alkyl; and p is 0, 1 or 2.

12. The compound according to claim 1, wherein $R^5$ is methyl, ethyl, isopropyl, oxo, fluorine, trifluoromethyl, hydroxyl, or ethoxycarbonyl, and $L^2$-$R^6$ is methyl, ethyl, isopropyl, 2-(methylamino)ethyl, benzyl, piperidin-4-ylmethyl, (methylamino)methyl, 2-(methylamino)ethyl, hydroxymethyl, trifluoromethyl, pyrrolidin-3-yl, pyrrolidin-2-yl, piperidin-4-yl, hydroxyl, ethoxycarbonyl, phenyl, methylamino, or amino.

13. The compound according to claim 1, wherein p is 0 or 1.

14. The compound according to claim 1, wherein the

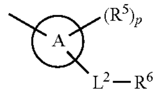

moiety is piperidin-4-yl, 1-methylpiperidin-4-yl, 1-(2-(methylamino)ethyl)piperidin-4-yl, 1-(pyrrolidin-3-yl)piperidin-4-yl, 1-(pyrrolidin-2-yl)piperidin-4-yl, 1-(piperidin-4-yl)piperidin-4-yl, 4-methylpiperidin-4-yl, 3-hydroxypiperidin-4-yl, 3-oxopiperidin-4-yl, 3-fluopiperidin-4-yl, 3,3-difluorpiperidin-4-yl, 3-benzylpiperidin-4-yl, 1-(piperidin-4-ylmethyl)piperidin-4-yl, 4-((methylamino)methyl)piperidin-1-yl, 2-ethylpiperidin-4-yl, 2-ethoxycarbonylpiperidin-4-yl, 2-hydroxymethylpiperidin-4-yl, 1-methyl-2-((methylamino)methyl)piperidin-4-yl, 1-isopropyl-2-((methylamino)methyl)piperidin-4-yl, 2,6-dimethylpiperidin-4-yl, 2,2-dimethylpiperidin-4-yl, 2-(trifluoromethyl)piperidin-4-yl, 2-phenylpiperidin-4-yl, 4-(methylamino)piperidin-1-yl, piperidin-2-yl, pyrrolidin-3-yl, azetidin-3-yl, azepan-4-yl, (R)-3-methylpiperazin-1-yl, (S)-3-methylpiperazin-1-yl, (S)-3-methylpiperazin-1-yl, (R)-3-methylpiperazin-1-yl, 2-hydroxy-7-azaspiro[3.5]non-2-yl, 3-azabicyclo[3.1.0]hex-6-yl, 2-azaspiro[3.3]hept-6-yl, 7-azaspiro[3.5]non-2-yl, 2-azaspiro[3.5]non-7-yl, 2-azabicyclo[2.2.1]hept-5-yl, 8-azabicyclo[3.2.1]oct-3-yl, 3-aminocyclobutyl, 1-(2-(methylamino)ethyl)-2-oxo-piperidin-4-yl, 2-azabicyclo[4.1.0]hept-5-yl, 1,2,3,6-tetrahydropyridin-4-yl, 3-aminobicyclo[1.1.1]pent-1-yl, or 3-((methylamino)methyl) bicyclo[1.1.1]pent-1-yl.

15. A pharmaceutical composition comprising the compound of claim 1 or a pharmaceutically acceptable salt thereof, and at least one pharmaceutically acceptable carrier or excipient.

16. A method for regulating TLR8, comprising administering the compound of claim 1 or a pharmaceutically acceptable salt thereof to an individual.

17. A compound, or a pharmaceutically acceptable salt or a stereoisomer thereof, selected from the group consisting of:

2-butoxy-7-(piperidin-4-ylmethyl)imidazo[2,1-f][1,2,4]triazin-4-amine;

2-(pent-2-yloxy)-7-(piperidin-4-ylmethyl)imidazo[2,1-f][1,2,4]triazin-4-amine;

2-butoxy-7-(2-(piperidin-4-yl)ethyl)imidazo[2,1-f][1,2,4]triazin-4-amine;

$N^2$-butyl-7-(piperidin-4-ylmethyl)imidazo[2,1-f][1,2,4]triazin-2,4-diamine;

$N^2$-(pent-2-yl)-7-(piperidin-4-ylmethyl)imidazo[2,1-f][1,2,4]triazin-2,4-diamine;

(S)-2-(pent-2-yloxy)-7-(piperidin-4-ylmethyl)imidazo[2,1-f][1,2,4]triazin-4-amine;

(R)-2-(pent-2-yloxy)-7-(piperidin-4-ylmethyl)imidazo[2,1-f][1,2,4]triazin-4-amine;

7-((4-methylpiperidin-4-yl)methyl)-2-(pent-2-yloxy)imidazo[2,1-f][1,2,4]triazin-4-amine;
2-(pent-2-yloxy)-7-(piperazin-1-ylmethyl)imidazo[2,1-f][1,2,4]triazin-4-amine;
2-(((S)-pent-2-yl)oxy)-7-(piperidin-3-ylmethyl)imidazo[2,1-f][1,2,4]triazin-4-amine;
2-pentyl-7-(piperidin-4-ylmethyl)imidazo[2,1-f][1,2,4]triazin-4-amine;
(S)-7-((1-(2-(methylamino)ethyl)piperidin-4-yl)methyl)-2-(pent-2-yloxy)imidazo[2,1-f][1,2,4]triazin-4-amine;
2-(((S)-pent-2-yl)oxy)-7-((1-(pyrrolidin-3-yl)piperidin-4-yl)methyl)imidazo[2,1-f][1,2,4]triazin-4-amine;
(S)-2-(pent-2-yloxy)-7-((1-(piperidin-4-ylmethyl)piperidin-4-yl)methyl)imidazo[2,1-f][1,2,4]triazin-4-amine;
7-(((R)-3-methylpiperazin-1-yl)methyl)-2-(pent-2-yloxy)imidazo[2,1-f][1,2,4]triazin-4-amine;
7-(((S)-3-methylpiperazin-1-yl)methyl)-2-(pent-2-yloxy)imidazo[2,1-f][1,2,4]triazin-4-amine;
7-(((S)-2-methylpiperazin-1-yl)methyl)-2-(pent-2-yloxy)imidazo[2,1-f][1,2,4]triazin-4-amine;
7-(((R)-2-methylpiperazin-1-yl)methyl)-2-(pent-2-yloxy)imidazo[2,1-f][1,2,4]triazin-4-amine;
(S)-7-((1-(3-(methylamino)propyl)piperidin-4-yl)methyl)-2-(pent-2-yloxy)imidazo[2,1-f][1,2,4]triazin-4-amine;
2-(((S)-pent-2-yl)oxy)-7-((1-(pyrrolidin-2-ylmethyl)piperidin-4-yl)methyl)imidazo[2,1-f][1,2,4]triazin-4-amine;
7-((4-(methylamino)piperidin-1-yl)methyl)-2-(pent-2-yloxy)imidazo[2,1-f][1,2,4]triazin-4-amine;
7-((4-(methylamino)methyl)piperidin-1-yl)methyl)-2-(pent-2-yloxy)imidazo[2,1-f][1,2,4]triazin-4-amine;
(S)-7-([1,4'-bipiperidin]-4-ylmethyl)-2-(pent-2-yloxy)imidazo[2,1-f][1,2,4]triazin-4-amine;
2-(4-amino-2-(pent-2-yloxy)imidazo[2,1-f][1,2,4]triazin-7-yl)-7-azaspiro[3.5]nona-2-ol;
7-(azepan-4-ylmethyl)-2-(((S)-pent-2-yl)oxy)imidazo[2,1-f][1,2,4]triazin-4-amine;
2-(((S)-pent-2-yl)oxy)-7-(pyrrolidin-3-ylmethyl)imidazo[2,1-f][1,2,4]triazin-4-amine;
7-((2-methylpiperidin-4-yl)methyl)-2-(((S)-pent-2-yl)oxy)imidazo[2,1-f][1,2,4]triazin-4-amine;
3-((4-amino-7-(piperidin-4-ylmethyl)imidazo[2,1-f][1,2,4]triazin-2-yl)oxy) hexan-1-ol;
7-(cyclohexylmethyl)-2-(pent-2-yloxy)imidazo[2,1-f][1,2,4]triazin-4-amine;
7-(((1s,3S)-3-aminocyclobutyl)methyl)-2-(((S)-pent-2-yl)oxy)imidazo[2,1-f][1,2,4]triazin-4-amine;
(S)-7-((4-(methylamino)cyclohexyl)methyl)-2-(pent-2-yloxy)imidazo[2,1-f][1,2,4]triazin-4-amine;
(S)-7-((1-methylpiperidin-4-yl)methyl)-2-(pent-2-yloxy)imidazo[2,1-f][1,2,4]triazin-4-amine;
7-(((1R,5S,6s)-3-azabicyclo[3.1.0]hex-6-yl)methyl)-2-(((S)-pent-2-yl)oxy)imidazo[2,1-f][1,2,4]triazin-4-amine;
7-(((1R,5S,6s)-3-azabicyclo[3.1.0]hex-6-yl)methyl)-2-(((S)-pent-2-yl)oxy)imidazo[2,1-f][1,2,4]triazin-4-amine;
2-((4-amino-7-(piperidin-4-ylmethyl)imidazo[2,1f][1,2,4]triazin-2-yl)oxy) pentan-1-ol;
(S)-2-(pent-2-yloxy)-7-(piperidin-4-ylidenemethyl)imidazo[2,1-f][1,2,4]triazin-4-amine;
2-(pent-2-yloxy)-7-((tetrahydro-2H-pyran-4-yl)methyl)imidazo[2,1-f][1,2,4]triazin-4-amine;
(S)-2-(pent-2-yloxy)-N7-(piperidin-4-yl)imidazo[2,1-f][1,2,4]triazin-4,7-diamine;
(S)-7-((1-(2-aminomethyl)piperidin-4-yl)methyl)-2-(pent-2-yloxy)imidazo[2,1-f][1,2,4]triazin-4-amine;
(S)-7-(azetidin-3-ylmethyl)-2-(pent-2-yloxy)imidazo[2,1-f][1,2,4]triazin-4-amine;
(S)-7-((3-aminobicyclo[1.1.1]pent-1-yl)methyl)-2-(pent-2-yloxy)imidazo[2,1-f][1,2,4]triazin-4-amine;
2-((5-methylisoxazol-3-yl) methoxy)-7-(piperidin-4-ylmethyl)imidazo[2,1-f][1,2,4]triazin-4-amine;
2-(((S)-pent-2-yl)oxy)-7-(pyrrolidin-2-ylmethyl)imidazo[2,1-f][1,2,4]triazin-4-amine;
(S)-7-((2-azaspiro[3.5]non-7-yl)methyl)-2-(pent-2-yloxy)imidazo[2,1-f][1,2,4]triazin-4-amine;
2-((5-methylthiazol-2-yl) methoxy)-7-(piperidin-4-ylmethyl)imidazo[2,1-f][1,2,4]triazin-4-amine;
2-((1-phenylpent-2-yl)oxy)-7-(piperidin-4-ylmethyl)imidazo[2,1-f][1,2,4]triazin-4-amine;
7-(piperidin-4-ylmethyl)-2-((tetrahydrofuran-3-yl) methoxy)imidazo[2,1-f][1,2,4]triazin-4-amine;
2-(hept-4-yloxy)-7-(piperidin-4-ylmethyl)imidazo[2,1-f][1,2,4]triazin-4-amine;
2-(pent-3-yloxy)-7-(piperidin-4-ylmethyl)imidazo[2,1-f][1,2,4]triazin-4-amine;
(S)-2-(hex-3-yloxy)-7-(piperidin-4-ylmethyl)imidazo[2,1-f][1,2,4]triazin-4-amine;
(S)-7-((7-azaspiro[3.5]non-2-yl)methyl)-2-(pent-2-yloxy)imidazo[2,1-f][1,2,4]triazin-4-amine;
2-(((S)-pent-2-yl)oxy)-7-(piperidin-2-ylmethyl)imidazo[2,1-f][1,2,4]triazin-4-amine;
(S)-7-((3,3-dimethylpiperidin-4-ylidene)methyl)-2-(pent-2-yloxy)imidazo[2,1-f][1,2,4]triazin-4-amine;
7-((3,3-dimethylpiperidin-4-yl)methyl)-2-(((S)-pent-2-yl)oxy)imidazol[2,1-f][1,2,4]triazin-4-amine;
7-((1-(2-(methylamino)propyl)piperidin-4-yl)methyl)-2-(((S)-pent-2-yl)oxy)imidazo[2,1-f][1,2,4]triazin-4-amine;
7-((8-azabicyclo[3.2.1]oct-3-ylene)methyl)-2-(((S)-pent-2-yl)oxy)imidazo[2,1-f][1,2,4]triazin-4-amine;
7-((8-azabicyclo[3.2.1]oct-3-yl)methyl)-2-(((S)-pent-2-yl)oxy)imidazo[2,1-f][1,2,4]triazin-4-amine;
7-((3,3-difluorpiperidin-4-yl)methyl)-2-(((S)-pent-2-yl)oxy)imidazo[2,1-f][1,2,4]triazin-4-amine;
7-((1-((R or S)-2-(methylamino)propyl)piperidin-4-yl)methyl)-2-(((S)-pent-2-yl)oxy)imidazo[2,1-f][1,2,4]triazin-4-amine;
7-((1-((S or R)-2-(methylamino)propyl)piperidin-4-yl)methyl)-2-(((S)-pent-2-yl)oxy)imidazo[2,1-f][1,2,4]triazin-4-amine; and
7-((3-methylpiperidin-4-yl)methyl)-2-(((S)-pent-2-yl)oxy)imidazo[2,1-f][1,2,4]triazin-4-amine.

18. A compound, or a pharmaceutically acceptable salt or a stereoisomer thereof, selected from the group consisting of:
2-(pent-2-yloxy)-7-(piperidin-4-ylmethyl)imidazo[2,1-f][1,2,4]triazin-4-amine;
2-butoxy-7-(piperidin-4-ylmethyl)imidazo[2,1-f][1,2,4]triazin-4-amine;
(S)-2-(pent-2-yloxy)-7-(piperidin-4-ylmethyl)imidazo[2,1-f][1,2,4]triazin-4-amine;
(S)-7-((1-(2-(methylamino)ethyl)piperidin-4-yl)methyl)-2-(pent-2-yloxy)imidazo[2,1-f][1,2,4]triazin-4-amine;
2-(pent-3-yloxy)-7-(piperidin-4-ylmethyl)imidazo[2,1-f][1,2,4]triazin-4-amine; and
(S)-2-(hex-3-yloxy)-7-(piperidin-4-ylmethyl)imidazo[2,1-f][1,2,4]triazin-4-amine.

* * * * *